US010172611B2

(12) United States Patent
Shelton, IV et al.

(10) Patent No.: US 10,172,611 B2
(45) Date of Patent: Jan. 8, 2019

(54) ADJUNCT MATERIALS AND METHODS OF USING SAME IN SURGICAL METHODS FOR TISSUE SEALING

(71) Applicant: Ethicon LLC, Guaynabo, PR (US)

(72) Inventors: Frederick E. Shelton, IV, Hillsboro, OH (US); Jason L. Harris, Lebanon, OH (US); Bret W. Smith, Kings Mills, OH (US)

(73) Assignee: Ethicon LLC, Guaynabo, PR (US)

( * ) Notice: Subject to any disclaimer, the term of this patent is extended or adjusted under 35 U.S.C. 154(b) by 666 days.

(21) Appl. No.: 14/300,954

(22) Filed: Jun. 10, 2014

(65) Prior Publication Data

US 2015/0351758 A1    Dec. 10, 2015

(51) Int. Cl.
*A61B 17/08*    (2006.01)
*A61D 1/00*    (2006.01)
(Continued)

(52) U.S. Cl.
CPC .... *A61B 17/0644* (2013.01); *A61B 17/00491* (2013.01); *A61B 17/068* (2013.01);
(Continued)

(58) Field of Classification Search
CPC ........ A61B 17/07292; A61B 17/00491; A61B 17/0057; A61B 17/04; A61B 17/401; A61B 17/0643; A61B 17/068; A61B 17/08; A61B 17/10; A61B 17/11; A61B 17/115; A61B 17/0682; A61B 17/0684; A61B 17/0686; A61B 17/072; A61B 17/07207; A61B 17/083; A61B 17/085; A61B 17/105; A61B 17/1114; A61B 17/1128; A61B 17/1146; A61B 17/1152; A61B 17/1155;
(Continued)

(56) References Cited

U.S. PATENT DOCUMENTS 5,690,675 A * 11/1997 Sawyer ............ A61B 17/00491
128/898
5,698,213 A    12/1997 Jamiolkowski et al.
(Continued)

FOREIGN PATENT DOCUMENTS

EP    2008595 A2    12/2008
WO    14016819 A1    1/2014

OTHER PUBLICATIONS

Chen et al. "Elastomeric Biomaterials for Tissue Engineering." Prog. Polymer. Sci. 38(2013):584-671.
(Continued)

*Primary Examiner* — Katherine M Shi
(74) *Attorney, Agent, or Firm* — Mintz Levin Cohn Ferris Glovsky and Popeo, P.C.

(57) ABSTRACT

Surgical methods involving cutting and sealing tissue include affixing a first adjunct material to tissue at a treatment site, such as by stapling the adjunct to tissue. A second adjunct material is applied to at least a portion of the first adjunct material such that the second adjunct material interacts with the first adjunct material to form a seal in an area of the tissue covered by at least one of the first and the second adjunct material. The resulting tissue sealing structure, which includes a combination of the two adjuncts, is believed to be superior to the sealing properties of either adjunct alone.

12 Claims, 103 Drawing Sheets

(51) Int. Cl.
*A61B 17/064* (2006.01)
*A61B 17/068* (2006.01)
*A61B 17/00* (2006.01)
A61B 17/072 (2006.01)
A61B 17/115 (2006.01)

(52) U.S. Cl.
CPC .. *A61B 17/07292* (2013.01); *A61B 17/07207* (2013.01); *A61B 17/1155* (2013.01); *A61B 2017/005* (2013.01); *A61B 2017/0046* (2013.01); *A61B 2017/00495* (2013.01); *A61B 2017/00893* (2013.01); *A61B 2017/00898* (2013.01); *A61B 2017/07271* (2013.01)

(58) Field of Classification Search
CPC ........... A61B 2017/00884; A61B 2017/00889; A61B 2017/00893; A61B 2017/00495; A61B 2017/005; A61B 2017/00504; A61B 2017/00584; A61B 2017/00588; A61B 2017/00592; A61B 2017/00597; A61B 2017/00646; A61B 2017/00668; A61B 2017/0404; A61B 2017/0406; A61B 2017/0408; A61B 2017/0688; A61B 2017/07214; A61B 2017/07221; A61B 2017/07228; A61B 2017/07235; A61B 2017/07242; A61B 2017/0725; A61B 2017/07257; A61B 2017/07264; A61B 2017/07271; A61B 2017/07278; A61B 2017/07285; A61B 2017/07292; A61B 2017/081; A61B 2017/086; A61B 2017/088; A61B 2017/1103; A61B 2017/1107; A61B 2017/111; A61B 2017/1117
See application file for complete search history.

(56) References Cited

U.S. PATENT DOCUMENTS

| | | | |
|---|---|---|---|
| 5,700,583 A | 12/1997 | Jamiolkowski et al. | |
| 6,736,823 B2* | 5/2004 | Darois ................. | A61F 2/0063 600/37 |
| 7,143,924 B2 | 12/2006 | Scirica et al. | |
| 7,143,925 B2 | 12/2006 | Shelton, IV et al. | |
| 7,772,352 B2 | 8/2010 | Bezwada | |
| 8,317,070 B2 | 11/2012 | Hueil et al. | |
| 8,393,514 B2 | 3/2013 | Shelton, IV et al. | |
| 8,551,058 B2 | 10/2013 | Measamer et al. | |
| 2005/0059997 A1 | 3/2005 | Bauman et al. | |
| 2005/0245965 A1* | 11/2005 | Orban, III ............ | A61B 17/068 606/214 |
| 2006/0257458 A1 | 11/2006 | Gorman et al. | |
| 2008/0140115 A1 | 6/2008 | Stopek | |
| 2009/0234193 A1 | 9/2009 | Weisenburgh, II et al. | |
| 2009/0270686 A1 | 10/2009 | Duke et al. | |
| 2011/0192882 A1 | 8/2011 | Hess et al. | |
| 2012/0024934 A1 | 2/2012 | Shelton, IV et al. | |
| 2012/0080335 A1 | 4/2012 | Shelton, IV et al. | |
| 2012/0083835 A1 | 4/2012 | Shelton, IV et al. | |
| 2012/0187179 A1* | 7/2012 | Gleiman ............... | A61B 17/072 227/176.1 |
| 2013/0112733 A1 | 5/2013 | Aranyi et al. | |
| 2013/0146642 A1 | 6/2013 | Shelton, IV et al. | |
| 2013/0153641 A1 | 6/2013 | Shelton, IV et al. | |
| 2013/0161374 A1 | 6/2013 | Swayze et al. | |
| 2013/0256365 A1 | 10/2013 | Shelton, IV et al. | |
| 2013/0256372 A1 | 10/2013 | Baxter, III et al. | |
| 2013/0256376 A1 | 10/2013 | Barton et al. | |
| 2013/0256377 A1 | 10/2013 | Schmid et al. | |
| 2014/0158741 A1 | 6/2014 | Woodard, Jr. et al. | |
| 2015/0173756 A1 | 6/2015 | Baxter, III et al. | |
| 2015/0272575 A1 | 10/2015 | Leimbach et al. | |

OTHER PUBLICATIONS

Lim et al. "Fabrication and Evaluation of Poly(epsilon-caprolactone)/Silk Fibroin Blend Nanofibrous Scaffold." Bioplolymers. 97(2012):265-275.

Zhao et al. "Biodegradable Fibrous Scaffolds Composed of Gelatin Coated Poly(?-caprolactone) Prepared by Coaxial Elecrospinning." J. Biomed. Mater. Res. 83A(2007):372-382.

European Search Report for Application No. EP 15171455, dated Sep. 30, 2015. (5 Pages).

* cited by examiner

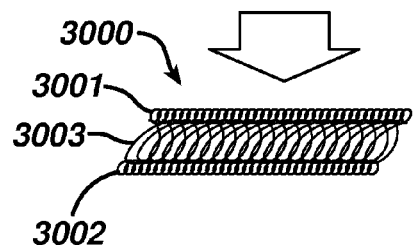 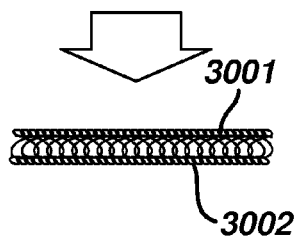 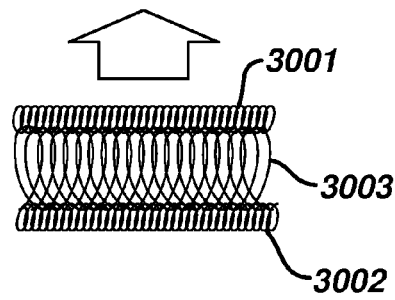
FIG. 49A  FIG. 49B  FIG. 49C
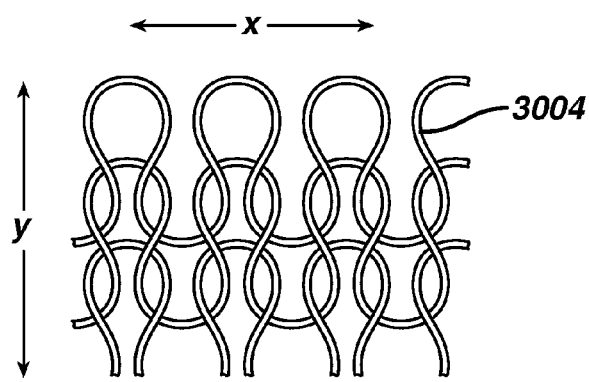
FIG. 50
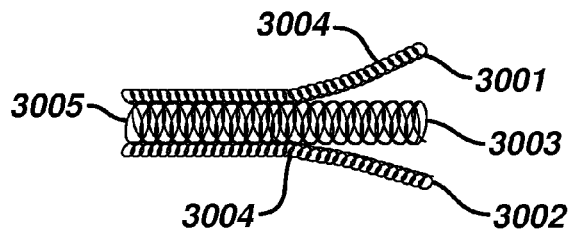 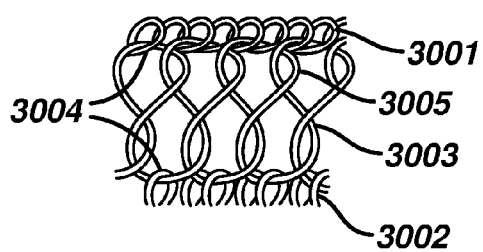
FIG. 51A  FIG. 51B

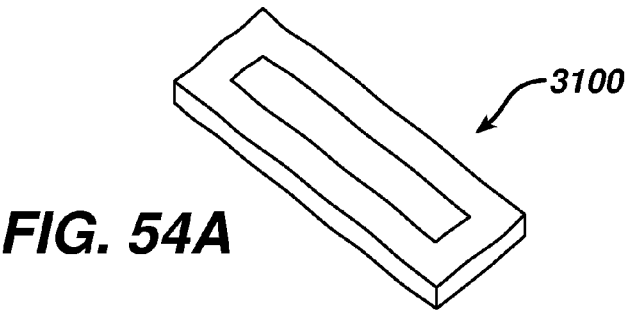
FIG. 54A
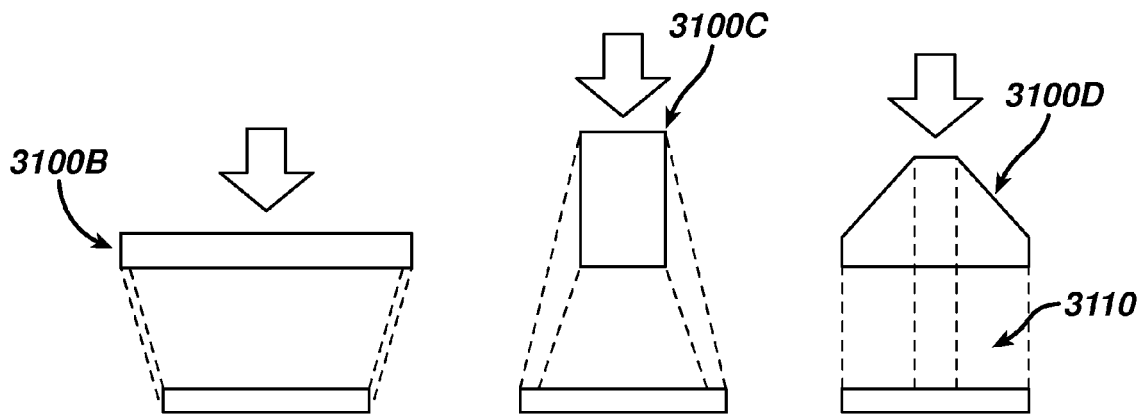
FIG. 54B  FIG. 54C  FIG. 54D
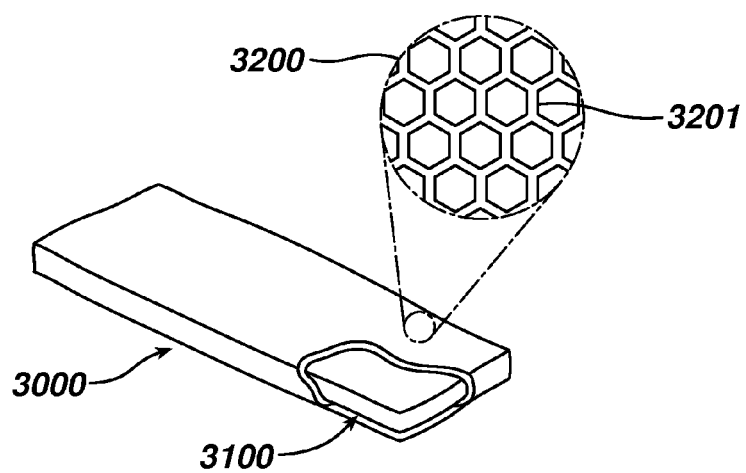
FIG. 55

FIG. 62
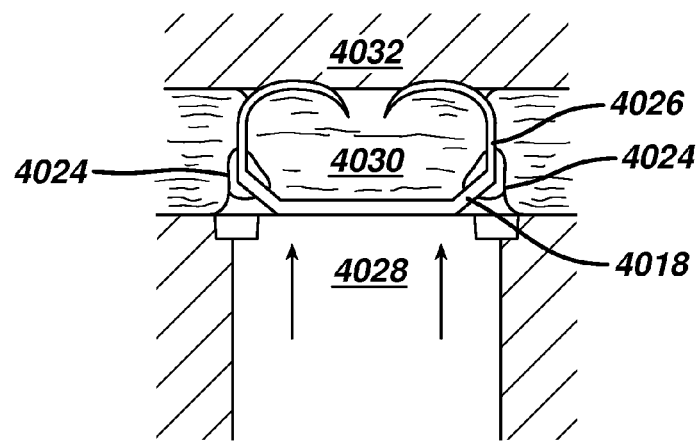
FIG. 63A FIG. 63B
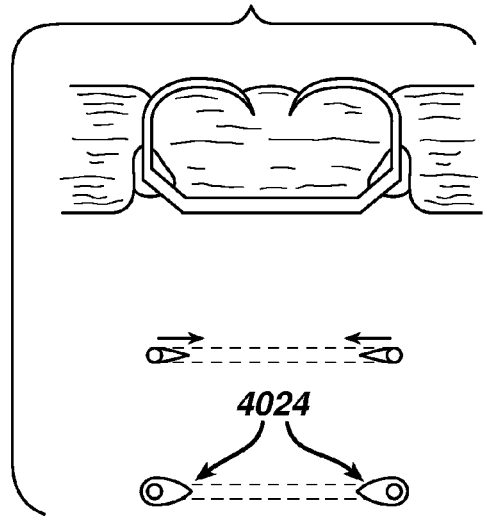 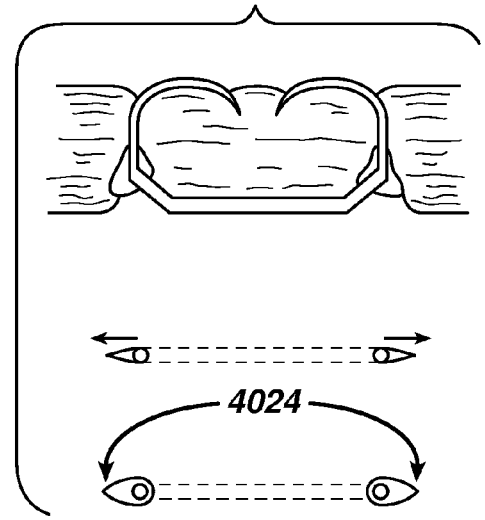

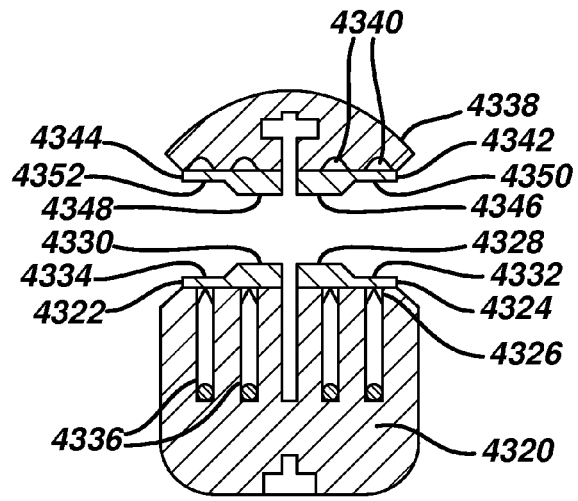
FIG. 116
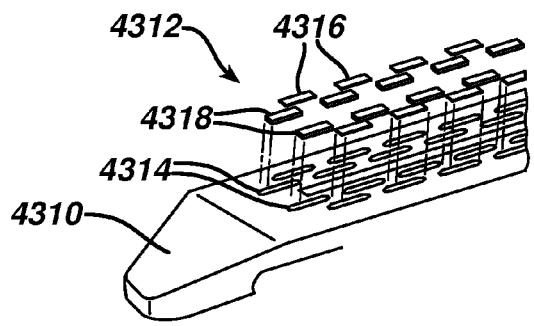
FIG. 117
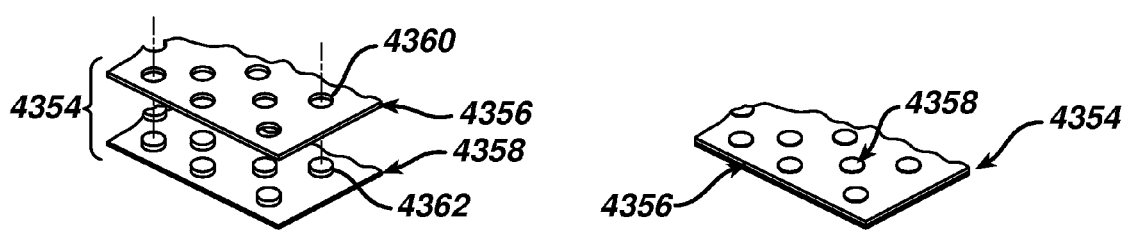
FIG. 118A          FIG. 118B

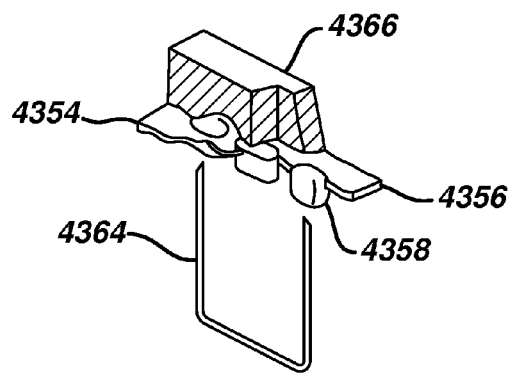
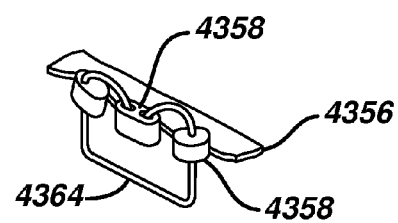
FIG. 119A      FIG. 119B
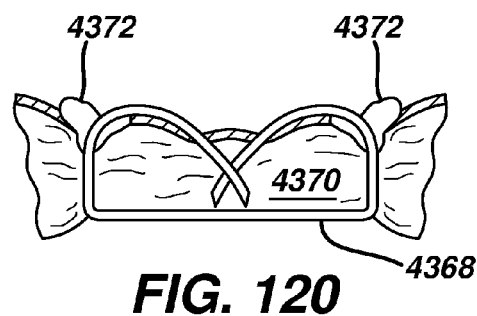
FIG. 120
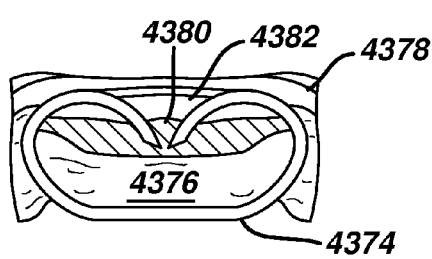    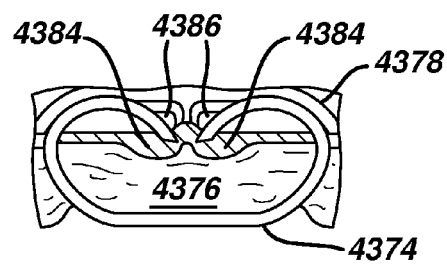
FIG. 121        FIG. 122

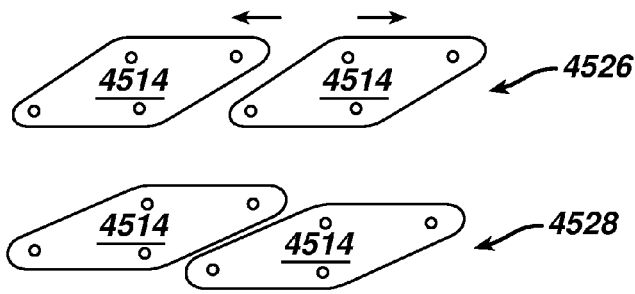
FIG. 128
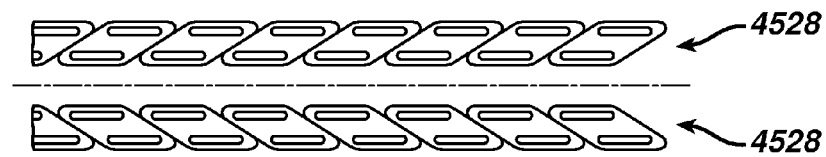
FIG. 129
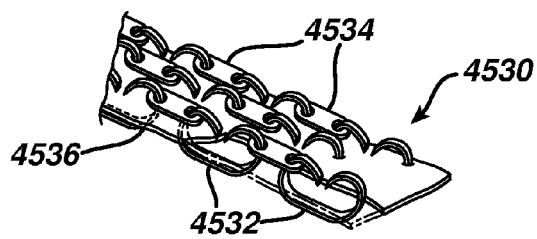   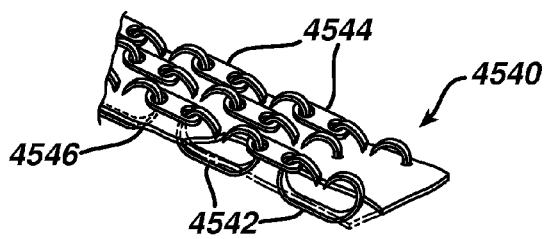
FIG. 130A   FIG. 130B
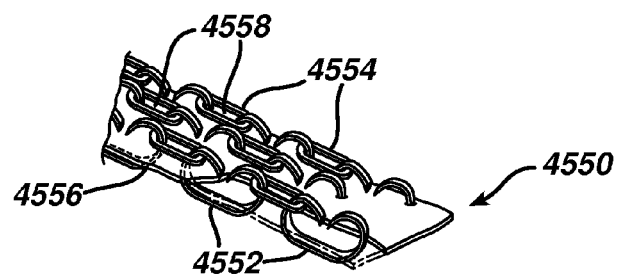
FIG. 130C

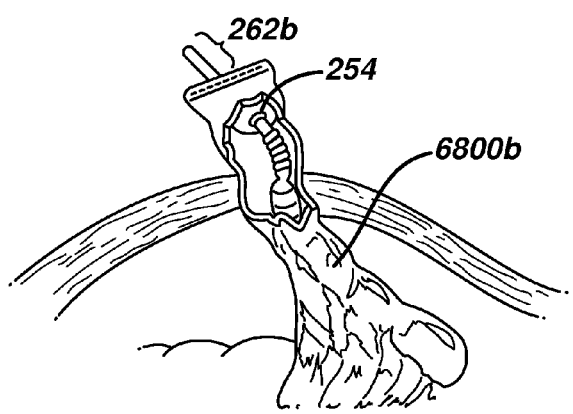
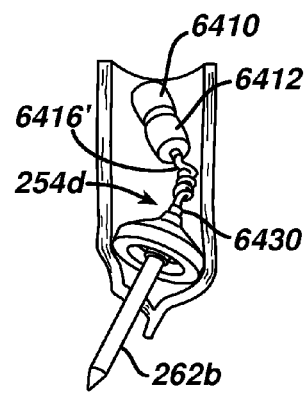
FIG. 210A  FIG. 210B
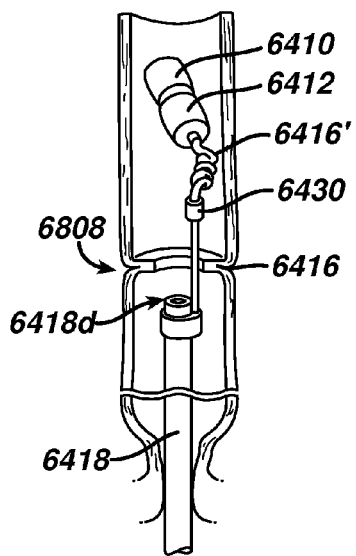 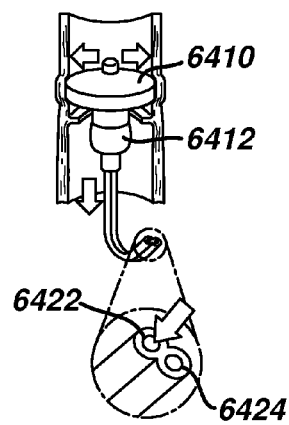 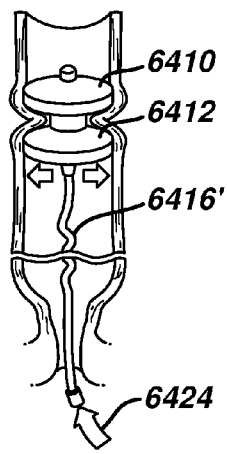
FIG. 210C  FIG. 210D  FIG. 210E

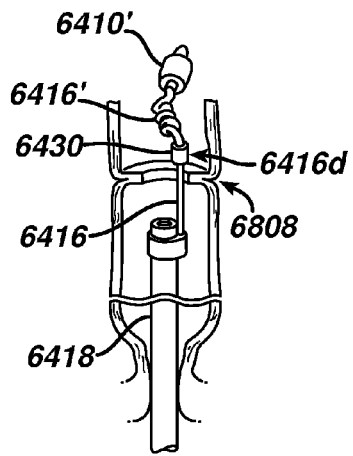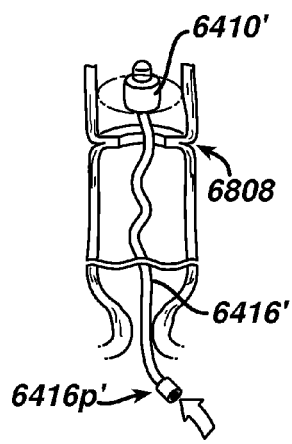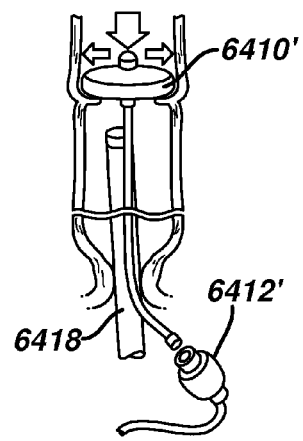
*FIG. 212A*  *FIG. 212B*  *FIG. 212C*
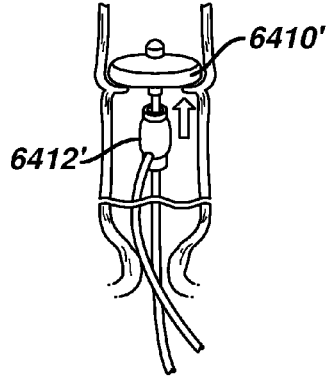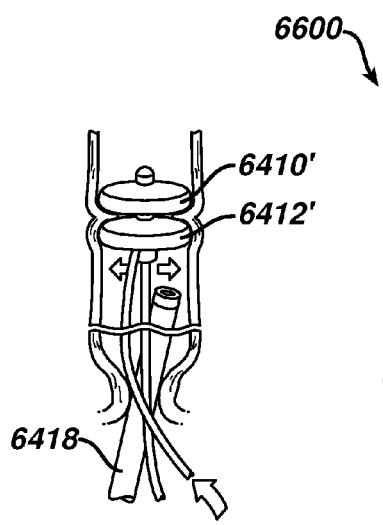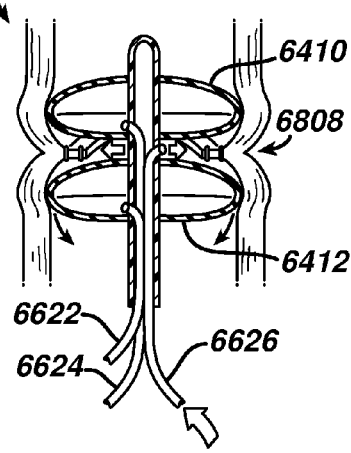
*FIG. 212D*  *FIG. 212E*  *FIG. 213*

ADJUNCT MATERIALS AND METHODS OF USING SAME IN SURGICAL METHODS FOR TISSUE SEALING

FIELD

The subject matter disclosed herein relates to surgical instruments, and in particular to methods, devices, and components thereof for cutting and stapling tissue.

BACKGROUND

Surgical staplers are used in surgical procedures to seal, divide, and/or transect tissues in the body by closing openings in tissue, blood vessels, ducts, shunts, or other objects or body parts involved in the particular procedure. The openings can be naturally occurring, such as passageways in blood vessels, airways or an internal lumen or organ like the stomach, or they can be formed by the surgeon during a surgical procedure, such as by puncturing tissue or blood vessels to form a bypass or an anastomosis, or by cutting tissue during a stapling procedure.

Most staplers have a handle with an elongate flexible or rigid shaft having a pair of opposed jaws formed on an end thereof for holding and forming staples therebetween. At least one of the opposed jaws is movable relative to the other jaw. In the case of laparoscopic surgery, often one jaw is fixed and the other is movable. In some devices (for example an open linear stapler), the opposed jaws can be separated by the operator and reassembled providing the relative motion needed for tissue placement. The staples are typically contained in a staple cartridge, which can house multiple rows of staples and is often disposed in one of the two jaws for ejection of the staples to the surgical site. In use, the jaws are positioned so that the object to be stapled is disposed between the jaws, and staples are ejected and formed when the jaws are closed and the device is actuated. Some staplers include a knife configured to travel between rows of staples in the staple cartridge to longitudinally cut the stapled tissue between the stapled rows. Placement of the device, manipulation of components or systems of the device, and other actuations of the device such as articulation, firing, etc. can be accomplished in a variety of ways, such as electromechanically, mechanically, or hydraulically.

There are various types of staplers suited for particular surgical procedures. For example, linear staplers include a handle with an elongate shaft having a pair of opposed jaws formed on an end thereof for holding and forming staples therebetween. At least one of the opposed jaws is movable relative to the other. The staples are typically contained in a staple cartridge assembly, which can house multiple rows of staples and is often disposed in one of the two jaws for ejection of the staples to the surgical site. Circular staplers have a handle and an elongate shaft with an anvil and a cartridge assembly disposed on a distal end of the elongate shaft, the anvil axially movable relative to the cartridge assembly and configured to form staples therebetween and deploy the staples into tissue.

While surgical staplers have improved over the years, a number of problems can potentially arise. Although rare, as illustrated in FIG. 1, one problem is that leaks can occur due to staples S forming tears H when penetrating a tissue T or other object in which the staples S are disposed. Blood, air, gastrointestinal fluids, and other fluids can seep through the tears H formed by the staples S, even after the staples S are fully formed. The tissue T being treated can also become inflamed due to the manipulations and deformations that can occur during stapling. Still further, staples, as well as other objects and materials implanted during stapling procedures, generally lack the same characteristics as tissue in which they are implanted. For example, staples and other objects and materials can lack the natural flexibility of the tissue in which they are implanted. A person skilled in the art will recognize that it is often desirable for tissue to maintain as much of its natural characteristics as possible after staples are disposed therein.

In the particular case of stapling bronchial tubes, such as during lung resection, it is important for no leaks to be present after stapling so that air does not inappropriately enter or exit the lung and/or the thoracic cavity. Air escaping a stapled bronchial tube through a leak can interfere with breathing and lung function, such as by preventing full intake of air. Air exiting a stapled bronchial tube into the thoracic cavity through a leak is unsterile and can cause infection and/or other complications in the otherwise sterile environment of the thoracic cavity. However, it can be difficult to prevent leaks in bronchial tubes for a variety of reasons. The small size of bronchial tubes can make delivery of any sealing materials into bronchial tubes difficult, inflammation due to implanted staples and/or other objects and materials can cause bronchial tubes to close or nearly close since they have small diameters, and/or it can be difficult for sealing materials introduced into a bronchial tube to withstand the repeated expansion and contraction of the lung without failing and/or moving within the tube so as to break the seal of the bronchial tube.

In the particular case of stapling a colon, it is important that the staple line of the anastomosis is substantially sealed so that gastrointestinal solids and fluid remain in the organ. Leakage from the tubular body organ, e.g. a colon, can interfere with normal digestive function and can introduce bacteria into other portions of the body, causing infection. However, it can be difficult to prevent leaks in a tubular body organ for a variety of reasons. For example, it can be difficult for the tissue disposed near the staple line to withstand repeated expansion and contraction that occurs when solids and fluid passes through the colon. Additionally, it can be difficult to deliver sealant to the tubular body organ and control the position of the sealant when it is curing from a liquid state to a solidified state Accordingly, there remains a need for improved devices, materials, and methods for stapling tissue, or other objects or body parts such that leaking and inflammation is minimized while substantially maintaining the natural characteristics of the treatment region.

SUMMARY

A staple cartridge for use with a surgical stapler is provided and can include a cartridge body and an adjunct material. The cartridge body can have a plurality of staple cavities configured to seat staples therein. The adjunct material can be mated to the cartridge body and configured to be detached therefrom as the staples are deployed from the cartridge body and into tissue. The adjunct material can include a solid central portion sized and shaped to substantially correspond to the cartridge body, and a wing portion extending along at least two sides of the solid central portion such that the wing portion extends beyond a lateral boundary of the cartridge body in a direction traverse to a longitudinal axis of the cartridge body.

The solid central portion of the adjunct material can vary in any number of ways. For example, the solid central portion of the adjunct material can be substantially rectangular shaped. In certain aspects, the solid central portion can include first and second opposed edges. In other aspects, the wing portion can extend along the first and second opposed edges of the adjunct material. In use, the solid central portion can be configured to reinforce a seal around staples when the adjunct material and the staples are coupled to tissue.

The wing portion can have various features. For example, the wing portion can include rounded corners. For another example, the wing portion can have a mesh structure. In certain aspects, the wing portion can have plurality of openings formed therein. In use, the wing portion can be configured to distribute or otherwise alter a strain or deformation present in tissue beyond the staple line when the adjunct material is disposed on tissue.

The solid and wing portions can be formed from various materials. In certain aspects, the solid and wing portions can be formed from a single polymer. In certain aspects, the solid and wing portions can be formed from more than one material or type of material. In certain aspects, the solid and wing portions can be formed from different materials. In other aspects, the wing portion can be more flexible than the solid central portion of the adjunct material.

An end effector for a surgical instrument is provided and can include first and second jaws, the first jaw having a cartridge body removably attached hereto and the cartridge body having a plurality of staple cavities configured to seat staples therein. The second jaw can include an anvil with a plurality of staples forming openings formed therein, at least one of the first and second jaws being movable relative to the other jaw. The end effector can include a buttress having a width greater than a width of at least one of the cartridge body and the anvil, the buttress having a compressible, central region configured to seal around a staple and a strain relief region adjacent to the compressible region. The strain relief region can have a plurality of openings formed therein and the strain relief region can extend from at least two sides of the central region. In use, the buttress can be releasably retained on at least one of the cartridge body and the anvil and can be configured to be released therefrom upon deployment of staples from the cartridge body and into the compressible region of the buttress.

The end effector can vary in a number of ways. In certain aspects, the plurality of openings include slits. When the buttress and the staples are deployed into tissue, the plurality of slits can extend parallel to longitudinal axes of the staples. In other aspects, the plurality of openings are spaced apart such that the strain relief region is more flexible along a lateral portion thereof than a portion of the strain relief region adjacent to the compressible region. In other aspects, the plurality of openings are shaped and spaced apart such that the strain relief region is more flexible along a longitudinal portion thereof than a portion of the strain relief region adjacent to the compressible region.

A method for implanting a tissue reinforcement material onto tissue is provided and includes engaging tissue between a cartridge assembly and an anvil of a surgical stapler at a surgical site, at least one of the cartridge assembly and the anvil having a tissue reinforcement material releasably retained thereon. The tissue reinforcement material can include a compressible, central region configured to seal around a staple and a flexible supportive region adjacent to the central region and defining an edge of the tissue reinforcement material. Actuating the surgical stapler can eject staples from the cartridge assembly so as to form a staple line through the central region and into the tissue to hold the tissue reinforcement material at the surgical site.

The method can vary in any number of ways. For example, actuating the surgical stapler can eject the staples through the central region and does not eject the staples through the flexible supportive region of the tissue reinforcement material. In certain aspects, the cartridge assembly and the anvil can be inserted into the surgical site with the flexible supportive region folded around at least one of the cartridge assembly and the anvil. Actuating the surgical stapler can advance a cutting member through the tissue reinforcement material and releases the tissue reinforcement material from the surgical stapler. In certain aspects, actuating the surgical stapler advances the cutting member through the central region of the tissue reinforcement material.

Methods for implanting a tissue reinforcement material onto tissue are provided. The method can include engaging tissue between a cartridge assembly and an anvil of a surgical stapler at a surgical site, at least one of the cartridge assembly and the anvil having a tissue reinforcement material retained thereon. The tissue reinforcement material can include a central region configured to provide a seal around a staple penetration site (e.g. in the tissue, in the central region, etc.) and an outer region adjacent to the central region and defining an edge of the tissue reinforcement material. Actuating the surgical stapler can eject staples from the cartridge assembly so as to form a staple line through the central region and into the tissue to hold the tissue reinforcement material at the surgical site. After actuating the surgical stapler, sealant can be delivered to the tissue reinforcement material when the sealant is in a first, liquid state such that the sealant solidifies thereon and reinforces a seal of the tissue at the staple line.

The method can vary in any number of ways. In certain aspects, actuating the surgical stapler ejects the staples through the central region of the tissue reinforcement material. The method can further include inserting the cartridge assembly and the anvil into the surgical site with the outer region of the tissue reinforcement material folded around at least one of the cartridge assembly and the anvil. Actuating the surgical stapler can release the tissue reinforcement material from the surgical stapler. In certain aspects, the surgical stapler advances the cutting member through the central region of the tissue reinforcement material. In other aspects, the surgical stapler forms a staple line having at least two rows of staples.

The sealant can be delivered to tissue in various ways. In certain aspects, the sealant is delivered through an applicator tool positioned adjacent to the tissue reinforcement material. Delivering the sealant can include depositing the sealant onto both the central and outer regions of the reinforcement material. In certain aspects, the sealant is delivered to the tissue reinforcement material in the first, liquid state, and the sealant penetrates a space in the tissue at the staple line and solidifies therein.

Systems for reinforcing a tissue seal are also provided. The system can include a sealant, a container, and an applicator tool. The sealant can be configured to transition from a first liquid state to a second solid state. The container can be configured to retain the sealant therein when the sealant is in the first liquid state, the container having a first port for receiving a gas and a second port for outputting nebulized sealant. The applicator tool can be coupled to the second port of the container, the applicator tool being configured to deliver the nebulized sealant to a surgical site.

The system can vary in any number of ways. In certain aspects, the applicator tool is a trocar. In other aspects, the gas includes carbon dioxide. In other aspects, the sealant includes a mixture of collagen, fibrinogen, and thrombin. These biologic materials may be derived from human and/or animal sources. The sealant can be configured to transition from the first liquid state to the second solid state after a predetermined amount of time. The system can include additional components. For example, a first tube can extend between the second port of the container and the applicator for receiving nebulized sealant.

Methods for delivering sealant to a body of a patient are also provided. The method can include delivering gas to a container having a sealant retained therein, thereby transitioning the sealant from a first, liquid state to a second, nebulized state. The nebulized sealant can be delivered through an applicator tool extending through an access port in a patient, the nebulized sealant solidifying onto tissue and forming a seal thereon.

The method can be performed in various ways. For example, the applicator tool can be positioned in a thoracic cavity of a patient prior to delivering the gas to the container. In certain aspects, the applicator tool includes a trocar, and nebulized sealant is delivered directly through the trocar and into the patient. The method can include positioning a distal end of the applicator tool adjacent to a staple line in the tissue prior to delivering the nebulized sealant to the tissue. In certain aspects, the hardened sealant is absorbed into the body after a predetermined passage of time.

Some embodiments relate to a staple cartridge assembly for use with a surgical stapler. In one embodiment, the staple cartridge assembly can include a cartridge body having a plurality of staple cavities configured to seat staples therein, and a tissue reinforcement construct removably attached to the cartridge body and configured to be delivered to tissue by deployment of the staples in the cartridge body. The tissue reinforcement construct can include a first, absorbable material encompassing a swellable, hydrophilic second material such that the second material is maintained within the first material in a constrained configuration. The second material can have a preconfigured shape such that, in an unconstrained configuration, the second material is adapted to expand to the preconfigured shape in which a peripheral edge portion of the second material has a thickness that is greater than a central portion of the second material.

The assembly can have any number of variations. For example, at least a portion of the first material can be less hydrophilic than the second material. For another example, the first material can be brittle. For yet another example, the second material can include a foam material. For another example, the first material can be selectively dissolvable such that portions of the first material encompassing the peripheral edge portions of the second material are adapted to dissolve at a faster rate than portions of the first material encompassing the central portion of the second material. For still another example, the first material can include at least one first portion and at least one second portion, and the first material can be selectively dissolvable such that the at least one first portion is adapted to dissolve at a faster rate than the at least one second portion. For another example, the first material can be selectively absorbable such that portions of the first material encompassing the peripheral edge portions of the second material are adapted to absorb at a faster rate than portions of the first material encompassing the central portion of the second material. For yet another example, the first material can include at least one first portion and at least one second portion, and the first material can be selectively absorbable such that the at least one first portion is adapted to absorb at a faster rate than the at least one second portion. For another example, the first material can be selected from the group consisting of polydioxanon, polyhydroxyalkanoate (PHA), polyglycerol sebacate (PGS), polyglycolic acid, polylactic acid (PLA), poliglecaprone 25, polyglactin 910, poly glyconate, polyglycolide (PGA), polyglycolide-trimethylene carbonate (PGA/TMC), polyhydroxybutyrate (PHB), poly(vinylpyrrolidone) (PVP), poly(vinyl alcohol) (PVA), absorbable polyurethanes, a blend thereof, and a copolymer thereof. For still another example, the second material can be selected from the group consisting of polydioxanon, polyhydroxyalkanoate (PHA), Polyglycerol sebacate (PGS), polyglycolic acid, polylactic acid (PLA), poliglecaprone 25, polyglactin 910, poly glyconate, polyglycolide (PGA), polyglycolide-trimethylene carbonate (PGA/TMC), polyhydroxybutyrate (PHB), poly(vinylpyrrolidone) (PVP), poly(vinyl alcohol) (PVA), absorbable polyurethanes, a blend thereof, and a copolymer thereof. For yet another example, the assembly can include at least one therapeutic agent incorporated into at least one of the first material and the second material, and the at least one therapeutic agent can be effective to be released upon one of absorption of the first material and expansion of the second material upon exposure to moisture. For another example, the tissue reinforcement construct can be shaped such that a cross-section of the peripheral edge portion of the tissue reinforcement construct is larger than a cross-section of the central portion of the tissue reinforcement construct, and the central portion can be closer to a longitudinal axis of the tissue reinforcement construct than the peripheral edge portion. The preconfigured shape can be such that the central portion of the second material transitions to a large radius at the peripheral edge.

In another embodiment, a staple cartridge assembly for use with a surgical stapler can include a cartridge body having a plurality of staple cavities configured to seat staples therein, and an adjunct material releasably retained on the cartridge body and configured to be delivered to tissue by deployment of the staples in the cartridge body. The adjunct material can include a first material encompassing a second material. The adjunct material can be configured to be penetrated by the staples being delivered to the tissue such that the first material is penetrated so as to expose the second material to moisture, and the second material can be configured to expand to form a seal around at least one staple of the staples inserted therethrough upon the exposure to moisture.

The first material can be formed from a variety of materials; particularly advantageous are those materials that are absorbable and capable bearing compressive and bending loads. They may be present in continuous form so as to fully encapsulate the materials making up the center of the device, or alternately they might be present in a non-continuous form. These non-continuous forms include, but are not limited to, otherwise encapsulating forms with minute openings allowing water or bodily fluids to access the materials making up the center of the device to facilitate rapid hydration to allow expansion of the center material; melt blend nonwoven forms with controlled porosity; immiscible polymer blends having a major blend component an absorbable polymer and a minor component being a biocompatible water soluble polymer which is capable of rapidly dissolving creating conduits to the central material allowing for its rapid hydration to generate an external force on the tissue.

The absorbable polymer making up the outer layer, although not limited to, can be selected from the group consisting of polydioxanone [AKA poly(1,4-dioxan-2-one), or poly(p-dioxanone)]; polyglycolide [AKA polyglycolic acid], polylactide [AKA polylactic acid] in all its forms based on the ring-opening of the corresponding lactone monomers, L(−)-lactide, D(+)-lactide, and meso-lactide, as well as all of its forms based upon polycondensation of L(+)-lactic acid and D(−)-lactic acid [e.g. poly(L(−)-lactide), poly(D(+)-lactide), poly(meso-lactide), poly(racemic-lactide), poly(L-lactic acid), poly(D-lactic acid), etc.]; the polycaprolactones, especially poly(epsilon-caprolactone); polyhydroxyalkanoate (PHA); the absorbable copolymers usually formed by the ring-opening polymerization of the lactone monomers, L(−)-lactide, (D+)-lactide, meso-lactide, glycolide, 1,4-dioxan-2-one, trimethylene carbonate, and the caprolactones, especially epsilon-caprolactone, in any molar combination or in an sequential distribution. These later copolymers include, but are not limited to epsilon-caprolactone/glycolide copolymers such as 25/75 poly(caprolactone-co-glycolide) [AKA poliglecaprone 25], 10/90 poly(L(−)-lacide-co-glycolide) [AKA polyglactin 910], polyglyconate, polyglycolide-trimethylene carbonate (PGA/TMC). The absorbable polymer can be a miscible or immiscible blend of the previously mentioned polymers [and copolymers] in any combination. It will be clear to one skilled in the art to select a biocompatible material.

The second material may be formed from a variety of materials. Advantageous materials include those that are absorbable and can undergo a controlled degree of swelling so as to create an external force on the tissue. Swelling might be accomplished by hydration based on an influx of water or bodily fluids. One class of materials that is particularly advantageous are absorbable dehydrated hydrogels. These include the materials described in U.S. Pat. No. 5,698,213, entitled "Hydrogels of Absorbable Polyoxaesters" and crosslinked aliphatic polyoxaesters containing amine and/or amido groups and blends thereof with other polymers as described in U.S. Pat. No. 5,700,583, each of which is incorporated herein by reference in its entirety. Other materials suitable for the second material include water soluble polymers such as poly(vinylpyrrolidone) (PVP), poly(vinyl alcohol) (PVA), and polyethylene glycol (PEG) or the higher molecular weight polyethylene oxide (PEO). Additionally suitable are absorbable polyurethanes. It is to be understood that suitable materials include copolymers that contain a hydrophilic section and an absorbable polyester section; this would include, by way of example, the copolymer made by reaction of a relatively low molecular weight alpha,omega-dihydroxy polyethylene glycol and a lactone monomer such as L(−)-lactide, (D+)-lactide, meso-lactide, glycolide, 1,4-dioxan-2-one, trimethylene carbonate, and the caprolactones, especially epsilon-caprolactone, in any molar combination or in an sequential distribution. Blends of materials and copolymers formed from a wide variety of suitable monomers, some already mentioned above, may be suitable. It will be clear to one skilled in the art to select a biocompatible material.

The assembly can have any number of variations. For example, the adjunct material can be positioned on the cartridge body such that at least a portion of the adjunct material extends beyond the cartridge body.

In another aspect, a method for joining tissue is provided that in one embodiment can include engaging tissue between a cartridge assembly and an anvil of a surgical stapler at a surgical site. At least one of the cartridge assembly and the anvil can have an adjunct material releasably retained thereon. The adjunct material can include a first material, at least a portion of which being configured to dissolve when exposed to bodily fluid, and a second material constrained within the first material in a constrained form. The method can further include actuating the surgical stapler to eject staples from the cartridge into the tissue such that at least one staple from the staples extends through the adjunct material to maintain the material at the surgical site. The second material can be configured to transition to a predetermined shape upon dissolution of the first material such that at least a peripheral edge portion of the adjunct material has a thickness greater than a central portion of the adjunct material. The method can have any number of variations.

Adjunct materials for use with end effectors like surgical stapling devices, and methods for using the same, are generally provided. In some embodiments a staple cartridge assembly for use with a surgical stapler can include a cartridge body having a plurality of staple cavities configured to seat staples therein and a biocompatible, compressible adjunct material releasably retained on the cartridge body. The adjunct material can be configured to be delivered to tissue by deployment of the staples in the cartridge body. The adjunct material can be a woven matrix such that the material can have a compressible elastic core layer configured to compress upon application of a compressive force and expand upon removal of the compressive force, and at least one flexible supportive layer coupled to at least one side of the compressible elastic core layer. In some embodiments, the adjunct material can contain a therapeutic substance such as a drug or other medicament. Additionally, in some embodiments the adjunct material can be selectively strengthened in certain areas.

The adjunct material can be a woven matrix such that the adjunct material will provide tissue support for tissue within and surrounding the staple line. In one embodiment, woven 3-D structures are created and compressed or otherwise formed into different shapes that have a higher density and different mechanical properties. This woven structure allows the adjunct to have different material characteristics in the compressed and uncompressed states. The amount of material and degree of compression can be used to determine the mechanical properties of the resultant brick. Multiple fiber types can be used in the weave to give it additional properties of interest including compressibility, abrasion resistance, bioabsorption profile, fluid absorption profile, substance elution characteristics, ability to be cut with a knife, ability to swell.

In other aspects, an end effector for a surgical instrument is provided. The end effector can include a first jaw having a cartridge body removably attached hereto, the cartridge body having a plurality of staple cavities configured to seat staples therein, a second jaw having an anvil with a plurality of staples forming openings formed therein. The adjunct material can be releasably retained on at least one of the tissue contacting surfaces of the cartridge body and the anvil so that it can be delivered to tissue upon deployment of the staples. The adjunct material can be comprised of a compressible elastic region configured to compress upon application of a compressive force and expand upon removal of the compressive force, and at least one flexible supportive region adjacent to the compressible elastic region.

In other aspects a method for stapling tissue is provided. The method can include engaging tissue between a cartridge assembly and an anvil of an end effector, one of which has an adjunct material releasable retained thereon, and actuating the end effector to eject staples from the cartridge assembly into tissue. The staples can extend through the adjunct material to maintain the adjunct material at the surgical site.

Embodiments described herein address these and other challenges by providing, for example, adjunct materials that seal punctures made by surgical staples in tissue. The adjunct materials described herein have a number of embodiments, including embodiments in which an adjunct is disposed about a single staple or leg thereof, or about a group of staples. Various embodiments disclosed herein include adjuncts that seal staples in tissue from the crown, or staple cartridge, side, or from the anvil or staple leg side (or both).

In one aspect, for example, a staple cartridge assembly for use with a surgical stapler is provided that can include a cartridge body having a plurality of staple cavities, where each staple cavity has a surgical staple disposed therein. The assembly can further include a plurality of adjuncts, where each adjunct can be disposed around at least one leg of a surgical staple such that each adjunct forms a seal around the at least one leg of the surgical staple upon deployment of the surgical staple from the cartridge body.

The assembly can have a number of different features and/or modifications, all of which are considered within the scope of the invention. For example, the adjuncts can have a number of different shapes and sizes. In some embodiments, for example, each of the plurality of adjuncts can be in the form of a plug. In certain embodiments, for each surgical staple of the assembly, a first adjunct plug can be disposed around a first leg of the surgical staple and a second adjunct plug can be disposed around a second leg of the surgical staple such that the first and second adjunct plugs form a seal around the first and second legs of the surgical staple.

In other embodiments, each of the plurality of adjuncts can be in the form of a pledget configured to seal around both a first leg and a second leg of a surgical staple. The pledget itself can have a number of different shapes and sizes. For example, in some embodiments the pledget can be in the form of a rectangular box extending along a length of a crown of a staple. Any of a variety of other shapes are also possible.

In still other embodiments, each of the plurality of adjuncts can be in the form of a coating disposed around a leg of a surgical staple. The adjuncts can be disposed about solely the legs of a staple (or a portion thereof), or about the entirety of a staple.

In addition to shape and/or size, the plurality of adjuncts can also be formed from a variety of materials. For example, in some embodiments each of the plurality of adjuncts can be formed from a swellable material that expands upon contact with body fluids. Forming the adjuncts from such a material can enhance the adjuncts' ability to seal a puncture in tissue created by a staple leg. Any of a variety of biocompatible swellable materials can be employed. For example, in certain embodiments, the swellable material can be a hydrogel. In yet other embodiments, each of the plurality of adjuncts can be formed from other materials, such as a foam.

The plurality of adjuncts can be located at a variety of positions with respect to the plurality of staples, and can be configured in certain embodiments to move relative to a staple during implantation in tissue. For example, in certain embodiments each of the plurality of adjuncts can be positioned adjacent to a crown of a surgical staple prior to deployment from the cartridge body. In other embodiments, each of the plurality of adjuncts can be positioned at a distal end of the at least one leg of the surgical staple opposite a crown of the surgical staple prior to deployment from the cartridge body. In such an embodiment, for example, each of the plurality of adjuncts can be configured to slide over the at least one leg of the surgical staple. By way of further example, if an adjunct is positioned at a distal end of a staple leg, the action of forcing the staple leg through tissue can slide the adjunct toward a crown of the staple such that the adjunct is sandwiched between the tissue and the crown of the staple, thereby sealing the puncture created by the staple leg. In other embodiments, adjuncts can be positioned at other locations, such as on an anvil of a surgical stapler opposite the cartridge body, as described in more detail below.

In another aspect, a staple cartridge assembly for use with a surgical stapler is provided that can include a cartridge body having a plurality of staple cavities and a plurality of surgical staples disposed within the plurality of staple cavities and configured to be ejected therefrom into tissue. The assembly can also include a plurality of sealing adjuncts disposed within the plurality of staple cavities and configured to be ejected therefrom along with the plurality of surgical staples without contacting the cartridge body. By avoiding contact between the cartridge body and the sealing adjuncts, the adjuncts can be prevented from interfering with sliding movement of the staples relative to the cartridge body.

The adjuncts can be prevented from contacting the cartridge body in a number of different ways. For example, in some embodiments each of the plurality of sealing adjuncts can be positioned such that a surgical staple shields the sealing adjunct from contact with the cartridge body during ejection. This can be accomplished, for example, by coupling one or more sealing adjuncts to a staple so that the staple leads the adjunct as it is ejected from the cartridge body, thereby shielding the adjunct from contact with the cartridge body.

Other configurations for coupling adjuncts to a staple are also possible. For example, in certain embodiments, each of the plurality of sealing adjuncts can be positioned adjacent to a junction between a leg of a surgical staple and a crown of the surgical staple.

In still other embodiments, each of the plurality of staple cavities can be shaped to accommodate passage of at least one sealing adjunct coupled to a surgical staple. For example, each of the plurality of staple cavities includes at least one cut-out formed on opposing ends of the staple cavity to accommodate the at least one sealing adjunct.

As mentioned above, the adjuncts can be formed from a variety of biocompatible materials and have any of a variety of shapes and/or sizes. In some embodiments, each of the plurality of sealing adjuncts can be configured to expand in volume upon contact with tissue.

In another aspect, a method for stapling tissue is provided that can include engaging tissue between a cartridge assembly and an anvil on a surgical stapler, and actuating the surgical stapler to eject at least one staple from the cartridge assembly into the tissue. Further, at least one leg of the at least one staple can extend through a sealing adjunct such that the adjunct forms a seal between the tissue and the leg.

In some embodiments, the sealing adjunct can be coupled to a distal end of the at least one leg of the at least one staple. In such an embodiment, actuating the surgical stapler can cause the adjunct to slide toward a crown of the at least one staple and seal a hole formed in the tissue by the at least one leg. In other embodiments, however, the sealing adjunct can be coupled to a crown of the at least one staple and actuating the surgical stapler can cause the adjunct to eject from the cartridge assembly with the crown such that the sealing adjunct is disposed between the crown of the at least one staple and the tissue.

As mentioned above, various embodiments described herein can include sealing adjuncts positioned away from the crown of a surgical staple, such as on the opposite side of stapled tissue near staple legs that are deformed by an anvil of a surgical stapler. And, in some embodiments, adjuncts can be positioned at both locations to seal punctures from both sides of the tissue and/or staple.

In one aspect, a surgical device includes an end effector that can include first and second jaws, where the first jaw has a cartridge body removably attached thereto and the second jaw having an anvil. The cartridge body can have a plurality of staple cavities configured to seat staples therein and the anvil can have a plurality of staple forming openings formed therein. Further, at least one of the first and second jaws can be movable relative to the other jaw. The end effector can also include a plurality of sealing adjunct segments coupled to one another and at least one of the first and second jaws such that a staple ejected from the cartridge body passes through one of the plurality of sealing adjunct segments and tissue disposed between the first and second jaws.

In some embodiments, each of the plurality of sealing adjunct segments can span a plurality of staple forming openings. In other embodiments, however, each of the plurality of sealing adjunct segments can cover a single staple forming opening.

The plurality of sealing adjunct segments can be coupled to one another in a variety of manners. For example, in some embodiments each of the plurality of sealing adjunct segments can be coupled to one another by a plurality of connecting branches. Further, at least one of the first and second jaws can includes a plurality of features formed thereon that are configured to sever the plurality of connecting branches when deploying staples into tissue disposed between the first and second jaws. Destroying the connecting branches between sealing adjuncts can allow for greater compliance of tissue between adjacent staples, thereby reducing forces that can otherwise act to enlarge a puncture surrounding a staple leg.

In other embodiments, the plurality of sealing adjunct segments can be coupled to one another by a plurality of threads, or by a woven mesh. In still other embodiments, the plurality of sealing adjunct segments can be coupled to one another by a connective film extending over a surface of at least one of the first and second jaws. The connective film can, in some embodiments, have a first thickness and each of the plurality of sealing adjunct segments can have a second, greater thickness. In certain embodiments, the greater thickness of the sealing adjunct segments can extend into the plurality of staple forming openings. The plurality of sealing adjunct segments in such an embodiment does not significantly reduce the available clearance between the jaws of a surgical stapler, thereby allowing use with thicker tissue.

In addition to features that sever connections between sealing adjunct segments, at least one of the first and second jaws of the end effector can include one or more features formed thereon that are configured to at least one of align and secure the plurality of sealing adjunct segments thereto. Such features can be configured to mate with complementary features coupled to the plurality of sealing adjuncts such that the plurality of sealing adjuncts can be temporarily coupled to the end effector in a proper position and/or orientation. Examples of such features can include hooks and loops, plastic retainers, etc.

In certain embodiments, the plurality of sealing adjunct segments can have the same shape and can be arrayed in a repeating pattern over a length of the end effector. In other embodiments, the plurality of sealing adjunct segments can have a plurality of shapes and can be arrayed in an alternating pattern over a length of the end effector. Regardless, the plurality of sealing adjunct segments can cover each of the plurality of staple cavities such that each staple ejected into tissue passes through one of the plurality of sealing adjuncts.

In another aspect, an end effector for a surgical instrument is provided that includes first and second jaws, the first jaw having a cartridge body removably attached thereto and the second jaw having an anvil with a plurality of staple forming openings formed therein. The cartridge body can have a plurality of staple cavities configured to seat staples therein and at least one of the first and second jaws can be movable relative to the other jaw. The end effector can further include a viscous sealant disposed within the plurality of staple forming openings of the anvil, wherein the viscous sealant within each staple forming opening is retained therein by a film extending across the staple forming opening. In such an embodiment, the plurality of discrete pockets of viscous sealant can be the plurality of sealing adjunct segments described herein.

In some embodiments, the film extending across each staple forming opening can be formed from viscous sealant that is at least partially cured by exposure to any of a chemical, ultraviolet light, and heat. In other embodiments, however, the film extending across each staple forming opening can be formed from a second material overlaid on the viscous sealant.

In addition the film extending across each staple forming opening, in some embodiments each of the plurality of staple forming openings can include at least one retainer formed thereon to aid in retaining the viscous sealant within the opening. Further, while in some embodiments the film can extend solely across each staple forming opening of the anvil, in other embodiments the film can also extend between adjacent staple forming openings.

In another aspect, a surgical method is provided that can include filling a plurality of staple forming openings in an anvil of a surgical stapler with a viscous sealant, and forming a film over the plurality of staple forming openings in the anvil such that the film retains the viscous sealant within the staple forming openings.

As mentioned above, in certain embodiments forming the film can include at least partially curing the viscous sealant by exposure to any of a chemical, ultraviolet light, and heat.

In other embodiments, however, forming the film can include overlaying a second material over the viscous sealant disposed within the staple forming openings.

In still other embodiments, the method can further include actuating the surgical stapler to drive a plurality of staples through tissue and into the plurality of staple forming openings such that the plurality of staples puncture the film and the viscous sealant forms a seal around the plurality of staples.

A surgical device is provided in the form of an applicator for coupling adjunct material to a surgical stapler. In one aspect, for example, a surgical device is provided that can include at least one nozzle formed at a proximal end of the device that is configured to receive a sealant, and an applicator formed at a distal end of the device that is configured to deliver the sealant received by the at least one nozzle. In one aspect, the applicator can be removably and replacably attached to the nozzle. The applicator can be configured to interface with at least one of a first and second jaw of a surgical stapler such that the sealant delivered from the applicator can be deposited into a plurality of openings formed in the surgical stapler. The plurality of openings can be, for example, any of a plurality of staple cavities located in a cartridge body, or a plurality of staple forming openings formed in an anvil.

In some embodiments, it can be desirable to prevent adjunct material, such as the sealant, from being deposited in certain areas of a surgical stapler. For example, in some embodiments, it can be desirable to keep a cutting member guide path free from sealant. Accordingly, in some embodiments, the surgical device can include a shield disposed within the applicator such that the shield prevents the sealant delivered by the applicator from entering a cutting guide slot formed in at least one of the first and second jaw of the surgical stapler.

Still further, it can be desirable to remove any excess sealant from the surgical stapler prior to use. In some embodiments then, the surgical device can include a squeegee formed on a distal-most edge of the applicator to remove excess sealant.

There are a variety of biocompatible sealants that can be used with the devices and methods described herein. Certain of these sealants can be multi-part, such as two-part sealants that must be mixed before being coupled to the surgical stapler. Therefore, in some embodiments, the surgical device can include two nozzles formed at a proximal end thereof, and the applicator can include a common lumen extending therethrough to allow sealant received from each nozzle to mix before being delivered from a distal end of the applicator. In still other embodiments, the two nozzles can be configured to introduce sealant into the common lumen at different rates, e.g., for multi-part sealants that require components at various mixing ratios.

In some embodiments, the surgical device can further include a container of sealant coupled to the at least one nozzle. The container can be sealed for sterility purposes in certain embodiments, and the at least one nozzle can include a piercing tip configured to puncture a seal formed on the container. The container can have any of a variety of shapes and/or sizes. In some embodiments, however, the container can be a syringe.

In another aspect, a method for applying sealant to a surgical device is provided that can include applying a viscous sealant to a jaw member of a surgical stapler, wherein the jaw member includes a plurality of openings formed therein that can receive the sealant. The method can further include removing excess viscous sealant from the jaw member such that only sealant deposited within the plurality of openings remains.

The viscous sealant can be applied to the jaw member in a variety of manners. For example, in some embodiments applying the viscous sealant to the jaw member can include sliding an applicator along a length of the jaw member as sealant is introduced through the applicator. Further, in certain embodiments removing excess viscous sealant can include sliding a squeegee along a length of the jaw member. In some embodiments, the applicator can include a squeegee formed on a distal-most edge thereof to allow both sealant application and removal of excess sealant with a single pass over the jaw member.

In order to help retain the viscous sealant within the plurality of openings of the jaw member (e.g., staple cavity openings in a cartridge body or staple forming openings in an anvil), the method can further include at least partially curing the viscous sealant after application to the jaw member. At least partially curing the viscous sealant can create a hardened layer extending across the opening that can retain the uncured sealant within the opening until, for example, ejection of a staple from the surgical stapler punctures the hardened layer of the sealant. Curing the viscous sealant can be accomplished in a variety of manners, including, for example, by exposing the sealant to any of a chemical, ultraviolet light, and heat.

In a further aspect, a method for stapling tissue is provided that can include applying a non-compressible sealant into a plurality of staple forming openings formed in an anvil of a surgical stapler, and compressing tissue between the anvil and a cartridge body of the surgical stapler. The method can further include actuating the surgical stapler to deliver a plurality of staples from the cartridge body through the tissue and into the plurality of staple forming openings containing the non-compressible sealant. The non-compressible sealant can prevent tissue compressed between the anvil and the cartridge body from entering the plurality of staple forming openings upon actuation of the surgical stapler. This can be beneficial to prevent staples from being formed within tissue (i.e., without being passed completely through tissue).

As in the embodiments described above, applying the non-compressible sealant can, in certain embodiments, include sliding an applicator along a length of the anvil. In other embodiments, applying the non-compressible sealant can include mixing a multi-part sealant just prior to delivery into the plurality of staple forming openings. The multi-part sealant can be mixed at any of a variety of ratios, depending on the type of sealant used.

In other embodiments, the method can further include removing excess sealant from the anvil. This can be accomplished using a separate squeegee or other scraping implement, or it can be accomplished in a single pass if an applicator used to deposit the non-compressible sealant includes a squeegee or scraper thereon.

In still other embodiments, the method can further include at least partially curing the non-compressible sealant after application to the anvil. Such a curing process can harden at least a portion of the non-compressible sealant extending across the plurality of staple forming openings, thereby assisting in retaining the non-compressible sealant within the plurality of staple forming openings.

The devices and methods described herein can be utilized in a variety of different types of tissue throughout the body. Certain embodiments described herein can provide a more effective procedure for forming an anastomosis between two body lumens. Such a procedure is often employed when, for example, resecting a portion of a patient's colon.

A staple cartridge assembly for use with a surgical stapler is provided that can include a cartridge body having a plurality of staple cavities, where each staple cavity has a surgical staple disposed therein. The assembly can also include a plurality of sealing adjuncts coupled to the cartridge body such that a staple ejected from the cartridge body passes through one of the plurality of sealing adjuncts before entering into tissue adjacent to the cartridge body. Further, the plurality of staple cavities can be arranged such that a greater density of staple cavities is present at a proximal end and a distal end of the cartridge body than a density of staple cavities that is present in a middle portion extending between the proximal and distal ends. Further still, the plurality of sealing adjuncts can be positioned at the proximal and distal ends of the cartridge body. Positioning the plurality of sealing adjuncts at a proximal and distal end of the cartridge body can keep the sealing adjuncts from interfering with operation of a circular stapler that can resect tissue extending along the middle portion to form an anastomosis.

In some embodiments, however, the assembly can further include at least one suture thread coupled to and extending between the plurality of sealing adjuncts positioned at the proximal and distal ends of the cartridge body. Furthermore, to prevent interference of the at least one suture thread with any staples ejected from the cartridge body, the at least one suture thread can be offset from any staple cavity positioned in the middle portion of the cartridge body.

In other embodiments, the assembly can also include a washer disposed between the plurality of sealing adjuncts at the proximal and distal ends of the cartridge body and coupled to the at least one suture thread extending therebetween. More particularly, in certain embodiments, a first suture thread can extend between at least one sealing adjunct at a proximal end of the cartridge body and the washer, and a second suture thread can extend between the washer and at least one sealing adjunct at a distal end of the cartridge body. The first and second suture threads can have identical or different lengths, depending on the particular embodiment employed.

The washer can be formed from a variety of materials and can have a number of different sizes. In some embodiments, for example, the washer can be configured to elastically compress when the cartridge body is compressed against tissue. In other embodiments, the washer can be rigid and the cartridge body can include a depression formed therein to accommodate the washer during actuation of the surgical stapler. In still other embodiments, a compressible washer can be utilized in combination with a cartridge body having a recess formed therein such that a required amount of elastic compression can be reduced.

Including a connecting suture thread and washer in the assembly can allow for complete resection of the staple line including the sealing adjuncts when forming an anastomosis, as described in more detail below.

In a further aspect, a surgical method is provided that can include transecting a body lumen using a linear surgical stapler that delivers a plurality of sealing adjuncts in combination with a plurality of surgical staples at a proximal end and a distal end of a staple line formed by the surgical stapler. Further, the plurality of sealing adjuncts positioned at the proximal and distal ends of the staple line can be coupled to one another by at least one suture thread. The method can further include positioning a circular surgical stapler to create an anastomosis with a second body lumen across the staple line. The method can also include drawing the proximal and distal ends of the staple line into a central lumen of the circular stapler using the at least one suture thread extending between the plurality of sealing adjuncts positioned at the proximal and distal ends of the staple line, and actuating the circular stapler to form the anastomosis and resect the staple line.

In certain embodiments, the linear surgical stapler can also deliver a washer positioned at a mid-point between the proximal and distal ends of the staple line, and the washer can be coupled to the at least one suture thread.

In some embodiments, positioning the circular stapler to create an anastomosis can include passing a stapler trocar across the staple line and through the washer. Still further, in certain embodiments drawing the proximal and distal ends of the staple line into the central lumen of the circular stapler can include retracting the stapler trocar and the washer into the central lumen of the circular stapler. This can allow the circular stapler to completely resect the staple line including the sealing adjuncts when forming the anastomosis, thereby reducing the possibility of future leakage through the staple line formed by the linear surgical stapler.

In still other embodiments, positioning the circular stapler to create an anastomosis can further include mating an anvil to the stapler trocar such that the anvil prevents the stapler trocar from retracting through the washer. In such an embodiment, mating the anvil to the stapler trocar can trap the washer therebetween, such that retraction of the trocar into the central lumen of the circular stapler will pull the washer into the central lumen as well.

In another aspect, a surgical method is provided that can include transecting a body lumen using a linear surgical stapler that delivers a plurality of sealing adjuncts in combination with a plurality of surgical staples at a proximal end and a distal end of a staple line formed by the surgical stapler. Further, the plurality of sealing adjuncts positioned at the proximal and distal ends of the staple line can be coupled to a washer positioned at a midpoint of the staple line by a plurality of suture threads. The method can further include extending a trocar out of a central lumen of a circular stapler cartridge disposed within the body lumen such that the trocar crosses the staple line and passes through the washer. The method can also include coupling the trocar to an anvil positioned in a second body lumen such that a portion of the anvil receives the trocar and the washer is trapped between the anvil and the trocar. The method can further include retracting the trocar into the central lumen of the circular stapler cartridge to draw the anvil toward the circular stapler body while simultaneously drawing the proximal and distal ends of the staple line into the central lumen.

In certain embodiments, the method can also include actuating the circular stapler cartridge to resect the staple line and form an anastomosis between the two body lumens. As described above, actuation can resect the entirety of the staple line formed by the linear surgical stapler because the proximal and distal ends of the staple line are drawn into the central lumen of the circular stapler by their attachment to the washer via the plurality of suture threads.

A surgical method is provided that in one embodiment includes transorally advancing a reinforcement material into a bronchial tube, and introducing a sealant into the bronchial tube and applying the sealant to the reinforcement material within the bronchial tube. The sealant can transition from a first state to a second, harder state within the bronchial tube so as to secure the reinforcement material in a fixed position relative to the bronchial tube.

The method can vary in any number of ways. For example, advancing the reinforcement material can includes advancing a distal end of a scoping device into the bronchial tube and introducing the reinforcement material into the bronchial tube through the scoping device. Introducing the sealant can include introducing the sealant into the bronchial tube through the scoping device with the sealant in the first state. For another example, the method can include stapling the bronchial tube and the reinforcement material that has been introduced into the bronchial tube. The sealant can be introduced and applied before the stapling of the bronchial tube and the reinforcement material, or the sealant can be introduced and applied after the stapling of the bronchial tube and the reinforcement material. A first component of the sealant can be introduced and applied before the stapling of the bronchial tube and the reinforcement material, and a second component of the sealant can be introduced and applied after the stapling of the bronchial tube and the reinforcement material.

In another embodiment, a surgical method is provided that includes positioning a reinforcement material within a bronchial tube, stapling the bronchial tube and the reinforcement material so as to form a staple line extending across the bronchial tube, and applying a sealant to the reinforcement material within the bronchial tube. The sealant can move from a first state to a second, more rigid state within the bronchial tube so as to facilitate sealing of the staple line.

The method can have any number of variations. For example, the method can include expanding an inner diameter of the bronchial tube with a balloon while at least one of the reinforcement material is being positioned and the sealant is being applied. For another example, the method can include, after positioning the reinforcement material and prior to the stapling, locating the reinforcement material within the bronchial tube by illuminating a light. For still another example, the reinforcement material can include at least one of a mesh, a non-woven matrix, a film, a melt-blown non-woven material, a felt material, a closed-cell foam, an open-cell foam, a sponge, a braided suture, poliglecaprone, polyglactin, polydioxanone, collagen, oxidized regenerated cellulose, regenerated cellulose, glycerol, glycolide, lactide, dioxanone, trimethylene carbonate, gut suture, polypropylene, polyethylene, polybutester fiber, stainless steel, nylon, polyester, silk, polyvinylidene difluoride, oxidized cellulose, and polypropylene. For another example, the sealant can include at least one of an adhesive, fibrin thrombin, a hydrogel, fibronectin, gelatin, collagen, Factor XIII, transglutaminase, Polyethylene glycol, alginate, carboxymethylcellulose, methylcellulose, hydroxypropylmethyl cellulose, pectin, polyvinyl alcohol, polyvinylpyrrolidone, benzocaine, cyanoacrylate, polyglycolic acid, hyaluronic acid, magnesium peroxide, 2-octyl cyanoacrylate, and hydrogen peroxide. For yet another example, the method can include, after positioning the reinforcement material and prior to the stapling, locating the reinforcement material within the bronchial tube by positioning a magnet outside the bronchial tube. The magnet can magnetically engage a target located within the bronchial tube adjacent to the reinforcement material. Positioning the reinforcement material can include introducing the reinforcement material into the bronchial tube using a delivery device, the target being attached to a distal end of the delivery device. The target can include one of a Hall sensor and a second magnet.

In another embodiment, a surgical method is provided that includes positioning a reinforcement material within a bronchial tube, and stapling the bronchial tube and the reinforcement material so as to form a staple line extending across the bronchial tube with the reinforcement material engaged within the staple line. An actuator coupled to the reinforcement material can move from a first state to a second, harder state after the stapling so as to facilitate sealing of the staple line.

The method can vary in any number of ways. For example, the method can include, after positioning the reinforcement material and prior to the stapling, locating the reinforcement material within the bronchial tube by illuminating a light inside the bronchial tube. For another example, the reinforcement material can include at least one of a mesh, a non-woven matrix, a film, a melt-blown non-woven material, a felt material, a closed-cell foam, an open-cell foam, a sponge, a braided suture, poliglecaprone, polyglactin, polydioxanone, collagen, oxidized regenerated cellulose, regenerated cellulose, glycerol, glycolide, lactide, dioxanone, trimethylene carbonate, gut suture, polypropylene, polyethylene, polybutester fiber, stainless steel, nylon, polyester, silk, polyvinylidene difluoride, and polypropylene. For yet another example, the actuator can include a biologic foam. For another example, the method can include, after positioning the reinforcement material and prior to the stapling, locating the reinforcement material within the bronchial tube by positioning a magnet outside the bronchial tube. The magnet can magnetically engage a target located within the bronchial tube adjacent to the reinforcement material.

In one embodiment, a surgical kit is provided that includes a liquid sealant and a sealing cuff. The liquid sealant can be configured to cure into a solidified state. The sealing cuff can have a sidewall with first and second ends removably mated to one another to form an enclosed loop, and the sidewall can define an interior chamber. In use, the sealing cuff can be configured to be disposed around a body lumen such that the interior chamber is sealed between the outer wall and the body lumen to allow the liquid sealant to be received therein and to directly contact the body lumen. The surgical kit can further include a tube coupled to the sealing cuff and configured to deliver the sealant to the interior chamber of the sealing cuff.

The sealing cuff can vary in any number of ways. For example, the sidewall can be substantially hemispherical and an inner surface of the sidewall can be substantially concave. The sealing cuff can include a plurality of protrusions formed on inner surface of the sidewall for facilitating distribution of the sealant within the interior chamber. In certain aspects, the plurality of protrusions can be spaced evenly about a circumference of the sidewall. For another example, the sealing cuff can include sutures coupled to an inner surface of the sidewall. In certain aspects, the sutures can be disposed in a criss-cross pattern. The sealing cuff can further include a locking mechanism for removably mating the first and second ends.

The surgical kit can further include at least one expandable member configured to move from a compressed position to an expanded position and having a shape that substantially corresponds to a shape of the interior chamber of the sealing cuff when the at least one expandable member is in the expanded position.

The sealant can also vary in a number of ways. For example, the sealant can be selected from the group consisting of fibrin, thrombin, a hydrogel, benzocaine, cyanoacrylate, polyglycolic acid, hyaluronic acid, magnesium peroxide, hydrogen peroxide, platelet rich plasma, and combinations thereof. In certain aspects, the sealant can be configured to transition from the liquid to the solidified state after a predetermined amount of time.

A surgical device is provided that includes a sealing cuff having a ring-shaped sidewall, the sidewall defining an interior chamber configured to hold a sealant therein. The sealing cuff can include a plurality of extensions for distributing the sealant within the interior chamber, the plurality of extensions being sized and shaped such that when the sealing cuff is disposed around a tubular body organ and sealant is delivered thereto, the sealant is distributing substantially uniformly in thickness within the interior chamber of the cuff and solidifies substantially circumferentially around the organ.

The surgical device can vary in any number of ways. The sealing cuff can further include a port formed therein and configured to mate with a delivery tube for delivering a sealant to the interior chamber of the cuff. The plurality of extensions can vary in a number of ways. For example, each of the extensions can be disposed radially around the sealing cuff. For another example, the plurality of extensions can be spaced along an inner surface of the interior chamber. In certain aspects, the plurality of extensions can be substantially cylindrical-shaped.

Methods for reinforcing an anastomosis of a tubular organ are also provided and in one embodiment, the method can include forming an anastomosis in a tubular organ, applying a sealing cuff around the anastomosis, the sealing cuff including at least one strand of suture extending along an inner surface of the sealing cuff and having a woven structure for containing a sealant, and injecting a sealant into an interior chamber of the sealing cuff such that the sealant directly contacts and forms a substantial seal around the anastomosis.

The method can be performed in various ways. In certain aspects, the anastomosis can be formed in the tubular organ prior to delivering the sealant into the interior chamber of the sealing cuff. In other aspects, the anastomosis can be formed in the tubular organ after the sealant is delivered into the interior chamber of the sealing cuff. Injecting the sealant into the interior chamber of the sealing cuff can cause the sealant to solidify around the at least one strand of suture. In certain aspects, after the sealant is solidified, the sealant can be released from the interior chamber of the cuff by detaching the at least one strand of suture from the sealing cuff.

In one embodiment a surgical method, comprises affixing a first adjunct material onto a tissue at a treatment site. A second adjunct material is applied to at least a portion of the first adjunct material such that the second adjunct material interacts with the first adjunct material to form a seal in an area of the tissue covered by at least one of the first and the second adjunct material. In one aspect the step of affixing the first and/or the second adjunct is effected by stapling the first adjunct material to the tissue. At least one of the first and second adjunct materials is formed from biocompatible, absorbable suture material, selected from the group consisting of polydioxanon, Polyglycerol sebacate, Polyglycolic acid, Polycaprolactone, Polylactic acid, Polyhydroxyalkanoate, Poliglecaprone 25, polyglactin 910, polyglyconate, polyglocolide-trimethylene carbonate, polyhydroxybutyrate, poly(vinylpyrrolidone), poly(vinyl alcohol), absorbable polyurethanes, and regenerated cellulose. In one embodiment at least one of the first and second adjunct materials is oxidized regenerated cellulose. At least one of the adjunct materials is made of a bioabsorbable material or a biofragmentable material The first and second adjunct materials can be made of a single layer of material or multiple layers, and one adjunct can be different from the other or the same as the other. Further, either or both of the adjunct materials can include a therapeutic agent.

BRIEF DESCRIPTION OF THE DRAWINGS

The invention will be more fully understood from the following detailed description taken in conjunction with the accompanying drawings, in which:

FIG. 49A is a side view of a woven adjunct material before a compressive force is applied thereto;

FIG. 49B is a side view of a woven adjunct material of FIG. 49A having a compressive force applied thereto;

FIG. 49C is a side view of the woven adjunct material of FIG. 49A after the compressive force is released therefrom;

FIG. 50 is a side view of one embodiment of a woven structure;

FIG. 51A is a side, cross-sectional view of a woven adjunct material having outer support layers woven onto an elastic core layer;

FIG. 51B is a detailed view of the woven adjunct material of FIG. 51A;

FIG. 51A is a perspective view of a fleece adjunct material;

FIG. 51B is a perspective view of a longitudinal fleece adjunct material with a compressive force applied thereto.

FIG. 51C is a perspective view of a rectangular fleece adjunct material with a compressive force applied thereto.

FIG. 54D is a perspective view of a polygonal fleece adjunct material with a compressive force applied thereto.

FIG. 55 is a perspective view of an adjunct material that includes a fleece core layer surrounded by woven support layers;

FIG. 62 is a cross-sectional view of the staple of FIG. 60 implanted in tissue;

FIG. 63A is an illustration of one embodiment of adjunct operation in non-thoracic tissue;

FIG. 63B is an illustration of one embodiment of adjunct operation in thoracic tissue;

FIG. 67A is a side view of one embodiment of adjuncts coupled to a staple;

FIG. 67B is a side view of an alternative embodiment of adjuncts coupled to a staple;

FIG. 67C is a side view of still another alternative embodiment of adjuncts coupled to a staple;

FIG. 68A is a cross-sectional view of the staple of FIG. 65 in a staple cartridge;

FIG. 68B is a cross-sectional view of the staple of FIG. 65 ejected into tissue;

FIG. 68C is a cross-sectional view of the adjuncts sealing the staple of FIG. 65 in tissue;

FIG. 69A is a side view of an alternative embodiment of a staple;

FIG. 69B is a side view of an alternative embodiment of a staple;

FIG. 70 is a perspective view of an alternative embodiment of an adjunct coupled to a staple;

FIG. 71A is a close perspective view of the adjunct of FIG. 70 before implantation in tissue;

FIG. 71B is a close perspective view of the adjunct of FIG. 70 after implantation in tissue;

FIG. 72A is a side view of the staple of FIG. 70;

Figure 70:
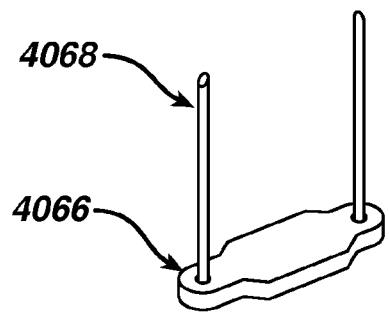
Figure 72A:
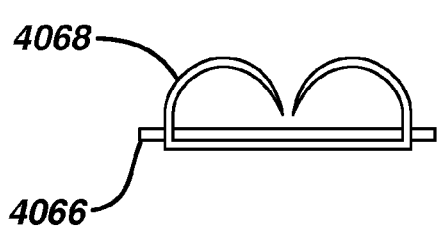
Figure 72B:
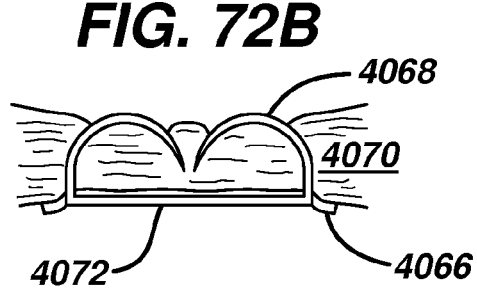
Figure 73:
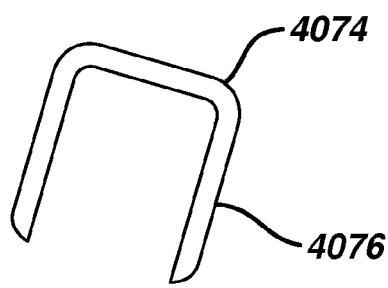
Figure 74:
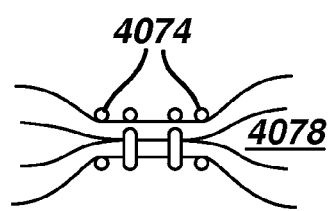
Figure 75:
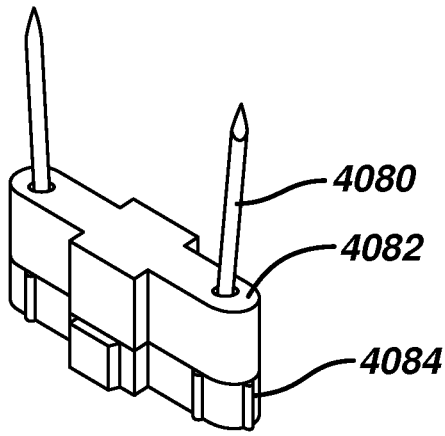
Figure 76:
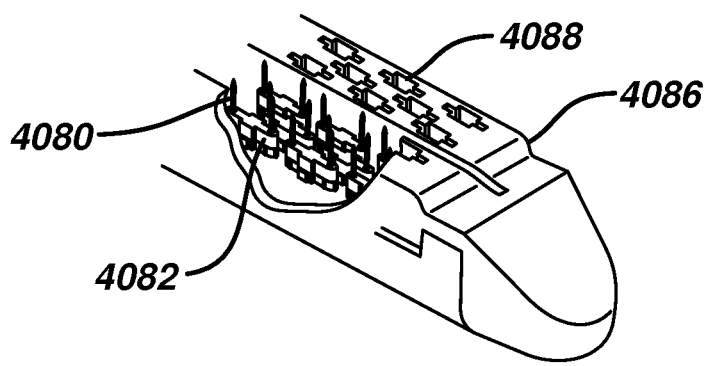
Figure 77:
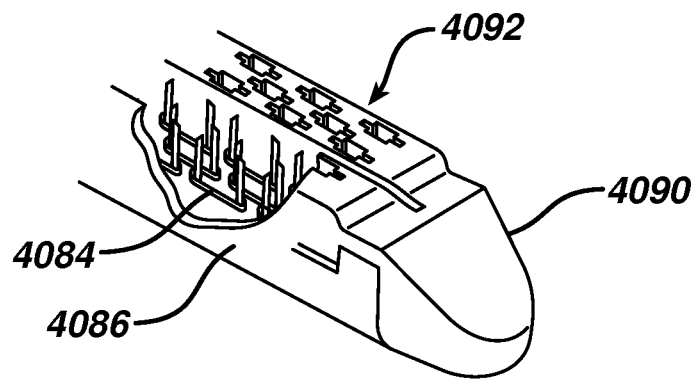
Figure 78A:
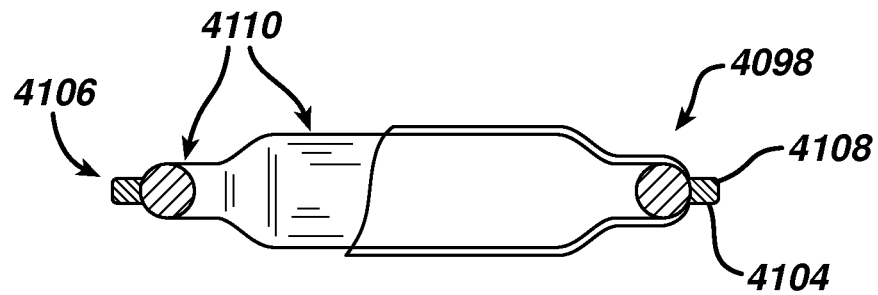
Figure 78B:
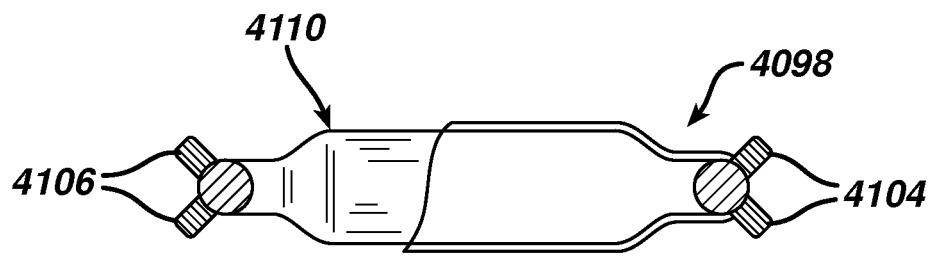
Figure 78C:
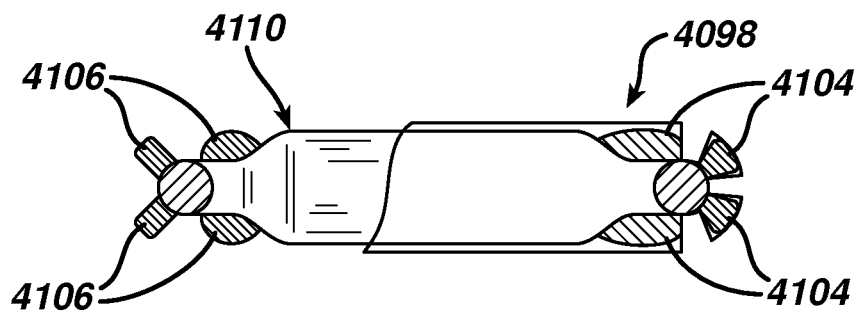
Figure 79:
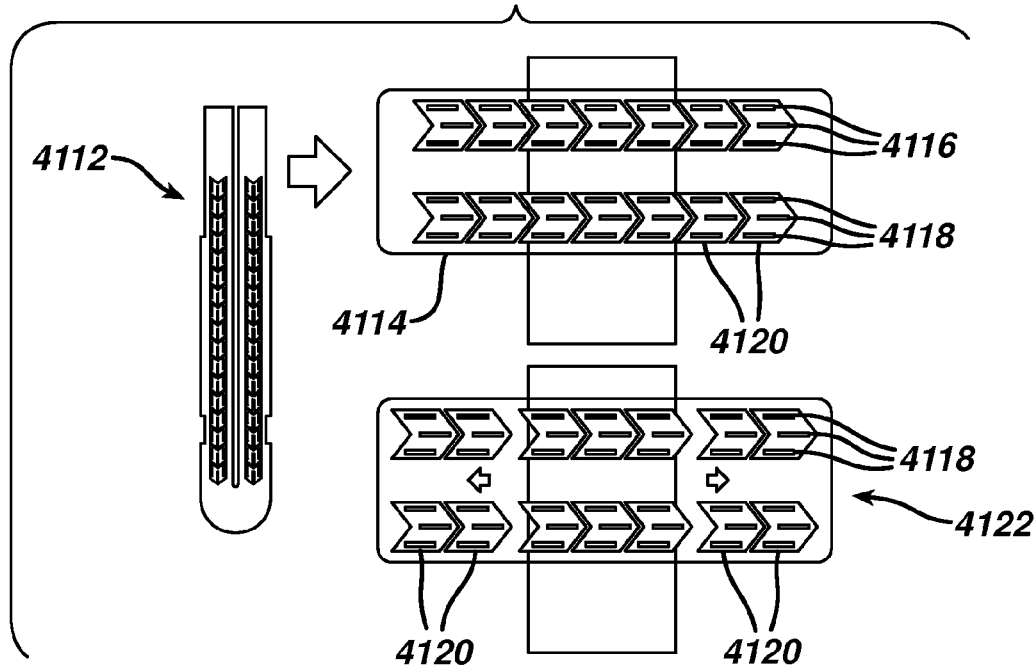
Figure 80:
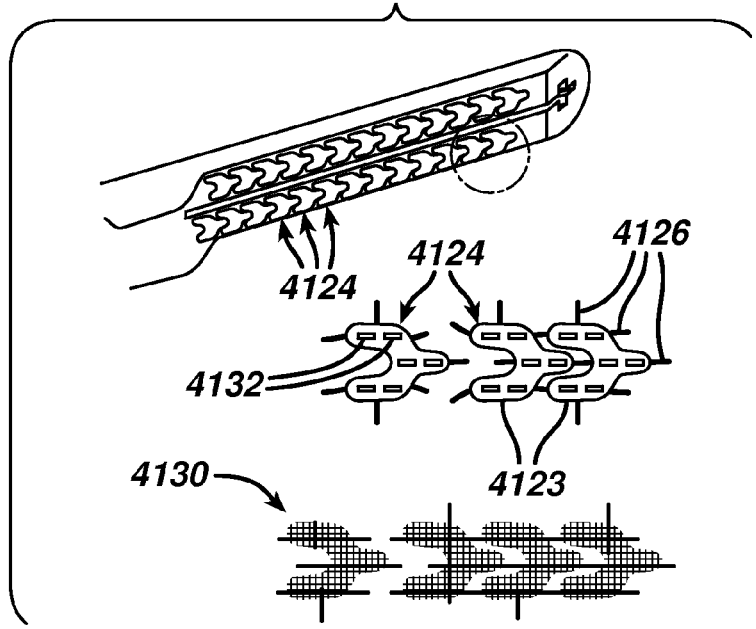
Figure 81A:
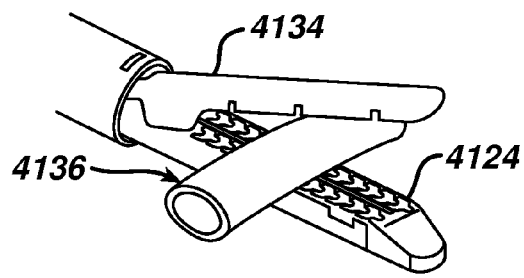
Figure 81B:
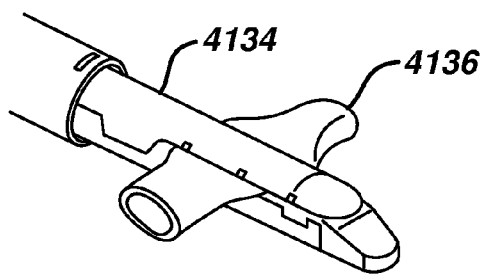
Figure 81C:
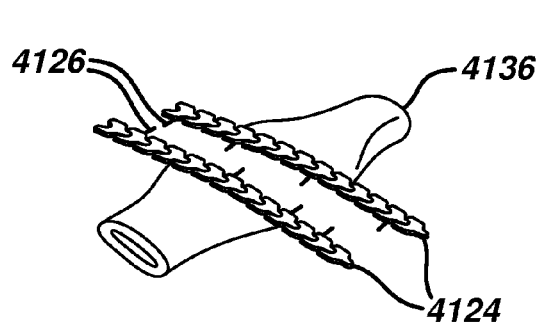
Figure 81D:
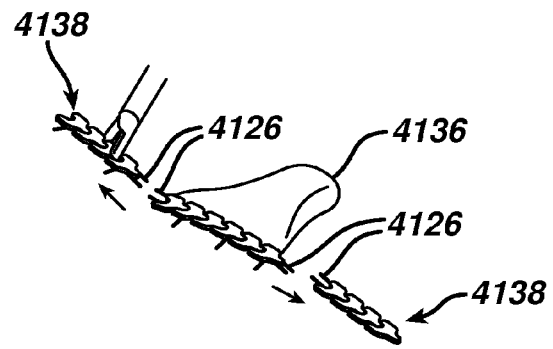
Figure 82:
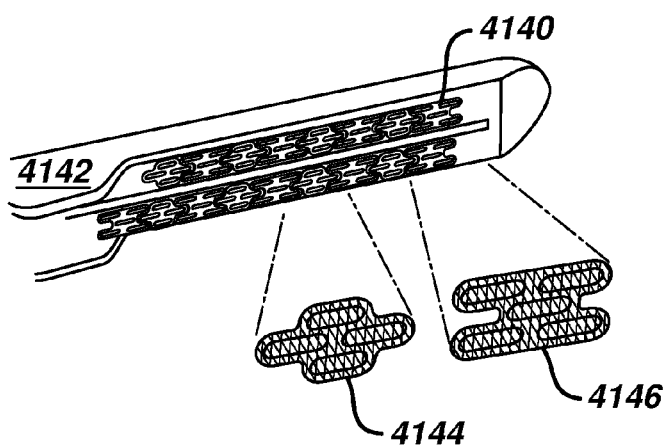
Figure 83:
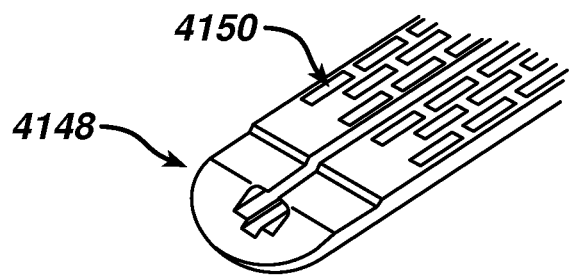
Figure 84:
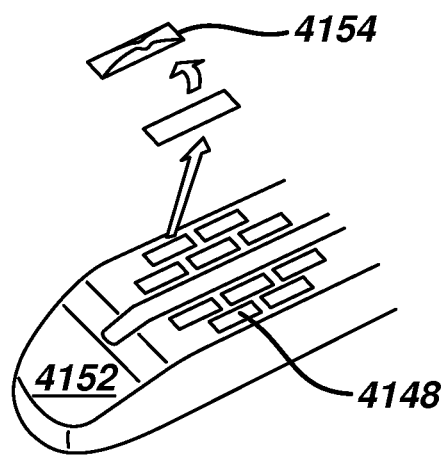
Figure 85:
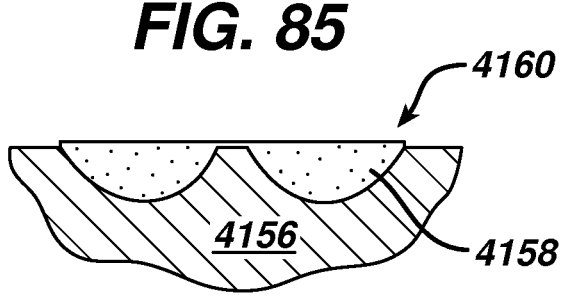
Figure 86A:
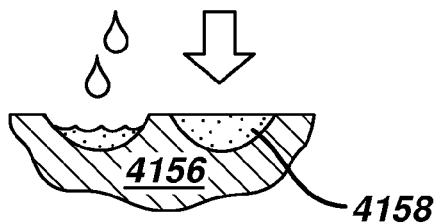
Figure 86B:
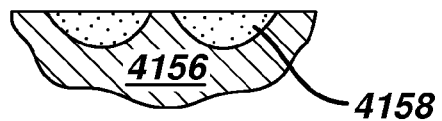
Figure 86C:
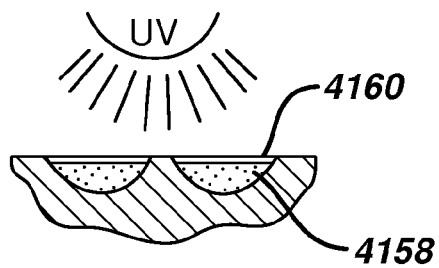
Figure 86D:
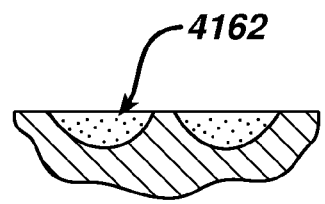
Figure 87:
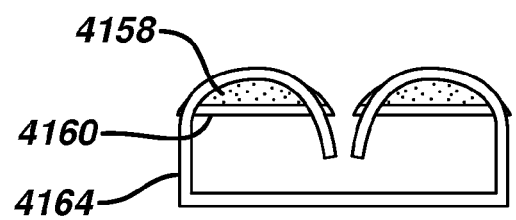
Figure 88:
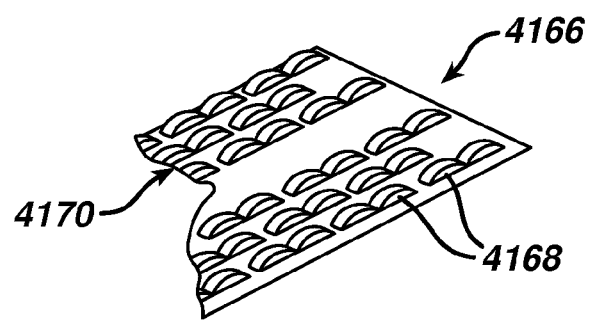
Figure 89:
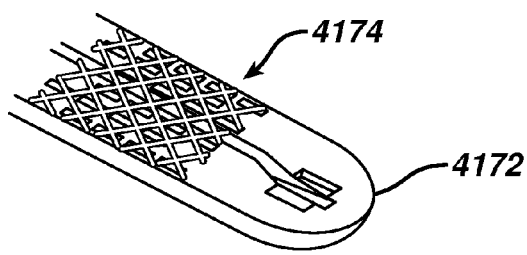
Figure 90:
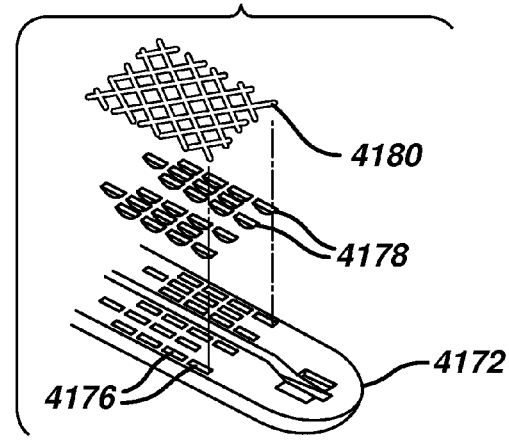
Figure 91A:
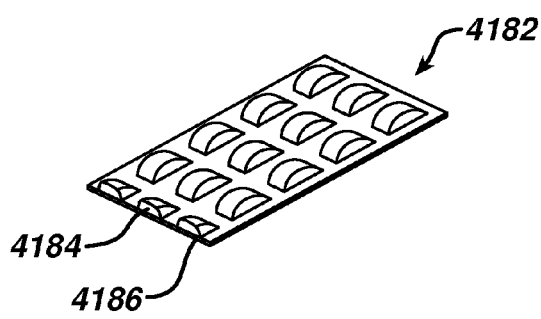
Figure 91B:
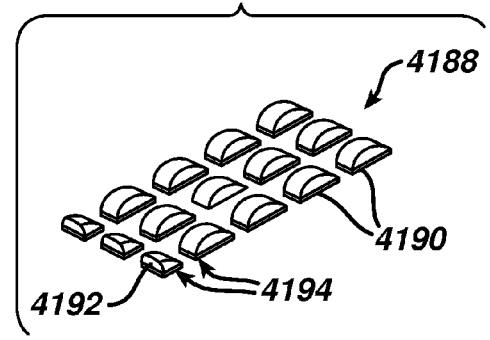
Figure 92:
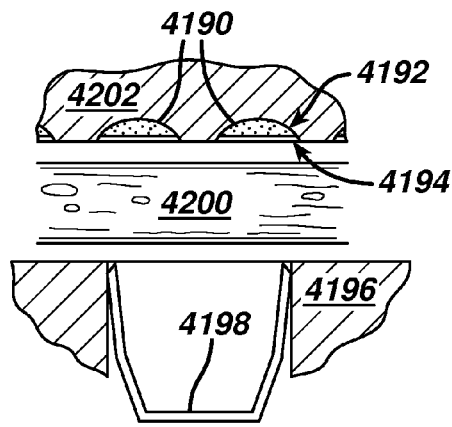
Figure 93:
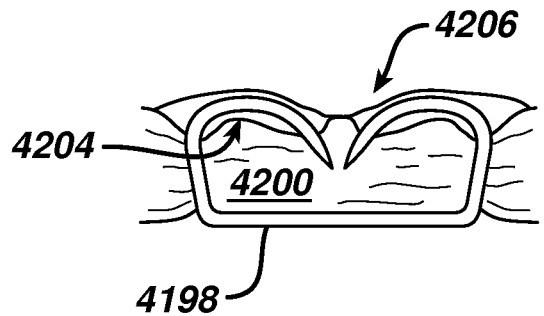
Figure 94:
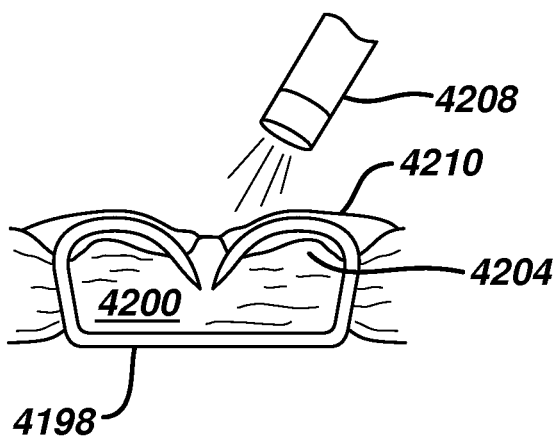
Figure 95:
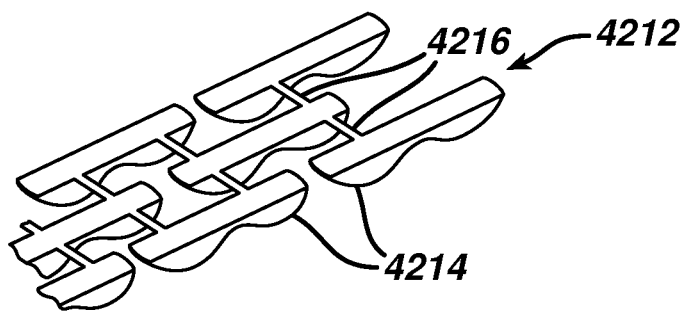
Figure 96:
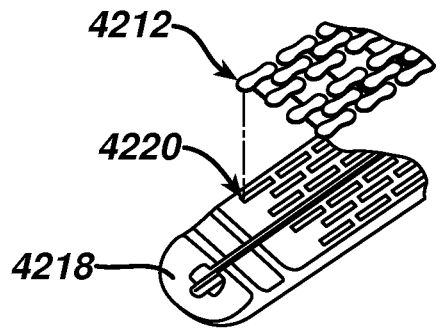
Figure 97:
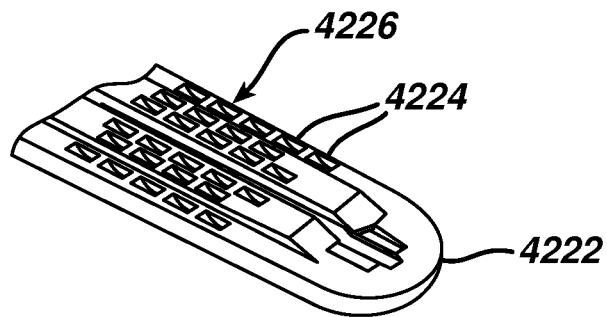
Figure 98:
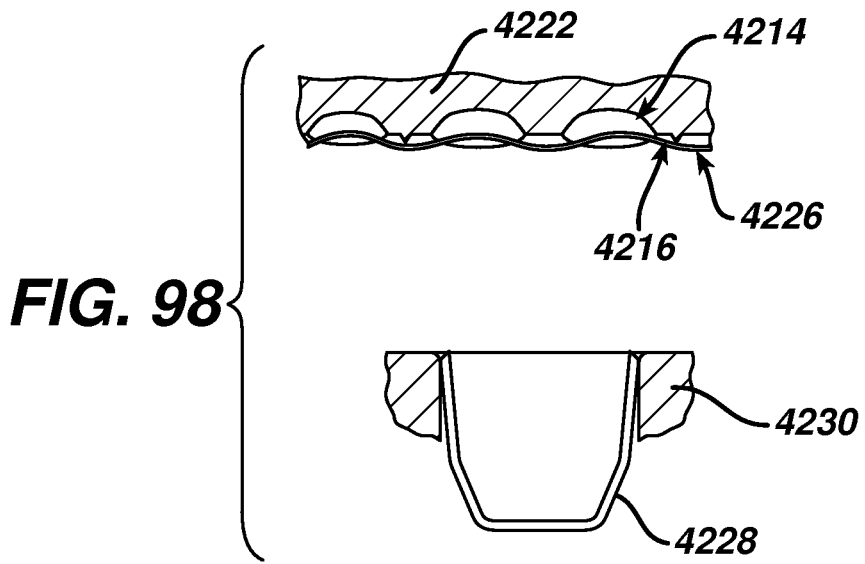
Figure 99:
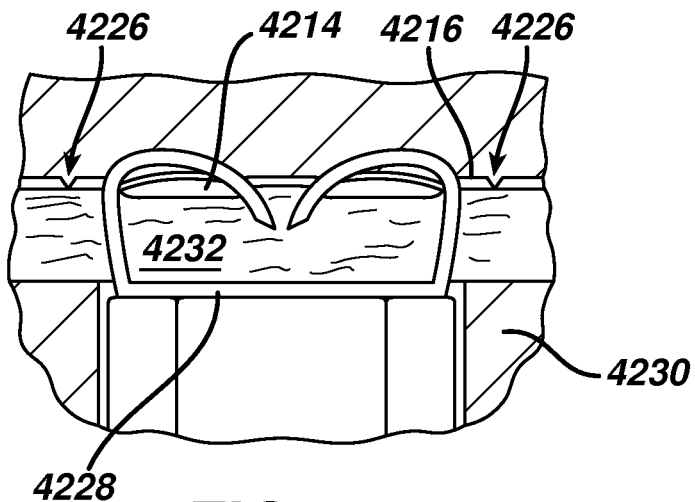
Figure 100:
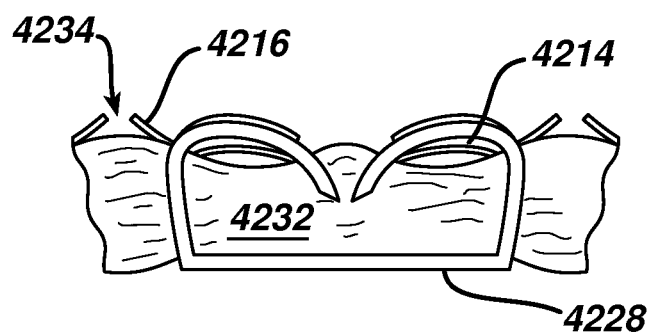
Figure 101:
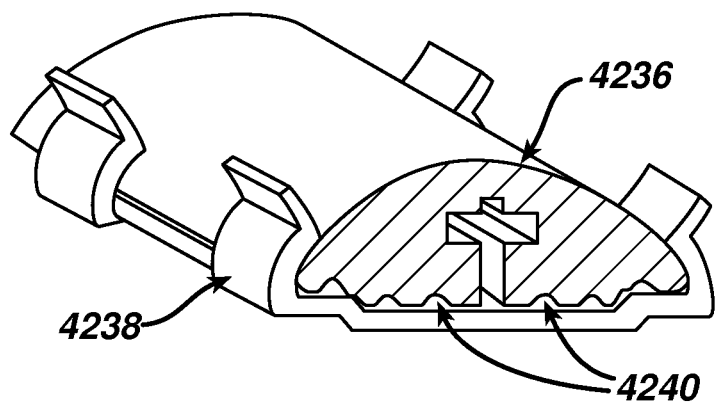
Figure 102A:
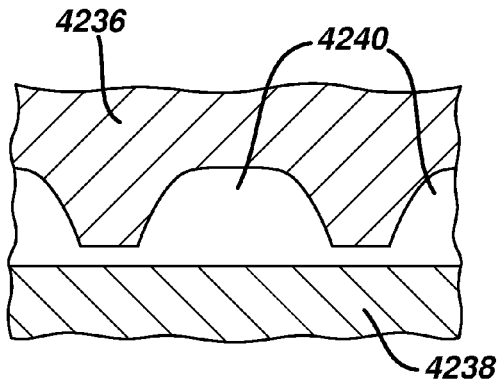
Figure 102B:
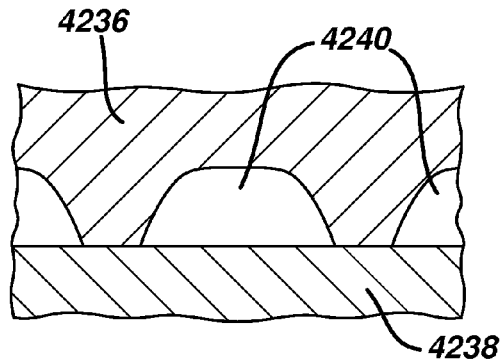
Figure 103:
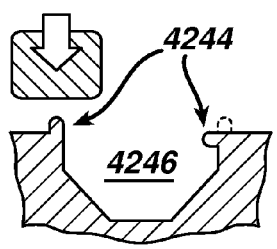
Figure 104:
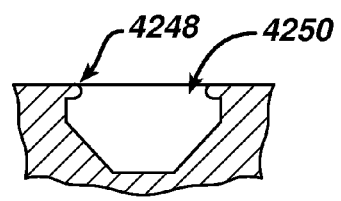
Figure 105:
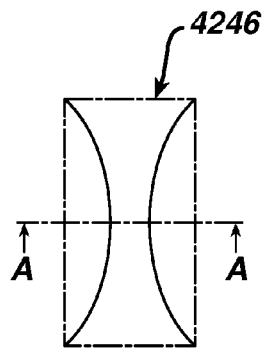
Figure 106:
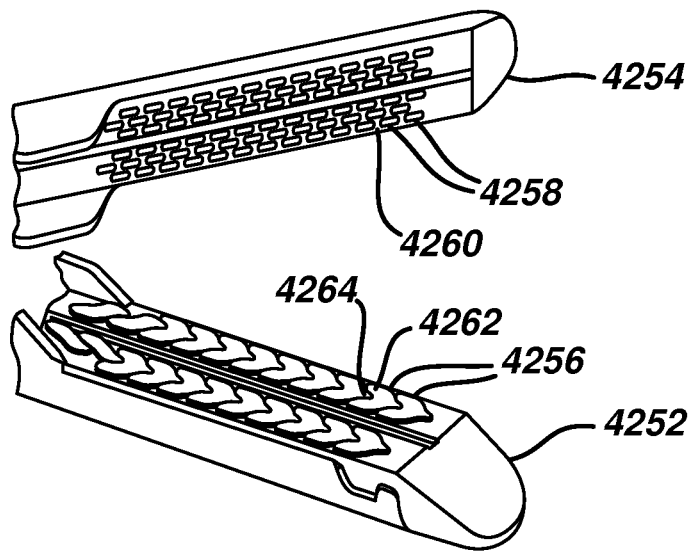
Figure 107:
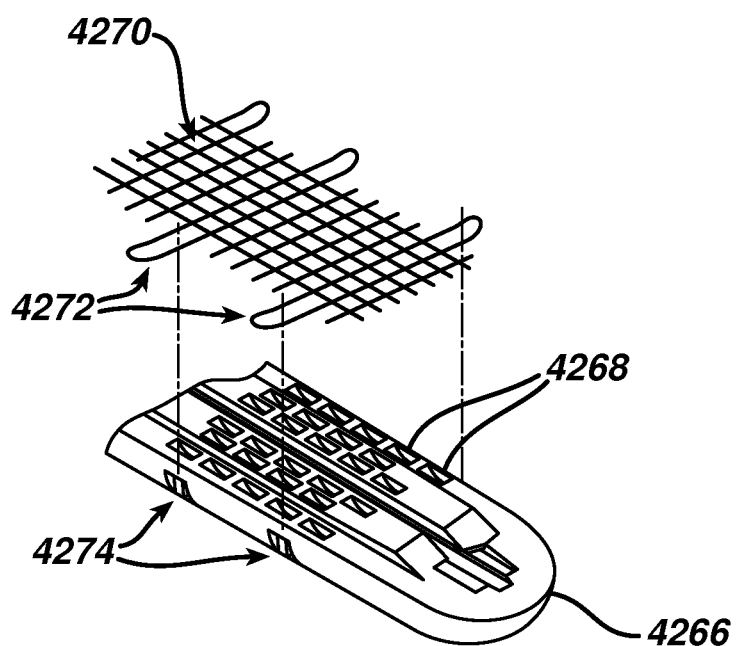
Figure 108:
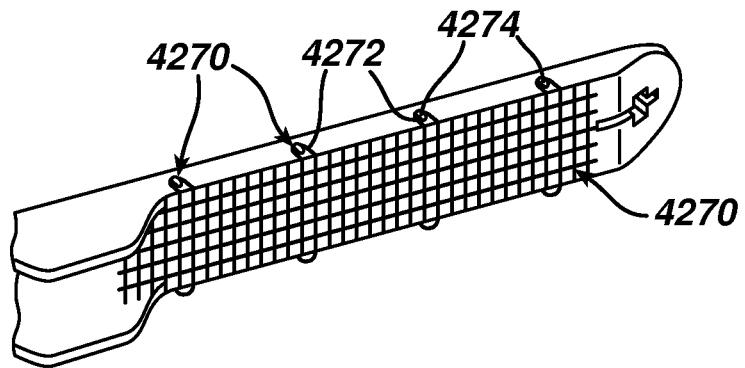
Figure 109:
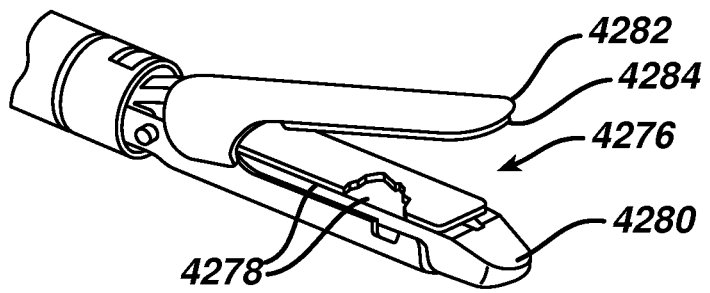
Figure 110:
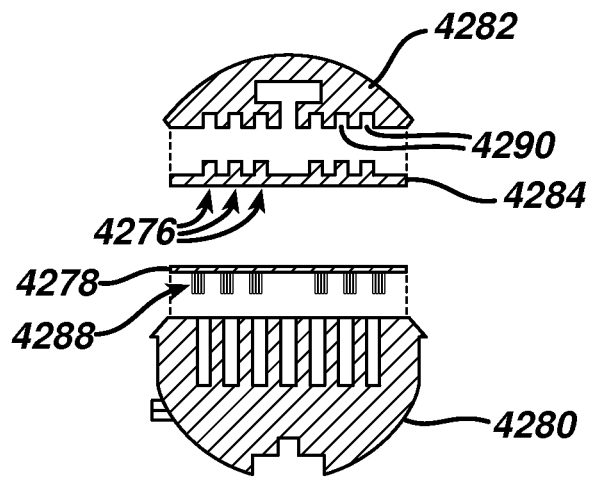
Figure 111:
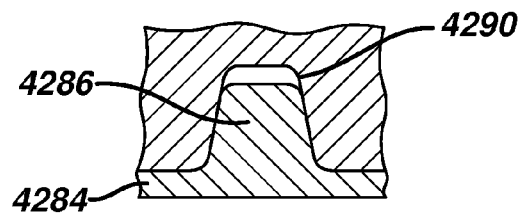
Figure 112:
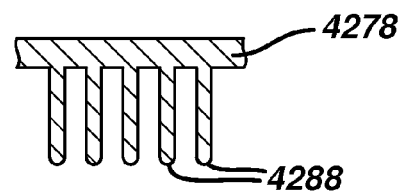
Figure 113A:
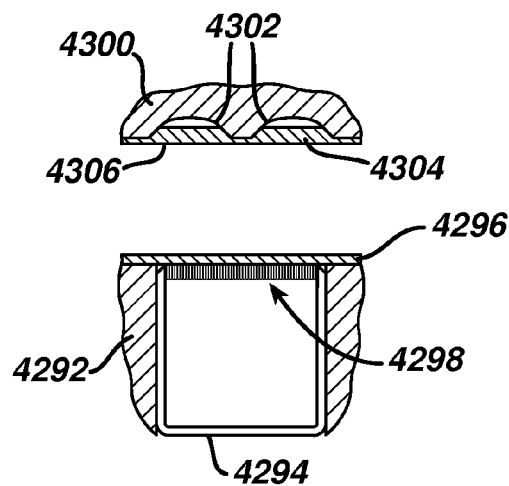
Figure 113B:
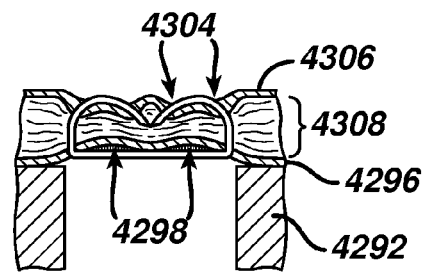
Figure 114A:
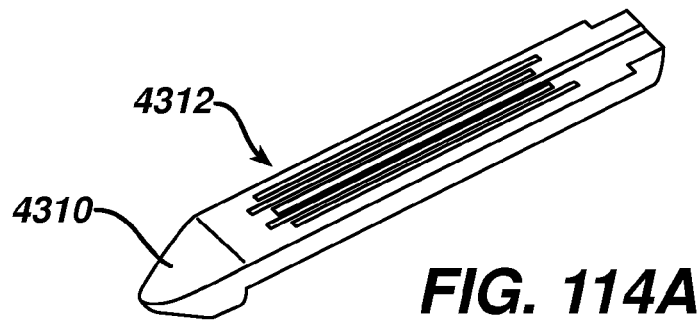
Figure 114B:
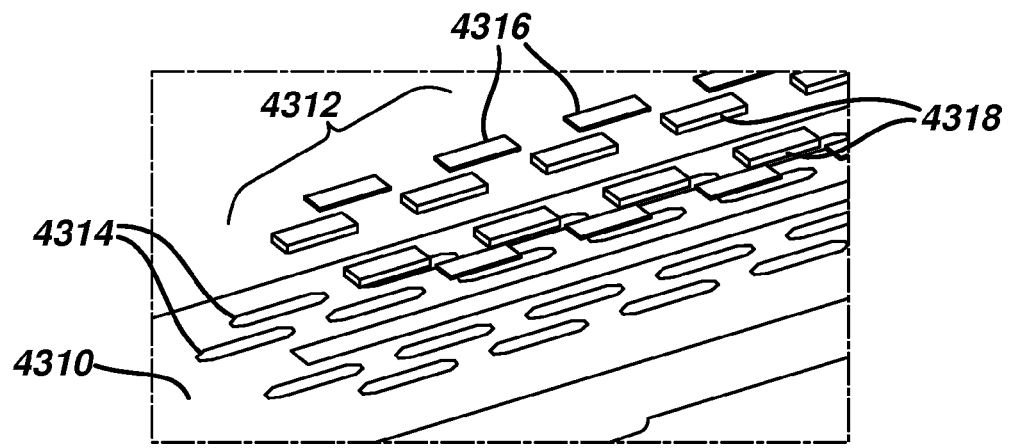
Figure 115:
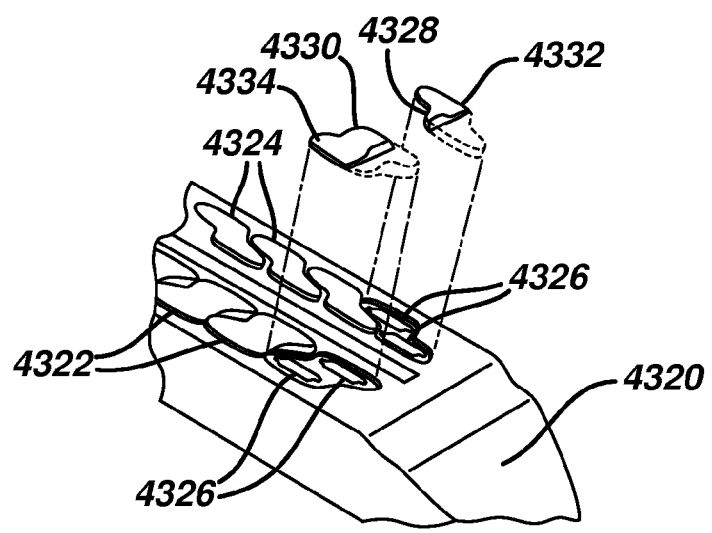
Figure 123A:
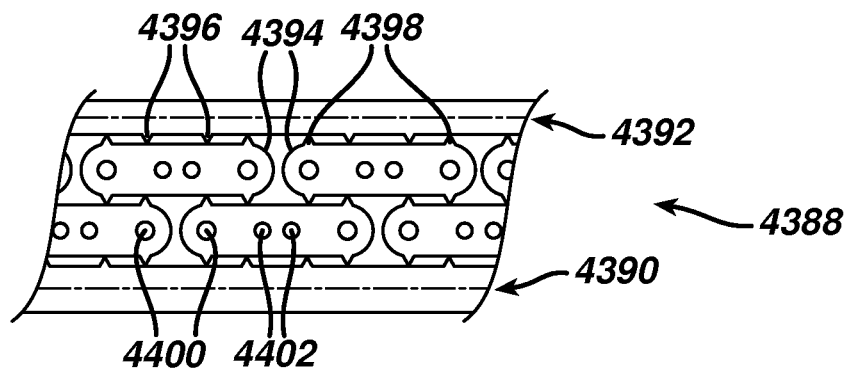
Figure 123B:
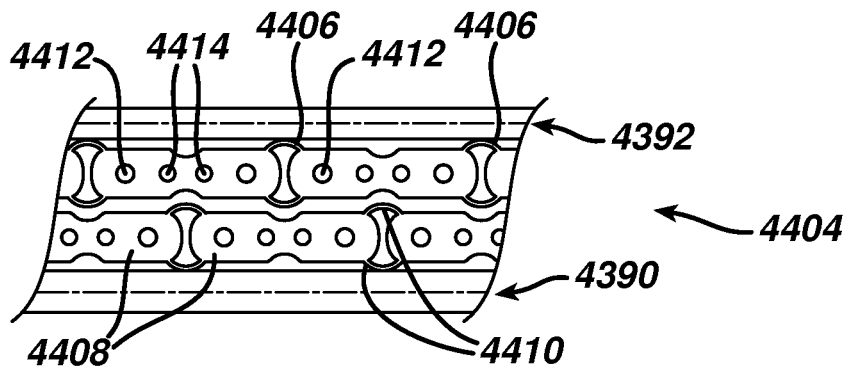
Figure 123C:
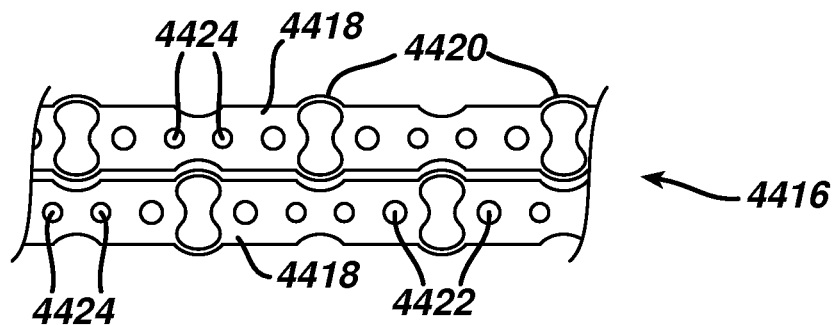
Figure 123D:
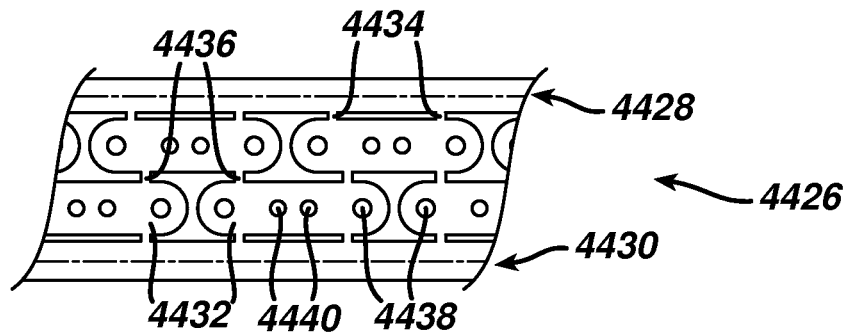
Figure 123E:
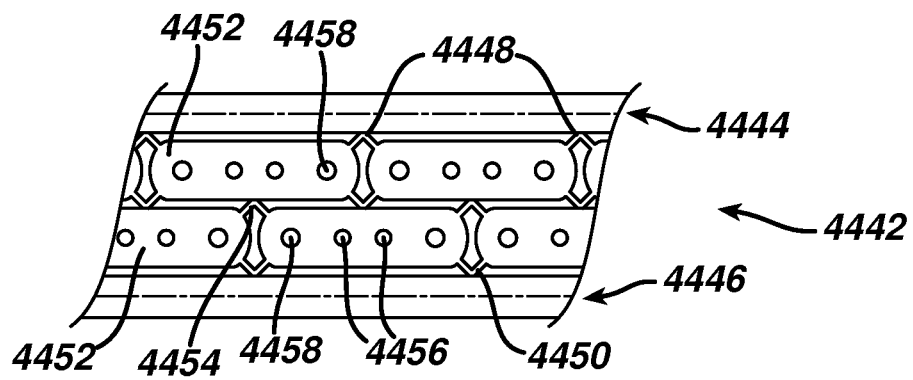
Figure 124:
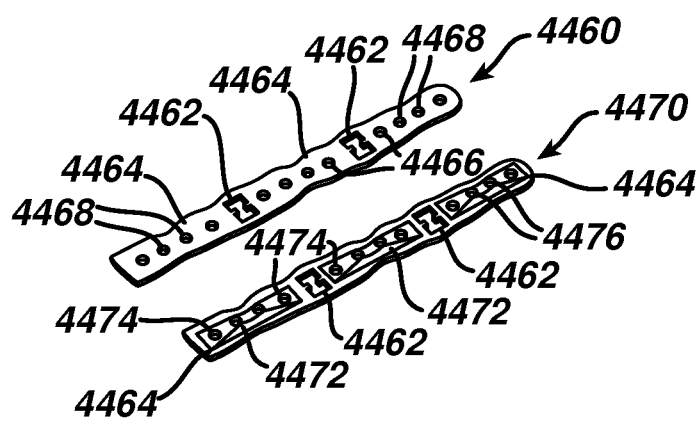
Figure 125:
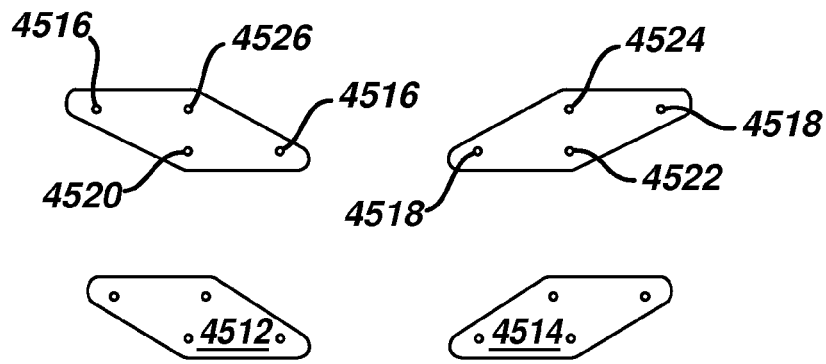
Figure 126:
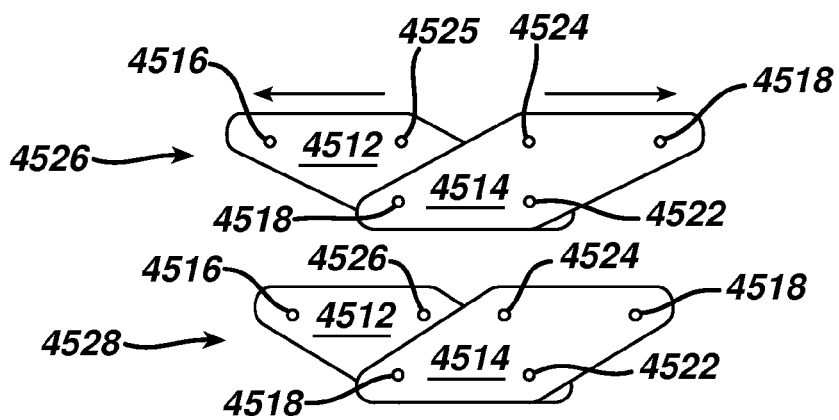
Figure 127:
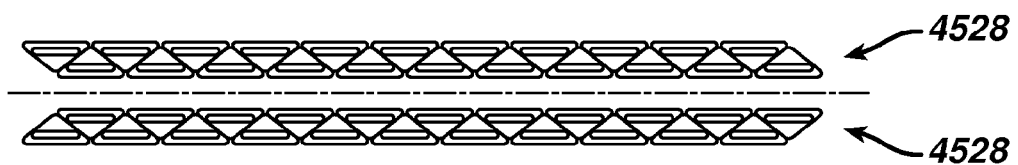
Figure 131:
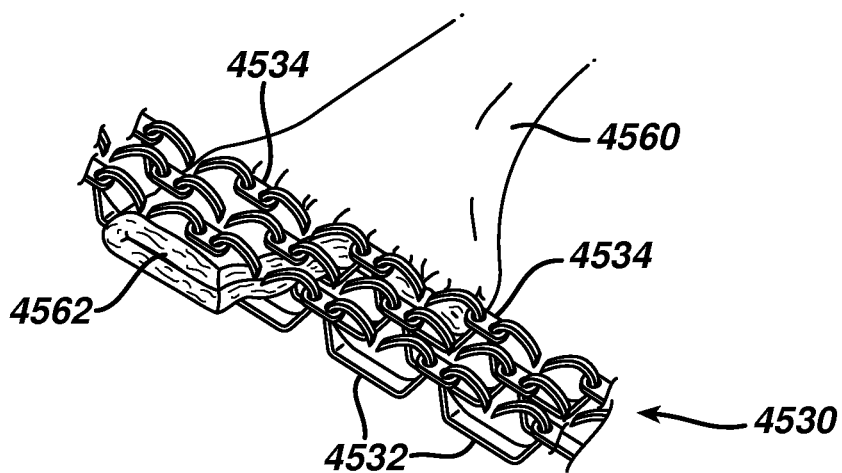
Figure 132:
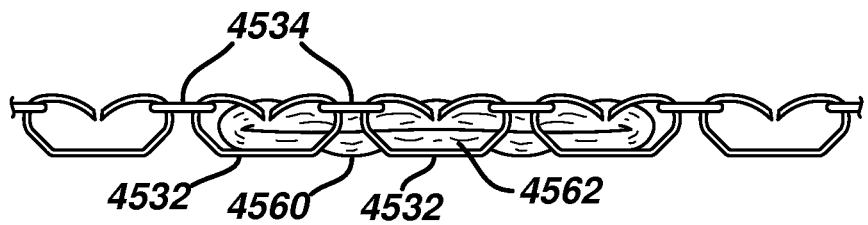
Figure 133:
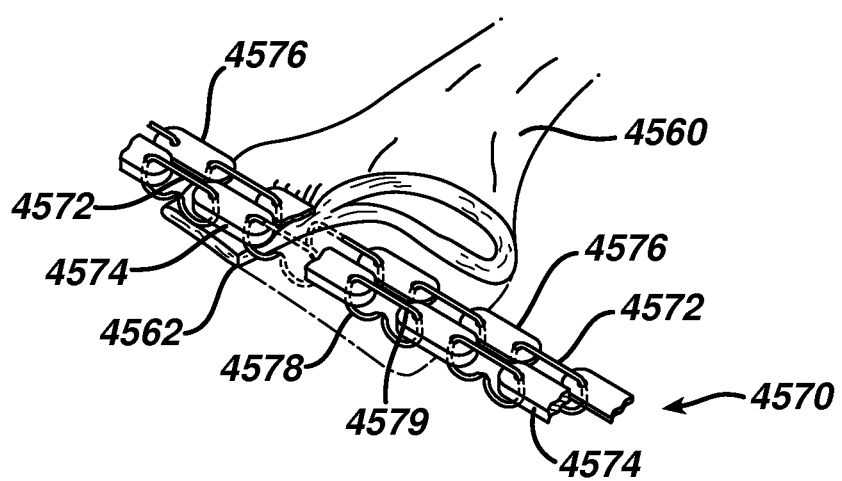
Figure 134:
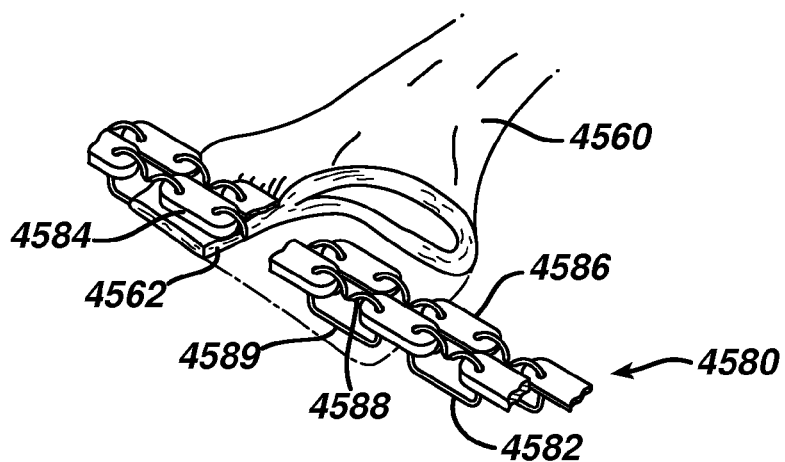
Figure 135:
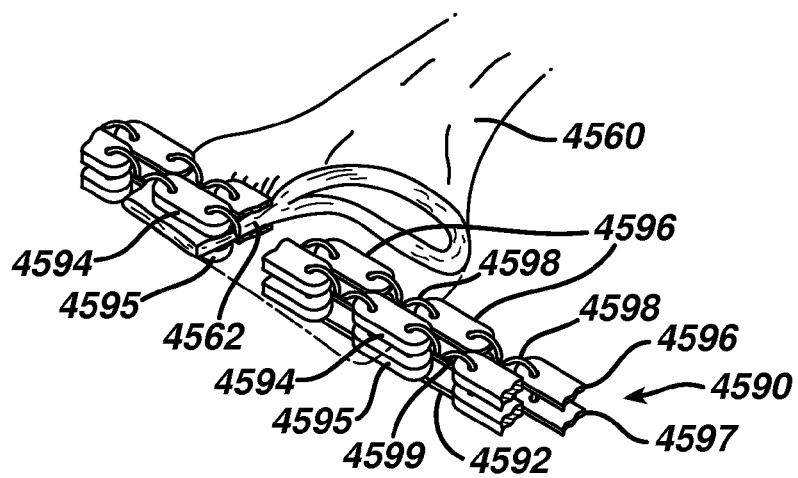
Figure 136:
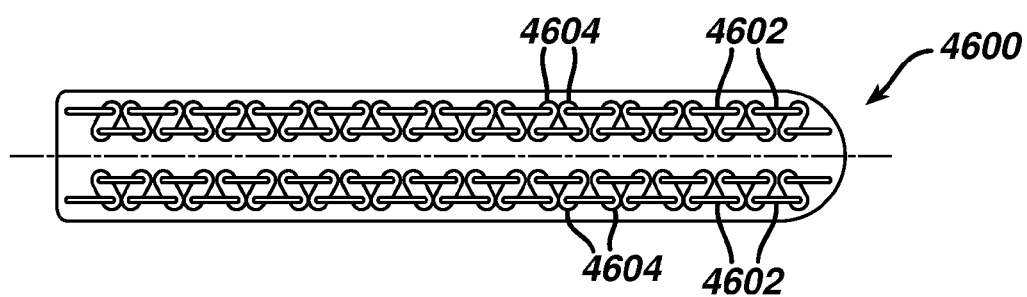
Figure 137:
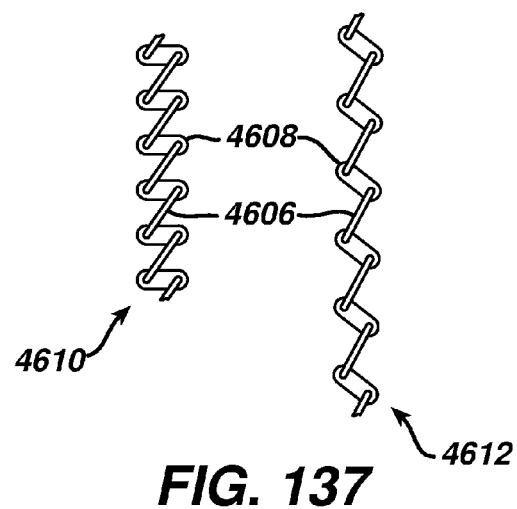
Figure 138A:
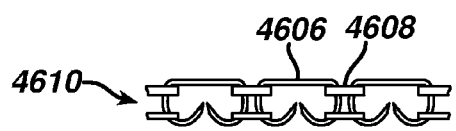
Figure 138B:
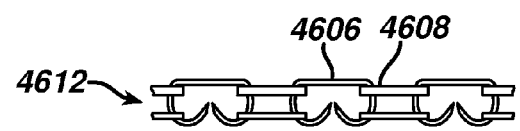
Figure 139:
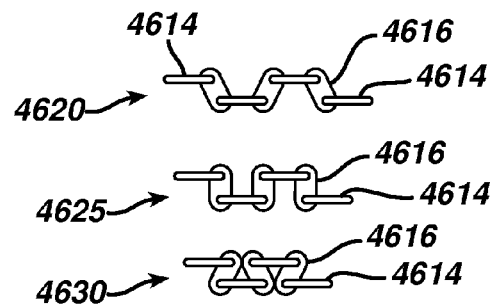
Figure 140A:
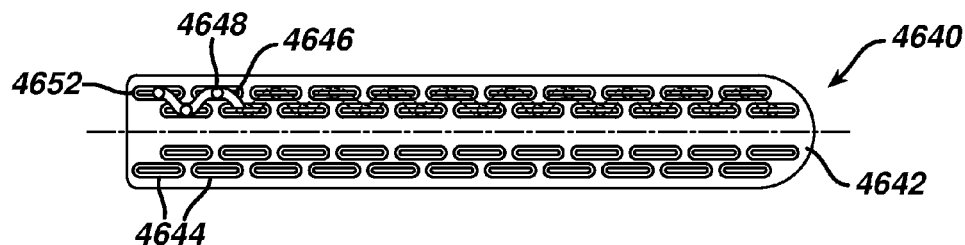
Figure 140B:
Figure 141A:
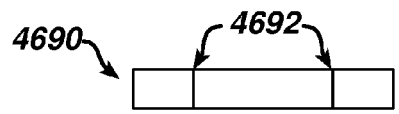
Figure 141B:
Figure 141C:
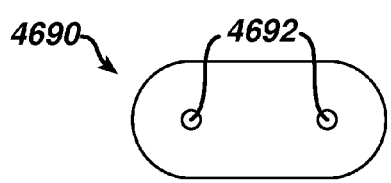
Figure 141D:
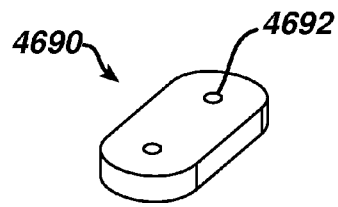
Figure 142A:
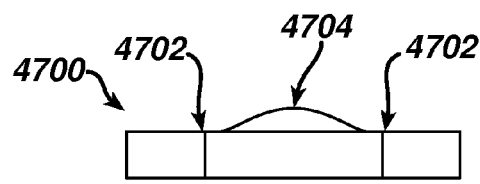
Figure 142B:
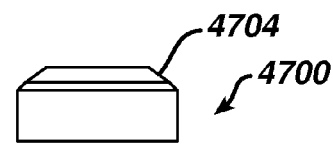
Figure 142C:
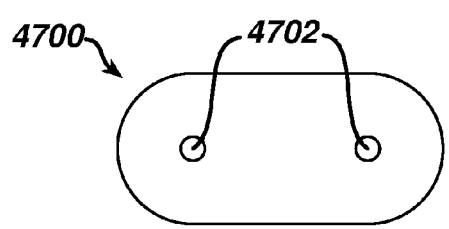
Figure 142D:
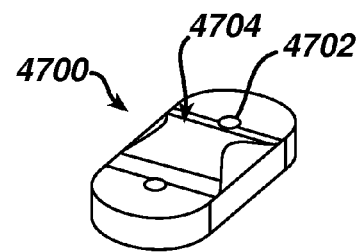
Figure 143:
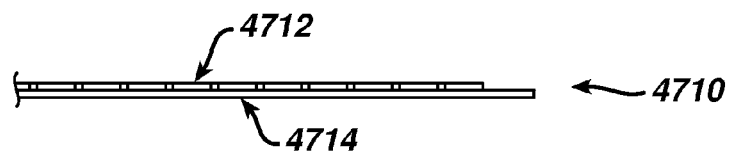
Figure 144A:
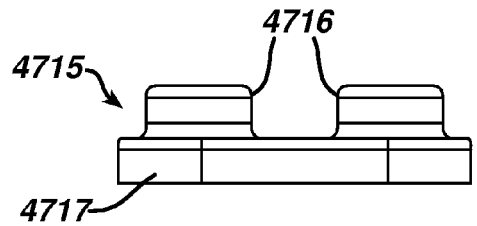
Figure 144B:
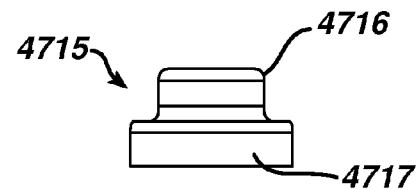
Figure 144C:
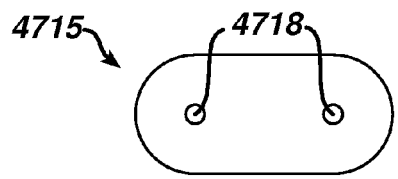
Figure 144D:
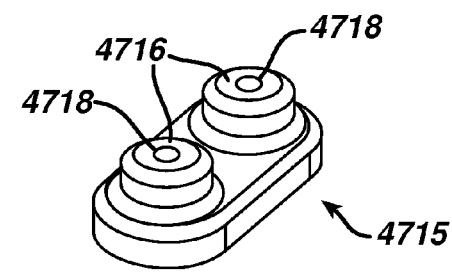
Figure 145A:
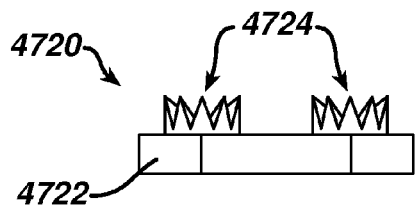
Figure 145B:
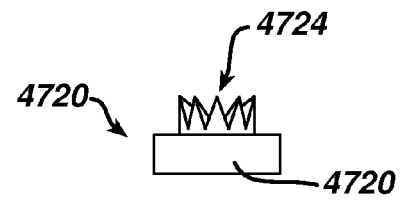
Figure 145C:
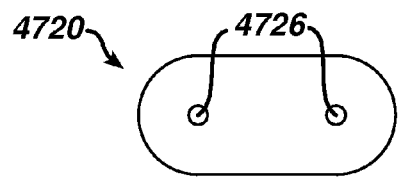
Figure 145D:
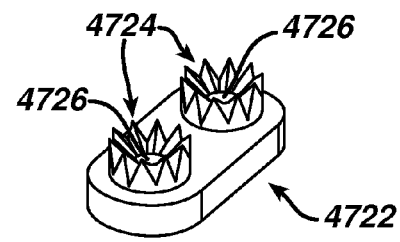
Figure 146:
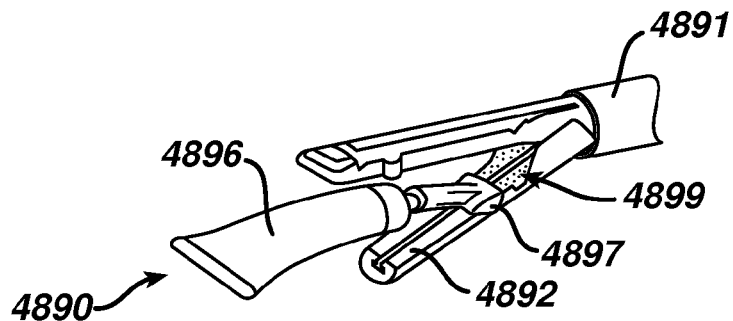
Figure 147:
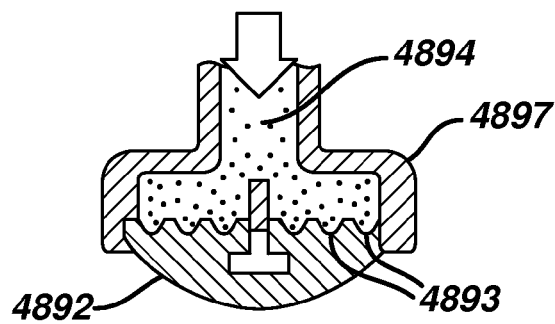
Figure 148:
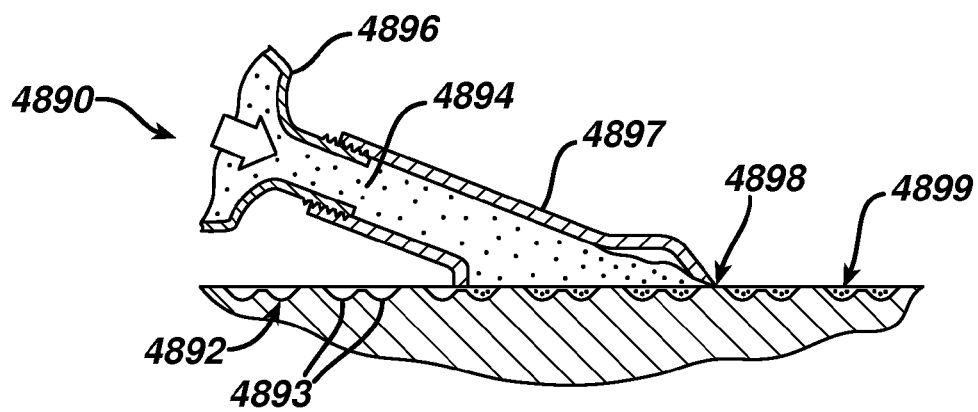
Figure 149A:
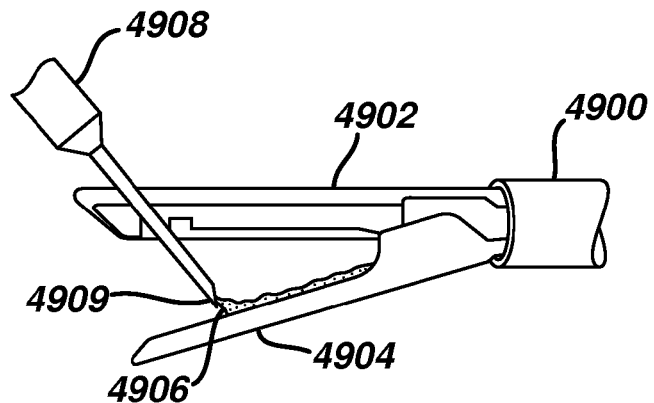
Figure 149B:
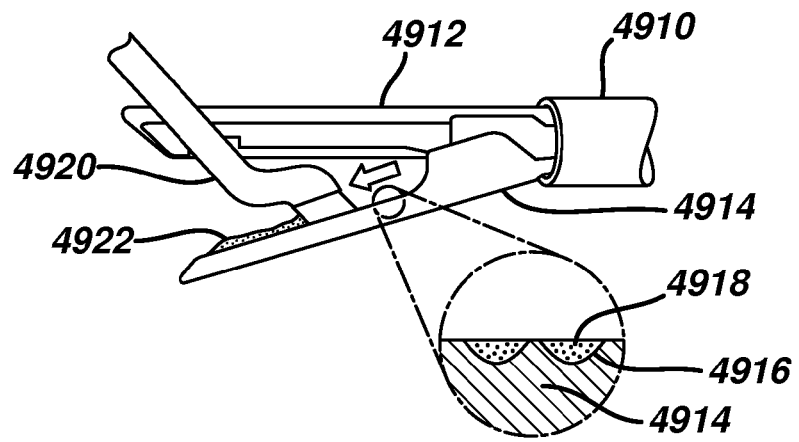
Figure 149C:
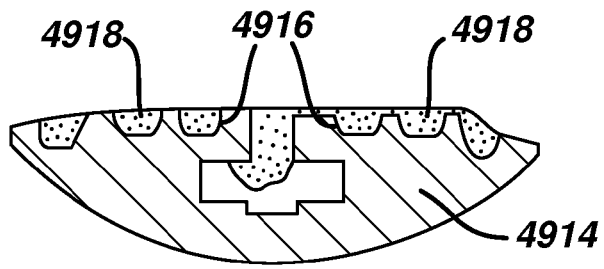
Figure 150:
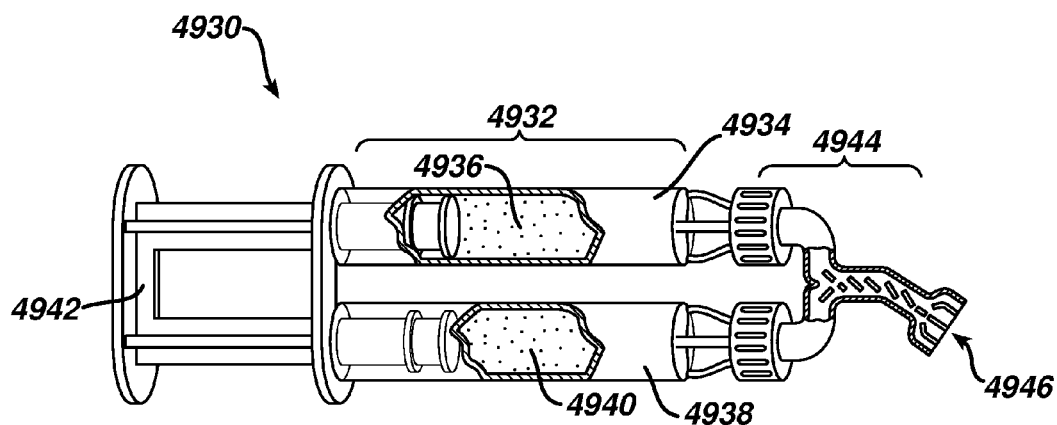
Figure 151:
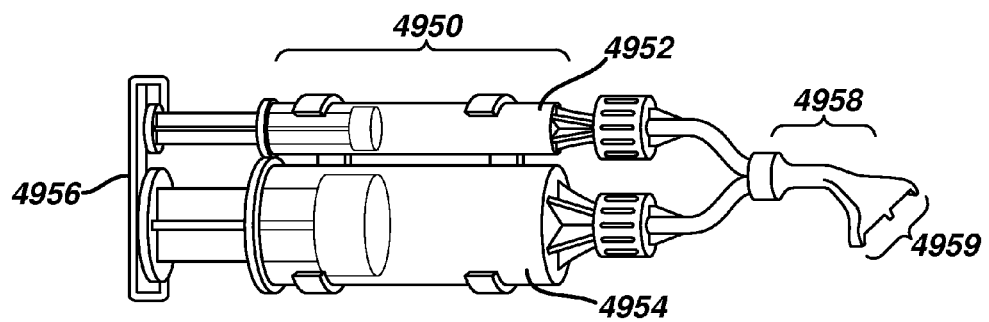
Figure 152A:
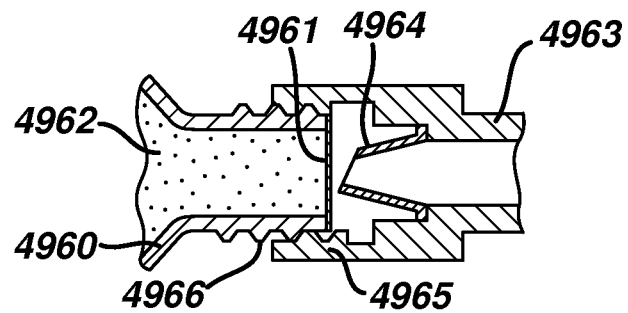
Figure 152B:
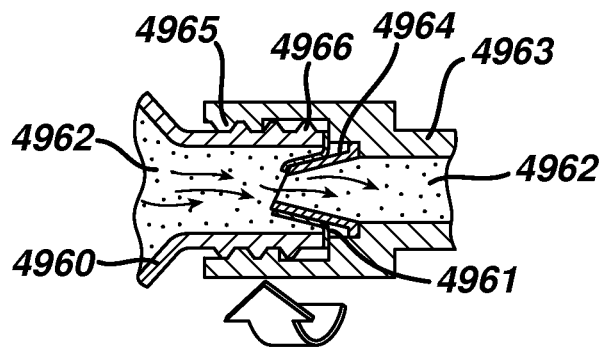
Figure 153:
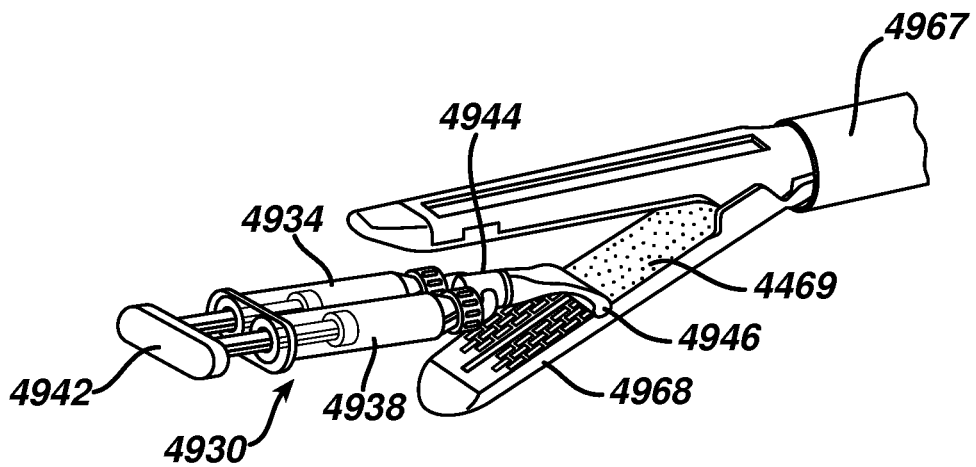
Figure 154:
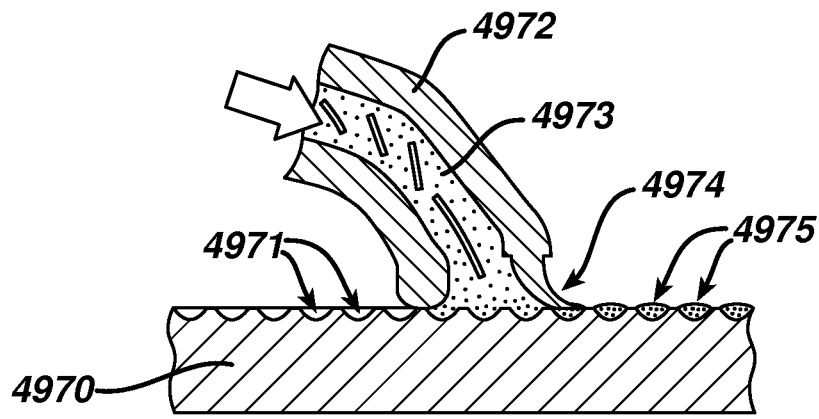
Figure 155:
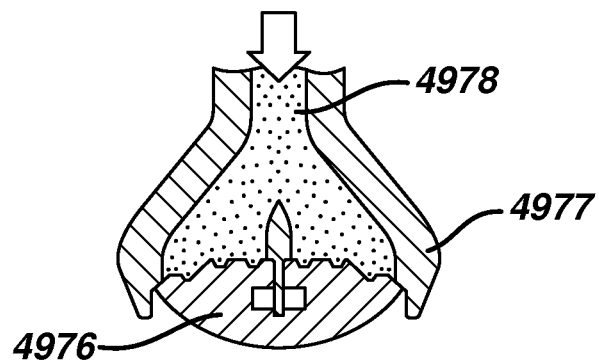
Figure 156:
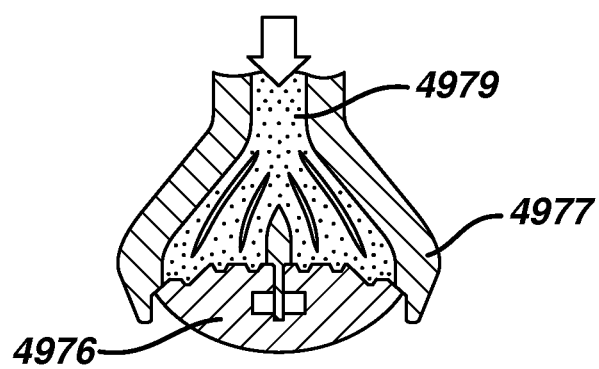
Figure 157:
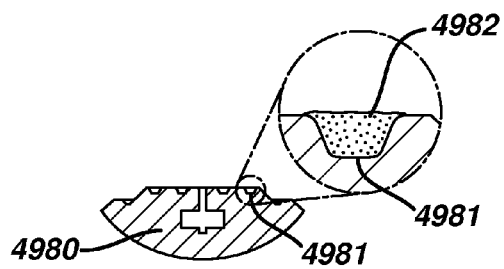
Figure 158:
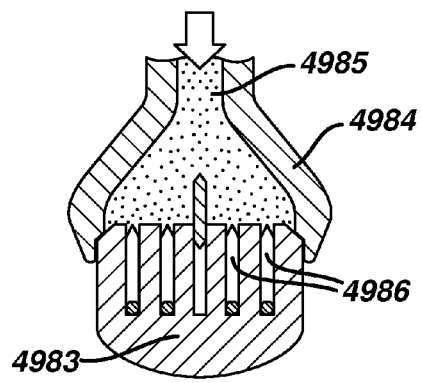
Figure 159:
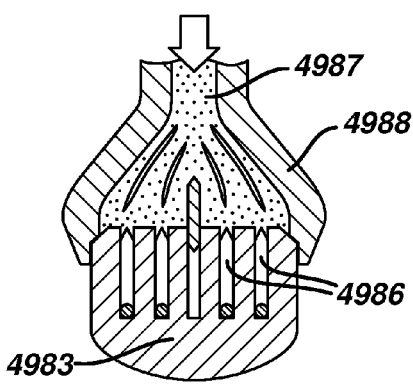
Figure 160:
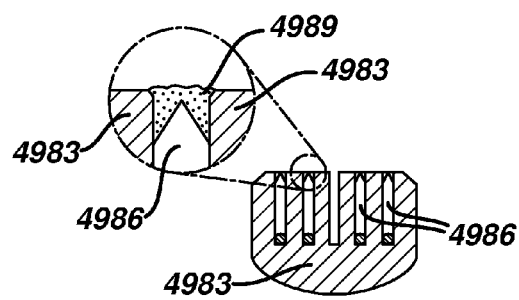
Figure 161:
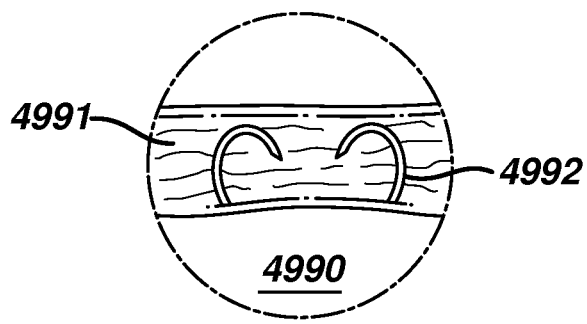
Figure 162:
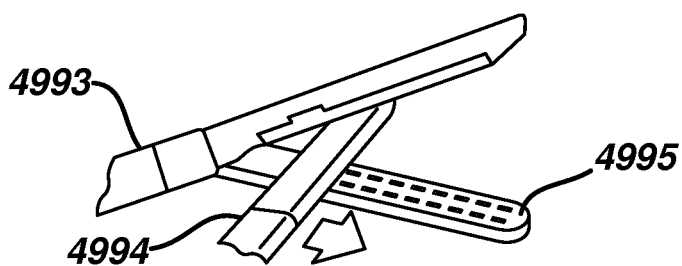
Figure 163:
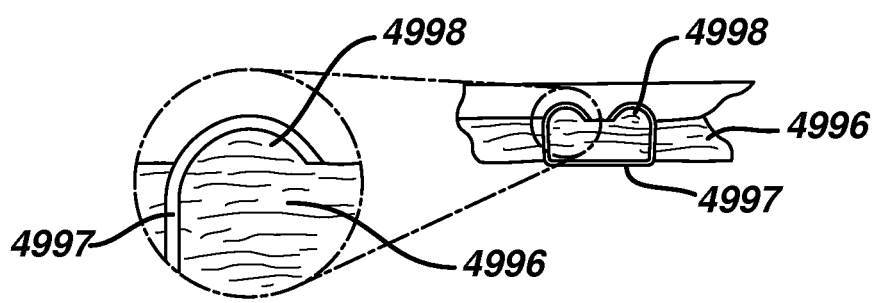
Figure 164A:
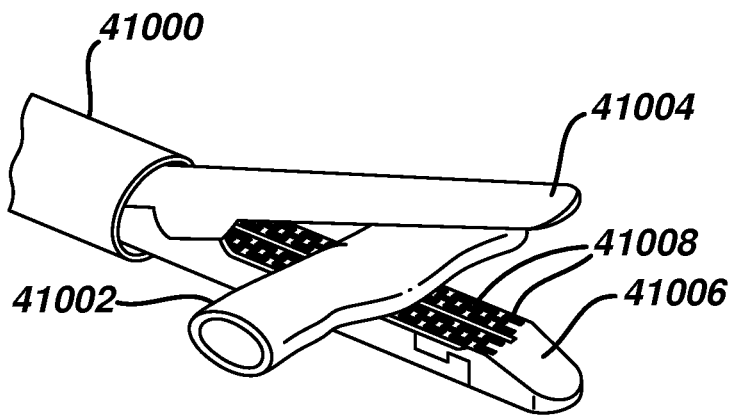
Figure 164B:
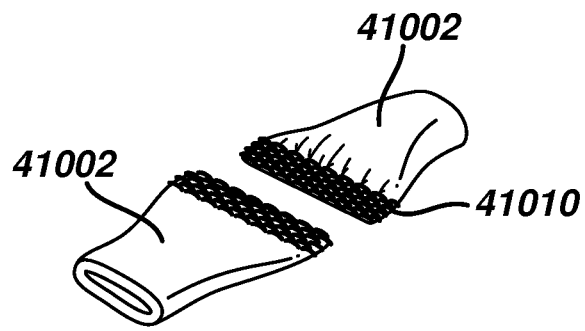
Figure 164C:
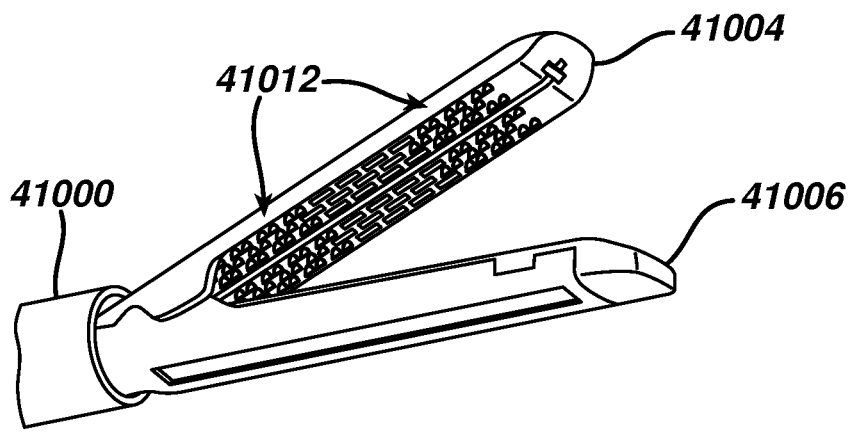
Figure 165:
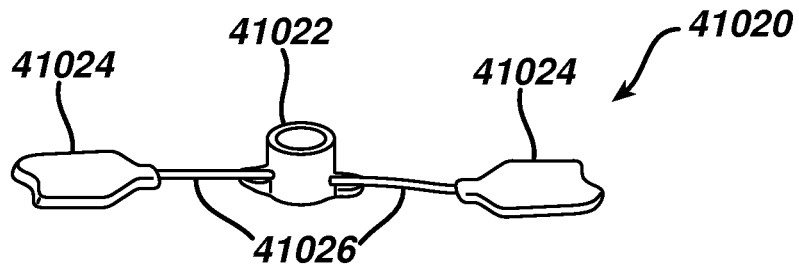
Figure 166:
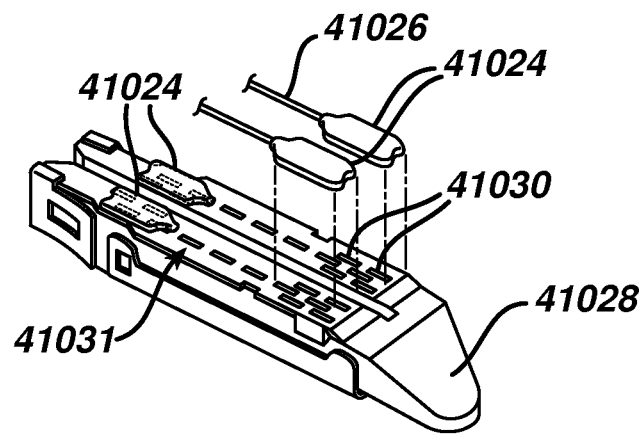
Figure 167:
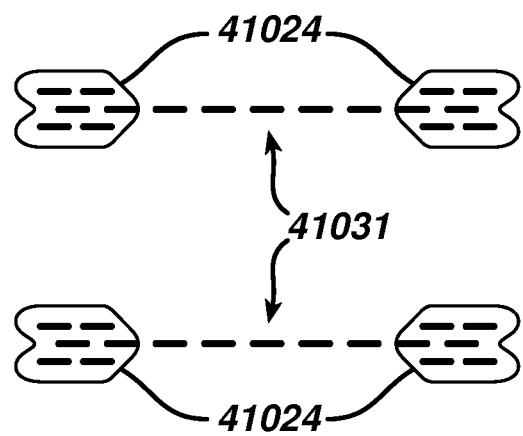
Figure 168:
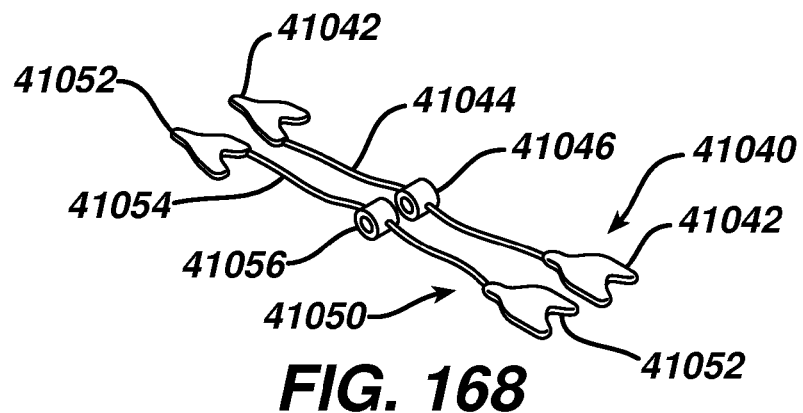
Figure 169:
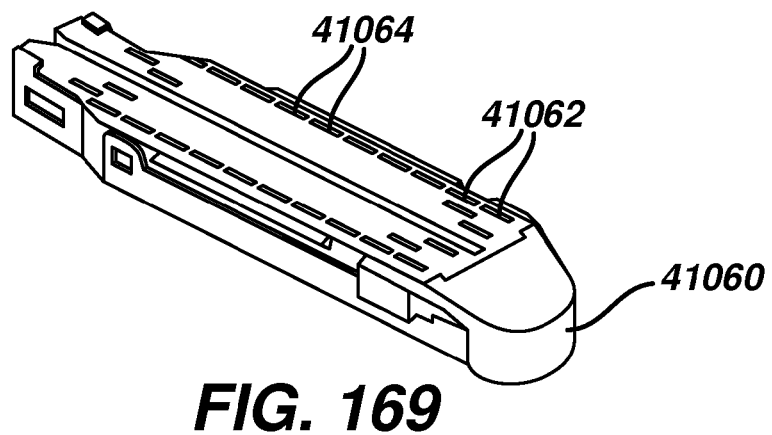
Figure 170:
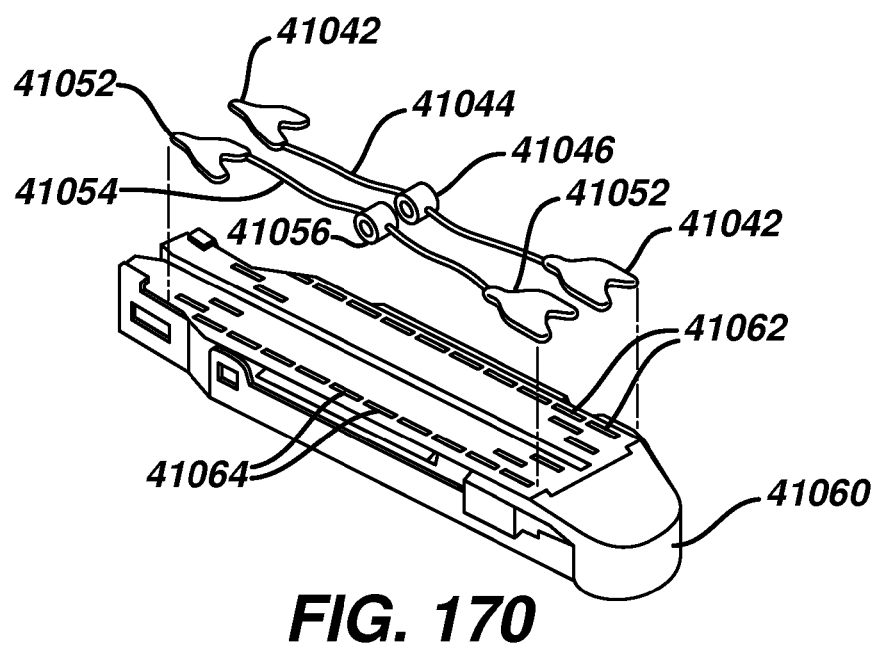
Figure 171:
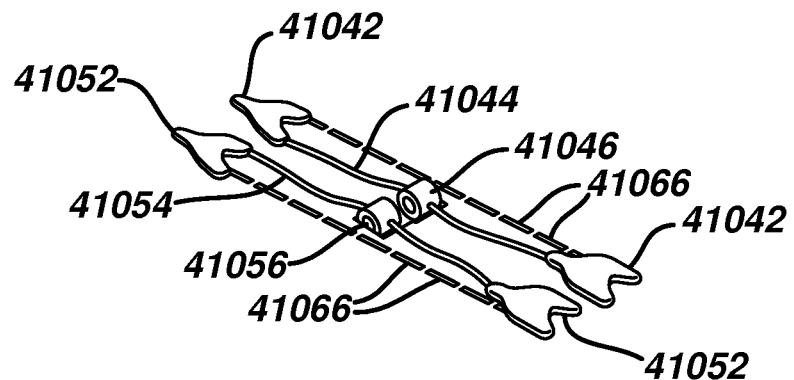
Figure 172:
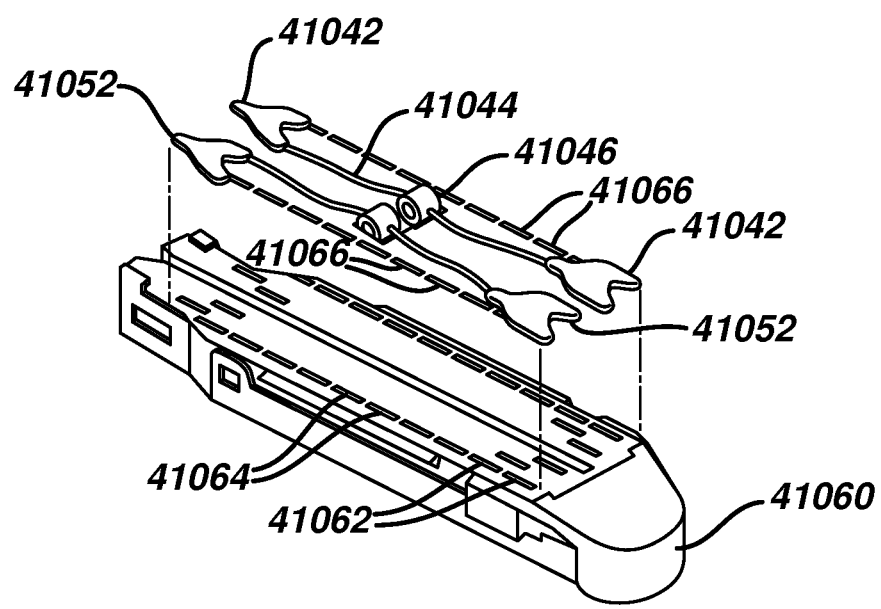
Figure 173:
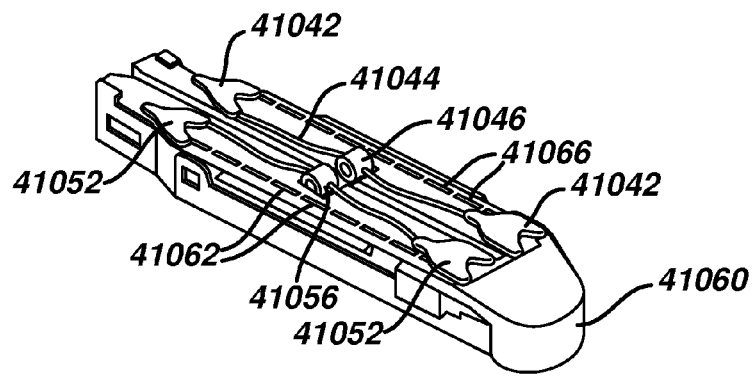
Figure 174:
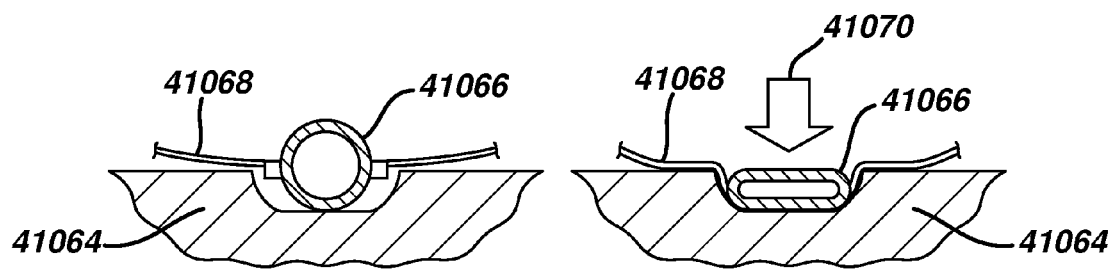
Figure 175:
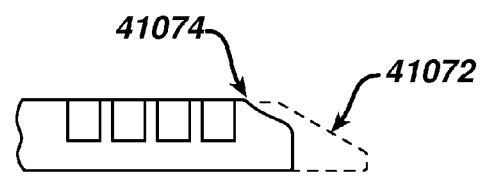
Figure 176:
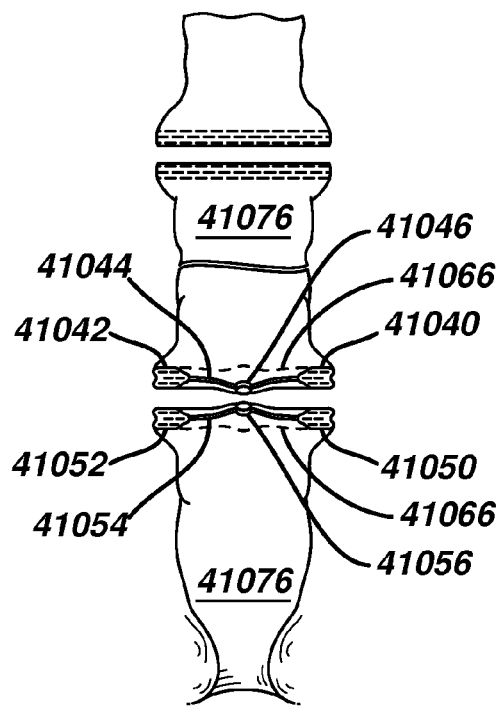
Figure 177A:
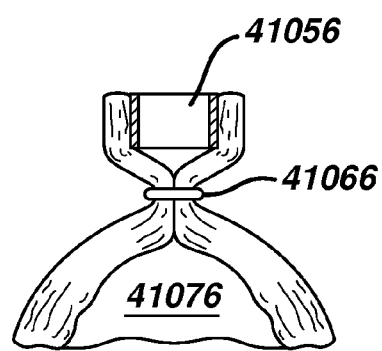
Figure 177B:
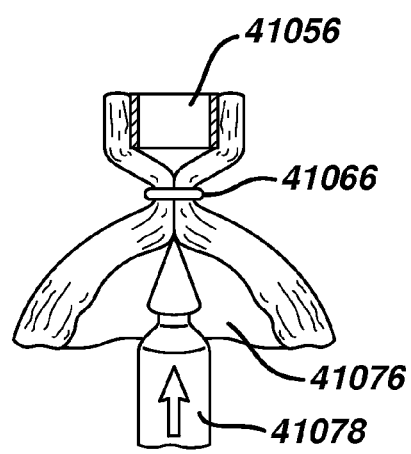
Figure 177C:
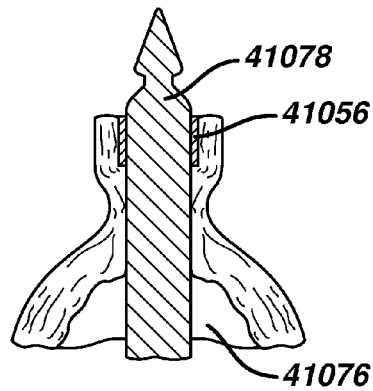
Figure 178:
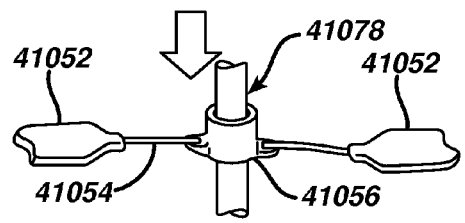
Figure 179:
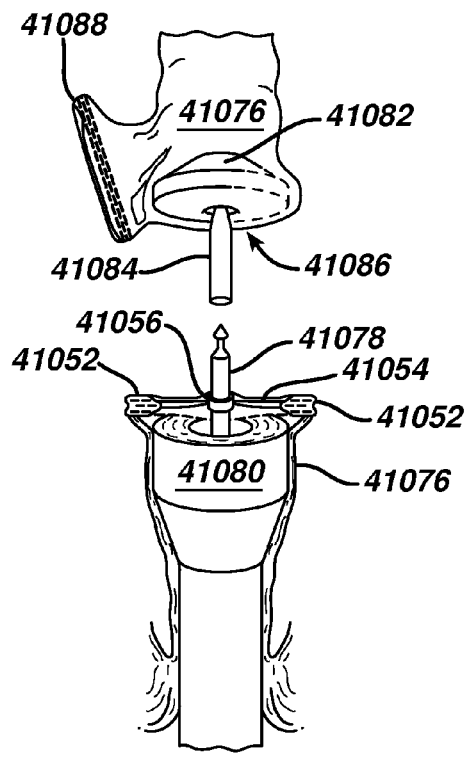
Figure 180:
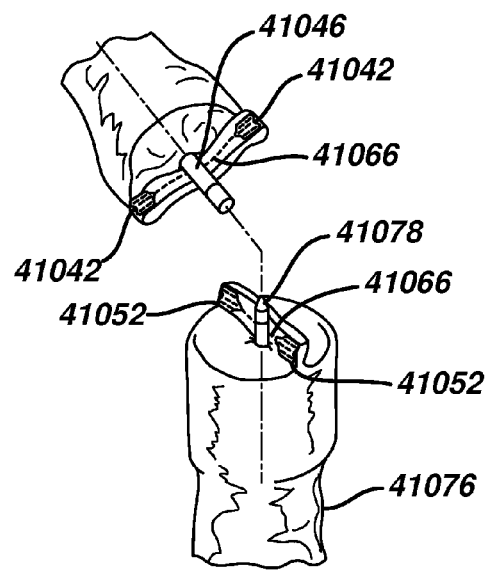
Figure 181:
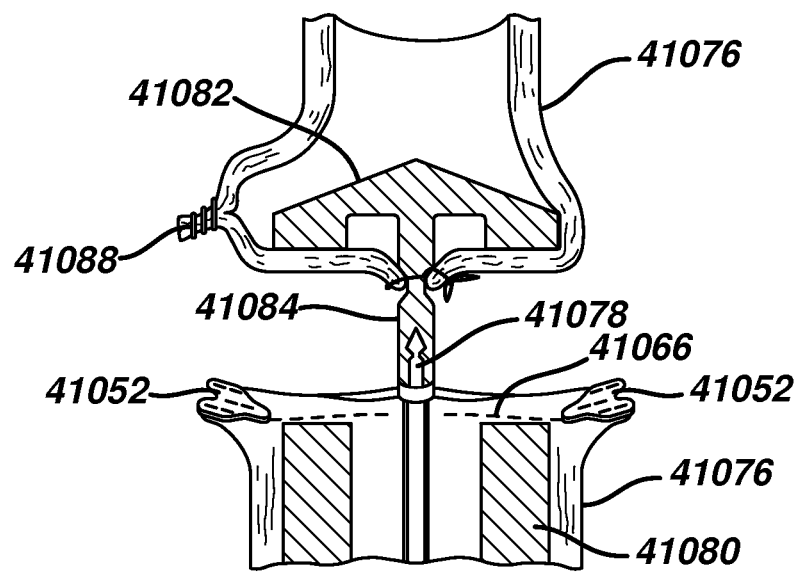
Figure 182:
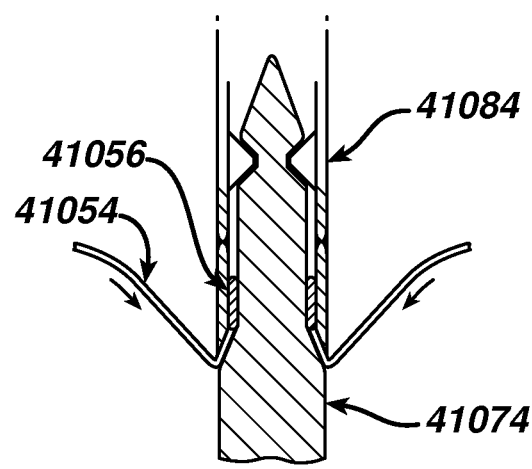
Figure 183:
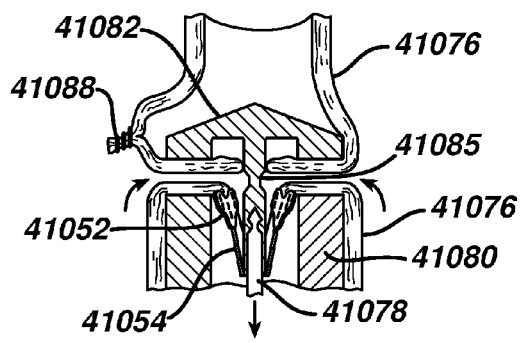
Figure 184:
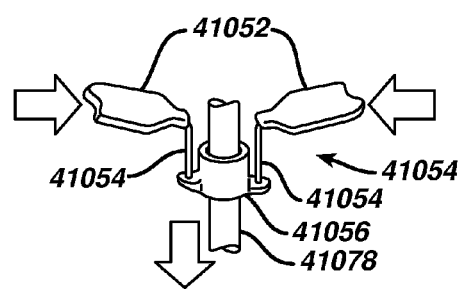
Figure 185:
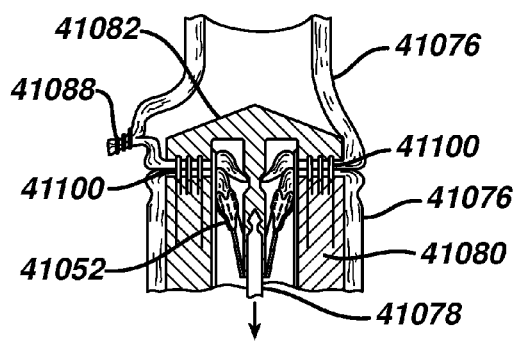
Figure 186:
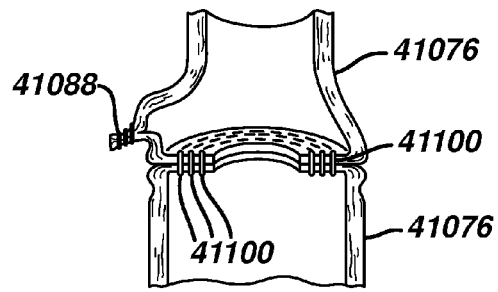

FIG. 72B is a cross-sectional view of the staple of FIG. 70 in tissue;

FIG. 73 is a perspective view of an alternative embodiment of an adjunct coupled to a staple;

FIG. 74 is a side view of the staple of FIG. 73 in tissue;

FIG. 75 is a perspective view of still another alternative embodiment of an adjunct coupled to a staple;

FIG. 76 is a perspective view of one embodiment of a staple cartridge housing a plurality of staples having adjuncts coupled thereto;

FIG. 77 is a perspective view of an alternative embodiment of a staple cartridge housing a plurality of staples having adjuncts coupled thereto;

FIG. 78A is a top view of one embodiment of a staple cartridge ejection slot that accommodates a staple having an adjunct coupled thereto;

FIG. 78B is a top view of an alternative embodiment of a staple cartridge ejection slot that accommodates a staple having an adjunct coupled thereto;

FIG. 78C is a top view of still another alternative embodiment of a staple cartridge ejection slot that accommodates a staple having an adjunct coupled thereto;

FIG. 79 is a top view of one embodiment of a plurality of adjunct segments coupled to one another;

FIG. 80 is a perspective view of an alternative embodiment of a plurality of adjunct segments;

FIG. 81A is a perspective view of one embodiment of a surgical end effector having a plurality of adjunct segments accepting a vessel;

FIG. 81B is a perspective view of the surgical end effector of FIG. 81A stapling and transecting the vessel;

FIG. 81C is a perspective view of the vessel and adjuncts of FIG. 81A after transection;

FIG. 81D is a perspective view of the vessel and adjuncts of FIG. 81A after excess adjuncts are removed;

FIG. 82 is a perspective view of an alternative embodiment of a plurality of adjunct segments;

FIG. 83 is a perspective view of one embodiment of a surgical stapler anvil having a plurality of staple forming openings filled with a viscous sealant;

FIG. 84 is a perspective view of an alternative embodiment of a surgical stapler anvil having a plurality of staple forming openings filled with a viscous sealant;

FIG. 85 is a cross-sectional view of one embodiment of a staple forming opening having a viscous sealant disposed therein and retained by a film;

FIG. 86A is a cross-sectional view of one embodiment of a staple forming opening with a viscous sealant;

FIG. 86B is a cross-sectional view of the staple forming opening of FIG. 86A prior to curing;

FIG. 86C is a cross-sectional view of the staple forming opening of FIG. 86A after partial curing;

FIG. 86D is a cross-sectional view of the staple forming opening of FIG. 86A after complete curing;

FIG. 87 is a side view of a surgical staple coupled to the adjunct of FIG. 85;

FIG. 88 is a perspective view of one embodiment of a film connecting a plurality of adjuncts;

FIG. 89 is a perspective view of one embodiment of a weave connecting a plurality of adjuncts;

FIG. 90 is an exploded view of the weave and adjuncts of FIG. 89;

FIG. 91A is a perspective view of one embodiment of a plurality of adjuncts coupled to one another by a film of cured adjunct material;

FIG. 91B is a perspective view of an alternative embodiment of a plurality of adjuncts separated from one another and including a layer of cured adjunct material;

FIG. 92 is a cross-sectional view of one embodiment of a staple in a staple cartridge, tissue, and an adjunct disposed in a staple forming opening of an anvil;

FIG. 93 is a cross-sectional view of a staple and the adjunct of FIG. 85 disposed in tissue;

FIG. 94 is a cross-sectional view of the staple and adjunct of FIG. 93 being cured after implantation in tissue;

FIG. 95 is a perspective view of one embodiment of a plurality of adjuncts coupled by a plurality of connecting branches of adjunct material;

FIG. 96 is an exploded view of the plurality of adjuncts of FIG. 95 disposed in a plurality of staple forming openings of a surgical stapler anvil;

FIG. 97 is a perspective view of one embodiment of a surgical stapler anvil having features to destroy connecting branches extending between a plurality of adjuncts;

FIG. 98 is a cross-sectional view of one embodiment of a surgical stapler including a staple disposed in a staple cartridge and a plurality of adjuncts coupled to the anvil of FIG. 97;

FIG. 99 is a cross-sectional view of the stapler of FIG. 98 ejecting a staple through tissue and into a staple forming opening of the anvil;

FIG. 100 is a cross-sectional view of the staple of FIG. 98 implanted in tissue;

FIG. 101 is a perspective cross-sectional view of one embodiment of a retainer to hold adjunct material against a surgical stapler anvil;

FIG. 102A is a cross-sectional view of the retainer and anvil of FIG. 101;

FIG. 102B is a cross-sectional view of an alternative embodiment of a retainer and anvil;

FIG. 103 is a cross-sectional view of one embodiment of a staple forming opening having a retainer formed thereon;

FIG. 104 is a cross-sectional view of the staple forming opening of FIG. 103 holding adjunct material therein;

FIG. 105 is a top view of the staple forming opening of FIG. 103;

FIG. 106 is a perspective view of one embodiment of a surgical stapler anvil and staple cartridge having adjunct segments coupled thereto;

FIG. 107 is an exploded view of one embodiment of attachment and alignment features of a surgical stapler anvil;

FIG. 108 is a perspective view of the anvil of FIG. 107;

FIG. 109 is a perspective view of one embodiment of a surgical stapler having a plurality of adjunct segments coupled thereto and connected to one another by a film;

FIG. 110 is an exploded cross-sectional view of the surgical stapler of FIG. 109;

FIG. 111 is a close cross-sectional view of a staple forming opening of the surgical stapler of FIG. 109;

FIG. 112 is a cross-sectional view of one embodiment of a plurality of adjunct segments connected to one another by a film;

FIG. 113A is a cross-sectional view of the surgical stapler of FIG. 109 prior to actuation;

FIG. 113B is a cross-sectional view of the surgical stapler of FIG. 109 after actuation that delivers a staple into tissue;

FIG. 114A is a perspective view of one embodiment of a surgical stapler having a plurality of adjunct segments of differing thicknesses;

FIG. 114B is a close exploded view of the surgical stapler of FIG. 114A;

FIG. 115 is an exploded perspective view of an alternative embodiment of a surgical stapler having a plurality of adjunct segments of differing thicknesses;

FIG. 116 is a cross-sectional view of the surgical stapler of FIG. 115;

FIG. 117 is a perspective view of an alternative embodiment of a surgical stapler having a plurality of adjunct segments of differing thicknesses;

FIG. 118A is an exploded view of one embodiment of a multi-material adjunct;

FIG. 118B is a perspective view of the adjunct of FIG. 118A;

FIG. 119A is a perspective cross-sectional view of the adjunct of FIG. 118A prior to actuation of a surgical stapler;

FIG. 119B is a perspective cross-sectional view of the adjunct of FIG. 118A after actuation of a surgical stapler;

FIG. 120 is a cross-sectional view of one embodiment of a surgical staple and adjunct formed in tissue;

FIG. 121 is a cross-sectional view of an alternative embodiment of a surgical staple and adjunct formed in tissue;

FIG. 122 is a cross-sectional view of still another embodiment of a surgical staple and adjunct formed in tissue;

FIG. 123A is a top view of one embodiment of a plurality of adjuncts coupled to a surgical stapler anvil;

FIG. 123B is a top view of an alternative embodiment of a plurality of adjuncts coupled to a surgical stapler anvil;

FIG. 123C is a top view of still another embodiment of a plurality of adjuncts coupled to a surgical stapler anvil;

FIG. 123D is a top view of yet another embodiment of a plurality of adjuncts coupled to a surgical stapler anvil;

FIG. 123E is a top view of still another embodiment of a plurality of adjuncts coupled to a surgical stapler anvil;

FIG. 124 is a perspective view of one embodiment of a plurality of adjuncts;

FIG. 125 is a top view of one embodiment of adjunct segment shapes;

FIG. 126 is a top view of the adjuncts of FIG. 125 coupled to one another;

FIG. 127 is a top view of one embodiment of a sheet of adjunct segments coupled to one another;

FIG. 128 is a top view of an alternative embodiment of adjunct segment shapes;

FIG. 129 is a top view of the adjuncts of FIG. 128 coupled to one another;

FIG. 130A is a perspective view of one embodiment of adjunct segments extending between adjacent surgical staples;

FIG. 130B is a perspective view of an alternative embodiment of adjunct segments extending between adjacent surgical staples;

FIG. 130C is a perspective view of another embodiment of adjunct segments extending between adjacent surgical staples;

FIG. 131 is a perspective view of the adjuncts and surgical staples of FIG. 130A disposed in tissue;

FIG. 132 is a cross-sectional view of the adjuncts and surgical staples of FIG. 131;

FIG. 133 is a perspective view of an alternative embodiment of surgical staples and adjuncts in tissue;

FIG. 134 is a perspective view of another embodiment of surgical staples and adjuncts in tissue;

FIG. 135 is a perspective view of still another embodiment of surgical staples and adjuncts in tissue;

FIG. 136 is a top view of one embodiment of surgical staples and adjuncts extending between adjacent staples;

FIG. 137 is a top view of an alternative embodiment of surgical staples and adjuncts extending between adjacent staples;

FIG. 138A is a side view of the surgical staples and adjuncts of FIG. 137 in a relaxed state;

FIG. 138B is a side view of the surgical staples and adjuncts of FIG. 137 in a tensioned state;

FIG. 139 is a top view of one embodiment of surgical staples and adjuncts extending between adjacent staples;

FIG. 140A is a top view of an alternative embodiment of surgical staples and adjuncts connected to one another by a serpentine carrier;

FIG. 140B is a side view of the surgical staples, adjuncts, and serpentine carrier of FIG. 140A;

FIG. 141A is a side view of one embodiment of an adjunct;

FIG. 141B is a front view of the adjunct of FIG. 141A;

FIG. 141C is a top view of the adjunct of FIG. 141A;

FIG. 141D is a perspective view of the adjunct of FIG. 141A;

FIG. 142A is a side view of an alternative embodiment of an adjunct;

FIG. 142B is a front view of the adjunct of FIG. 142A;

FIG. 142C is a top view of the adjunct of FIG. 142A;

FIG. 142D is a perspective view of the adjunct of FIG. 142A;

FIG. 143 is a side view of one embodiment of a plurality of adjuncts coupled to a backing material;

FIG. 144A is a side view of one embodiment of an adjunct;

FIG. 144B is a front view of the adjunct of FIG. 144A;

FIG. 144C is a top view of the adjunct of FIG. 144A;

FIG. 144D is a perspective view of the adjunct of FIG. 144A;

FIG. 145A is a side view of an alternative embodiment of an adjunct;

FIG. 145B is a front view of the adjunct of FIG. 145A;

FIG. 145C is a top view of the adjunct of FIG. 145A;

FIG. 145D is a perspective view of the adjunct of FIG. 145A;

FIG. 146 is an illustration of one embodiment of an adjunct applicator;

FIG. 147 is a cross-sectional view of the applicator of FIG. 146 applying an adjunct to a surgical stapler anvil;

FIG. 148 is a side view of the applicator of FIG. 146 applying an adjunct to a surgical stapler anvil;

FIG. 149A is an illustration of an alternative embodiment of an adjunct applicator;

FIG. 149B is an illustration of one embodiment of a squeegee that can remove excess adjunct applied to a surgical stapler;

FIG. 149C is a cross-sectional view of a surgical stapler anvil having an adjunct applied thereto;

FIG. 150 is an illustration of one embodiment of a two-part adjunct applicator;

FIG. 151 is an illustration of an alternative embodiment of a two-part adjunct applicator;

FIG. 152A is a cross-sectional view of one embodiment of an applicator nozzle coupled to an adjunct container;

FIG. 152B is a cross-sectional view of the applicator nozzle of FIG. 152A piercing a seal formed on the adjunct container;

FIG. 153 is an illustration of the applicator of FIG. 150 applying an adjunct to a surgical stapler;

FIG. 154 is a side cross-sectional view of one embodiment of an applicator applying an adjunct to a surgical stapler;

FIG. 155 is a front cross-sectional view of one embodiment of an applicator applying an adjunct to a surgical stapler anvil;

FIG. 156 is a front cross-sectional view of one embodiment of an applicator applying a two-part adjunct to a surgical stapler anvil;

FIG. 157 is a cross-sectional view of one embodiment of an adjunct disposed within a staple forming opening of a surgical stapler anvil;

FIG. 158 is a front cross-sectional view of one embodiment of an applicator applying an adjunct to a surgical stapler cartridge;

FIG. 159 is a front cross-sectional view of one embodiment of an applicator applying an adjunct to a surgical stapler cartridge;

FIG. 160 is a cross-sectional view of one embodiment of an adjunct disposed within a surgical stapler cartridge cavity;

FIG. 161 is a cross-sectional view of one embodiment of a surgical staple formed within tissue;

FIG. 162 is an illustration of one embodiment of an adjunct applicator and surgical stapler;

FIG. 163 is a cross-sectional view of one embodiment of a surgical staple formed so as to trap adjunct material;

FIG. 164A is an illustration of one embodiment of a surgical stapler positioned to transect tissue;

FIG. 164B is an illustration the tissue of FIG. 164A transected with staples and adjunct segments coupled thereto;

FIG. 164C is an illustration of the surgical stapler of FIG. 164A having excess staples and adjuncts coupled thereto;

FIG. 165 is an illustration of one embodiment of a non-continuous adjunct for use in forming an anastomosis;

FIG. 166 is an illustration of one embodiment of a surgical stapler cartridge for use with the adjunct of FIG. 165;

FIG. 167 is an illustration of one embodiment of a staple pattern for use with the adjunct of FIG. 165;

FIG. 168 is an illustration of an alternative embodiment of a non-continuous adjunct for use in forming an anastomosis;

FIG. 169 is an illustration of one embodiment of a surgical stapler cartridge for use with the adjunct of FIG. 168;

FIG. 170 is an exploded view of the adjunct of FIG. 168 and surgical stapler cartridge of FIG. 169;

FIG. 171 is an illustration of one embodiment of a staple pattern and the adjunct of FIG. 168;

FIG. 172 is an exploded view of the surgical stapler cartridge of FIG. 169 and the adjunct of FIG. 171;

FIG. 173 is an illustration of the surgical stapler cartridge of FIG. 169 and the adjunct of FIG. 171;

FIG. 174 is a cross-sectional view of one embodiment of an adjunct washer before and during actuation of a surgical stapler;

FIG. 175 is an illustration of one embodiment of a surgical stapler cartridge for use in forming an anastomosis;

FIG. 176 is an illustration of one embodiment of a body lumen transected by a surgical stapler;

FIG. 177A is a cross-sectional view of a staple line including an adjunct with a washer;

FIG. 177B is a cross-sectional view of a circular stapler trocar advancing toward the staple line of FIG. 177A;

FIG. 177C is a cross-sectional view of the circular stapler trocar of FIG. 177B crossing the staple line of FIG. 177A;

FIG. 178 is an illustration of a circular stapler trocar passing through a washer of the non-continuous adjunct of FIG. 175;

FIG. 179 is an illustration of a circular stapler anvil being positioned over the circular stapler trocar of FIG. 177B;

FIG. 180 is an illustration of an alternative embodiment of a circular stapler anvil being positioned over the circular stapler trocard of FIG. 177B;

FIG. 181 is a cross-sectional view of one embodiment of a circular stapler anvil trapping an adjunct washer over a circular stapler trocar;

FIG. 182 is a close cross-sectional view of the circular stapler anvil, adjunct washer, and circular stapler trocar of FIG. 181;

FIG. 183 is a cross-sectional view of the circular stapler trocar of FIG. 181 being withdrawn into a central lumen of the circular stapler;

FIG. 184 is an illustration of one embodiment of forces exerted on a non-continuous adjunct upon withdrawal of a circular stapler trocar coupled thereto;

FIG. 185 is a cross-sectional view of the circular stapler of FIG. 181 being actuated to resect the staple line including the non-continuous adjunct; and FIG. 186 is a cross-sectional view of an anastomosis produced by actuation of the circular stapler of FIG. 181.

Figure 6:
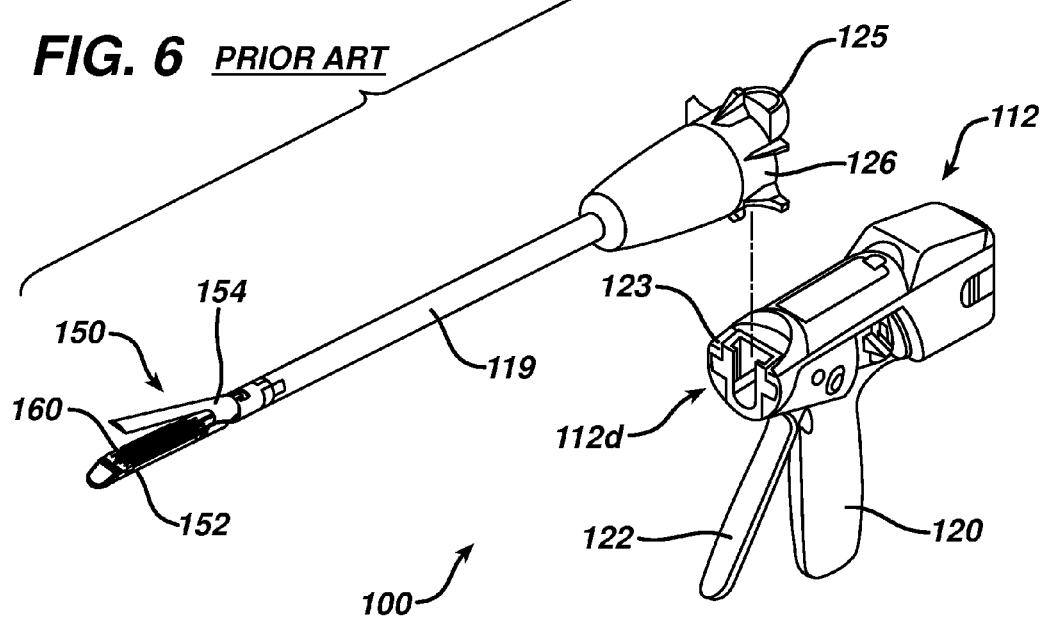
FIG. 6 is a perspective view of another prior art surgical instrument which can be used with one or more adjunct materials.
Figure 187:
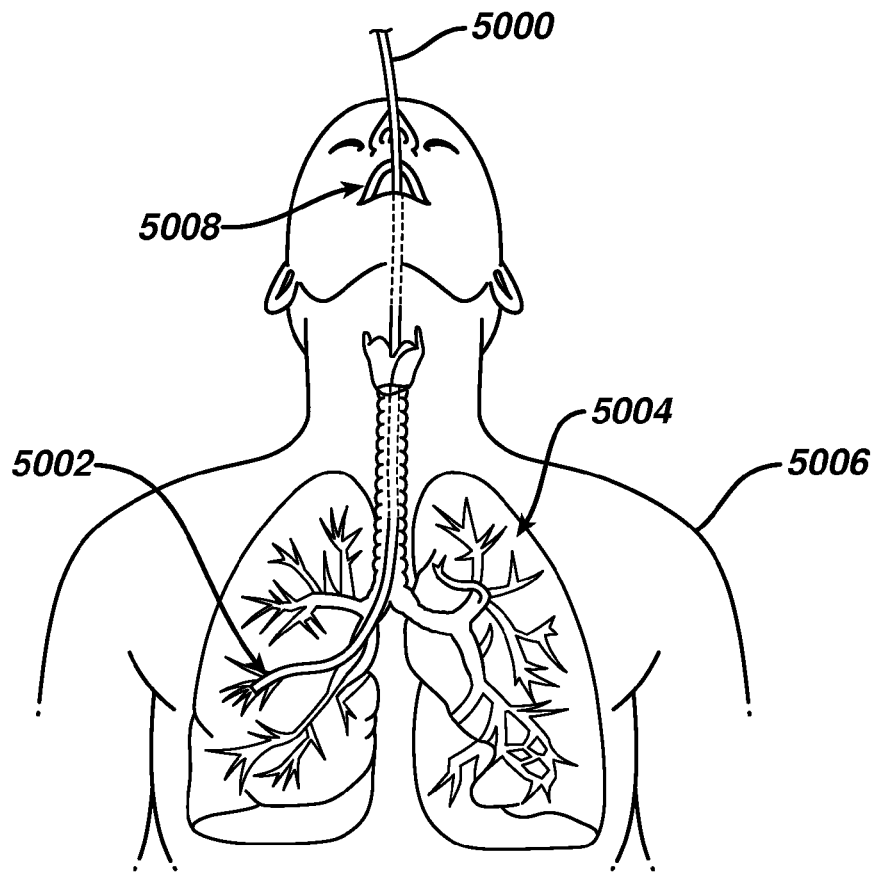
Figure 188:
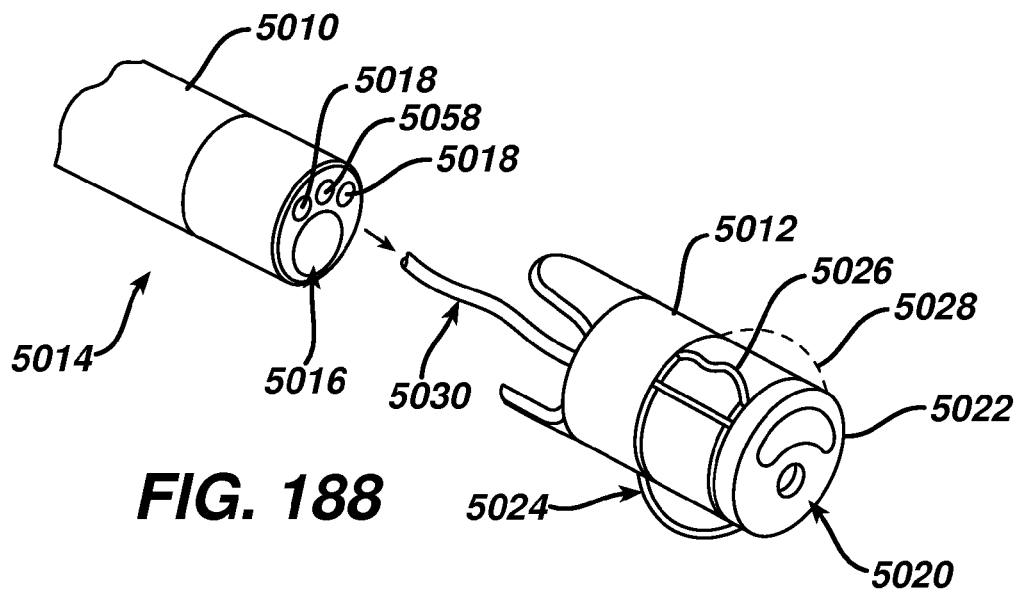
Figure 189:
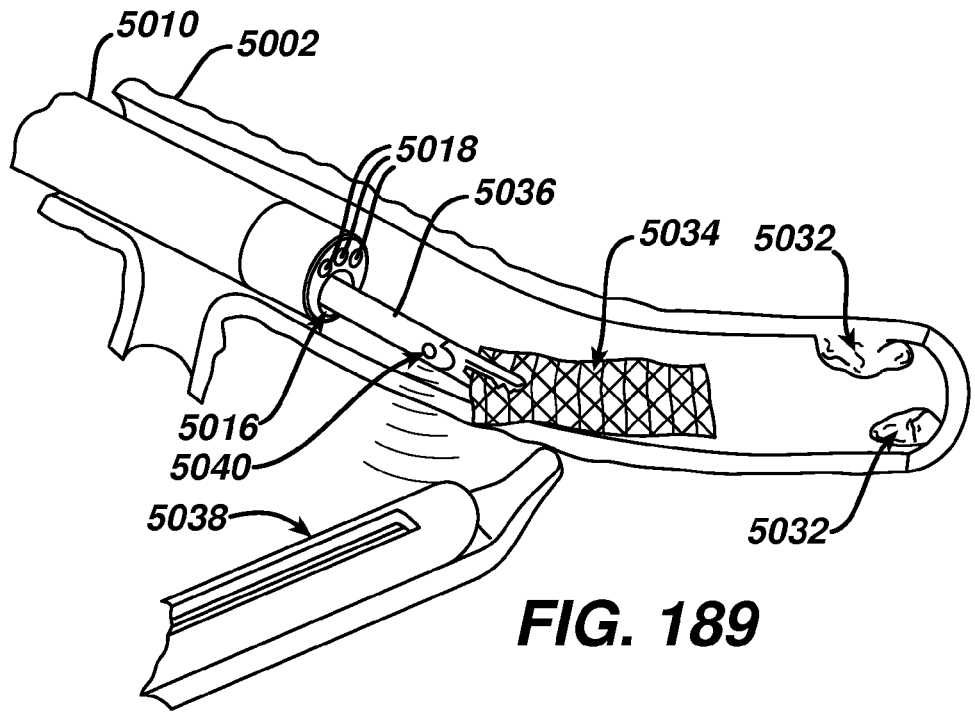
Figure 190:
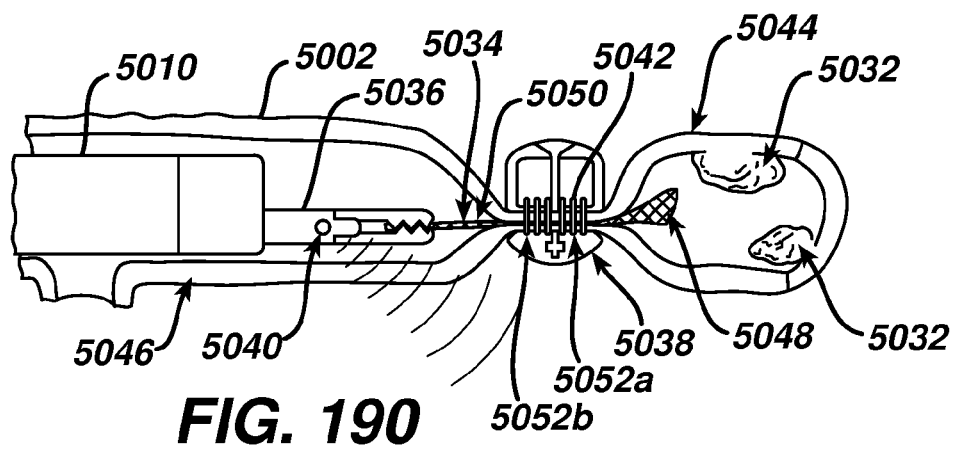
Figure 191:
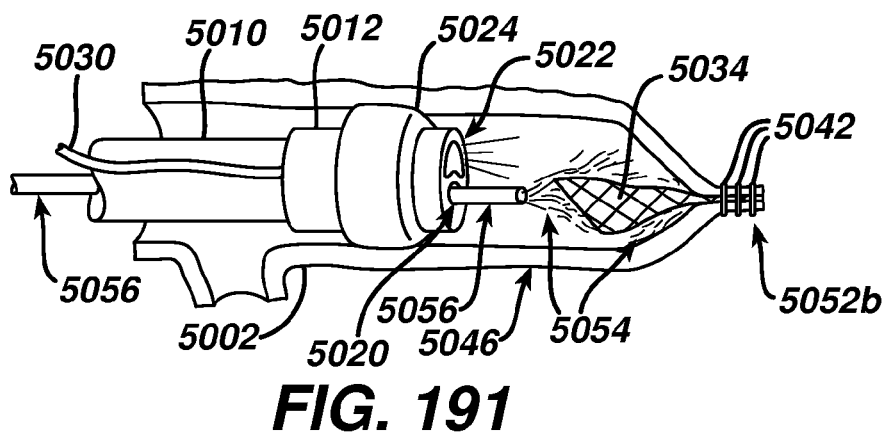
Figure 192:
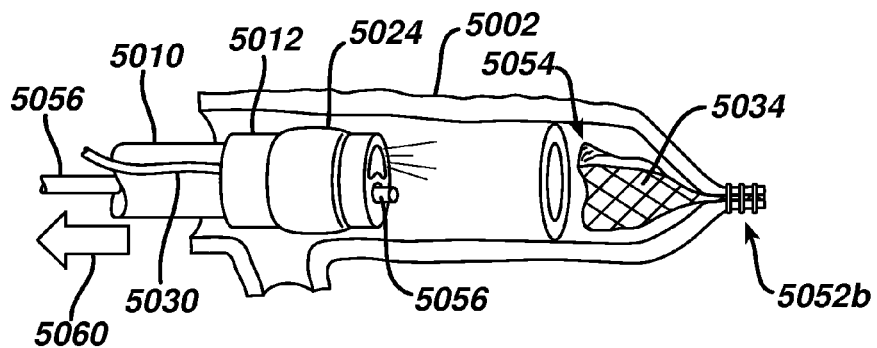
Figure 193:
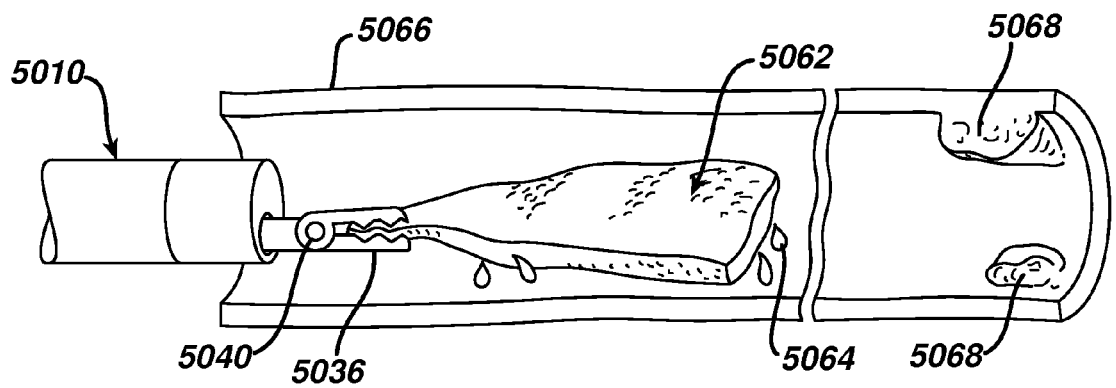
Figure 194:
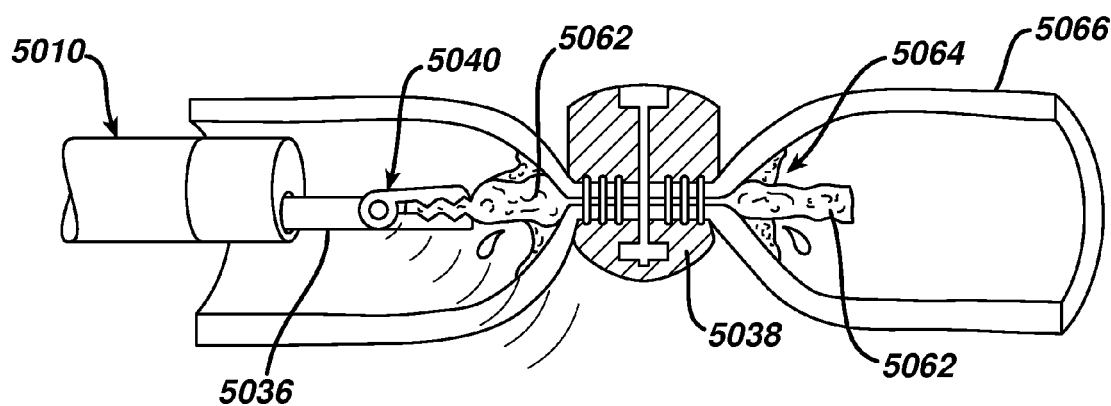
Figure 195:
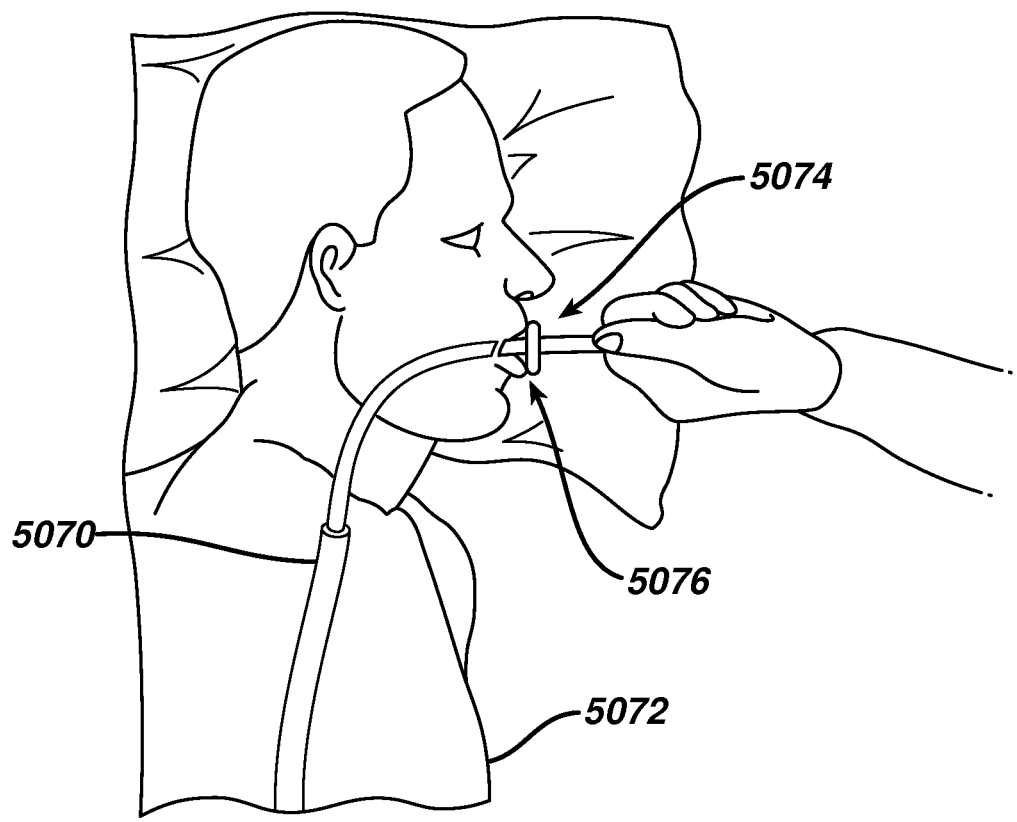
Figure 196:
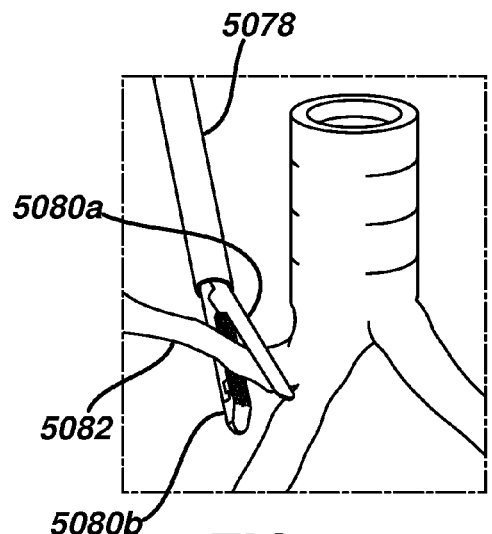
Figure 197:
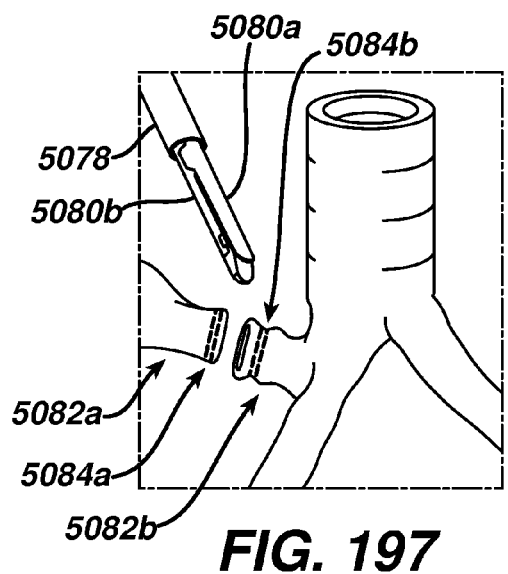
Figure 198:
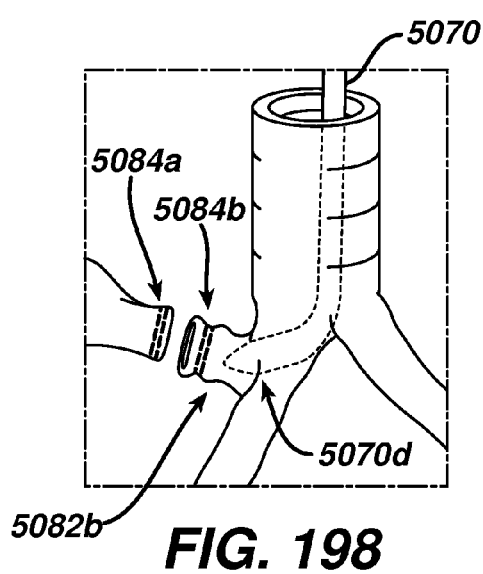
Figure 199:
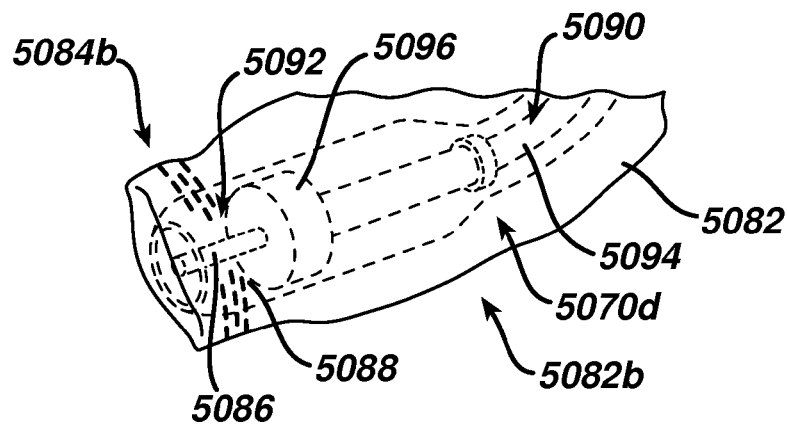
Figure 200:
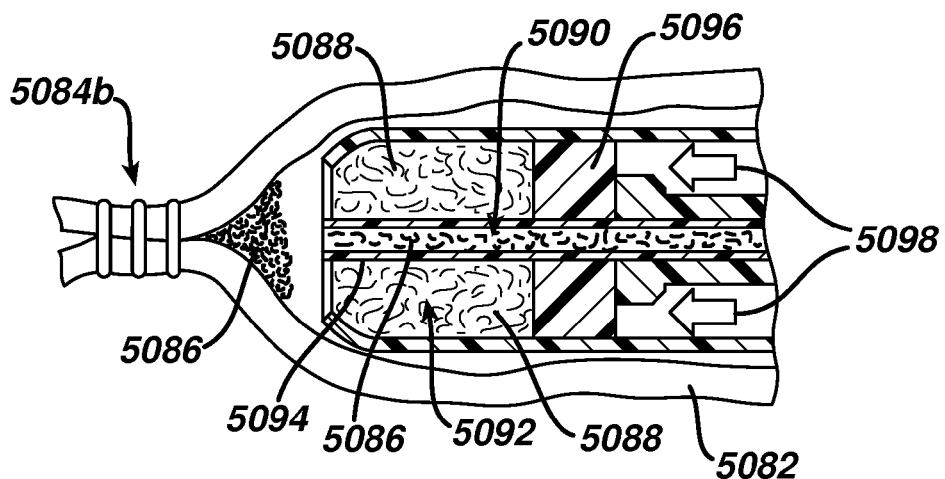
Figure 201:
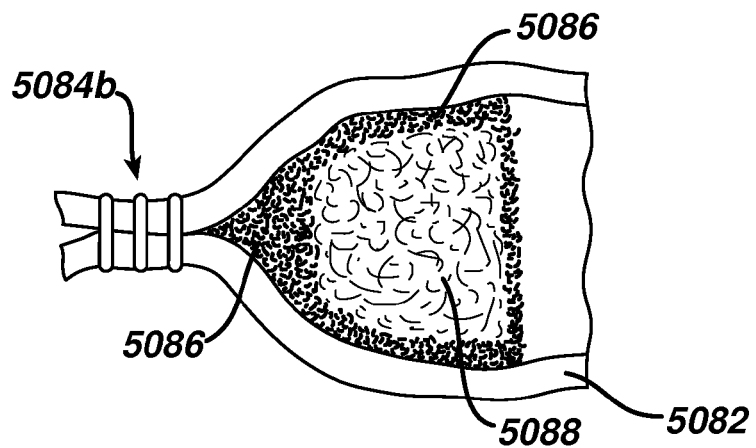

FIG. 187 is a perspective, partially transparent view of a patient with one embodiment of a surgical instrument transorally advanced into a bronchial tube of the patient;

FIG. 188 is an exploded perspective view of a distal end of the surgical instrument of FIG. 187 including a scoping device and an end cap;

FIG. 189 is a perspective, partially cross-sectional view of the scoping device of FIG. 188 advanced into the bronchial tube of FIG. 187, one embodiment of a grasper advanced through a working channel of the scoping device and grasping one embodiment of a reinforcement material, and one embodiment of a stapler having a distal end positioned outside and adjacent to the bronchial tube;

FIG. 190 is a perspective, partially cross-sectional view of the stapler of FIG. 189 stapling the bronchial tube and the reinforcement material;

FIG. 191 is a perspective, partially cross-sectional view of the scoping device of FIG. 188, with the end cap of FIG. 188 attached thereto, within a portion of the bronchial tube of FIG. 190 stapled and cut by the stapler, and one embodiment of an applicator advanced through the working channel of the scoping device and a working port of the end cap, the applicator applying one embodiment of a sealant, the sealant being in a first state;

FIG. 192 is a perspective, partially cross-sectional view of the scoping device and the end cap of FIG. 6 being removed from the bronchial tube with the applied sealant being in a hardened state;

FIG. 193 is a perspective, partially cross-sectional view of the scoping device of FIG. 188 disposed within a bronchial tube and the grasper of FIG. 189 advanced through the working channel of the scoping device and grasping another embodiment of a reinforcement material coupled to another embodiment of a sealant;

FIG. 194 is a perspective, partially cross-sectional view of the stapler of FIG. 189 stapling the bronchial tube, the reinforcement material, and the sealant of FIG. 193;

FIG. 195 is a perspective, partially transparent view of another patient with another embodiment of a surgical instrument transorally advanced into a bronchial tube of the patient;

FIG. 196 is a perspective view of another embodiment of a stapler with jaws thereof positioned on either side of the bronchial tube of FIG. 195;

FIG. 197 is a perspective view of the bronchial tube of FIG. 196 after being stapled and cut by the stapler;

FIG. 198 is a perspective, partially transparent view of the instrument of FIG. 195 advanced into the stapled and cut bronchial tube of FIG. 197 with a distal end of the instrument positioned adjacent a stapled and cut end of the bronchial tube;

FIG. 199 is another perspective view of the distal end of the instrument of FIG. 198 positioned adjacent the stapled and cut end of the bronchial tube;

FIG. 200 is a side, cross-sectional view of the stapled and cut end of the bronchial tube of FIG. 199 having another embodiment of a sealant disposed therein, the sealant having been advanced into the bronchial tube from the instrument; and FIG. 201 is a side, cross-sectional view of the and cut end of the bronchial tube of FIG. 200 having another embodiment of a reinforcement material and additional sealant disposed therein, the reinforcement material and the additional sealant having been advanced into the bronchial tube from the instrument.

Figure 202A:
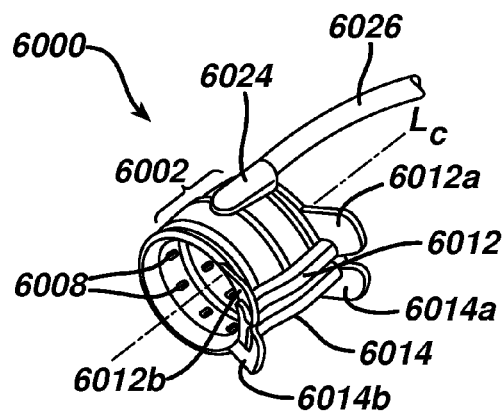
Figure 202B:
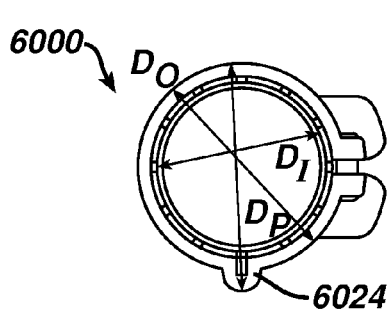
Figure 202C:
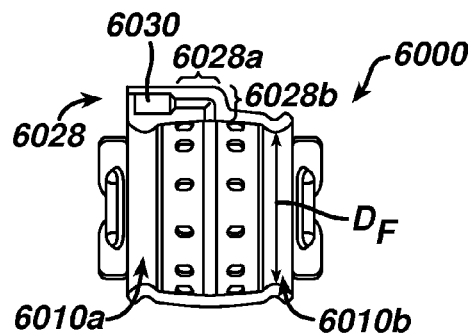
Figure 203:
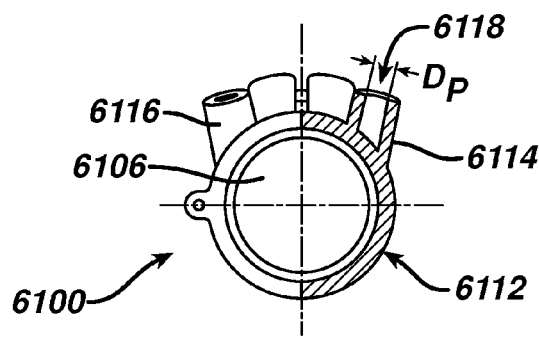
Figure 204A:
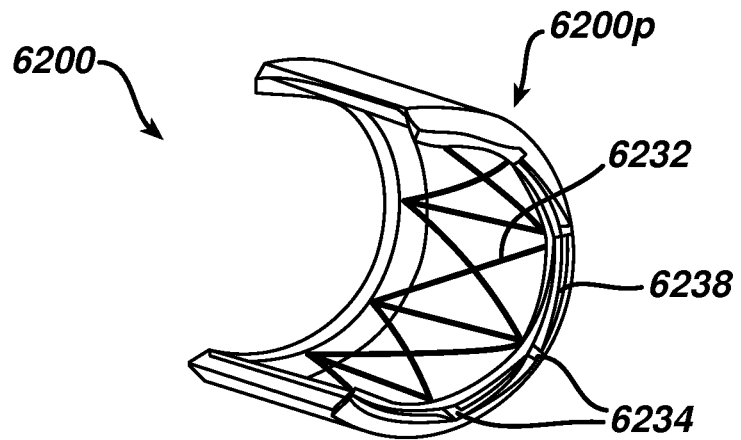
Figure 204B:
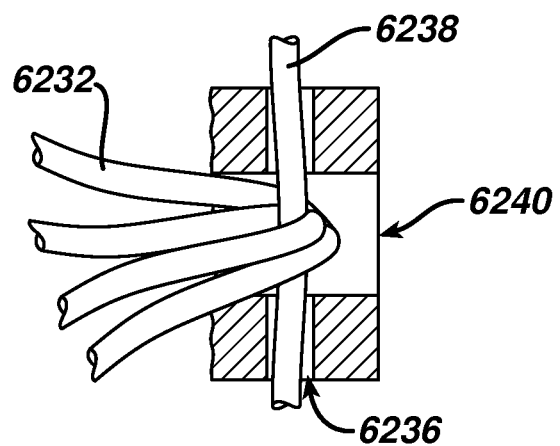
Figure 205A:
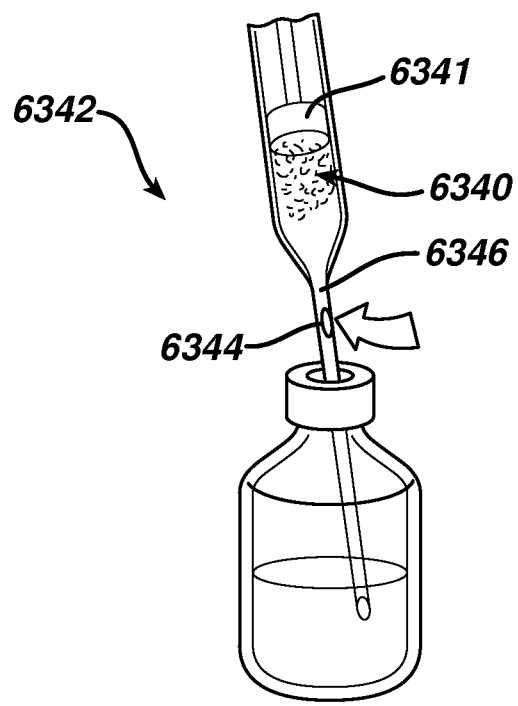
Figure 205B:
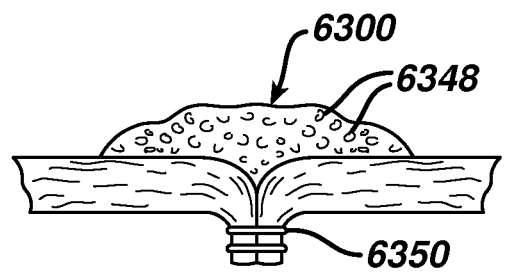
Figure 206A:
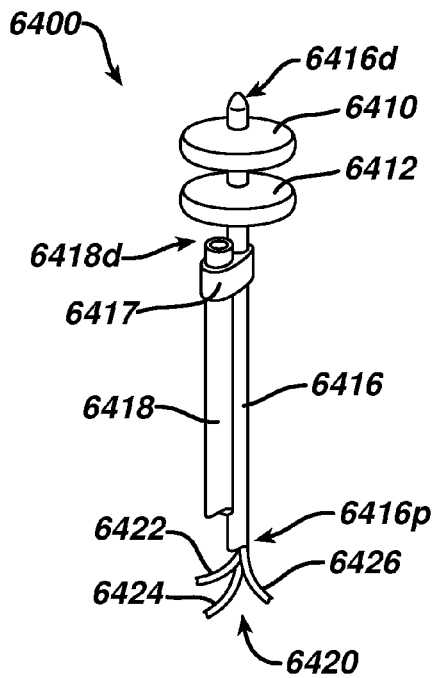
Figure 206B:
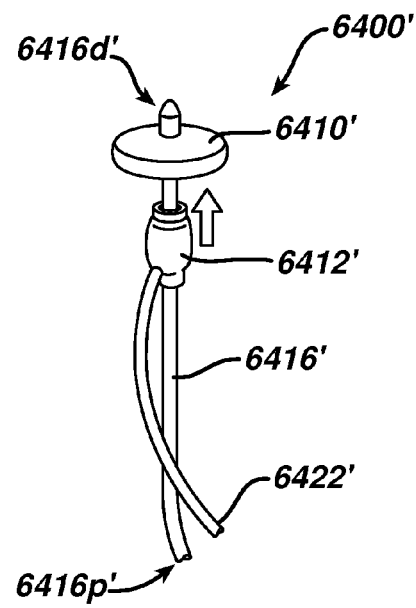
Figure 206C:
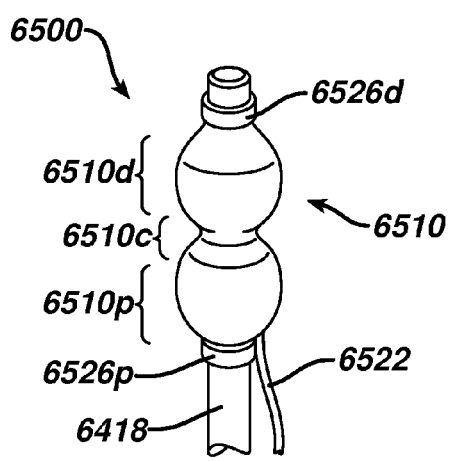
Figure 206D:
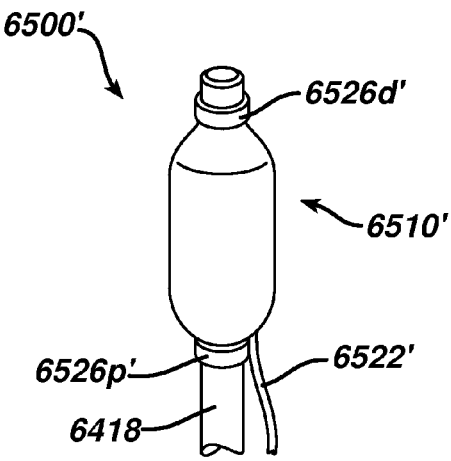
Figure 207:
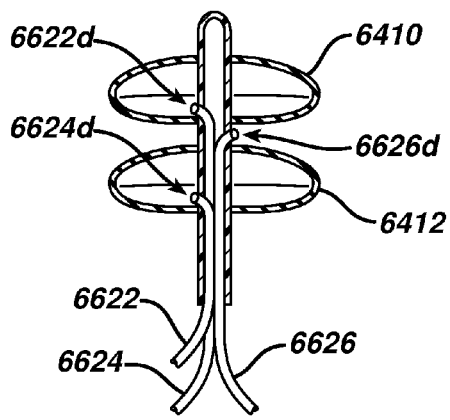
Figures 208A, 208B, 208C:
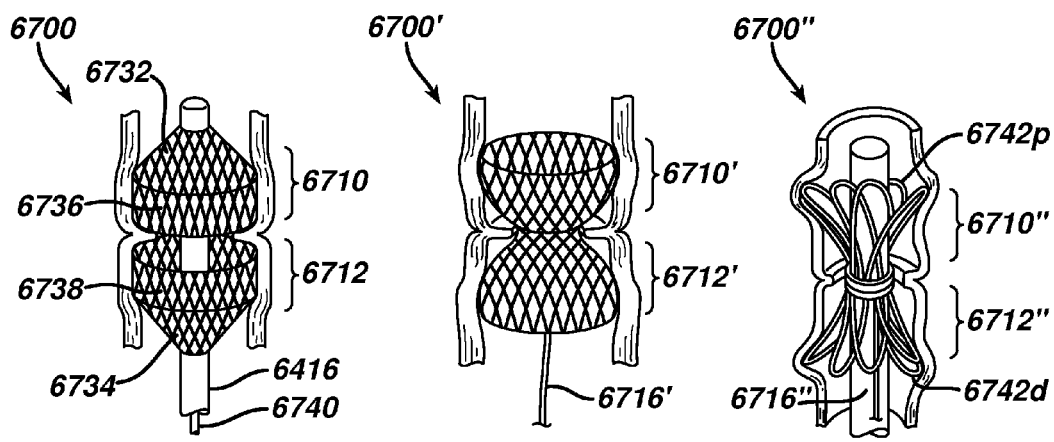
Figure 209A:
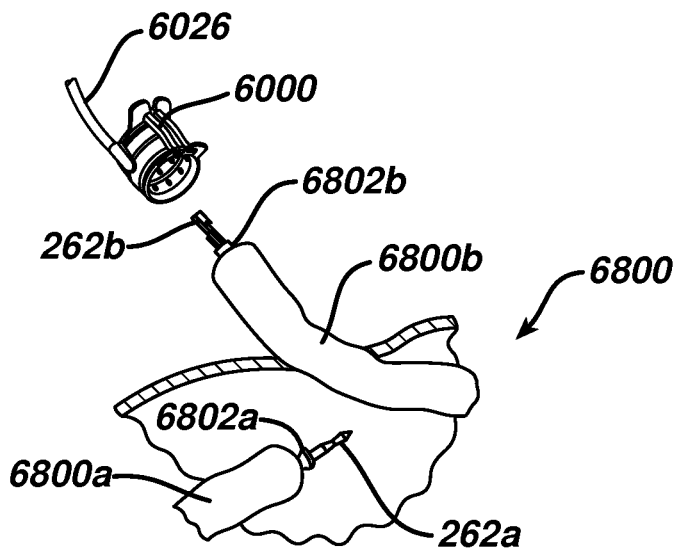
Figure 209B:
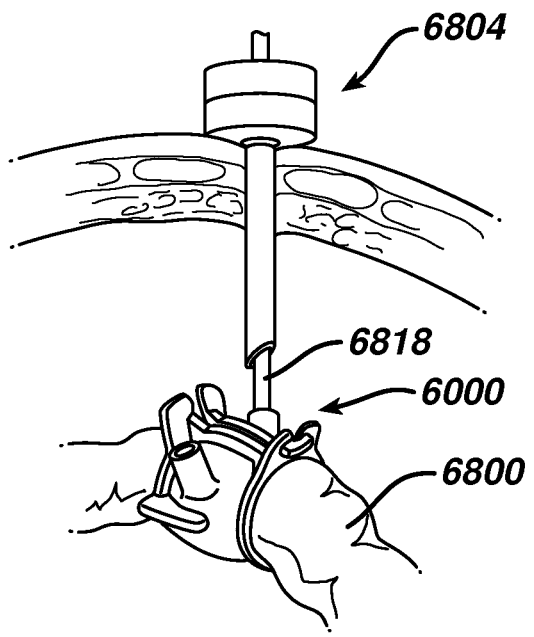
Figure 209C:
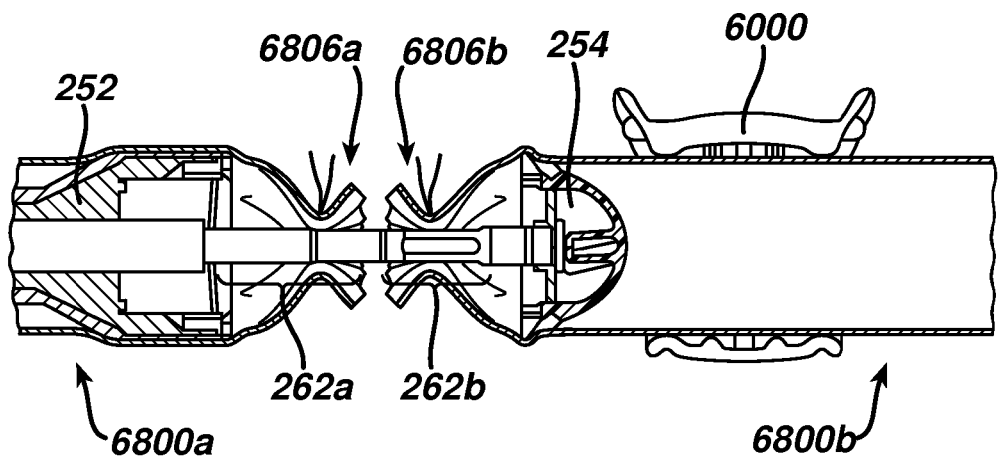
Figure 209D:
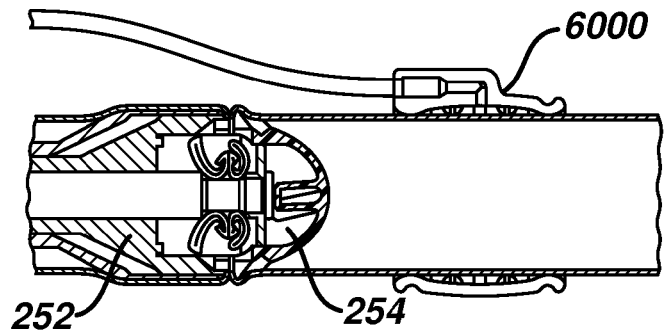
Figure 209E:
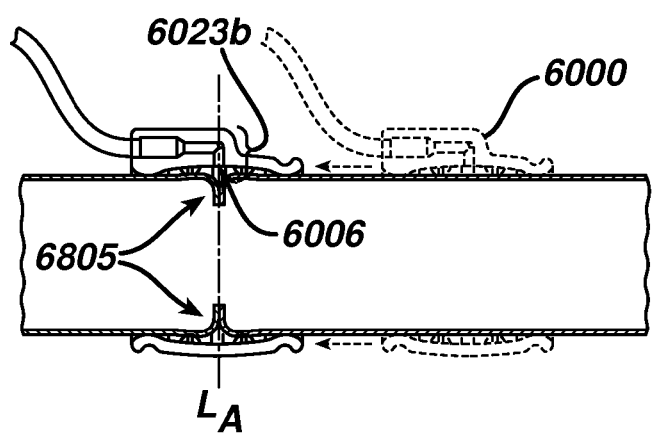
Figure 209F:
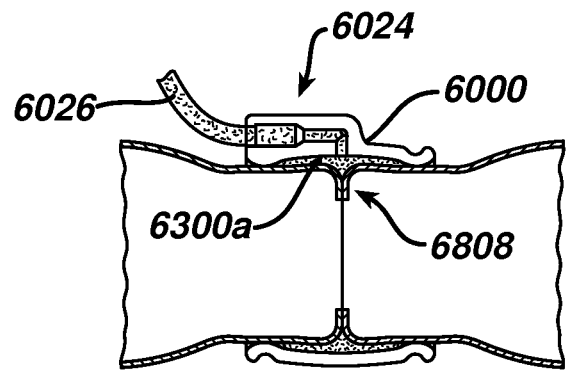
Figure 209G:
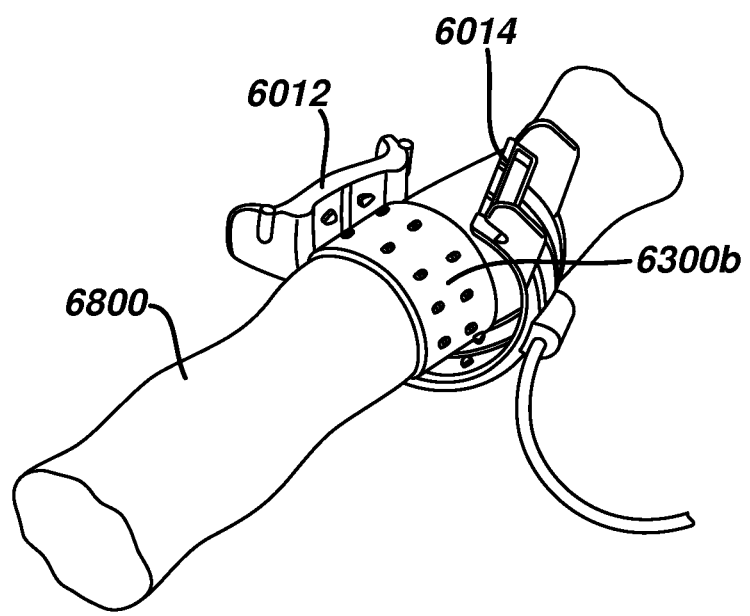
Figure 211A:
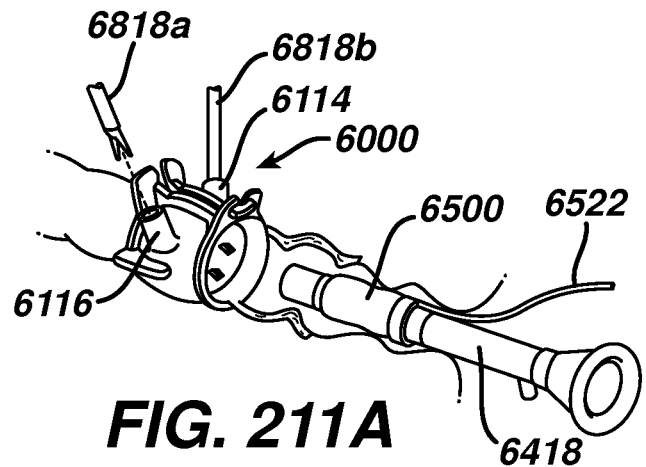
Figure 211B:
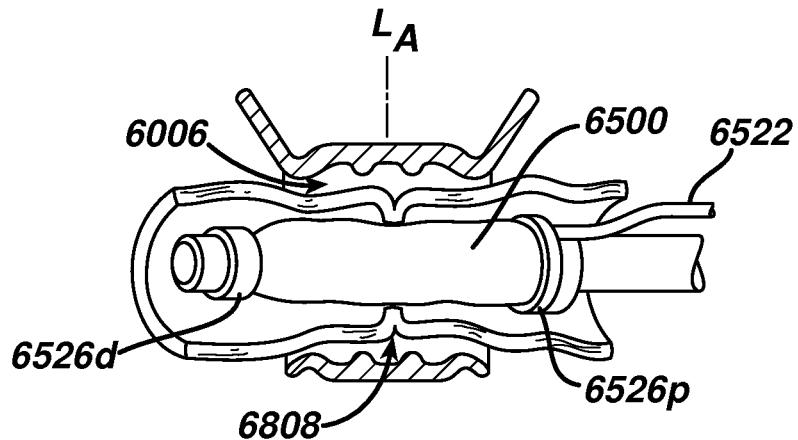
Figure 211C:
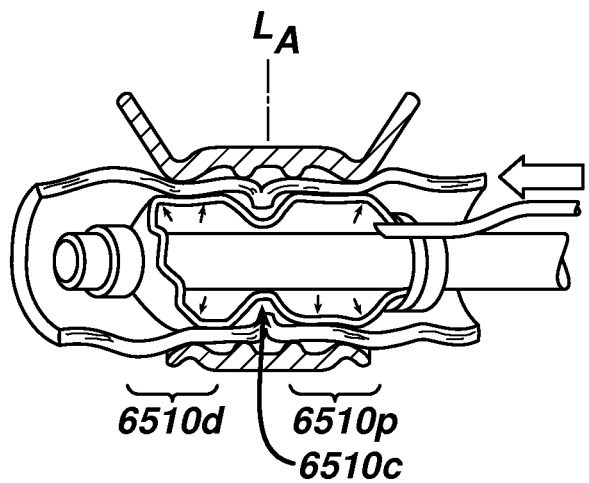
Figure 214A:
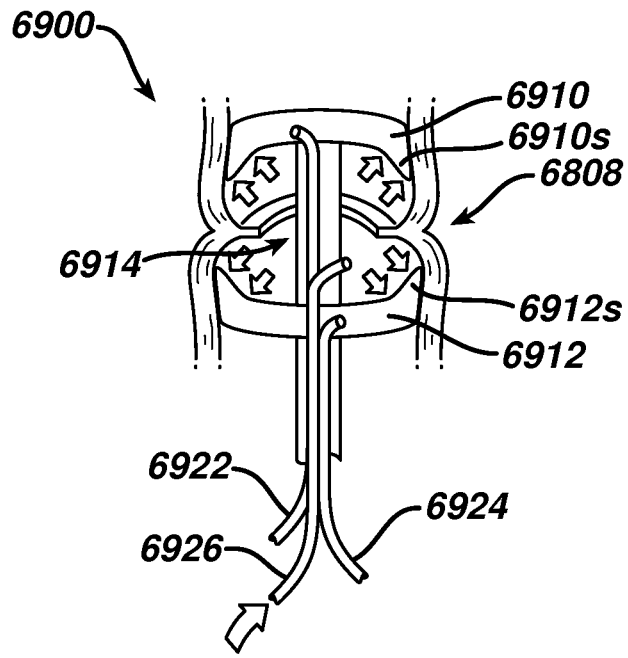
Figure 214B:
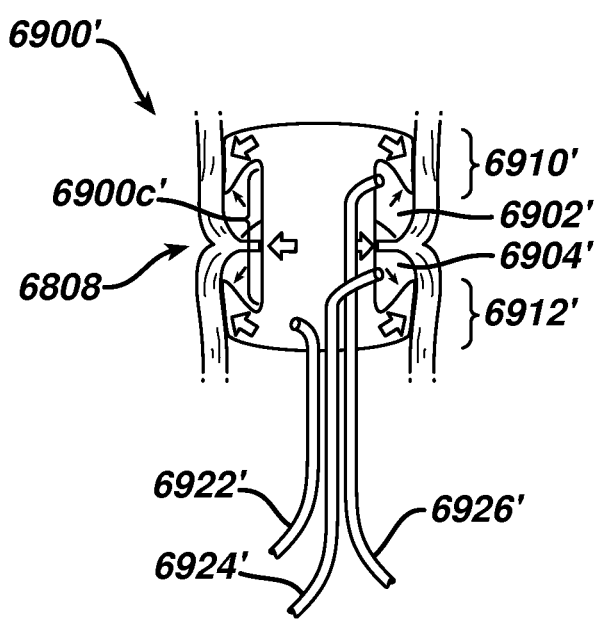

FIG. 202A is a perspective view of a sealing cuff, according to one exemplary embodiment;

FIG. 202B is a side view of the sealing cuff of FIG. 202A;

FIG. 202C is a cross-sectional view of the sealing cuff of FIG. 202A;

FIG. 203 is another embodiment of a sealing cuff having one or more extension ports that facilitate positioning the cuff around a body lumen;

FIG. 204A is a partial, cross-sectional view of a sealing cuff having suture woven across an inner surface thereof for contacting a sealant;

FIG. 204B is partial, side view of the sealing cuff of FIG. 204A showing a passageway formed in a wall of the cuff and having suture extending therethrough;

FIG. 205A is an exemplary embodiment of a foamed sealant;

FIG. 205B is a side view of the foamed sealant of FIG. 205A penetrating into an anastomosis;

FIG. 206A is a side view of an expandable device including first and second expandable members;

FIG. 206B is a side view of another embodiment of an expandable device having first and second expandable members;

FIG. 206C is a side view of an expandable device having a single expandable member;

FIG. 206D is a side view of another embodiment of an expandable device having a single expandable member;

FIG. 207 is a side view of an expandable device having a lumen for delivering fluid to a space between first and second expandable members;

FIG. 208A is a side view of one embodiment of a stent having first and second expandable portions;

FIG. 208B is a side view of another embodiment of a stent having first and second expandable portions;

FIG. 208C is a side view of yet another embodiment of a stent having first and second expandable portions;

FIG. 209A is a perspective view of the sealing cuff of FIG. 202A being positioned over a first section of a tubular body organ;

FIG. 209B is a perspective view of a trocar having a tool extending therethrough and into a positioning port formed on the sealing cuff;

FIG. 209C is a cross-sectional view of the organ of FIG. 209A showing an anvil and cartridge assembly of a surgical stapler, the anvil positioned inside of the first section of the tubular organ and the cartridge assembly positioned inside of the second section of the tubular organ;

FIG. 209D is a cross-sectional view of the stapler and tubular organ of FIG. 209A, the anvil moved toward the cartridge assembly and deploying staples to form the anastomosis as the sealing cuff is positioned away from the anastomosis;

FIG. 209E is a cross-sectional view of the sealing cuff of FIG. 209A illustrating the cuff's direction of movement along the tubular organ and toward the anastomosis;

FIG. 209F is a cross-sectional view of the sealing cuff of FIG. 209A showing sealant being delivered to the sealing cuff and into the anastomosis;

FIG. 209G is a perspective view of the sealing cuff of FIG. 209A being removed from the tubular organ after the sealant has cured around the anastomosis;

FIG. 210A is a perspective, semi-transparent view of an anvil of a circular stapler positioned inside of a tubular organ;

FIG. 210B is a side, semi-transparent view of the anvil and tubular organ of FIG. 210A, the anvil having first and second expandable members coupled thereto;

FIG. 210C is a side, semi-transparent view of the tubular organ of FIG. 10B formed into an anastomosis and having the first and second expandable members coupled to a scope;

FIG. 210D is a side, semi-transparent view of the first expandable member positioned proximal to the anastomosis, in an expanded position;

FIG. 210E is a side, semi-transparent view of the first and second expandable members disposed on opposite sides of the anastomosis, in their expanded positions;

FIG. 211A is a perspective view of an expandable member disposed on a scope, the scope extending through an anus and moving toward the sealing cuff;

FIG. 211B is a partial cross-sectional view of the tubular organ having the scope of FIG. 211A extending therethrough, the expandable member being in a first, compressed position adjacent to the anastomosis and to the sealing cuff;

FIG. 211C is a partial cross-sectional view of the tubular organ of FIG. 211B showing the expandable member in a second, expanded position;

FIG. 212A is a partial cross-sectional view of an anastomosis of a tubular organ, along with a scope having a tether coupled thereto that is attached to a first expandable member;

FIG. 212B is a partial cross-sectional view of the first expandable member being positioned proximal to the anastomosis as a terminal end of the tether is positioned outside of the patient's body;

FIG. 212C is a partial cross-sectional view of the first expandable member being inflated to an expanded position and the second expandable member being positioned over the tether;

FIG. 212D is a partial cross-sectional view of the second expandable member moving toward the anastomosis in a compressed position;

FIG. 212E is a partial cross-sectional view of showing the second expandable member being inflated to an expanded position through its inflation lumen;

FIG. 213 is a cross-sectional view of a first and second expandable members forming a seal inside of the tubular organ and gas being delivered to the sealed space between the expandable members so as to test leakage from the anastomosis;

FIG. 214A is a cross-sectional view of another embodiment of first and second expandable members with gas delivered to a space therebetween so as to test leakage from the anastomosis; and FIG. 214B is a cross-sectional view of an embodiment of an expandable member having a central portion configured to support the anastomosis as fluid is delivered to the space adjacent to the anastomosis so as to test leakage therefrom.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of such devices and methods is defined solely by the claims. The features illustrated or described in connection with one exemplary embodiment may be combined with the features of other embodiments. Such modifications and variations are intended to be included within the scope of the devices and methods described herein. Further, in the present disclosure, like-numbered components of the various embodiments generally have similar features when those components are of a similar nature and/or serve a similar purpose.

Reference throughout the specification to "various embodiments," "some embodiments," "one embodiment," or "an embodiment," or the like, means that a particular feature, structure, or characteristic described in connection with the embodiment is included in at least one embodiment. Thus, appearances of the phrases "in various embodiments," "in some embodiments," "in one embodiment," or "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features structures, or characteristics of one or more other embodiments without limitation. Such modifications and variations are intended to be included within the scope of the methods, apparatus, devices, and systems described herein.

Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

The terms "proximal" and "distal" are used herein with reference to a clinician manipulating the handle portion of the surgical instrument. The term "proximal" referring to the portion closest to the clinician and the term "distal" referring to the portion located away from the clinician. It will be further appreciated that, for convenience and clarity, spatial terms such as "vertical," "horizontal," "up," and "down" may be used herein with respect to the drawings. However, surgical instruments are used in many orientations and positions, and these terms are not intended to be limiting and/or absolute.

It can be desirable to use one or more biologic materials and/or synthetic materials, collectively referred to herein as "adjunct materials," in conjunction with surgical instruments to help improve surgical procedures. These biologic materials may be derived from human and/or animal sources. A person skilled in the art may refer to these types of materials as buttress materials as well as adjunct materials.

Various exemplary devices and methods are provided for performing surgical procedures. In some embodiments, the devices and methods are provided for open surgical procedures, and in other embodiments, the devices and methods are provided for laparoscopic, endoscopic, and other minimally invasive surgical procedures. The devices may be fired directly by a human user or remotely under the direct control of a robot or similar manipulation tool. However, a person skilled in the art will appreciate that the various methods and devices disclosed herein can be used in numerous surgical procedures and applications. Those skilled in the art will further appreciate that the various instruments disclosed herein can be inserted into a body in any way, such as through a natural orifice, through an incision or puncture hole formed in tissue, or through an access device, such as a trocar cannula. For example, the working portions or end effector portions of the instruments can be inserted directly into a patient's body or can be inserted through an access device that has a working channel through which the end effector and elongated shaft of a surgical instrument can be advanced.

End effectors of the surgical instruments as described herein can be configured to deliver one or more synthetic materials and/or biologic materials, collectively referred to herein as "adjunct materials," to a surgical site to help improve surgical procedures. These biologic materials may be derived from human and/or animal sources. While a variety of different end effectors can benefit from the use of adjunct materials, in some exemplary embodiments the end effector can be a surgical stapler. When used in conjunction with a surgical stapler, the adjunct material(s) can be disposed between and/or on jaws of the stapler, incorporated into a staple cartridge disposed in the jaws, or otherwise placed in proximity to the staples. When staples are deployed, the adjunct material(s) can remain at the treatment site with the staples, in turn providing a number of benefits. In some instances, the adjunct material(s) can be used to help seal holes formed by staples as they are implanted into tissue, blood vessels, and various other objects or body parts, and/or can be used to provide tissue reinforcement at the treatment site. Tissue reinforcement may be needed to keep the staples from tearing through the tissue if the tissue is diseased, is healing from another treatment such as irradiation, medications such as chemotherapy, or other tissue property altering situation. In some instances, the adjunct material(s) may minimize tissue movement in and around the staple puncture sites that can occur from tissue deformation that occurs after stapling (e.g., lung inflation, gastrointestinal tract distension, etc.). It will be recognized by one skilled in the art that a staple puncture site may serve as a stress concentration and that the size of the hole created by the staple will grow when the tissue around it is placed under tension. Restricting the tissues movement around these puncture sites can minimize the size the holes may grow to under tension. In some instances, the adjunct material(s) can be configured to wick or absorb beneficial fluids, e.g., sealants, blood, glues, that further promote healing, and in some instances, the adjunct material(s) can be configured to degrade to form a gel, e.g., a sealant, that further promotes healing. In some instances, the adjunct may carry materials that when placed into a wet environment (e.g., blood, water, saline, or other bodily fluids) form a sealant to create a seal (e.g., human or animal derived fibrinogen and thrombin can be lyophilized into a powder form that when mixed with water creates a sealant). Still further, the material(s) can help reduce inflammation, promote cell growth, and otherwise improve healing.

Figure 1:
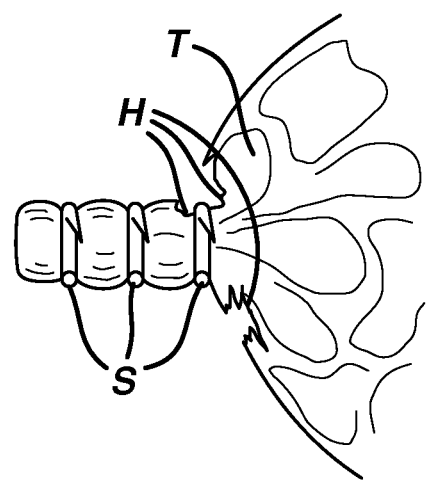
FIG. 1 is a side view of damaged stapled tissue.
Figure 2:
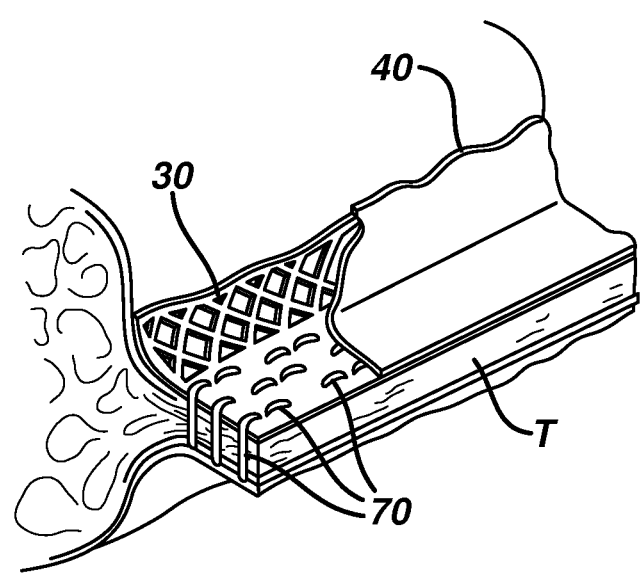
FIG. 2 is a perspective view of one embodiment of an adjunct material as described herein that is fixed to stapled tissue.

FIG. 2 illustrates one embodiment of an adjunct material that includes a porous buttress 30 that can be fixed to a tissue T to be treated by a surgical stapler and that remains at the treatment site with staples 70. The buttress 30 can be made from one or more absorbent materials and can be stamped, pressed, cut, molded, woven, melted, blown, comprised from composite structures and/or methods or otherwise shaped to facilitate absorption, reinforcement, delivery and/or retention of beneficial fluids such as sealants, glues, blood, etc. The absorption and/or retention of beneficial fluids, for example a fibrin sealant 40, at the treatment site can further help to prevent leaks and to reinforce the buttress 30.

In use, the adjunct material can come pre-loaded onto the device and/or the staple cartridge, while in other instances the adjunct material can be packaged separately. In instances in which the adjunct material comes pre-loaded onto the device and/or the staple cartridge, the stapling procedure can be carried out as known to those skilled in the art. For example, in some instances the firing of the device can be enough to disassociate the adjunct material from the device and/or the staple cartridge, thereby requiring no further action by the clinician. In other instances any remaining connection or retention member associating the adjunct material with the device and/or the staple cartridge can be removed prior to removing the instrument from the surgical site, thereby leaving the adjunct material at the surgical site. In instances in which the adjunct material is packaged separately, the material can be releasably coupled to at least one of a component of the end effector and the staple cartridge prior to firing the device. The adjunct material may be refrigerated, and thus removed from the refrigerator and the related packaging, and then coupled to the device using a connection or retention member as described herein or otherwise known to those skilled in the art. The stapling procedure can then be carried out as known to those skilled in the art, and if necessary, the adjunct material can be disassociated with the device as described above.

A person skilled in the art will recognize a variety of other ways by which the adjunct material can be temporarily retained with respect to the end effector. In various embodiments a connection or retention member can be configured to be released from an end effector and deployed along with a piece of adjunct material. In at least one embodiment, head portions of retention members can be configured to be separated from body portions of retention members such that the head portions can be deployed with the adjunct material while the body portions remain attached to the end effector. In other various embodiments, the entirety of the retention members can remain engaged with the end effector when the adjunct material is detached from the end effector.

Adjunct materials described herein may be used in any surgery where a surgical stapler or other instrument creating tissue punctures is utilized. In some embodiments, adjunct materials described herein may be used for sealing staple punctures created when a surgical stapler is used in lung surgery. When surgery is performed on a lung (e.g., lobectomy, segmentectomy, wedge resection, lung volume reduction surgery, etc.), the lung is typically collapsed, and the required procedure, including application of the stapler to tissue to be removed, is then performed on the collapsed lung. After the procedure is completed, the collapsed lung is re-inflated. The reinflation of the lung stretches the lung parenchyma, which may result in increased stress at a junction between the stapled tissue and surrounding tissue that was not punctured. Furthermore, airtight sealing is required for the staple punctures of the lung. Such airtight sealing may be difficult to achieve due to lung tissue movement. While leaks around staple punctures typically heal within approximately five days, in some cases, staple punctures may persist for longer periods of time, such as, for example, up to six months.

Accordingly, some embodiments provide adjunct material that may be used to seal staple punctures created by a surgical stapler used to secure lung tissue. However, it should be appreciated that the adjunct materials can also be used to seal punctures created by surgical staplers used to secure any other type of tissue, such as, for example, blood vessels, intestinal, stomach and esophageal tissue.

Various exemplary sealants and methods of sealing a tubular body organ are provided herein. In general, the sealants can facilitate sealing around a stapled body lumen, such as around a colon or around an intestinal anastomosis. A sealant can be formulated in various ways and can have various properties, but is generally provided in a first, liquid state and then cures to a second, solidified state after a predetermined amount of time. For example, the sealant can be introduced to the tubular body organ and can help reinforce a seal at the staple line of an anastomosis. When the sealant is in its liquid state, the sealant can seep into the staple line and can solidify therein, thereby facilitating a complete sealing of the tubular body organ at the staple line. The sealant can facilitate short term sealing of the tubular body organ and can be formulated so that it is absorbed into the body after the tubular body organ has healed at the anastomosis. In certain aspects, a sealing cuff is provided that can act as a mold or form for holding the sealant at the desired location, e.g. adjacent to a staple line, when the sealant is in the first, liquid state. One or more expandable members can be configured to expand the tubular body organ to further maintain contact between the sealant and the sealing cuff. In this way, the sealing cuff can be configured to hold the sealant at the desired location so that the sealant is more likely to completely seal the staple line and remain sealed as liquid and solid material passes through the tubular body organ during normal bodily functions.

The method can be performed in various ways. For example, at least one expandable member can be inserted into the tubular organ within an anastomosis. The expandable member can be inserted in a first, compressed position and can be moved to a second, expanded position to increase a diameter of a portion of the tubular organ. In general, one or more expandable members can be positioned adjacent to the staple line so that the tissue surrounding the staple line can be expanded. A sealing cuff can be positioned around an outer surface of the tubular organ and around the staple line. When the expandable member is expanded, the tissue can move toward the sealing cuff. The sealant can be predisposed within or introduced into the sealing cuff to reinforce a seal at the staple line of the anastomosis. A method for conducting a leak test of an anastomosis is also provided and can be performed before or after a sealant is applied thereto allow a surgeon to visually identify whether there are openings between the tissue and the staple line during expansion and contraction of the organ. Liquid or gas can be delivered into the organ using various techniques and visualization techniques can be used to allow a user can visually identify whether the liquid/gas is leaking out of the organ through the staple line. This can help a user determine whether sealant should be applied to reinforce the tissue during the surgical procedure, or if sealant has already been applied, whether additional sealant or other sealing techniques should be used to reinforce the seal. As described further below, the sealing cuff and expandable member(s) can be used in conjunction with the leak test, such as to reinforce the tissue after a user identifies leakage through the anastomosis.

Surgical Stapling Instrument

Figure 3:
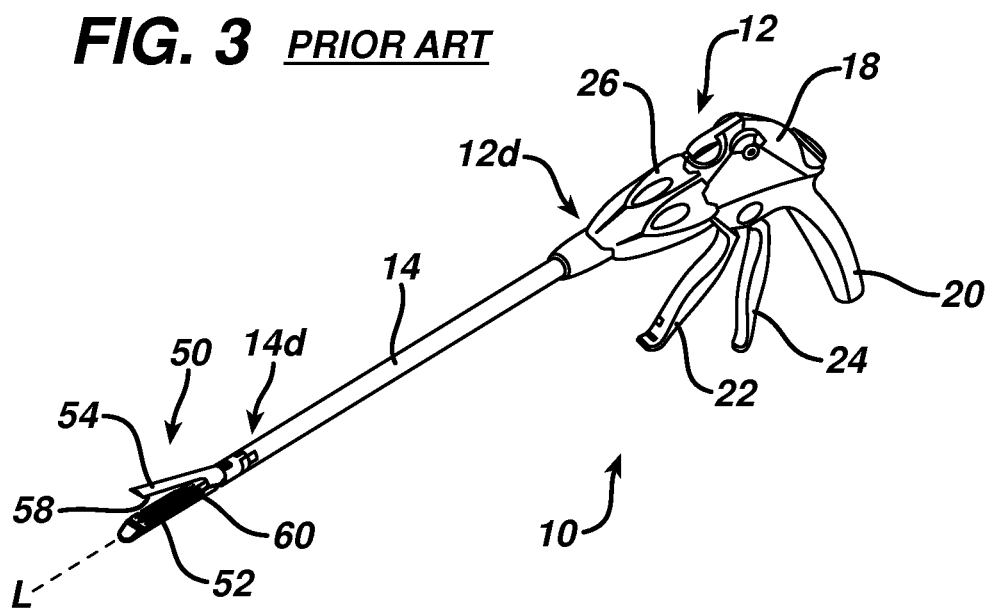
FIG. 3 is a perspective view of a prior art surgical instrument which can be used with one or more adjunct materials.

While a variety of surgical instruments can be used in conjunction with the adjunct materials disclosed herein, FIG. 3 illustrates one, non-limiting exemplary embodiment of a surgical stapler 10 suitable for use with one or more adjunct materials. The instrument 10 generally includes a handle assembly 12, a shaft 14 extending distally from a distal end 12d of the handle assembly 12, and an end effector 50 at a distal end 14d of the shaft 14. Because the illustrated embodiment is a surgical stapler, the end effector 50 has jaws 52, 54, although other types of end effectors can be used with the shaft 14, handle assembly 12, and components associated with the same. The surgical stapler 10 includes opposed lower and upper jaws 52, 54 with the lower jaw 52 including a staple channel 56 (FIG. 4) configured to support a staple cartridge 60, and the upper jaw 54 having an inner surface 58 that faces the lower jaw 52 and that is configured to operate as an anvil to help deploy staples 70 of the staple cartridge 60. The jaws 52, 54 are configured to move relative to one another to clamp tissue or other objects disposed therebetween, and components of a firing system can be configured to pass through at least a portion of the end effector 50 to eject the staples into the clamped tissue. In various embodiments a knife blade 81 can be associated with the firing system to cut tissue during the stapling procedure. At least one of the opposed lower and upper jaws 52, 54 will be moveable relative to the other lower and upper jaws 52, 54. At least one of the opposed lower and upper jaws 52, 54 may be fixed or otherwise immovable. In some embodiments, both of the opposed lower and upper jaws 52, 54 will be movable.

Operation of the end effector 50 can begin with input from a clinician at the handle assembly 12. The handle assembly 12 can have many different configurations designed to manipulate and operate the end effector 50 associated therewith. In the illustrated embodiment, the handle assembly 12 has a pistol-grip type housing 18 with a variety of mechanical and/or electrical components disposed therein to operate various features of the instrument. For example, the handle assembly 12 can include a rotation knob 26 mounted adjacent a distal end 12d thereof which can facilitate rotation of the shaft 14 and/or the end effector 50 with respect to the handle assembly 12 about a longitudinal axis L of the shaft 14. The handle assembly 12 can further include clamping components as part of a clamping system actuated by a clamping trigger 22 and firing components as part of the firing system that are actuated by a firing trigger 24. The clamping and firing triggers 22, 24 can be biased to an open position with respect to a stationary handle 20, for instance by a torsion spring. Movement of the clamping trigger 22 toward the stationary handle 20 can actuate the clamping system, described below, which can cause the jaws 52, 54 to collapse towards each other and to thereby clamp tissue therebetween. Movement of the firing trigger 24 can actuate the firing system, described below, which can cause the ejection of staples from a staple cartridge disposed therein and/or the advancement the knife blade 81 to sever tissue captured between the jaws 52, 54. A person skilled in the art will recognize that various configurations of components for a firing system, mechanical, hydraulic, pneumatic, electromechanical, robotic, or otherwise, can be used to eject staples and/or cut tissue, and thus a detailed explanation of the same is unnecessary.

Figure 4:
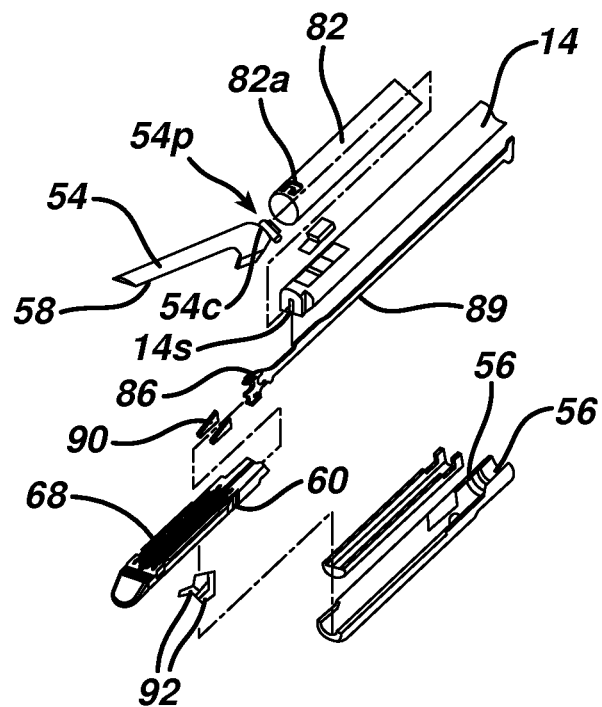
FIG. 4 is an exploded perspective view of an end effector and a distal end of a shaft of the instrument of FIG. 3.

As shown in more detail in FIG. 4, the end effector 50 of the illustrated embodiment is a surgical stapling tool having a lower jaw 52 that serves as a cartridge assembly or carrier and an opposed upper jaw 54 that serves as an anvil. The staple cartridge 60, having a plurality of staples 70 therein, is supported in a staple tray 57, which in turn is supported within the cartridge channel of the lower jaw 52. The upper jaw 54 has a plurality of staple forming pockets 66 (FIG. 11), each of which is positioned above a corresponding staple from the plurality of staples 70 contained within the staple cartridge 60. The upper jaw 54 can be connected to the lower jaw 52 in a variety of ways, although in the illustrated embodiment the upper jaw 54 has a proximal pivoting end 54p that is pivotally received within a proximal end 56p of the staple channel 56, just distal to its engagement to the shaft 14. When the upper jaw 54 is pivoted downwardly, the upper jaw 54 moves the anvil surface 58 and the staple forming pockets 66 formed thereon move toward the opposing staple cartridge 60.

Various clamping components can be used to effect opening and closing of the jaws 52, 54 to selectively clamp tissue therebetween. In the illustrated embodiment, the pivoting end 54p of the upper jaw 54 includes a closure feature 54c distal to its pivotal attachment with the staple channel 56. Thus, a closure tube 82, whose distal end includes a horseshoe aperture 82a that engages the closure feature 54c, selectively imparts an opening motion to the upper jaw 54 during proximal longitudinal motion and a closing motion to the upper jaw 54 during distal longitudinal motion of the closure tube 82 in response to the clamping trigger 22. It will be appreciated by a person skilled in the art that opening and closure of the end effector 50 may be effected by relative motion of the lower jaw 52 with respect to the upper jaw 54, relative motion of the upper jaw 54 with respect to the lower jaw 52, or by motion of both jaws 52, 54 with respect to one another.

Figure 5:
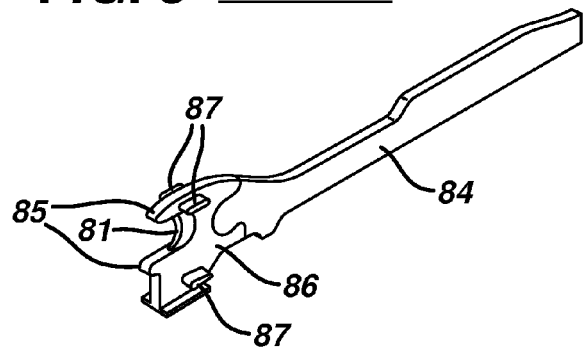
FIG. 5 is a perspective view of an E-beam component of the instrument of FIG. 3.

The firing components of the illustrated embodiment can include a firing bar 84, as shown in FIG. 5, having an E-beam 86 on a distal end thereof. The firing bar 84 is encompassed within the shaft 14, for example in a longitudinal firing bar slot 14s of the shaft 14, and guided by a firing motion from the handle 12. Actuation of the firing trigger 24 can affect distal motion of the E-beam 86 through at least a portion of the end effector 50 to thereby cause the firing of staples 70 contained within the staple cartridge 60. In the illustrated embodiment, guides 85 projecting from a distal end of the E-Beam 86 can engage a wedge sled 90, which in turn can push staple drivers 92 upwardly through staple cavities 68 formed in the staple cartridge 60. Upward movement of the staple drivers 92 applies an upward force on each of the plurality of staples 70 within the cartridge 60 to thereby push the staples 70 upwardly against the anvil surface 58 of the upper jaw 54 and to create formed staples 70'.

In addition to causing the firing of staples, the E-beam 86 can be configured to facilitate closure of the jaws 52, 54, spacing of the upper jaw 54 from the staple cartridge 60, and/or severing of tissue captured between the jaws 52, 54. In particular, a pair of top pins 87 and a pair of bottom pins 89 can engage one or both of the upper and lower jaws 52, 54 to compress the jaws 52, 54 toward one another as the firing bar 84 advances through the end effector 50. Simultaneously, a knife 81 extending between the top and bottom pins 87, 89 can be configured to sever tissue captured between the jaws 52, 54.

In use, the surgical stapler 10 can be disposed in a cannula or port and disposed at a surgical site. A tissue to be cut and stapled can be placed between the jaws 52, 54 of the surgical stapler 10. Features of the stapler 10 can be maneuvered as desired by the clinician to achieve a desired location of the jaws 52, 54 at the surgical site and the tissue with respect to the jaws 52, 54. After appropriate positioning has been achieved, the clamping trigger 22 can be pulled toward the stationary handle 20 to actuate the clamping system. The trigger 22 can cause components of the clamping system to operate such that the closure tube 82 advances distally through at least a portion of the shaft 14 to cause at least one of the jaws 52, 54 to collapse towards the other to clamp the tissue disposed therebetween. Thereafter, the trigger 24 can be pulled toward the stationary handle 20 to cause components of the firing system to operate such that the firing bar 84 and/or the E-beam 86 are advanced distally through at least a portion of the end effector 50 to effect the firing of staples 70 and optionally to sever the tissue captured between the jaws 52, 54.

Another embodiment of a surgical instrument 100 is illustrated in FIG. 6. Like surgical instrument 10, surgical instrument 100 includes a handle assembly 112 with a shaft 114 extending distally therefrom and having an end effector 150 on a distal end thereof for treating tissue. Upper and lower jaws 154, 152 of the end effector 150 can be configured to capture tissue therebetween, staple the tissue by firing of staples from a cartridge 160 disposed in the lower jaw 154, and/or to create an incision in the tissue. In this embodiment, an attachment portion 116 on a proximal end of the shaft 114 can be configured to allow for removable attachment of the shaft 114 and the end effector 150 to the handle assembly 112. In particular, mating features 125 of the attachment portion 116 can mate to complementary mating features 123 of the handle assembly 112. The mating features 123, 125 can be configured to couple together via, e.g., a snap fit coupling, a bayonet type coupling, etc., although any number of complementary mating features and any type of coupling can be used to removably couple the shaft 114 to the handle assembly 112. Although the entire shaft 114 of the illustrated embodiment is configured to be detachable from the handle assembly 112, in some embodiments the attachment portion 116 can be configured to allow for detachment of only a distal portion of the shaft 114. Detachable coupling of the shaft 114 and/or the end effector 150 can allow for selective attachment of a desired end effector 150 for a particular procedure, and/or for reuse of the handle assembly 112 for multiple different procedures.

The handle assembly 112 can have one or more features thereon to manipulate and operate the end effector 150. By way of non-limiting example, a rotation knob 126 mounted on a distal end of the handle assembly 112 can facilitate rotation of the shaft 114 and/or the end effector 150 with respect to the handle assembly 112. The handle assembly 112 can further include clamping components as part of a clamping system actuated by trigger 122 and firing components as part of a firing system that can also be actuated by the trigger 122. Thus, in some embodiments, movement of the trigger 122 toward a stationary handle 120 through a first range of motion can actuate clamping components to cause opposed jaws 152, 154 to approximate toward one another to a closed position. Further movement of the trigger 122 toward the stationary handle 120 through a second range of motion can actuate firing components to cause the ejection of staples from the staple cartridge 160 and/or the advancement of a knife to sever tissue captured between the jaws 152, 154.

Figure 7:
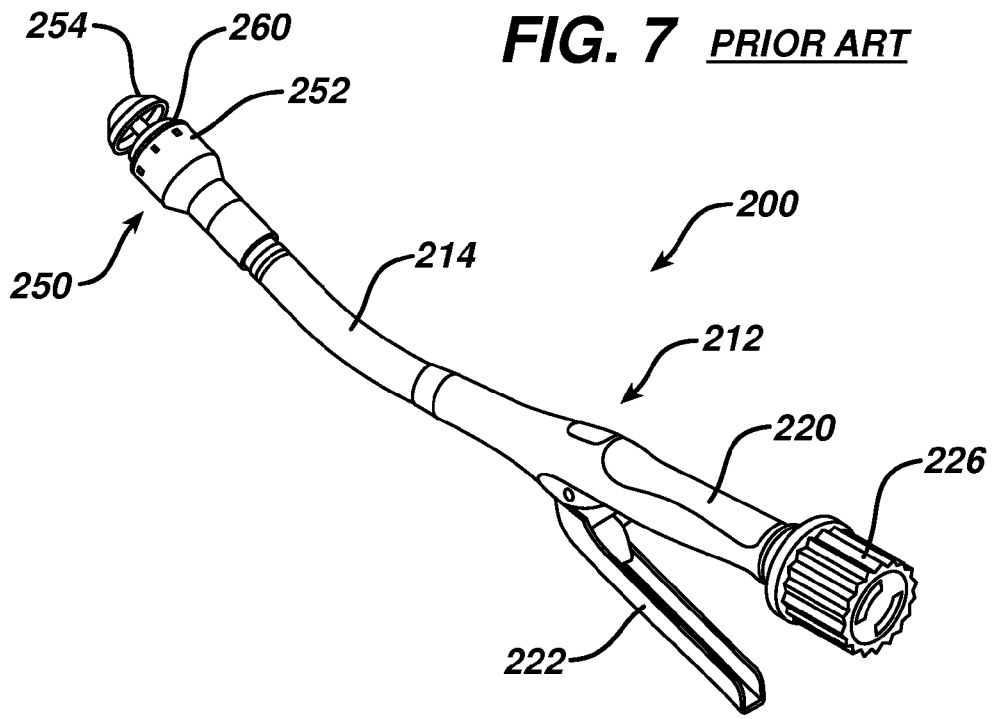
FIG. 7 is a perspective view of another prior art surgical instrument which can be used with one or more adjunct materials.

Yet another embodiment of a surgical instrument 200 is illustrated in FIG. 7 Like surgical instruments 10 and 100, surgical instrument 200 includes a handle assembly 212 with a shaft 214 extending distally therefrom and having an end effector 250 on a distal end thereof for treating tissue. The end effector 250 can include a cartridge assembly 252 and an anvil 254, each having a tissue-contacting surface 260p, 260d that is substantially circular in shape. The cartridge assembly 252 and anvil 254 can be coupled together via a shaft 262 extending from the anvil 254 to the handle assembly 212 of the stapler 200, and manipulating an actuator 222 on the handle assembly 220 can retract and advance the shaft 262 to move the anvil 254 relative to the cartridge assembly 252. In one embodiment, the shaft 262 can be formed of first and second portions (not shown) configured to releasably couple together to allow the anvil 254 to be detached from the cartridge assembly 252, allowing greater flexibility in positioning the anvil 254 and the cartridge assembly 252 in a body. For example, the first portion of the shaft can be disposed within the cartridge assembly 252 and extend distally outside of the cartridge assembly 252, terminating in a distal mating feature. The second portion of the shaft 214 can be disposed within the anvil 254 and extend proximally outside of the cartridge assembly 252, terminating in a proximal mating feature. In use, the proximal and distal mating features can be coupled together to allow the anvil 254 and cartridge assembly 252 to move relative to one another. The anvil 254 and cartridge assembly 252 can perform various functions and can be configured to capture tissue therebetween, staple the tissue by firing of staples from a cartridge assembly 252 and/or can create an incision in the tissue. In general, the cartridge assembly 252 can house a cartridge containing the staples and can deploy staples against the anvil 254 to form a circular pattern of staples around a circumference of a tubular body organ.

The handle assembly 212 of the stapler 200 can have various actuators disposed thereon that can control movement of the stapler. For example, the handle assembly 212 can have a rotation knob 226 disposed thereon to facilitate positioning of the end effector 250 via rotation, and/or a trigger 222 for actuation of the end effector 250. Movement of the trigger 222 through a first range of motion can actuate components of a clamping system to approximate the jaws, i.e. move the anvil 254 toward the cartridge assembly 252. Movement of the trigger 222 through a second range of motion can actuate components of a firing system to cause the staples to deploy from the staple cartridge assembly 252 and/or cause advancement of a knife to sever tissue captured between the cartridge assembly 252 and the anvil 254.

The illustrated embodiments of surgical stapling instruments 10, 100, and 200 provide only a few examples of many different configurations, and associated methods of use, that can be used in conjunction with the disclosures provided herein. Although the illustrated embodiments are all configured for use in minimally invasive procedures, it will be appreciated that instruments configured for use in open surgical procedures, e.g., open linear staplers as described in U.S. Pat. No. 8,317,070, can be used in conjunction with the disclosures provided herein. Greater detail on the illustrated embodiments, as well as additional exemplary embodiments of surgical staplers, components thereof, and their related methods of use, that can be used in accordance with the present disclosure include those devices, components, and methods provided for in U.S. Publication No. 2013/0256377, U.S. Pat. Nos. 8,393,514, 8,317,070, 7,143,925, U.S. patent application Ser. No. 14/074,884, entitled "Sealing Materials for Use in Surgical Procedures, and filed on Nov. 8, 2013, U.S. patent application Ser. No. 14/074,810, entitled "Hybrid Adjunct Materials for Use in Surgical Stapling," and filed on Nov. 8, 2013, U.S. patent application Ser. No. 14/075,438, entitled "Positively Charged Implantable Materials and Method of Forming the Same," and filed on Nov. 8, 2013, U.S. patent application Ser. No. 14/075,459, entitled "Tissue Ingrowth Materials and Method of Using the Same," and filed on Nov. 8, 2013, U.S. patent application Ser. No. 14/074,902, entitled "Hybrid Adjunct Materials for Use in Surgical Stapling," and filed on Nov. 8, 2013, U.S. patent application Ser. No. 14/226,142, entitled "Surgical Instrument Comprising a Sensor System," and filed on Mar. 26, 2014, each of which is incorporated by reference herein in its entirety.

End Effector Variations

End effectors of the surgical stapling instruments described herein can have one or more features for adjusting an amount of compression applied to tissue captured by the end effector. In some embodiments, the end effector can be configured to create a desired compression profile in tissue captured therein, for example a profile that helps to minimize bleeding, tearing, and/or leakage of the treated tissue. By way of non-limiting example, the desired tissue compression profile can be obtained using variations in a gap between upper and lower jaws of the end effector and/or variations in the orientation, size, and/or shape of staples applied to tissue by the end effector. As described in detail herein, adjunct material(s) used in conjunction with such an end effector can be configured to assist in creating the desired tissue compression profile and/or to accommodate features used to create the desired tissue compression profile.

Any such variations described herein can be used alone or together to provide the desired tissue compression profile. Although exemplary end effectors and components thereof are described in conjunction with a particular surgical instrument, e.g., instruments 10, 100, and 200, it will be appreciated that the end effectors and components thereof can be configured for use with other embodiments of surgical instruments as described herein.

Figure 8:
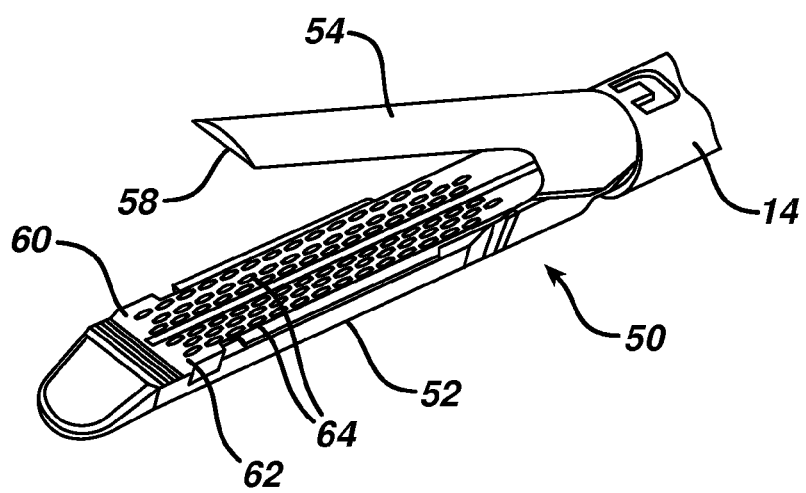
FIG. 8 is a perspective view of the end effector of FIG. 4.

In some embodiments, a staple cartridge disposed within an end effector of a surgical stapling instrument can have a first portion configured to compress tissue captured by the end effector more than a second portion when the end effector is in a closed position. The first portion of the cartridge can be spaced longitudinally and/or laterally from the second portion to create a desired compression gradient. For example, as shown in FIGS. 4 and 8, the staple cartridge 60 can have a stepped tissue contacting surface. In particular, the cartridge 60 can have an inner tissue contacting surface 62 and outer tissue contacting surfaces 64 that extend upwardly to a taller height than the inner tissue contacting surface 62. In this way, when the upper jaw 54 is in the closed position in close approximation with the cartridge 60, the anvil surface 58 can be configured to compress the outer surfaces 64 more than the inner surface 62 due to the taller height of the outer surfaces 64. In some circumstances, including circumstances where tissue positioned between the anvil surface 58 and the cartridge 60 has a constant, or at least substantially constant, thickness, the pressure generated within the tissue can be greater at outer portions of the end effector 50 than at inner portions of the end effector 50. Whereas a compression gradient generated by the cartridge 60 varies in a stepped manner, it will be appreciated by a person skilled in the art that a gradual compression gradient can be generated within the tissue by a gradual increase in height of various portions of the cartridge 60. It will also be appreciated that a compression gradient can be obtained by variations in height of the anvil surface 58, alone or in combination with height variations of the cartridge 60, and that height variations can be spaced laterally and/or longitudinally across the end effector 50.

Figure 9:
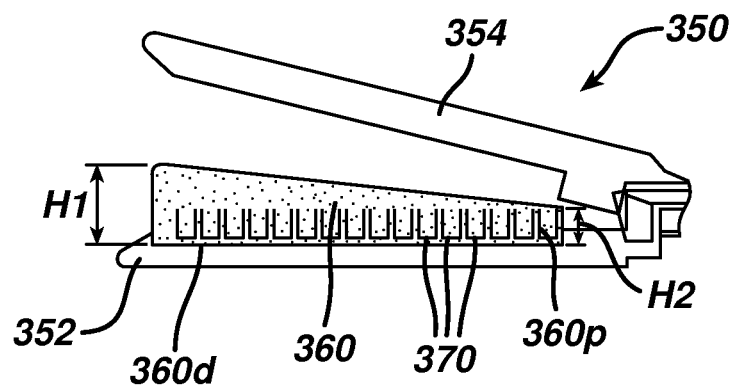
FIG. 9 is a side view of a prior art end effector having an implantable staple cartridge therein.

In some embodiments, one or more adjunct materials fixed to an end effector of a surgical stapling instrument can be used to create a desired compression profile in tissue captured by the end effector. Referring now to FIG. 9, a compressible, implantable staple cartridge 360 can be formed from one or more adjunct materials as described herein and can be configured to be seated within an end effector of a surgical instrument, e.g., an end effector 350. The cartridge 360 can have a height that decreases from a tallest height H1 at a distal end 360*d* thereof to a smallest height H2 at a proximal end 360*p* thereof. In this way, when an upper jaw 354 of the end effector 350 is in the closed position in close approximation with the cartridge 360, an upper jaw 354 of the end effector 350 can be configured to compress the distal end 360*d* more than the proximal end 360*p*. Although the compression gradient created in the captured tissue by the cartridge 360 decreases linearly from the distal end 360*d* to the proximal end 360*p*, it will appreciated by a person skilled in the art that any compression gradient can be created by different shapes of the cartridge 360. In at least one embodiment, a thickness of the cartridge 360 can vary across its width, similar to the cartridge 360.

Figure 10:
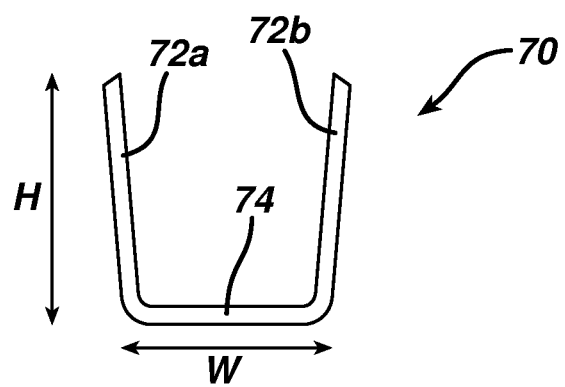
FIG. 10 is a side view of a prior art staple.
Figure 11:
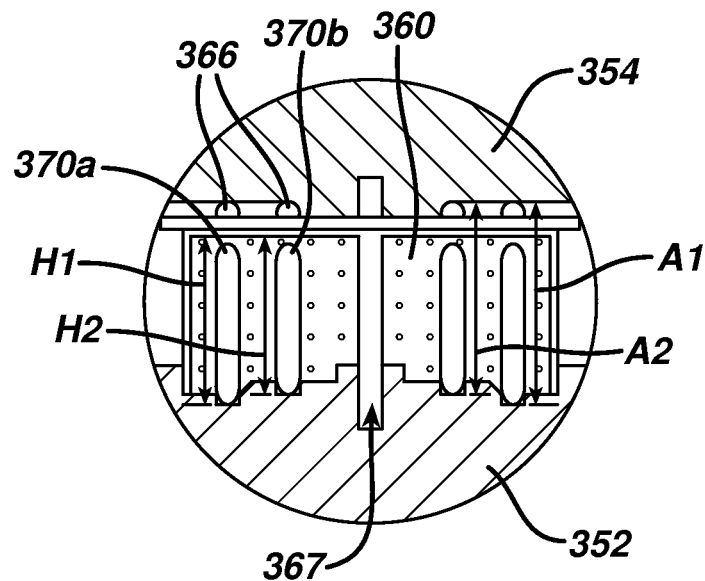
FIG. 11 is a cross-sectional view of the end effector of FIG. 9.

In some embodiments, staples contained within a staple cartridge of an end effector can be configured to create a desired compression profile within tissue captured by the staples. The desired compression profile can be created in stapled tissue, for example, where staples within the staple cartridge have different unformed staple heights. As shown in FIG. 10, an unformed height H of the exemplary staple 70 can be measured from a base 74 of the staple 70 to a top, or tip, of legs 72*a*, 72*b* of the staple 70. Referring now to FIG. 11, which illustrates a cross section of the end effector 350, a first group of staples 370*a* can have first staple height H1 that is taller than a second staple height H2 of a second group of staples 370*b*. The first group of the staples 370*a* can be positioned in a first portion of the staple cartridge 360, for example in an outer portion, and the second group of staples 370*b* can be positioned in a second portion of the staple cartridge 360, for example in an inner portion. In the illustrated embodiment, the cartridge 360, and therefore the compression gradient, can be configured to be symmetrical about a slot 367 configured to receive a cutting instrument, e.g., the E-beam 86, therethrough. It will be appreciated by a person skilled in the art that the first and second groups of staples 370*a*, 370*b* can be arranged in any pattern and can be spaced laterally and/or longitudinally along the cartridge 360. In certain embodiments, a plurality of staple groups, each group having different unformed staple heights, can be utilized. In at least one such embodiment, a third group having an intermediate staple height can be positioned in the cartridge intermediate the first group of staples and the second group of staples. In various embodiments, each staple within a staple row in the staple cartridge can comprise a different staple height. In at least one embodiment, the tallest staple within a staple row can be positioned on a first end of a staple row and the shortest staple can be positioned on an opposite end of the staple row. In at least one such embodiment, the staples positioned intermediate the tallest staple and the shortest staple can be arranged such that the staple heights descend between the tallest staple and the shortest staple, for example.

Figure 12:
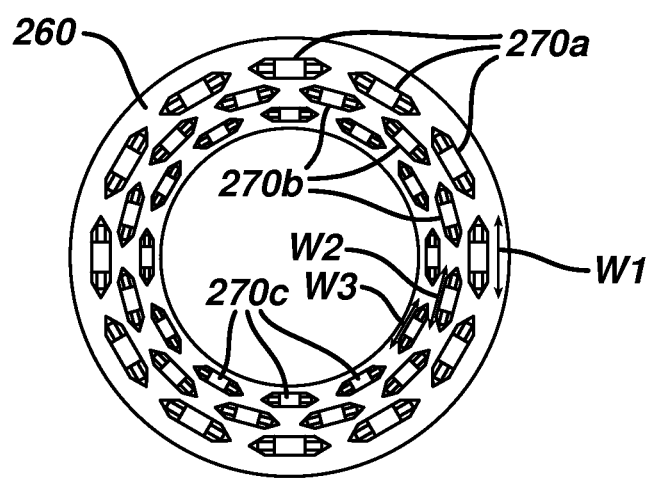
FIG. 12 is a top view of a prior art staple cartridge for use with the instrument of FIG. 7.

Similarly, staples within a staple cartridge can have different crown widths to create a desired compression profile in the stapled tissue. As shown in FIG. 10, a crown width W of the exemplary staple 70 can be measured from one side of the base 74 of the staple 70 to an opposite side. Like the above-described variations in staple height H, variations in the staple width W can be spaced throughout the staple cartridge to create a plurality of staple groups dispersed longitudinally and/or laterally across the cartridge. By way of non-limiting example, FIG. 12 illustrates a staple cartridge 260 for use with the surgical instrument 200 and having staples 270 therein with different crown widths W.

The staple cartridge 260 houses three groups of staples 270a, 270b, 270c, each having different widths W1, W2, and W3, respectively, although any number of staple groups is possible. As shown, the groups of staples 270a, 270b, 270c can be arranged in circumferential rows, with the staples 270c having the largest width W1 positioned on an outermost edge of the cartridge 260 and the staples 270a having the smallest width W3 positioned on an innermost edge of the cartridge 260. In other embodiments, staples having a larger crown width can be positioned near an inner most edge of a cartridge and staples having a smaller crown width can be positioned near an outer edge of the cartridge. In still further embodiments, staples along the same row can have different crown widths.

Figure 13:
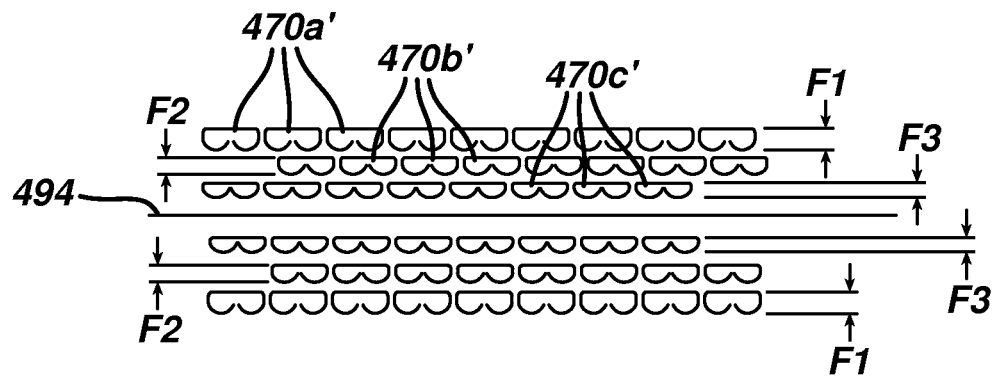
FIG. 13 is a diagrammatic representation of lines of staples installed using a prior art surgical stapling instrument.

Additionally or alternatively, it may be possible to create a desired tissue compression profile by the creation of different formed (final) staple heights. FIG. 13 illustrates an exemplary embodiment of lines of formed staples 470' installed using a surgical stapling instrument as described herein and configured to apply staples 470' having different formed heights as well as to cut tissue to thereby create a cut line 494. As shown in FIG. 13, formed heights F1 of a first group of staples 470a' in a first row that is the farthest distance away from the cut line 494 are greater than formed heights F3 of a third group of staples 470c' in a third row that is closest to the cut line 494. A second group of staples 470b' in a second row that is formed between the first and third rows can have staples 470b' with a formed height F2 that is between the heights F1, F3. In other embodiments, formed heights of the staples can decrease from an innermost row to an outermost row. In still further embodiments, formed heights of the staples in a single row can increase or decrease from staple to staple.

Referring again to FIG. 11, differences in formed staple heights can be attained by, for example, altering a staple forming distance A. Forming distances A1, A2 can be measured from a seat of staples 370a, 370b, respectively, within the cartridge 360, and an apex of a corresponding forming pocket 366 of the anvil surface 358 when the upper jaw 354 is in the closed position. In one embodiment, for example, a first staple forming distance A1 is different from a second staple forming distance A2. Because the forming distance A1 is greater than the forming distance A2, the staples 370a are not compressed as much as the staples 370b, which can alter the formed heights of the staples 370a, 370b. In particular, greater amounts of compression, corresponding to smaller forming distances, can result in staples with smaller formed (final) heights. It will be understood that similar results may be attained in any desired pattern.

Figure 14:
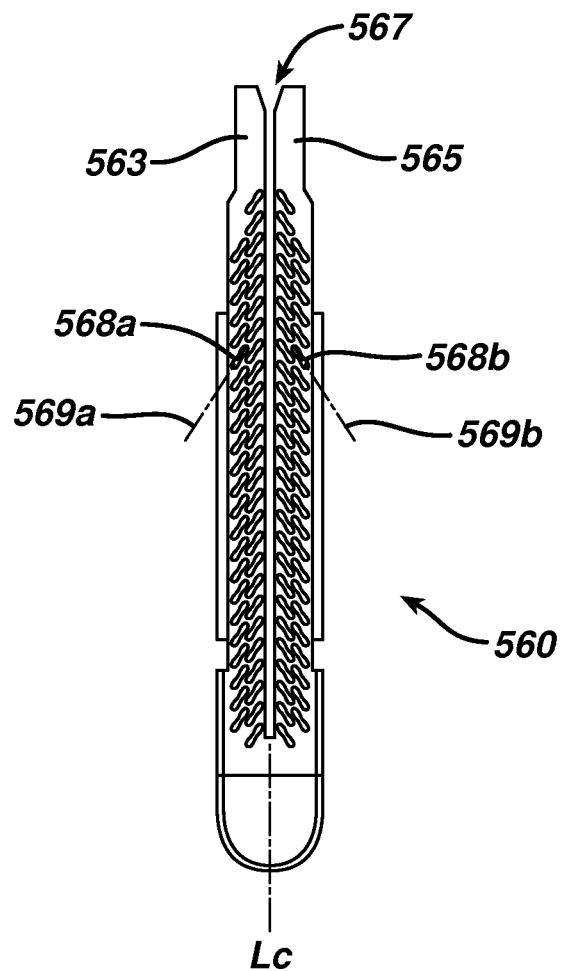
FIG. 14 is a top view of a prior art staple cartridge having a staple pattern.
Figure 15A:
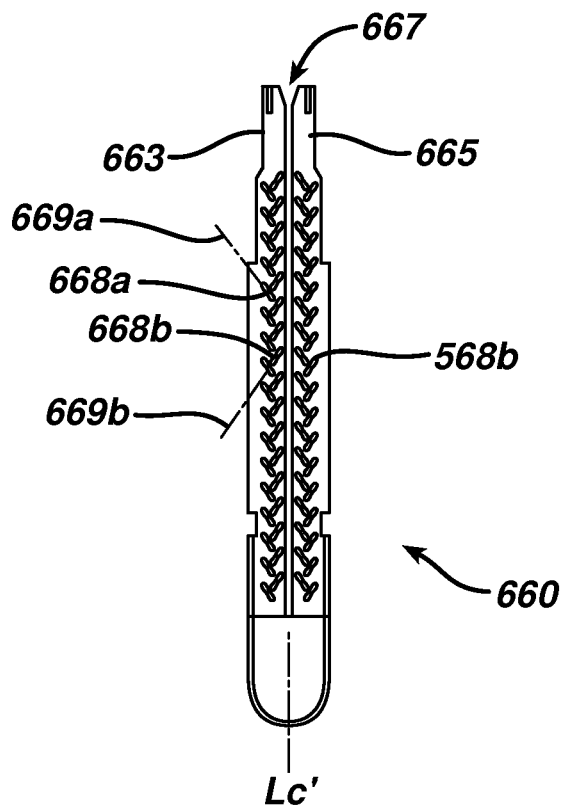
FIG. 15A is a side view of an end effector with a staple cartridge loaded with an adjunct material.

Varied tissue compression gradients can be obtained via patterns in staple orientation within a staple cartridge, for example by the patterns illustrated in FIGS. 14 and 15A. In the embodiment depicted in FIG. 14, staple cartridge 560 can include at least one first staple cavity 568a and at least one second staple cavity 568b for housing staples 570 therein. The first cavity 568a can be situated on first lateral side 563 of the cartridge 560 and the second cavity 568b can be situated on a second lateral side 565 of the cartridge 560, the first and second lateral sides 563, 565 being separated by a slot 567 configured to receive a cutting instrument, e.g., the E-beam 86, therethrough. The first cavity 568a can define a first longitudinal axis 569a and the second cavity 568b can define a second longitudinal axis 569b. In the illustrated embodiment, the first axis 569a is perpendicular, or substantially perpendicular, to the second axis 569b. In other embodiments, the first axis 569a can be transverse to the second axis 569b such that axes 569a, 569b can create an acute or obtuse angle therebetween. In still other embodiments, the first axis 569a can be parallel to, or substantially parallel to, the second axis 569b. In some embodiments, at least a portion of the staple cavities 568a, 568b can overlap, such that staples 570 therein can be interlocked when formed. The cartridge 560 can have a plurality of each of the first and second cavities 568a, 568b, which can be arranged in any pattern on first and second sides 563, 565 of the cartridge 560, for example in rows extending along both sides 563, 565 of the cartridge 560 along a longitudinal axis Lc of the cartridge 560. The staples 570 housed within the cavities 568a, 568b can be implanted into tissue in a pattern determined by the orientation and positioning of the cavities 568a, 568b. The cartridge 560, for example, can be used to implant staples 570 having different orientations of the staples 570 on opposite sides of an incision line created by a surgical instrument carrying the cartridge 560.

In other embodiments, for example the embodiment of a cartridge 660 illustrated in FIG. 15A, staple cavities 668a and 668b having different orientations can both be disposed on a single lateral side of the cartridge 660. As shown in FIG. 15A, an axis 669a of the first staple cavity 668a is perpendicular, or substantially perpendicular, to an axis 669b of the second staple cavity 668b, both of which are disposed on each of first and second lateral sides 663, 665 of the cartridge 660. In other embodiments, the axes 669a, 669b can form an acute or obtuse angle therebetween, or can be parallel to one another. A plurality of the first and second cavities 668a, 668b can be aligned in adjacent rows along a longitudinal axis Lc' of the cartridge 660 on each of the first and second sides 663, 665 of the cartridge 660. In this embodiment, staples 670 housed within the cavities 668a, 668b can be implanted into tissue in a symmetrical pattern about an incision line created by a surgical instrument carrying the cartridge 660. Greater detail on staple patterns, as well as additional embodiments of such patterns, can be found in U.S. Publication No. 2011/0192882, incorporated herein by reference in its entirety.

Exemplary Compositions for Adjunct Materials

Figure 15B:
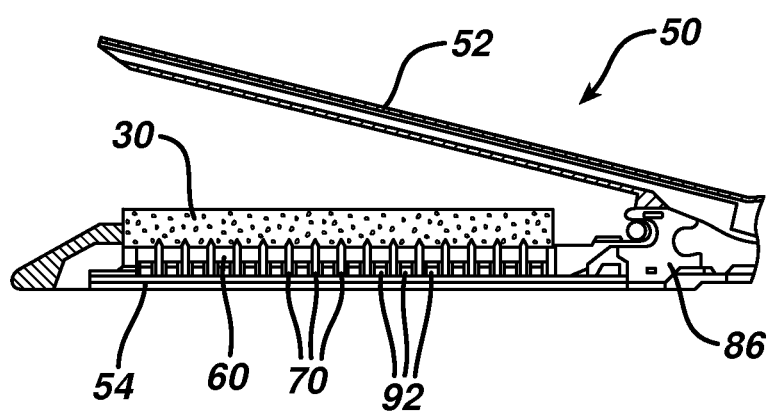
FIG. 15B is a side, cross-sectional view of the end effector of FIG. 4 having an adjunct material thereon.

Regardless of the configuration of the surgical instrument, the present disclosure provides for the use of implantable materials, e.g., synthetic and/or biological materials, collectively "adjunct materials," in conjunction with instrument operations. As shown in FIG. 15B, the end effector 50 can include at least one piece of adjunct material 30 positioned intermediate the lower and upper jaw members 52, 54 and it can be releasably retained to one of the staple channel 56 and/or the anvil surface 58. In use, the adjunct material 30 and patient tissue can be captured by staples 70 when the staples 70 are fired. Then, the adjunct material 30 can be separated from the surgical stapler and can remain in the patient when the stapler is removed from the patient. Exemplary devices and methods for attaching one or more adjunct materials to an end effector of a surgical instrument can be found in U.S. Publication No. 2013/0256377 and U.S. Publication No. 2013/0153641, incorporated herein by reference in their entirety.

Regardless of the configuration of the surgical instrument, the embodiments described herein can provide for the use of implantable materials, e.g., synthetic and/or biological materials, collectively "adjunct materials," in conjunction with instrument operations. As explained in more detail below, adjunct materials as disclosed herein can be releasably coupled to the lower and upper haw members 52, 54 in a variety of manners to allow the adjunct materials to separate from the jaw members upon actuation of the end effector 50. More particularly, the adjunct materials can be captured by staples 70 along with tissue disposed between the jaw members 52, 54. The adjunct materials can remain in the patient when the stapler removed from the patient. While a number of devices and methods for attaching adjunct materials to an end effector of a surgical instrument are described below, others can be found in U.S. Pat. Pub. No. 2013/0256377 and U.S. Pat. Pub. No. 2013/0153641, incorporated herein by reference in their entirety.

In at least one embodiment, a surface on the adjunct material 30 can be configured to contact tissue as the tissue is clamped between the lower and upper jaw members 52, 54. In such an embodiment, the adjunct material can be used to distribute the compressive clamping force over the tissue, absorb, reinforce, and/or retain beneficial fluids at the treatment site, improve the purchase of the staples, and/or promote improved clinical outcomes such as hemostasis, pneumostasis, healing, etc. In various embodiments, one or more pieces of adjunct material can be positioned within the end effector 50. In some embodiments, one piece of adjunct material 30 can be attached to the staple cartridge 60 and a second piece of adjunct material 30' can be attached to the anvil surface 58; however, any suitable number of adjunct materials can be situated within the end effector 50.

Adjunct material used in conjunction with the disclosures provided for herein can have any number of configurations and properties. Generally, they can be made from a bioabsorbable material, a biofragmentable material, and/or a material otherwise capable of being broken down, for example, such that the adjunct material can be absorbed, dissolved, fragmented, and/or broken down during the healing process. In at least one embodiment, the adjunct material can be configured to degrade over time to form a gel, e.g., a sealant, to assist in wound healing. In other embodiments, the adjunct material can include a therapeutic drug that can be configured to be released over time to aid the tissue in healing, for example. In further various embodiments, the adjunct materials can include a non-absorbable and/or a material not capable of being broken down, for example.

Some particularly advantageous adjunct materials can include porous polymer scaffolds that can be configured to be broken down, for example by exposure to water such that the water attacks the linkage of a polymer of the material. The degraded material can be configured to gel over a wound site to thereby coat the wounded tissue, e.g., wounded soft tissue, which can aid in compressing, sealing and/or generally creating an environment at the wound site that promotes healing of the tissue. In particular, such degradable polymers can allow for the tissue itself to become the weight-bearing component. In some embodiments, the degraded material can include chemoattractant agents that attract natural healing compounds to the wound site. The polymer scaffolds can be configured to have a desired rate of degradation, for example within minutes to hours after attachment to tissue, to thereby assist in the healing process almost immediately after attachment. For more details on porous polymer scaffolds as described herein, see Q. Chen et al., Elastomeric biomaterials for tissue engineering, Progress in Polymer Science 38 (2013) 584-671, incorporated herein by reference in its entirety.

In some embodiments, the porous polymer scaffolds described herein can be physically crosslinked, which can allow for shaping of the polymer into various complicated three-dimensional shapes, e.g., fibers, sheets, films etc., having any desired porosity, surface-to-volume ratio, and mechanical properties. The scaffold can be shaped into a desired form via a number of methods, for example by extrusion, wet spinning, electrospinning, thermally induced phase separation (TIPS), salt leaching/freeze-drying, etc. Where the scaffold is formed into a film or sheet, the film or sheet can have any desired thickness, for example in a range of about 50 to 750 µm or in a range of about 1 to 3 mm, depending on the desired application.

One embodiment of a porous polymer scaffold includes multiple layers, each of which can perform different wound healing functions. In an exemplary embodiment, the scaffold includes three layers. The first layer can be made from polyester carbonate urethane urea (PECUU), the second layer can be made from poly(ester urethane) urea (PEUU), and the third layer can be made from poly(carbonate urethane) urea (PCUU) lysine triisocyanate (LTI) or hexamethylene diisocyanate (HDI). A person skilled in the art will appreciate that the properties of each layer can be optimized to achieve desired results and performance. In some embodiments, the desired properties of the scaffold can be achieved by blending or copolymerizing the material of the third layer or copolymerized with various polymers or copolymers. By way of non-limiting examples, the material of the third layer can be blended with a polyester copolymer, for example polycaprolactone (PCL), polyglycolic acid PGA, poly(D,L-lactic acid) (PDLLA), PGA, and/or polyethylene glycol (PEG). Where the material of the third layer is blended with both the polyester copolymer and the PEG, a ratio of the polyester to the PEG in the third layer can be about 50:50. In another exemplary embodiment, the PCL can be present in a range of about 60-70% weight/volume, the PGA can be present in a range of about 20-30% weight/volume, the PEG can be present in a range of about 50% weight/volume, and the PDLLA can be present in a range of about 10% weight/volume.

The three-layered film can be configured to degrade almost immediately upon attachment to tissue, for example within about 1 to 2 hours after attachment, although each of the three layers can be configured to degrade differently to have different healing benefits. The order, number, and thickness of each of the layers can vary, and can be tailored to create desired degradation and/or compression ratios. In some embodiments, the first, second, and third layers can be formed on top of a base material or substrate, for example on top of PCL, which can be configured to aid in mechanical compression of the wounded tissue.

Another exemplary embodiment of a porous polymer scaffold can be synthesized from polyhydroxyalkanoate (PHA). In an exemplary embodiment, the PHA can be naturally produced from a variety of microorganisms, e.g., Gram-negative or Gram-positive bacteria, or it can be synthesized, e.g., similar to the production of Biopol®, available from Zeneca of London, United Kingdom. Because PHAs are very quick to dissolve, scaffolds made from PHA can begin to degrade within 20 to 30 minutes after attachment to tissue via contact with heat and/or water. Where the PHA scaffold has a higher molecular weight, the degradation time can be higher, for example in a range of about 30 minutes to about 10 hours. The PHA can be formed into a very thin film, for example a film having a thickness of less than 0.1 mm, e.g., in a range of between 50 to 750 µm. In some embodiments, the PHA can be copolymerized and/or blended with one or more additional materials. By way of non-limiting example, the PHA can be copolymerized with hydroxlvalerate (HV), hydroxylbutyrate (HB), and/or hydroxylhexanoate (HH), which can reduce a level or crystallinity and/or brittleness of the PHA. In other embodiments, the PHA can be blended with one or more thermoplastics, e.g., poly(lactic acid) (PLA), PGA, PCL, starch, etc., to thereby customize a molecular weight and resultant mechanical properties of the scaffold. In certain aspects, one or more of the polymers can be a thermoplastic polymer.

In other embodiments, the scaffold can be synthesized from poly(polyol sebacate) (PPS), e.g., from poly(glycerol-sebacate) (PGS). Such scaffolds can be particularly biocompatible and can provide an additional advantage of reducing a risk of infection in addition to promoting healing. Other exemplary embodiments can be synthesized from xylitol-based elastomers, for example polyxylitol sebacates (PXSs), which can offer structural stability over a clinically required period and/or can enter the metabolic pathway slowly without causing rapid fluctuations of blood glucose levels. Scaffolds made from PXS's can be formed into a thicker film to thereby provide greater compression to the wound site, and can be configured to degrade within a range of about 10 hours to 8 days after attachment. Still other exemplary embodiments can be synthesized from poly(glycerol sebacate-co-acrylate) (PGSA), which can promote tissue ingrowth into the scaffold, particularly when formed as a fiber, and/or can serve as an antibacterial agent. PGSA scaffolds can be useful as a replacement for traditional surgical sutures and staples, and/or can serve as a waterproof sealant for hollow organ anastomoses (e.g., ducts, intestine, etc.), 2D mesh grafts (e.g., treatment of hernias, ulcers, burns, etc.), and/or wound dressings (e.g., hemostatic patches, etc.). The PGSA can be combined with glycerol, which can allow the scaffold to last longer in situ, for example up to 20 days.

In yet another embodiment, the scaffold can be made from poly(ε-caprolactone) (PCL), which can be blended with silk fibroin (SF) and which can be formed into a very thin film. The PCL/SF blend can have highly biocompatible properties and/or can improve cell attachment and/or proliferation to the scaffold. For example, when implanted onto tissue, the scaffold can release fibroin into the tissue to thereby promote faster healing, nearly immediate hemostasis, and/or to attract fibroblasts in greater numbers. The PCL component can further assist in the healing process by providing mechanical compression of the wounded tissue. A higher PCL content can provide better mechanical properties, while a higher SF content can provide better degradation properties. In general, the PCL content can be in a range of about 50 to 90% weight/volume and the SF content can be in a range of about 10 to 50% weight/volume. More details on the properties and manufacturing methods for scaffolds made from PCL and SF can be found in Jun Sik Lim et al., Fabrication and Evaluation of Poly(epsilon-caprolactone)/Silk Fibroin Blend Nanofibrous Scaffold, Biopolymers 97: 265-275 (2012), incorporated herein by reference in its entirety.

In still further embodiments, the scaffold can include PCL coated with a gelatin. The scaffold can be arranged in one or more layers, for example with the PCL serving as a substrate. The PCL can function to increase a mechanical strength of the scaffold and/or can support fibroblast adhesion and cell proliferation. More details on the properties and manufacturing methods for scaffolds made from gelatin-coated PCL can be found in Pengcheng Zhao et al., Biodegradable fibrous scaffolds composed of gelatin coated poly (ε-caprolactone) prepared by coaxial electrospinning, J. Biomed Mater Res 83A: 372-382 (2007), incorporated herein by reference in its entirety.

Table 1 below outlines exemplary molecular weight ranges, approximate absorption times, and average dimensions of films made from the aforementioned porous polymer scaffold materials. It will be appreciated by a person skilled in the art that the ranges provided in Table 1 are not intended to be limiting, and that a molecular weight of any of the polymers described herein can be altered to obtain the desired degradation properties.

TABLE 1

| Film | Average molecular weight in Daltons | Approximate absorption times | Average thickness | Average length | Average width |
|---|---|---|---|---|---|
| Polyester carbonate urethane urea (PECUU) | 5,000 to 80,000 | 14 to 60 days | 10 μm to 1 mil | 25.4 to 100 mm | 10.3 to 12.7 mm |
| Poly(ester urethane)urea (PEUU) | 5,000 to 80,000 | 14 to 60 days | 10 μm to 1 mil | 25.4 to 100 mm | 10.3 to 12.7 mm |
| Poly(carbonate urethane)urea (PCUU) | 10,000 to 200,000 (preferably 15,000 to 50,000) | 14 to 60 days | 100 μm to 1 mil | 25.4 to 100 mm | 10.3 to 12.7 mm |
| Polyhydroxyalkanoate (PHA) | $2.107 \times 10^{29}$ to $2.589 \times 10^{29}$ | 7 to 60 days | 100 μm to 1 mil | 25.4 to 100 mm | 10.3 to 12.7 mm |
| Poly(polyol sebacate) (PPS) | 89,000 and 124,000 | 7 to 60 days | 100 μm to 1 mil | 25.4 to 100 mm | 10.3 to 12.7 mm |
| Polyxylitol sebacates (PXS's) | $1.47 \times 10^{27}$ to $3.73 \times 10^{27}$ | 7 to 60 days | 100 μm to 1 mil | 25.4 to 100 mm | 10.3 to 12.7 mm |
| Poly(glycerol sebacate-co-acrylate) (PGSA) | $5.8 \times 10^{26}$ to $7.5 \times 10^{26}$ | 7 to 60 days | 10 μm to 1 mil | 25.4 to 100 mm | 10.3 to 12.7 mm |
| Poly(ε-caprolactone); silk fibroin; scaffold (PCL/SF) Blend PCL/SF (50/50) | 25,000 to 325,000 (SF) $4.21 \times 10^{28}$ to $4.81 \times 10^{28}$ (PCL) | 21 to 60 days (SF) 2 to 3 years (PCL) | 10 μm to 1 mil | 25.4 to 100 mm | 10.3 to 12.7 mm |
| Gelatin coated PCL (poly (ε-caprolactone) | $3.01 \times 10^{28}$ to $1.98 \times 10^{29}$ (gelatin) $4.21 \times 10^{28}$ to $4.81 \times 10^{28}$ (PCL) | 7 days (gelatin) 2 to 3 years (PCL) | 100 μm to 1 mil | 25.4 to 100 mm | 10.3 to 12.7 mm |

Other suitable adjunct materials can include absorbable polyurethanes, e.g., polyurethanes derived from aromatic absorbable isocyanates that can be similar to methylene bis(phenyl isocyanate) (MDI) and chain extender diols. The absorbable polyurethanes can be configured to hydrolytically degrade into safe and biocompatible products upon hydrolysis. Non-limiting examples of hydrolysable aromatic isocyanates that can be used to form the absorbable polyurethanes include glycolate-diisocyante, caprolactone-diisocyanate, glycolate-ethylene glycol-glycolate, glycolate-diethylene glycol-glycolate, lactate-diethylene glycol-lactate, trimester of gycolic acid with trimethylpropane, and tetraester of glycolic acid with pentaerythritol.

Another particularly advantageous adjunct material that can be used in conjunction with the disclosures provided herein are the materials that form the multilayered dressings disclosed in U.S. Publication No. 2006/0257458, incorporated herein in its entirety, which are particularly suited to absorb and retain fluids when compressed, e.g., by the application of staples. Other exemplary, non-limiting examples of synthetic materials that can be used in conjunction with the disclosures provided for herein, e.g., as a buttress, include biodegradable synthetic absorbable polymer such as a polydioxanon film sold under the trademark PDS® or with a Polyglycerol sebacate (PGS) film or other biodegradable films formed from PGA (Polyglycolic acid and various forms thereof, marketed under the trademarks Vicryl, Dexon, and/or Neoveil), PCL (Polycaprolactone), PLA or PLLA (Polylactic acid), PHA (polyhydroxyalkanoate), PGCL (poliglecaprone 25, sold under the trademark Monocryl), PANACRYL (Ethicon, Inc., Somerville, N.J.), Polyglactin 910, Poly glyconate, PGA/TMC (polyglycolide-trimethylene carbonate sold under the trademark Biosyn), polyhydroxybutyrate (PHB), poly(vinylpyrrolidone) (PVP), poly(vinyl alcohol) (PVA), polydioxanone (PDO) and various forms thereof (e.g., marketed under the trademark PDS) or a blend or copolymerization of any of the above. Blends and/or copolymerizations of any of the aforementioned materials can be tailored to have a desired molecular weight and/or degradation rate.

Some non-limiting examples of biologic derived materials that can be used in conjunction with the disclosures provided for herein, e.g., as a sealant material, include platelet poor plasma (PPP), platelet rich plasma (PRP), starch, chitosan, alginate, fibrin, thrombin, polysaccharide, cellulose, collagen, bovine collagen, bovine pericardium, gelatin-resorcin-formalin adhesive, oxidized regenerated cellulose, regenerated cellulose, mussel-based adhesive, poly (amino acid), agarose, polyetheretherketones, amylose, hyaluronan, hyaluronic acid, whey protein, cellulose gum, starch, gelatin, silk, Progel®, available from Davol Inc. of Warwick, R.I., TachoSil®, available from Baxter of Deerfield, Ill., or other material suitable to be mixed with biological material and introduced to a wound or defect site, including combinations of materials, or any material apparent to those skilled in the art in view of the disclosures provided for herein. Biologic materials can be derived from a number of sources, including from the patient in which the biologic material is to be implanted, a person that is not the patient in which the biologic material is to be implanted, or other animals.

Additional disclosures pertaining to synthetic or polymer materials and biologic materials that can be used in conjunction with the disclosures provided herein can be found in U.S. Pat. No. 7,772,352, PCT Publication No. WO 2014/016819, U.S. Patent Application Publication No. 2006/0257458, U.S. Patent Application Publication No. 2012/0080335, U.S. Patent Application Publication No. 2012/0083835, U.S. Patent Application Publication No. 2013/0256372, U.S. Patent Application Publication No. 2013/0256365, U.S. Patent Application Publication No. 2013/0256376, U.S. patent application Ser. No. 13/710,931, entitled "Electrosurgical End Effector with Tissue Tacking Features," and filed on Dec. 11, 2012, and U.S. patent application Ser. No. 13/763,192, entitled "Multiple Thickness Implantable Layers for Surgical Stapling Devices," and filed on Feb. 8, 2013, each of which is incorporated by reference herein in its entirety.

In use, the adjunct material can come pre-loaded onto the device and/or the staple cartridge, while in other instances the adjunct material can be packaged separately. In instances in which the adjunct material comes pre-loaded onto the device and/or the staple cartridge, the stapling procedure can be carried out as known to those skilled in the art. For example, in some instances the firing of the device can be enough to disassociate the adjunct material from the device and/or the staple cartridge, thereby requiring no further action by the clinician. In other instances any remaining connection or retention member associating the adjunct material with the device and/or the staple cartridge can be removed prior to removing the instrument from the surgical site, thereby leaving the adjunct material at the surgical site. In instances in which the adjunct material is packaged separately, the material can be releasably coupled to at least one component of the end effector, e.g., the staple cartridge, prior to firing the device. The adjunct material may be refrigerated, and thus removed from the refrigerator and the related packaging, and then coupled to the device using a connection or retention member as described herein or otherwise known to those skilled in the art. The stapling procedure can then be carried out as known to those skilled in the art, and if necessary, the adjunct material can be disassociated with the device as described above.

Adjuncts Having Strain Relieving Features

A tissue adjunct can have various configurations, but can generally be configured to contact tissue as the tissue is clamped between a cartridge assembly and an anvil of a surgical stapler. One advantage of tissue adjuncts is their propensity to prevent or minimize leaks, such as fluid or gas leaks. Tissue adjuncts can perform this function by one or more of the following mechanisms: plugging holes or tears that occur at the staple puncture sites; restricting movement of tissue around staple puncture sites to prevent an increase in the size of staple holes and/or to prevent tissue tears; and minimizing strain gradients that occur between constrained tissues within the staple line and free tissue adjacent to the staple line.

In certain aspects, the adjunct material can be used to distribute the compressive clamping force over the tissue, absorb and retain beneficial fluids at the treatment site, improve the purchase of the staples, and/or promote hemostasis. In some embodiments, a first piece of adjunct material can be attached to a cartridge assembly and a second piece of adjunct material can be attached to an anvil; however, any suitable number of adjunct materials can be situated within the end effector.

The tissue adjunct can include various features and be formed from various materials for assisting with sealing of tissue at a staple line and/or for preventing the formation of leaks in the tissue. For example, a tissue adjunct can have a central region configured to be deployed onto tissue and attached thereto via staples. The tissue adjunct can further include an outer region, also referred to herein as a wing region or wing portion, which can be positioned outside of a staple line when the adjunct is stapled to tissue. The wing portion can help to more evenly distribute strain and/or minimize strain gradients across a tissue as the tissue deforms or otherwise expands and contracts during normal bodily functions. In some embodiments, a sealant can be used in conjunction with the adjunct to help seal the stapled tissue. The sealant can be introduced into a patient in a first, liquid state and can be configured to transition to a second, hardened or solid state after a predetermined amount of time. When the sealant is in the first, liquid state, the sealant can seep into the adjunct and/or the staple line and then harden therein, thereby facilitating complete sealing of the tissue. The adjunct and the sealant can thus cooperate to provide a better, more complete seal of the staple line than if only the tissue adjunct or the sealant were used.

Figure 16A:
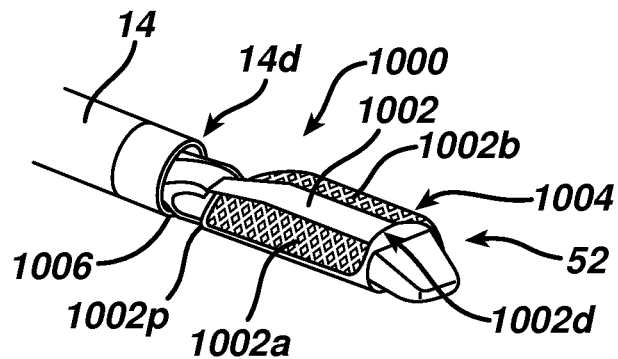
FIG. 16A is a perspective view of adjunct material having a central portion and a wing portion, the adjunct material being coupled to a cartridge assembly.
Figure 16B:
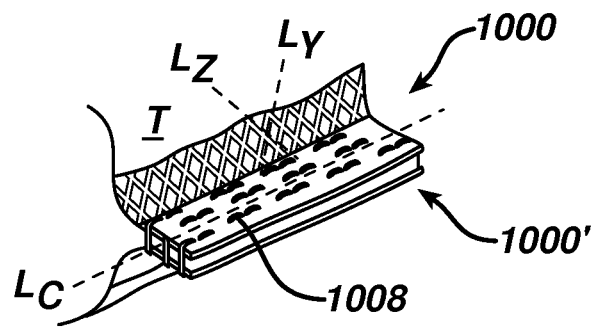
FIG. 16B is a perspective view of an adjunct material stapled onto tissue.

Exemplary adjuncts having central and wing regions are shown deployed onto tissue in FIGS. 16A and 16B. As shown in FIG. 16A, an adjunct 1000 can include a central 1002 for receiving staples therethrough and a wing portion 1004 adjacent to the central region 1002. The central region 1002 of the adjunct 1000 can be sized and shaped to correspond to a size and shape of a cartridge assembly 52 and/or an anvil (not shown). For example, FIG. 16A illustrates an adjunct 1000 having a central region 1002 that corresponds in size and shape to a tissue-contacting surface of the cartridge assembly 52. That is, the central region 1002 can be substantially equal in size to the tissue-contacting surface. The central region 1002 of the adjunct 1000 shown in FIG. 16A can have a substantially elongate rectangular shape defined by proximal and distal edges 1002p, 1002d and first and second lateral edges 1002a, 1002b. The proximal edge 1002p of the central region 1002 can terminate in a proximal mating feature 1006 for coupling to a distal end 14d of a shaft 14 of a stapler 10. At least two of the remaining three edges of the central region 1002 can include a wing portion 1004 extending therearound and forming a perimeter of the adjunct 1000. For example, as shown in FIG. 16A, the wing portion 1004 of the adjunct 1000 can extend around the first and second lateral edges 1002a, 1002b and can extend distally beyond the distal edge 1002d of the central region 1002. In one embodiment, adjunct 1000 is sized and position in such a way on cartridge assembly 52 so that in can be separated by a cutting member in the stapler during use. In fact, a distal region of the wing portion 1004 is always cut. As shown, the wing portion 1004 can have a modified structure that is different from a structure of the central region 1002. In the illustrated embodiment, the central region 1002 can be substantially solid, e.g. a film, and the wing portion 1004 can be a mesh. As shown in FIG. 16B, when the adjunct 1000 is stapled to tissue T, the central region 1002 can have one or more rows/lines of staples 1008 extending therethrough and the wing portion 1004 can extend laterally away from the staples 1008. As shown, the adjunct 1000 stapled to the tissue T includes half of the adjunct shown in FIG. 16A because the cutting member in the stapler severs the tissue while the staples 1008 are deployed thereon. The meshed wing portion 1004 can flex as the tissue expands and contracts and more evenly distribute a strain (or minimize a strain gradient) across a greater area of tissue than if the adjunct 1000 only included the central region 1002. For example, the wing portion 1004 can expand and contract in a direction transverse to the longitudinal axis LC of the central region 1002. This can help prevent the formation of pressure points which can create leaks in the stapled tissue after repeated expansion and contraction of the tissue. In certain aspects, the mesh can be formed from threads of the same film material as the central region 1002 extending in a criss-cross pattern. The longitudinal axis of half of the threads L1 can be disposed at an angle θ1 of about a 45 degrees relative to the longitudinal axis LC of the central region 1002, as shown, and a longitudinal axis L2 of the other half of the threads can be disposed at an angle θ2 of about a 45 degree angle relative to the longitudinal axis LC of the central region 1002, or can be positioned at other angles relative to the central region 1002. As will be appreciated by a person skilled in the art, the wing portion 1004 of the adjunct 1000 can be formed using various known manufacturing techniques, such as laser cutting or punching shapes such as squares, circles, diamonds, out of the film to produce a mesh wing region and the solid central region 1002. Two identical adjuncts 1000, 1000' can be stapled to tissue, as shown in FIG. 16B, and in certain aspects, these adjuncts 1000, 1000' can be substantially the same in size, shape, and configuration.

Figure 17:
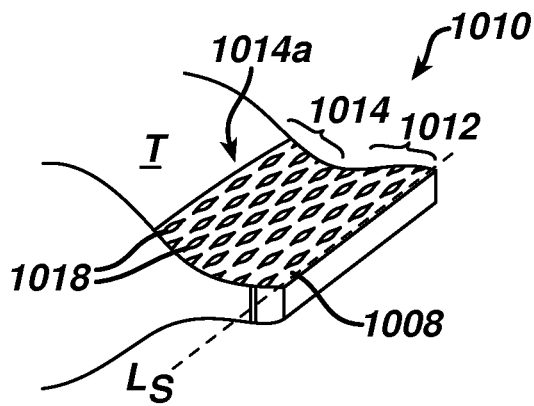
FIG. 17 is a perspective view of another exemplary embodiment of adjunct material stapled to tissue.

Another embodiment of an adjunct 1010 is shown in FIG. 17 and also includes a central region and wing region. In this embodiment, a wing portion 1014 has a plurality of openings 1018 formed therein which can allow the wing portion 1014 to flex with the tissue T during expansion and contraction of the tissue T. The openings 1018 can have various sizes, shapes, and configurations, and can be circular, oval, rectangular, etc., and can be positioned at various locations across the wing portion 1014. In the illustrated embodiment, the openings 1018 are slits positioned in multiple rows, the rows being substantially parallel to the longitudinal axis LC of a central region 1012. A longitudinal axis of the slits 1018 can be parallel to a longitudinal axis LS of the staples 1008. A number of longitudinal rows and a number of openings 1018 disposed in each row can vary. In the illustrated embodiment, a row adjacent to the central region 1012 can have a smaller number of openings 1018 than a row adjacent to an outermost edge 1014a of the wing portion 1014. For example, the row adjacent to the central region 1012 can have about three openings 1018 formed therein while the row adjacent to the outermost edge 1014a of the wing portion 1014 can have about four openings 1018 formed therein. In this way, a flexibility of the wing portion 1014 can increase from the central region 1012 to the lateral edge and can further facilitate distribution of strain across the tissue T.

Figure 18A:
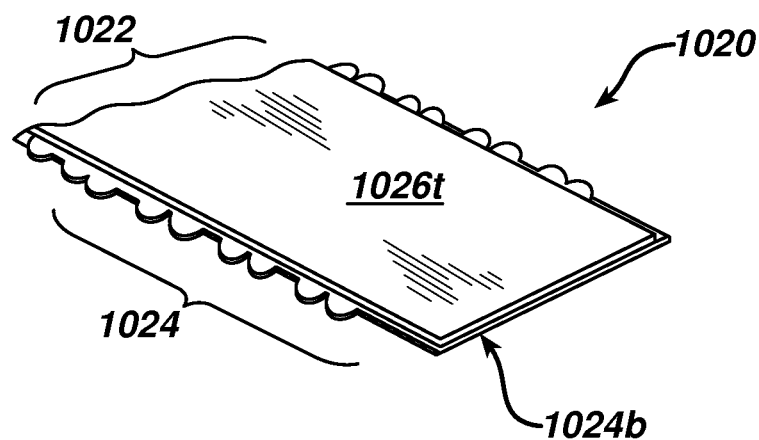
FIG. 18A is a perspective view of an adjunct material having edge protrusions configured to distribute a strain to tissue beyond a staple line.
Figure 18B:
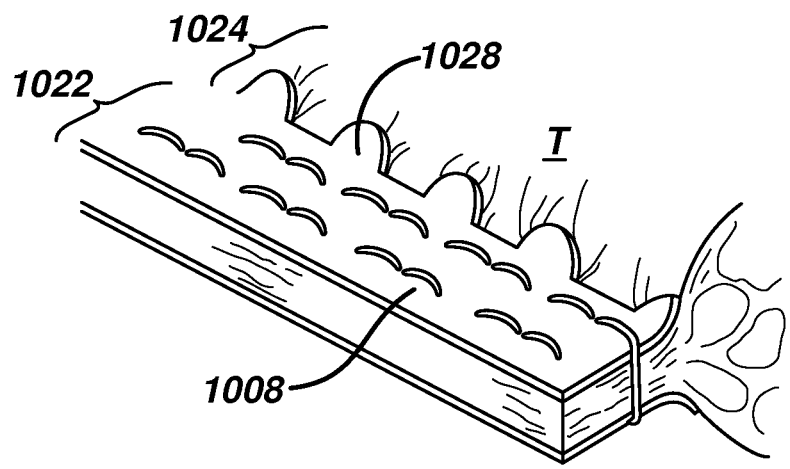
FIG. 18B is a perspective view of another adjunct material having edge protrusions, the adjunct material being stapled to tissue.

FIGS. 18A and 18B illustrate another embodiment of a tissue adjunct having wings for distributing strain across the tissue. FIG. 18A illustrates an adjunct 1020 having a central region 1022 and a wing region 1024, both regions being formed from a plurality of layers. As in the previous embodiments, the central region 1022 can have a substantially rectangular shape. A top layer of material can define the central region 1022 and both regions 1022, 1024 can be formed from a plurality of layers. The central region 1022 can have a substantially rectangular shape, but can be shaped in other ways. As shown in FIG. 18A, a top layer of material 1026t can define the central region and can be formed from a flexible material, such as PDS®, PGA, Neoveil®, ORC or other polymers and biologically derived material constructs or combinations disclosed herein. Material geometry and structure (material thickness, fiber orientation, polymer chain orientation, hole patterns, etc.) may be used to create desired isotropic or anisotropic deformation characteristics. A bottom layer of material 1026b can also be substantially flexible, and in certain aspects can have a greater flexibility than the top layer 1026t. The bottom layer 1026b can have a shape that corresponds to a shape of the top layer 1026t, and is shown having a substantially rectangular shape. The bottom layer 1026b can have a larger surface area than the top layer 1026t such that the bottom layer 1026b extends beyond lateral edges of the top layer 1026t. As shown, lateral edges of the bottom layer 1026b can be scalloped, having a plurality of semicircular protrusions 1028 along the wing portion 1024. These semicircular protrusions can be spaced at equal distances apart along the edges, or can be spaced in groups of two, three, four, and the groups of protrusions can be disposed at equal distances apart along the edge. When the adjunct 1020 is stapled to tissue, the top layer 1026*t* of material 1026*t* will be positioned away from and will not directly contact the tissue, while the bottom layer 1026*b* will directly contact tissue. Additionally, the protrusions can be positioned away from the staple rows and can distribute a strain across the tissue T to prevent formation of leaks. The bottom layer 1062*b* may be formed from a flexible material, such as PDS®, PGA, Neoveil®, ORC or other polymers and biologically derived material constructs or combinations disclosed herein. Material geometry and structure (material thickness, fiber orientation, polymer chain orientation, hole patterns, etc.) may be used to create desired isotropic or anisotropic deformation characteristics. In an embodiment, at least one of top layer 1062*t* and bottom layer 1062*b* is at least partially comprised of PDS® to aid in attachment of adjacent layers. In an embodiment, both the top layer 1062*t* and bottom layer 1062*b* are created from absorbable materials.

The adjunct material can be constructed in various ways. For example, the adjunct material can be formed from a continuous material. That is, as shown in FIG. 18B, the adjunct 1020 can include a single layer with the central region 1022 and the wing portion 1024 having the plurality of protrusions 1024 for distributing a strain. In other aspects, the adjunct can include more than two layers of material. For example, one or more intermediate layers of material (not shown) can be positioned between the top layer and the bottom layer and can be more rigid than the top and bottom layers. The layers can be coupled together using known manufacturing techniques, such as lamination, adhesive, etc. The protrusions 1028 on the wing portion 1024 of the adjunct can also be formed using known manufacturing techniques, such as laser cutting, stamping, punching, etc.

Figure 19:
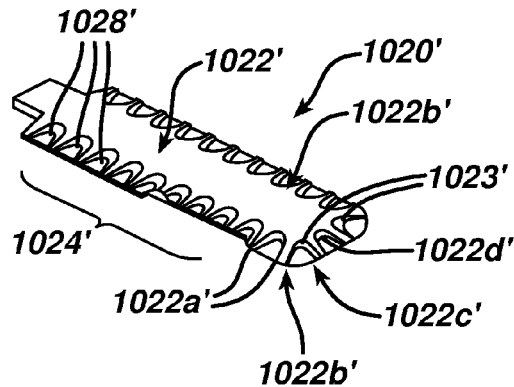
FIG. 19 is a perspective view of an adjunct material including an outer region with a plurality of cuts formed therein.

Another exemplary adjunct is shown in FIG. 19 and includes a wing region having a varied geometry. As shown, an adjunct 1020' can have a wing region 1024' extending around a perimeter of the central region 1022' and can have a plurality of surface features 1028' formed therein and spaced evenly along the wing region 1024'. The surface features 1028' can be generally shaped as a boomerang and can include an elbow 1023' and first and second arms 1025', 1027' extending therefrom. As shown in FIG. 19, the elbow 1023' can be positioned along edges 1022*a'*, 1022*b'*, 1022*c'* of the central region 1022' while terminal ends 1025*t'*, 1027*t'* of the arms 1025', 1027' can be positioned at an outer edge of the wing region 1024'. In this way, a thickness of the wing region 1024' in a direction transverse to a longitudinal axis of the central region 1022' can vary and a thickness of the wing region 1024' in a direction parallel to the longitudinal axis of the central region 1022' can also vary. These surface features 1028' can be formed by removing a portion of the adjunct material 1020' using known manufacturing techniques, such as laser cutting, stamping, punching, etc.

Figure 20A:
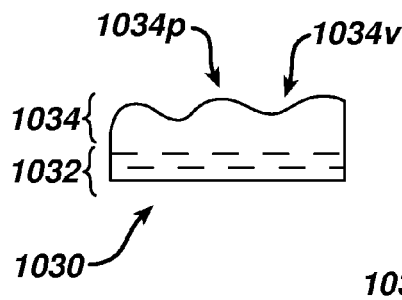
FIGS. 20A-20C are side views of adjunct material having modified outer regions.
Figure 20B:
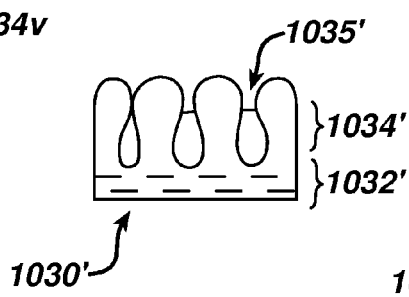
Figure 20C:
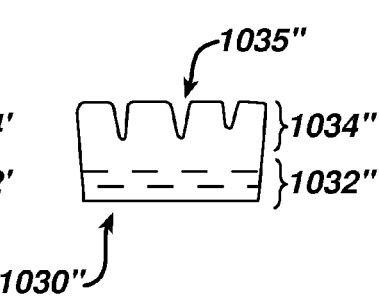
Figure 20D:
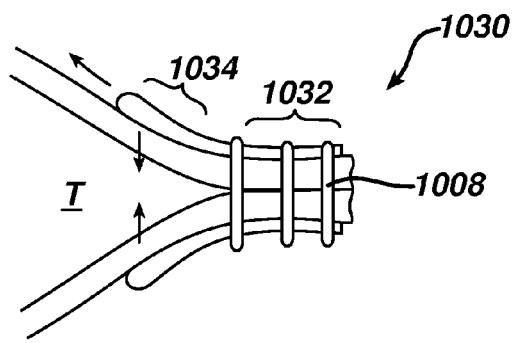
FIG. 20D is a side, cross-sectional view of adjunct material stapled to a body lumen.

FIGS. 20A-20C illustrate adjunct material including wing portions with modified edges. For example, a wing portion 1034 of an adjunct 1030 of FIG. 20A can have an outer edge in the shape of a sine wave with peaks 1034*p* and valleys 1034*v* along its length so that the wing portion 1034 is atraumatic and does not increase a likelihood of forming leaks in tissue. A wing portion 1034' of FIG. 20B includes a first material 1036' forming a central region 1032' and the wing portion 1034', the wing portion 1034' having curved edges which loop around and extend toward the central region 1032', and back toward the edge forming an oblong opening 1035'. In certain aspects, a second material 1038' is disposed in the oblong, teardrop shaped openings 1035', such as by being laminated to the first material 1036' to form the adjunct 1030'. A thickness of this second material 1038' can vary from a thickness of the first material 1036'. For example, the thickness of the second material 1038' can be less than the thickness of the first material 1036', as shown. A wing portion 1034" of FIG. 20C can have a plurality of openings 1035" formed therein, such as triangular shaped openings, that can form protrusions 1038" similar to those protrusions 1028 shown in FIG. 18B, but the protrusions 1038" can have corners rather than rounded edges. The adjuncts 1030, 1030', 1030" of FIGS. 20A-20C can be formed from different materials, such as any flexible or stretchable polymer material described herein. In use, any one of the adjuncts 1030, 1030', 1030" can be stapled to tissue and any of the respective wing portions can extend beyond the staple line. A shown in FIG. 20D, the adjunct 1030 can be stapled to tissue T and the wing portion 1034 can be positioned outside of the staples 1008 which form a staple line and the central portion 1032 can be positioned inside of the staple line. In certain aspects, as the tissue expands and contracts, the adjuncts can stretch or flex in a direction transverse to the staple rows or can be configured to stretch in multiple directions, such as along an outer surface of the tissue T as shown. A person skilled in the art will appreciate that the edges of the wing portions can be shaped in other ways than the illustrated embodiments.

Figure 21A:
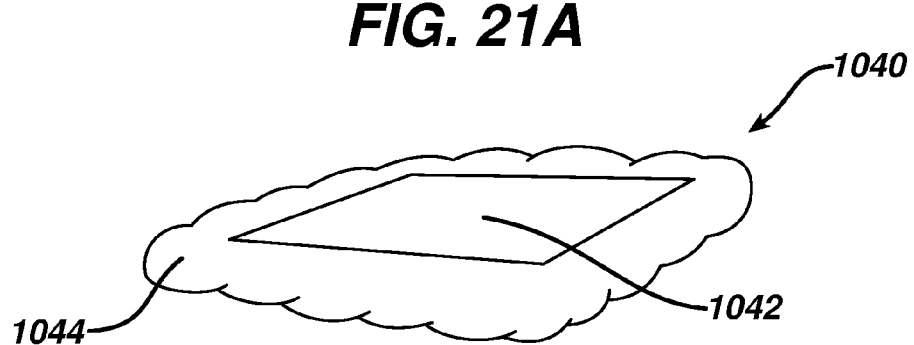
FIG. 21A is a perspective view of adjunct material having first and second layers and woven, atraumatic edges.
Figure 21B:
FIG. 21B is a side view of the adjunct material of FIG. 21A showing the first and second layers.
Figure 21C:
FIG. 21C is a side view of the adjunct material of FIG. 21A absorbing fluid in between the first and second layers.

FIGS. 21A-21C illustrate another embodiment of adjunct material including a wing portion with modified edges. As shown in FIG. 21A, an adjunct material 1040 can be woven. A central region 1042 of the adjunct 1040 can be formed from a woven material of higher density than a woven material at a wing portion 1044 of the adjunct 1040. In other aspects, a less dense woven material can encase a denser woven material on all sides, as shown in FIG. 21B. In both embodiments, the wing portion 1044 can have soft, atraumatic edges 1046 that have a decreased likelihood of puncturing or otherwise damaging the tissue and causing holes to form therein. The adjunct 1040 can be configured to wick and/or absorb liquid therein. For example, in the embodiment of FIG. 21C, a top layer 1048*t'* of material of an adjunct 1040' is shown positioned over a bottom layer of material 1048*b'*, liquid 1047' being wicked through the top layer of material and into a space between the top and bottom layers 1048*b'*, 1048*t'*. These adjunct materials can be formed from various woven materials known in the art, such as ETHISORB® (Ethicon, Inc., Somerville, N.J.). In one embodiment, central region 1042 may be a film comprised of solid, but deformable absorbable material.

Figure 22A:
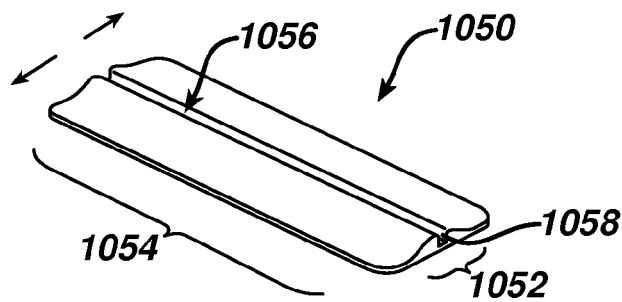
FIG. 22A is a perspective view of adjunct material having a variable thickness in a lateral direction.
Figure 22B:
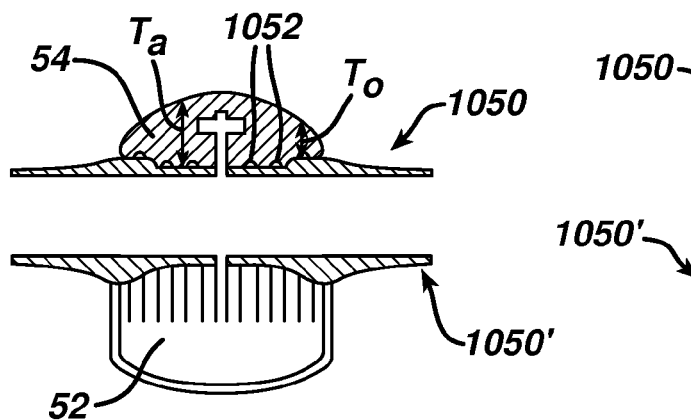
FIG. 22B is an end view of an anvil and cartridge assembly and two variable thickness adjuncts, a first adjunct material associated with the anvil and a second adjunct material associated with the cartridge assembly.
Figure 22C:
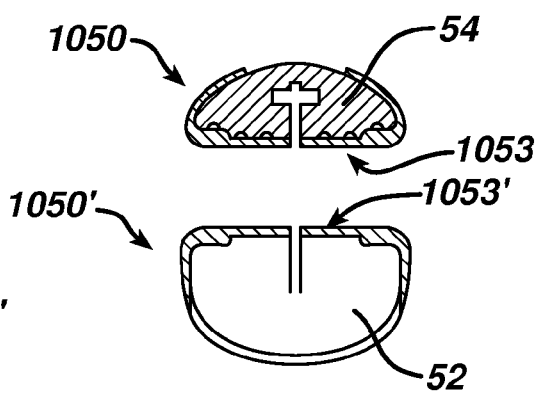
FIG. 22C is an end view of the anvil and cartridge assembly of FIG. 22B having the first and second adjunct materials coupled thereto.
Figure 22D:
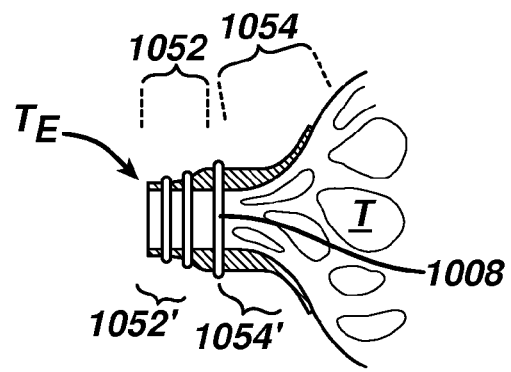
FIG. 22D is a side view of the first and second adjunct material stapled to tissue.

An adjunct material for use with a stapler that deploys variable thickness staples is shown in FIGS. 22A-22D. As shown, a thickness of an adjunct 1050 can vary from a central axis 1056 to an outer edge of the adjunct 1050 in a lateral direction indicated by arrows. That is, the adjunct 1050 can have a decreasing/tapering thickness from the central axis 1056 of the adjunct 1050 to the outer edge thereof in the lateral direction. As in the previous embodiments, the adjunct material 1050 can include a central region 1052 and wing portion 1054. The adjunct 1050 can include an elongate slot 1058 formed along the central axis 1056 of the adjunct 1050 and having a size and shape that corresponds to a size and shape of a cutting member (not shown). In the illustrated embodiment, the elongate slot 1058 has a substantially rectangular shape. FIGS. 22B and 22C provide end views of a cartridge assembly 52 and an anvil 54 having a varying thickness in a lateral direction such that the stapler 10 can deploy staples (not shown) of varying heights. As shown, a thickness TO of the anvil 54 near the cutting member slot can be greater than a thickness TE of the anvil 54 near its lateral edge. The adjunct 1050 can be coupled to the cartridge assembly 52 and/or to the anvil 54 with at least the central region 1052 of the adjunct 1050 directly contacting the tissue-contacting surface 60, 58 of the cartridge assembly 52/anvil 54. The tissue-contacting surface 58 of the anvil 54 can include one or more mating points 1057 attaching the adjunct 1050 to the anvil 54, as shown. The wing portion 1054 of the adjunct 1050 can be folded around the cartridge assembly 52 and/or the anvil 54 and attached thereto, as will be described in greater detail below. In this way, a tissue-contacting surface 1053 of the first adjunct 1050 can be substantially planar and can be disposed parallel to a tissue contacting surface 1053' of the second adjunct 1050' disposed on the cartridge assembly 52. When the adjuncts 1050, 1050' are stapled onto tissue, as shown in FIG. 22D, the wing portion of the adjunct 1050 can be disposed between the staples 1008 and extend toward a cut terminal end TE of the tissue T, while a second portion of the adjunct 1050 can extend away from the cut terminal end TE of the tissue T and distribute strain to the tissue T, similar to the wing portions described above. The adjunct 1050' can have similarly positioned portions 1052', 1054', as shown.

Figure 23A:
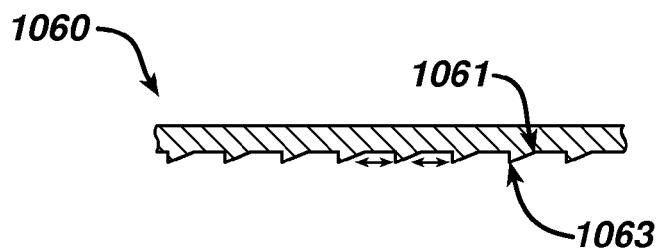
FIG. 23A is a side view of an adjunct material having surface features formed thereon for penetrating and gripping into tissue.
Figure 23B:
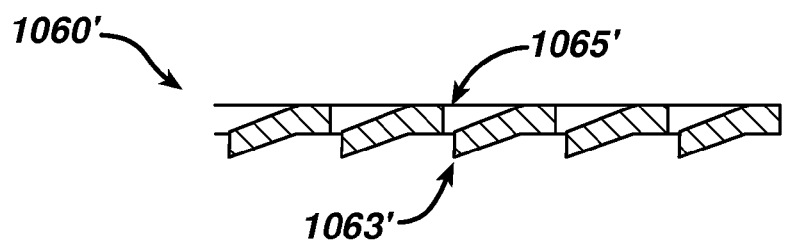
FIG. 23B is a side view of another adjunct material having surface features for penetrating and gripping into tissue.
Figure 23C:
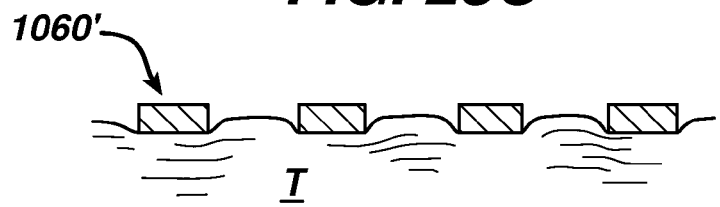
FIG. 23C is an end view of four rows of adjunct material, each row of adjunct material having a surface feature locked in a tissue.
Figure 23D:
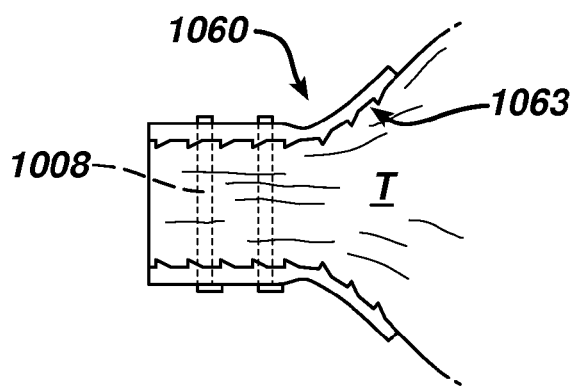
FIG. 23D is a side view of an adjunct material having surface features penetrated into tissue.
Figure 24A:
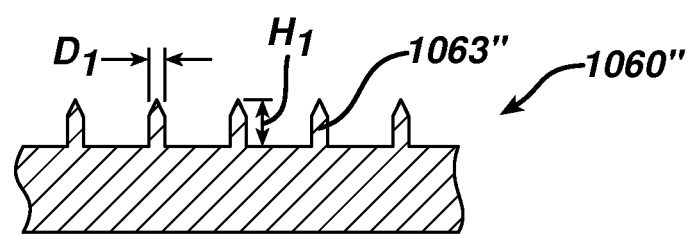
FIG. 24A is a side view of another exemplary adjunct material having a plurality of pointed surface features for penetrating into tissue.
Figure 24B:
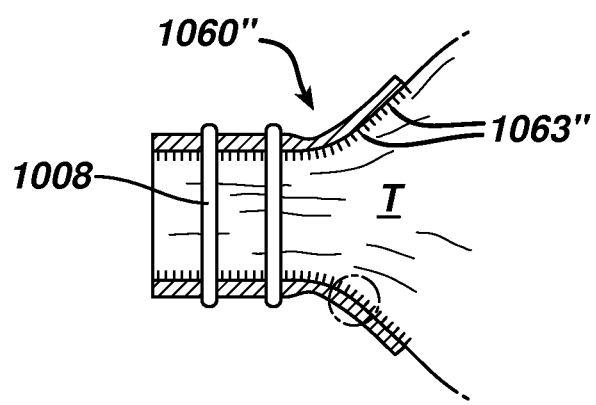
FIG. 24B is a side view of the adjunct material of FIG. 24A having the pointed surface features piercing into tissue.

Any of the adjunct materials can include various features for increasing friction between the adjunct material and the tissue to ensure that the adjunct material remains in a desired position. For example, adjuncts 1060, 1060' in FIGS. 23A and 23B include a plurality of teeth 1061, 1061' formed on a tissue-contacting surface thereof and terminating in points 1063, 1063' that can penetrate into tissue. As shown, the plurality of teeth 1061, 1061' can be spaced at equal distances apart in the lateral direction of the adjunct 1060, 1060'. The teeth 1061, 1061' can be formed in the adjunct 1060, 1060' using various known manufacturing techniques, such as via compression molding, cut/stamping, punching, etc. For example, the adjunct 1060 of FIG. 23A can be compression molded while the adjunct 1060' of FIG. 23B can be formed from stamping slits 1065' into material to form the teeth 1061'. The gaps between the teeth 1061, 1061' can push into tissue T and create a lock that prevents sliding of the adjunct 1060, 1060', as in FIG. 23C which illustrates multiple rows of adjuncts 1060'. In another embodiment shown in FIG. 24A, the adjunct 1060" can include a plurality of micropillars 1063" formed on a tissue-contacting surface thereof, the micropillars 1063" being shaped as needles configured to penetrate into tissue T. The teeth 1063 and/or micropillars 1063" can directly penetrate into the tissue T as shown in FIGS. 23D and 24B and can thereby prevent the adjunct 1060, 1060" from sliding relative to the staples 1008 as the tissue T expands and contracts. In certain aspects, the micropillars 1063" can have a diameter D1 in the range of about 0.01 to 0.50 mm and a height H1 in the range of about 0.05 to 0.50 mm.

Figure 25A:
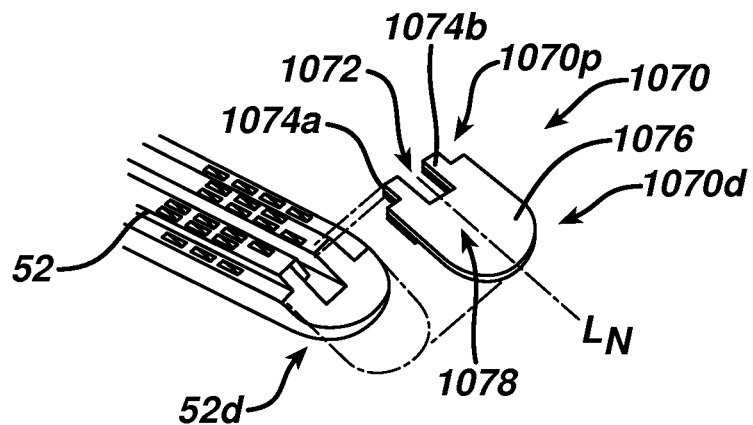
FIG. 25A is a perspective view of a cartridge assembly having an adjunct material for detachable coupling to a distal end of the cartridge assembly.
Figure 25B:
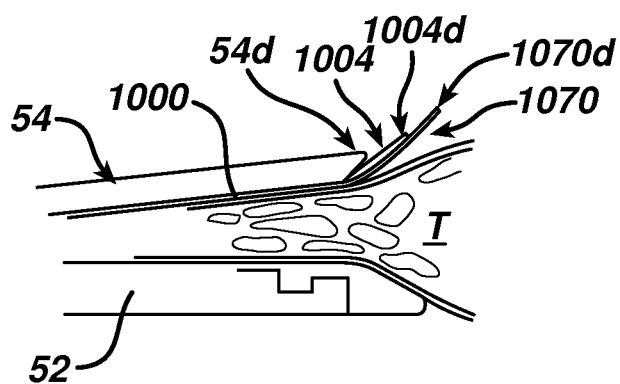
FIG. 25B is a side view of the cartridge assembly and an anvil of a surgical stapler grasping tissue with the adjunct material of FIG. 25A extending beyond a distal end of the cartridge assembly.
Figure 25C:
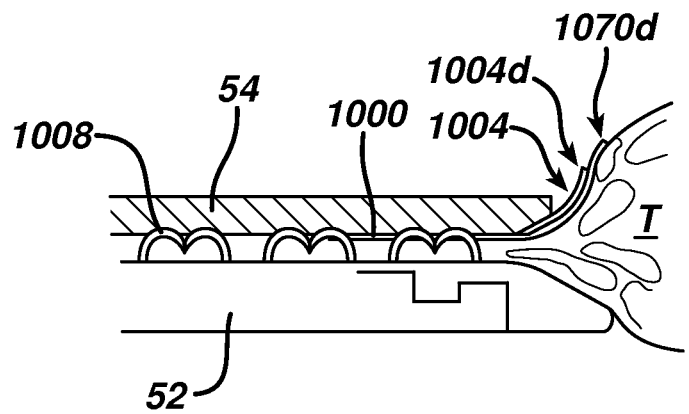
FIG. 25C is a side view of the cartridge assembly and the anvil of FIG. 25B deploying staples through the adjunct material and the tissue.

Another embodiment of an adjunct material is shown in FIGS. 25A-25C. In this embodiment, an adjunct material such as the adjunct 1000 of FIGS. 16A and 16B is used in conjunction with a nose extension member 1070 that can be coupled to an anvil 54 and/or a cartridge assembly 52 of a surgical stapler 10. As shown in FIG. 25A, a distal end 1004d of the adjunct 1000, that is, the distal end 1004d of the wing portion 1004 can terminate at or proximal to a distal-most end 52d of the cartridge assembly 52. As shown in FIG. 25B, a distal end 1004d of the adjunct 1000, that is, the distal end 1004d of the wing portion 1004 can terminate at or proximal to a distal-most end 54d of the anvil 54. The nose extension member 1070 can be added onto the cartridge assembly 52 and/or the anvil 54 to replace or supplement a distal portion of the adjunct material 1000. A proximal end 1070p of the nose extension member 1070 can have a cutout 1072 formed therein and sized so as to not obstruct or cover a slot formed in the anvil 54 for receiving a cutting member (not shown). The cutout 1072 can define first and second extension arms 1074a, 1074b which can be releasably coupled to the distal end 54d of the anvil 54 along a curved portion of the anvil 54 that is distal to the anvil's 54 tissue contacting surface in various ways, such as using an adhesive. A distal-most end 1070d of the nose extension member 1070 can be substantially rounded. A mechanism for releasing a distal portion 1076 of the nose extension 1070 from the proximal end 1070p of the nose extension 1070 can also be provided. In certain aspects, this releasing mechanism can consist of a perforation 1078 extending transverse to a longitudinal axis LN of the nose extension member 1070. In use, an adjunct 1000 can be positioned on the anvil 54 and the nose extension member 1070 can also be coupled to the anvil 54. The anvil 54 and cartridge assembly 52 can grasp tissue T therebetween, and a portion of the adjunct 1000 can extend distally beyond the nose extension member 1070, as shown in FIG. 25B. That is, the distal end 1070d of the nose extension member 1070 can be positioned distal to the distal end 1004d of the adjunct 1000. The anvil 54 and the cartridge assembly 52 can deploy staples 1008 through the tissue T and through the adjunct 1000, while the wing region 1004 of the adjunct 1000 does not include staples 1008 extending therethrough. The wing region 1004 of the adjunct 1000 can directly contact the tissue T and the nose extension member 1070 can be positioned above the wing region 1004. In certain aspects, the nose extension member 1070 can be a semi-flexible material and can be used in conjunction with the adjunct 1000 to help relieve a strain on tissue T and/or provide strength to the adjunct 1000. In use, the distal end of the nose extension member 1070 can be removed from the anvil 54 and/or the cartridge prior to, during, and/or after the tissue T is stapled.

While features of the adjunct described above were illustrated as separate embodiments, an adjunct can have any combination of features described above.

Mechanisms for Attaching and Releasing Adjuncts from an End Effector

Figure 26A:
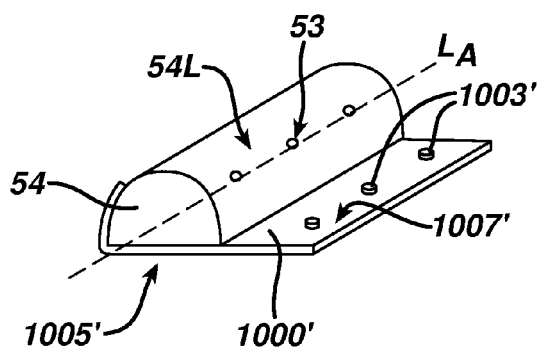
FIG. 26A is a perspective view of adjunct material having protrusions configured to mate with corresponding depressions formed in a cartridge assembly.
Figure 26B:
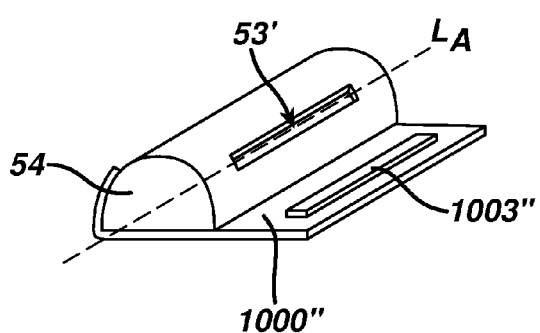
FIG. 26B is a perspective view of adjunct material having a single protrusion configured to mate with a corresponding depression formed in a cartridge assembly.

Various mechanisms can be used to attach and then release an adjunct having wings from an end effector, e.g. a cartridge assembly 52 or an anvil 54. While the embodiments described below include features formed on an anvil 54, any of these features can be formed on a cartridge assembly 52 for mating an adjunct to the cartridge assembly 52. FIGS. 26A-26B illustrate adjunct material 1000', 1000" having mating features keyed to corresponding mating features formed on an anvil 54. More specifically, FIG. 26A shows an adjunct 1000' having a plurality of cylindrical protrusions 1003' formed on a surface 1007' that is oriented away from a tissue contacting surface 1005' of the adjunct 1000'. While FIG. 26A illustrates three cylindrical protrusions 1003' spaced apart along an axis parallel to a longitudinal axis LA of the anvil 54, any number of protrusions 1003' can be formed at various locations along the adjunct 1000'. A lateral surface 54L of the anvil 54 can have a plurality of depressions 53 configured to receive the plurality of protrusions 1003' from the adjunct 1000' therein. In one embodiment, a height (not shown) of the cylindrical protrusions 1003' can vary, and can be in the range of about 0.25 to 1.00 mm, the height measured perpendicular to the surface 1007' of the adjunct 1000'. The protrusions 1003' formed on the adjunct 1000' can have other sizes and shapes. As shown in FIG. 26B, in another embodiment, an adjunct 1000" can have a single elongate rectangular protrusion 1003" extending parallel to the longitudinal axis LA of the anvil 54. A lateral surface of the anvil 54 can also include a corresponding elongate rectangular depression 53' for receiving the rectangular protrusion 1003" therein when the adjunct 1000" is folded around the anvil 54. A height (not shown) of the rectangular protrusion 1003" can also vary, but can be in substantially the same range as the height of the cylindrical protrusions 1003' described above. While only a first lateral surface 54L of the anvil 54 is shown in FIGS. 26A and 26B, a person skilled in the art will appreciate that identical protrusion(s) can be formed on a second lateral surface (not shown) of the anvil 54. Similarly, identical depression(s) can be formed on a second lateral surface (not shown) of the adjuncts 1000', 1000".

Figure 27A:
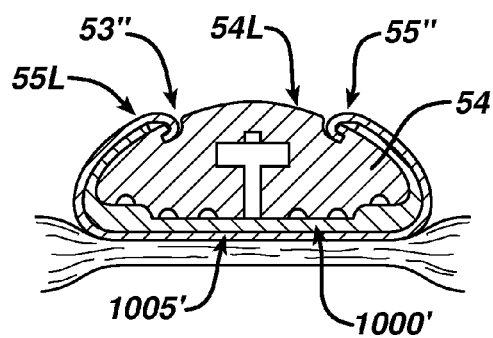
FIG. 27A is an end view of an adjunct material extending around a cartridge assembly and having first and second lateral edges coupled to the cartridge assembly.
Figure 27B:
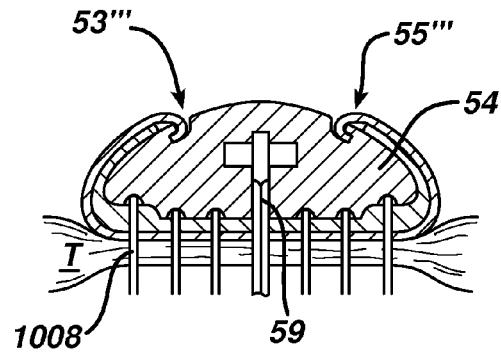
FIG. 27B is an end view of the adjunct material and the cartridge assembly of FIGS. 27A and a cutting member being advanced through the cartridge assembly to release the adjunct material from the cartridge assembly.
Figure 28A:
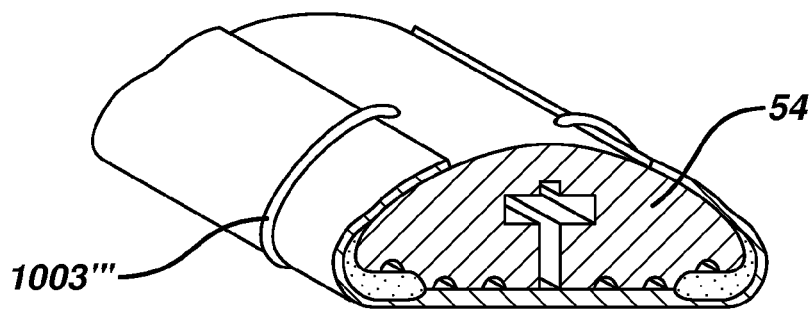
FIG. 28A is a perspective view of a cartridge assembly including suture coupling an adjunct material to the cartridge assembly.
Figure 28B:
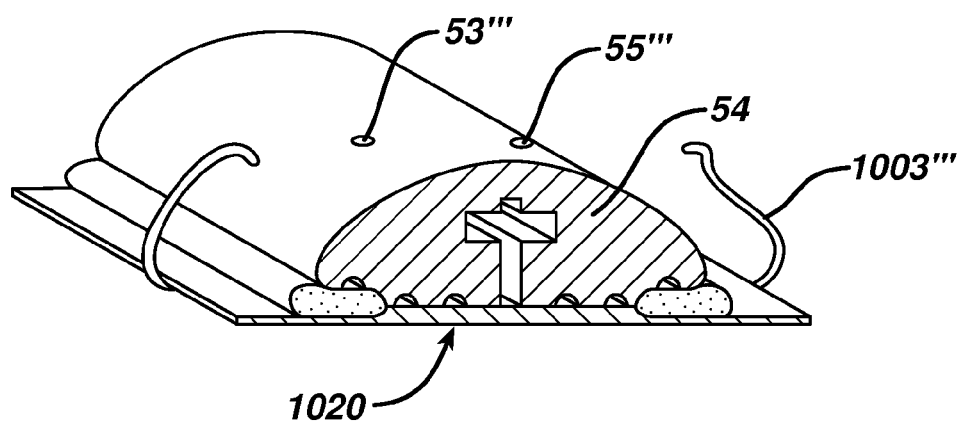
FIG. 28B is a perspective view of the cartridge assembly and adjunct material of FIG. 28A, the suture detached from the cartridge assembly to release the adjunct material.

An adjunct can be coupled to an anvil/cartridge assembly in other ways. As shown in FIGS. 27A and 27B, a strand of suture 1003''' can couple the adjunct to the anvil 54. The suture 1003''' can extend from the first lateral surface 54L of the anvil 54, across a tissue-contacting surface of the adjunct, and to the second lateral surface 55L of the anvil 54. First and second depressions 53''', 55''' can be formed in the first and second lateral surfaces of the anvil 54, and a first terminal end of the suture 1003''' can be received in the first depression 53''' and a second terminal end can be received in the second depression 55'''. A length of the suture 1003''' and/or a size of the depressions 53''', 55''' can be selected so that the suture 1003''' is taught when the terminal ends of the suture 1003''' are positioned within the depressions 53''', 55'''. As a cutting member 59 advances through the anvil 54 during and/or after the staples 1008 are deployed into the tissue T, as shown in FIG. 27B, the cutting member 59 can sever the suture 1003''', causing the terminal ends of the suture 1003''' to slide out of the depressions 53''', 55''' and thereby releasing the adjunct from the anvil. FIGS. 28A and 28B illustrate the strand of suture 1003''' extending around an anvil 54 and coupling a multi-layer adjunct 1020 to the anvil 54. As in the previous embodiment, advancement of the cutting member (not shown) relative to the anvil 54 can sever the suture 1003''' and release the suture 1003''' from the depressions 53''', 55''' in the anvil 54 to release the adjunct 1020. As will be appreciated by a person skilled in the art, any number of strands of suture can be used to couple the adjunct to one of the cartridge assembly 52 and the anvil 54 and the depressions formed therein can vary so long as they are configured to receive a portion of the suture therein.

Figure 29A:
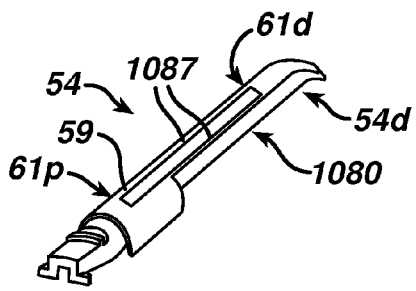
FIG. 29A is a perspective view of a shaft of a surgical stapler including an adjunct material coupled thereto.
Figure 29B:
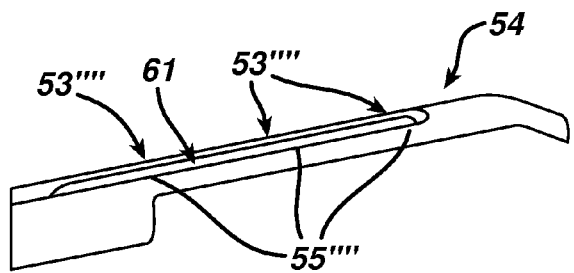
FIG. 29B is a side view of the shaft of FIG. 29A showing attachment points for attaching the adjunct material to the shaft.
Figure 29C:
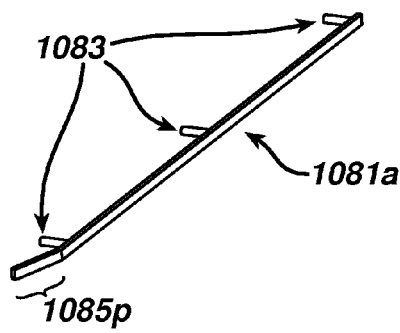
FIG. 29C is a perspective view of a driver insertable within the shaft and having a plurality of lateral extension portions.
Figure 29D:
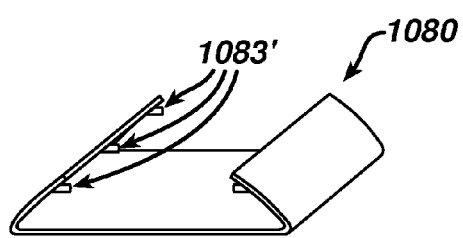
FIG. 29D is a perspective view of adjunct material for attaching to the shaft.
Figure 29E:
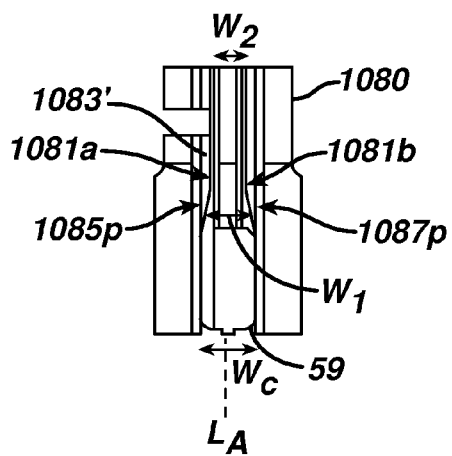
FIG. 29E is a partial top view of the shaft of FIG. 29A with a cutting member of the stapler in a first, retracted position.
Figure 29F:
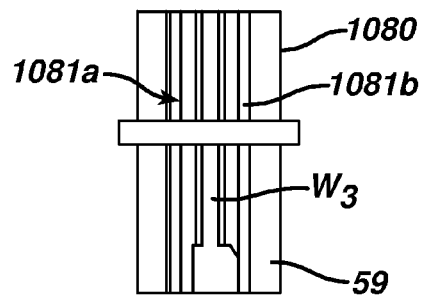
FIG. 29F is a partial top view of the shaft of FIG. 29A with the cutting member in a second, advanced position that releases the adjunct material from the shaft.

FIGS. 29A-29B illustrate other mechanisms for attaching an adjunct to an anvil/cartridge assembly. In this embodiment, the anvil 54 of a surgical stapler 10 includes a cutting member 59 that can advance within the slot 61, referred to as a longitudinal track, and can move between proximal and distal ends 61p, 61d of the track 61. A driver 1081 including first and second elongate members (not shown) can be disposed in the longitudinal track 61, as in FIG. 29B. Three cylindrical protrusions (not shown) extend from the elongate members and into depressions 53"", 55"" formed in both lateral surfaces of the anvil 54, but there can be any number of protrusions spaced along the driver and having various other shapes. As shown in FIG. 29C, a first driver 1081a can be generally elongate and can have a plurality of protrusions 1083, such as three protrusions 1083, oriented transverse to a longitudinal axis of the driver, the protrusions 1083 being cylindrical shaped. A wing portion 1084 of an adjunct material 1080 can be disposed around a lateral surface of the anvil 54 and can include a plurality of protrusions 1083' oriented transverse to the longitudinal axis LA of the anvil 54 when the adjunct material 1080 is coupled thereto. As shown in FIG. 29D, the adjunct material 1080 can have a first set of protrusions 1083' for mating with the first lateral surface of the anvil 54 and a second set of protrusions 1083" for mating with the second lateral surface of the anvil 54. Prior to use, the first driver 1081a can be positioned on a first lateral wall of the track 61 and the second driver 1081b can be positioned on a second lateral wall of the track 61. A proximal end of each driver 1081a, 1081b can have an angled portion 1085p, 1087p such that when the drivers 1081a, 1081b are disposed in the track 61, a width W1 between the drivers 1081a, 1081b at a proximal end of the track 61 is greater than a width W2 between the drivers 1081a, 1081b at and/or distal to the protrusions 1083', the width being measured transverse to the longitudinal axis LA of the anvil 54 as shown in FIG. 29E. Additionally, the width W2 between the drivers 1081a, 1081b distal to the proximal end 61p of the track 61 can be less than a width WC of the cutting member 59. In this way, the cutting member 59 can be advanced toward the distal end 54d of the anvil 54 and can increase a width between the drivers 1081a, 1081b and the protrusions 1083 can push the corresponding protrusions 1083' on the adjunct 1080 off of and away from the anvil as in FIG. 29F, thereby releasing the adjunct from the anvil 54. In certain aspects, the adjunct 1080 can be biased to a flattened, substantially planar configuration such that when the cutting member 59 advances within the track 61 and exerts a force on the drivers 1081a, 1081b, the adjunct 1080 is more able to release from the anvil 54.

Figure 30A:
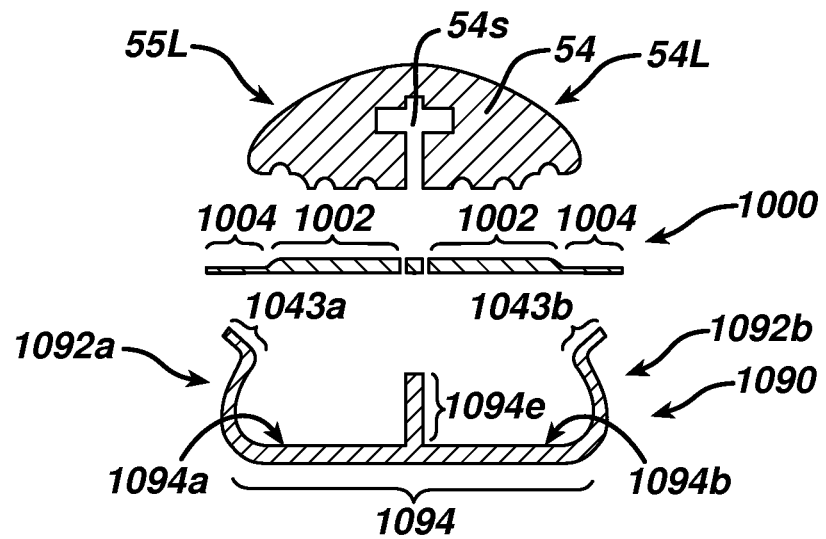
FIG. 30A is an end view of a cartridge assembly, an adjunct material, and an insertion tool for attaching the adjunct material to the cartridge assembly.
Figure 30B:
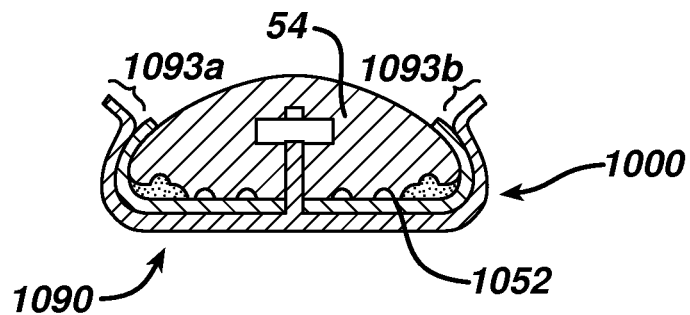
FIG. 30B is an end view of the insertion tool pressing the adjunct material onto the cartridge assembly of FIG. 30A.
Figure 30C:
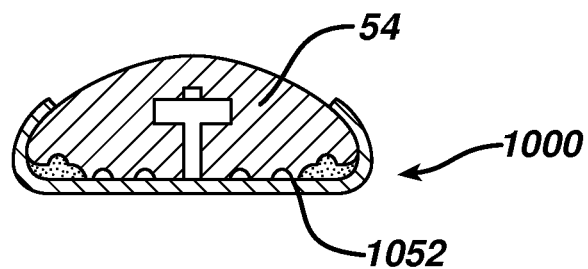
FIG. 30C is an end view of the cartridge assembly of FIG. 30A having the adjunct material attached thereto and after the insertion tool has been removed from the cartridge assembly.

A loading mechanism for loading an adjunct onto an anvil/cartridge assembly is shown in FIGS. 30A-30B. A loading mechanism 1090 can have various sizes, shapes, and configurations, and can include a first curved arm 1092a and a second curved arm 1092b having a radius of curvature that corresponds to a radius of curvature of the first and second lateral surfaces 54L, 55L of the anvil 54 and the arms 1092a, 1092b can terminate in angled features 1093a, 1093b that can be grasped by a user. The loading mechanism 1090 can have a planar base 1094 from which each of the first and second curved arms 1092a, 1092b extend. The base 1094 of the loading mechanism 1090 can further include a track extension 1094e extending perpendicular to the base 1094 and disposed along a central longitudinal axis of the loading mechanism 1090 for insertion into the cutting member slot 54s in the anvil 54, as shown in FIG. 30B. A first inner surface 1094a of the loading mechanism 1090 can be defined by the first curved arm 1092a and a first portion of the base 1094 from the first arm 1092a to the track extension, as shown in FIG. 30A Likewise, a second inner surface 1094b of the loading mechanism 1090 can be defined by the second curved arm 1092b and a second portion of the base 1094 from the second arm 1092b to the track extension 1094e. In this way, the loading mechanism 1090 can be generally E-shaped for receiving the anvil 54. An adjunct 1000 having a central region 1002 and a wing region 1004 can be positioned and sandwiched between inner surfaces of the loading mechanism 1090 and the tissue-contacting surface of the anvil 54, as in FIG. 30B, the loading mechanism 1090 clamping onto the anvil 54 as shown. The track extension 1094e can facilitate achieving a tight fit between the loading mechanism 1090, the adjunct 1000, and the anvil 54 with substantially no gaps between. After the adjunct 1000 is coupled to the anvil 54, such as using any attachment mechanisms described herein, such as attachment mechanisms 1052, the loading mechanism 1090 can be removed from the anvil 54. This can be accomplished, for example, by pressing the angled features 1093a, 1093b of the curved arms away 1092a, 1092b from one another, leaving the anvil 54 loaded with the adjunct 1000 as in FIG. 30C.

Figure 31A:
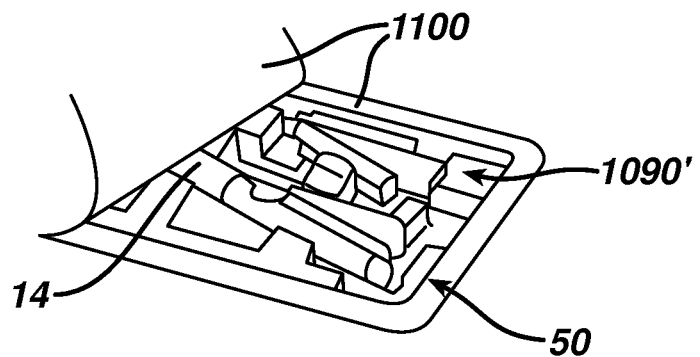
FIG. 31A is an exemplary kit including a retaining tool and a surgical stapler, the retaining tool being configured for wrapping the adjunct material around a cartridge assembly/anvil.
Figure 31B:
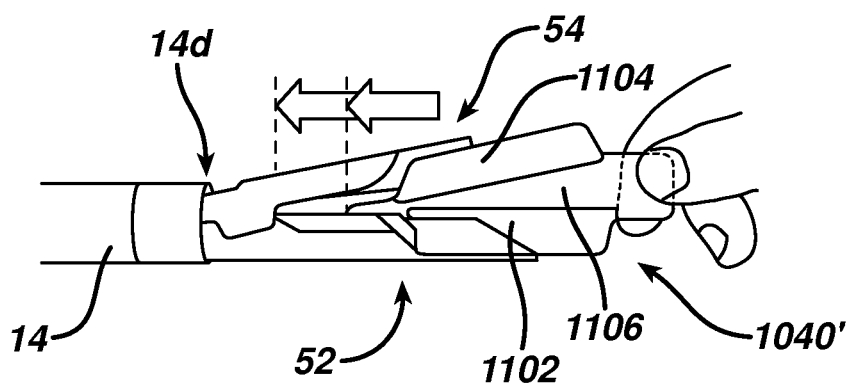
FIG. 31B is a side view of the retaining tool of FIG. 31A being advanced proximally along a longitudinal axis of the anvil and the cartridge assembly.
Figure 31C:
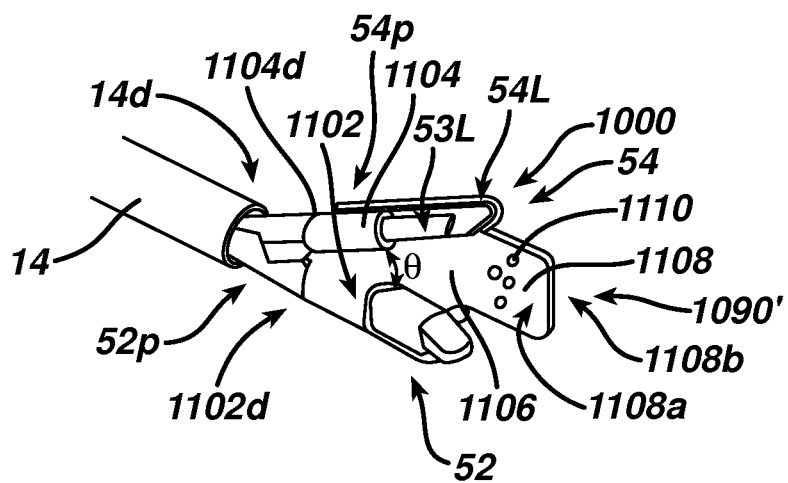
FIG. 31C is a perspective view of the retaining tool and stapler of FIG. 31A, the retaining tool being in a proximal most position.

Another exemplary loading mechanism is shown in FIGS. 31A-31C. A loading mechanism 1090' can be packaged as a kit along with an end effector of a stapler. Alternatively, loading mechanism 1090' may be packaged separately. As in FIG. 31A, the anvil 54 and cartridge assembly 52 of the end effector 50 can include an adjunct material 1000 preloaded thereon or in another non-illustrated embodiment, the adjunct material 1000 can be fixed to the anvil 54 and the cartridge assembly 52 after being removed from packaging 1100. This loading mechanism 1090' can be configured to wrap the wing portion 1004 of the adjunct 1000 around the lateral surfaces 54L, 53L of the anvil/cartridge assembly 54, 52 such that the wing portion is passively coupled to the anvil/cartridge assembly 54, 52. As shown in FIG. 31B, the loading mechanism 1090' can be configured to contact the central region (not shown) of the adjunct 1000 against the tissue-contacting surface of the anvil/cartridge assembly 54, 52 and, if needed, can be configured to shape the wing portion (not shown) around the anvil 54. The loading mechanism 1090' can be formed of a single molded material having an upper retaining portion 1104 and a lower retaining portion 1102, the retaining portions having a channel (not shown) sized and shaped for receiving the anvil/cartridge assembly 54, 52 therein. A shape of the channel can be substantially similar to the shape of the loading mechanism 1090 previously described and can include any of the same features, such as the track extension. The upper and lower retaining portions 1104, 1102 can be disposed at an angle θL relative to one another, the angle being in the range of about 10 to 40 degrees. A support member 1106 can extend between a lower surface of the upper retaining portion 1104 and an upper surface of the lower retaining portion 1102 such that the angle θL between the retaining portions 1102, 1104 is fixed. The support member 1106 can be a substantially solid member, as shown, so as to provide rigidity to the loading mechanism 1090'. A first end of the support member 1106 can terminate in a grasping feature 1108, and the grasping feature 1108 can have first and second planar surfaces 1108a, 1108b configured to be grasped by a user, such as between a thumb and finger of a user. The grasping feature 1108 can further include one or more surface features 1110 for increasing friction between a user's fingers. A longitudinal axis of the grasping feature 1108 can be oriented perpendicular to a longitudinal axis of the stapler 10 or can be parallel to the longitudinal axis of the stapler 10. In use, a user can grasp the grasping feature 1108 and position distal ends 1102d, 1104d of the retaining portions adjacent to proximal ends ends 52p, 54p of the cartridge assembly 52 and the anvil 54. A user can advance the distal end of the loading mechanism 1090' toward the proximal end of the end effector 50, as shown in FIG. 31B, and the retaining portions 1102, 1104 can slide along the anvil/cartridge assembly 54, 52 and force the adjunct material 1000 around the lateral surfaces thereof, as shown in FIG. 31C. This can temporarily secure the wing region 1004 along the lateral surfaces of the cartridge assembly 52 and the anvil 54. With the wing region 1004 so positioned, a user can retract the loading mechanism 1090' in the opposite direction, distally away from the end effector 50, leaving the end effector 50 prepared for insertion into a patient. While reference is made to a single adjunct material 1000 loaded onto the anvil 54, adjunct material 1000' can similar be loaded onto the cartridge assembly 52. The adjunct material 1000, such as the material shown in FIGS. 31A-31C, can be a shape memory material such that the adjunct 1000 is biased to a substantially straightened configuration. That is, when the end effector 50 is positioned inside of the patient, the wing regions can automatically move back to the substantially straightened configuration prior to being deployed off of the end effector 50 and onto tissue.

Delivering Adjuncts into a Patient

Figure 32A:
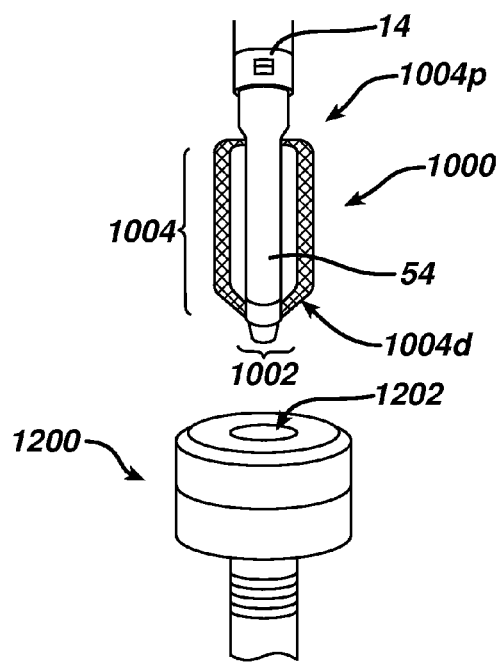
FIG. 32A is a perspective view of an end effector of a stapler having an adjunct material coupled thereto and positioned above a trocar.
Figure 32B:
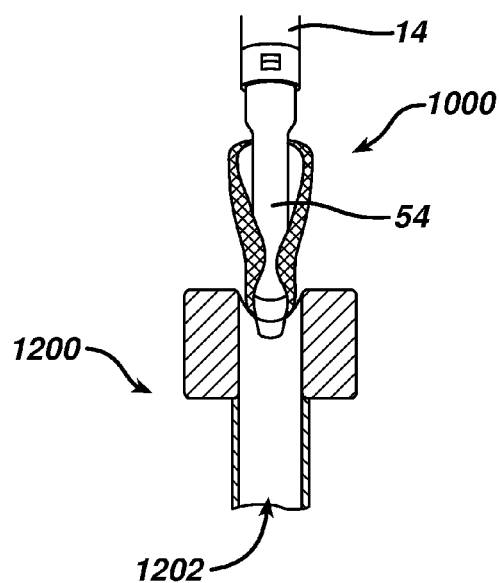
FIG. 32B is a perspective view of the end effector of FIG. 32A having the adjunct material wrapped around the end effector as the end effector is inserted through the trocar.

End effectors having one or more adjuncts coupled thereto can be delivered into various areas of a patient, such as a chest cavity, stomach, etc. As will be appreciated by a person skilled in the art, an adjunct can be delivered through an access port, such as a trocar extending into the patient. Any of the adjuncts herein can include features that assist with delivery of the adjunct into a patient's body. For example, FIG. 32A illustrate an adjunct 1000 having a solid central region 1002 and mesh wing region 1004 coupled to an anvil 54 of a surgical stapler 10. While a single adjunct 1000 is shown coupled to the anvil 54, another adjunct 1000' can be coupled to the cartridge assembly 52 prior to inserting the end effector 50 into a patient's body. A distal portion of the adjunct 1000, such as a distal portion 1004d of the wing region 1004, can be configured to guide proximal portions 1004p of the wing region 1004 around the lateral surfaces (not shown) of the anvil 54 so as to minimize width of the adjunct material, as shown in FIG. 32B. This can facilitate insertion of the end effector 50 and the adjunct 1000 into an access port, such as a port 1202 formed in a trocar 1200, because a width of the anvil/cartridge assembly 54, 52 including the adjunct 1000 thereon will be about the same as a width of the anvil/cartridge assembly 54, 52 without an adjunct. In certain aspects, this distal portion 1004d of the wing region 1004 can be formed from a more rigid material than remaining portions of the wing region 1004 to help guide the adjunct material 1000 into the port 1202.

Stapling Adjuncts onto Tissue

Figure 33A:
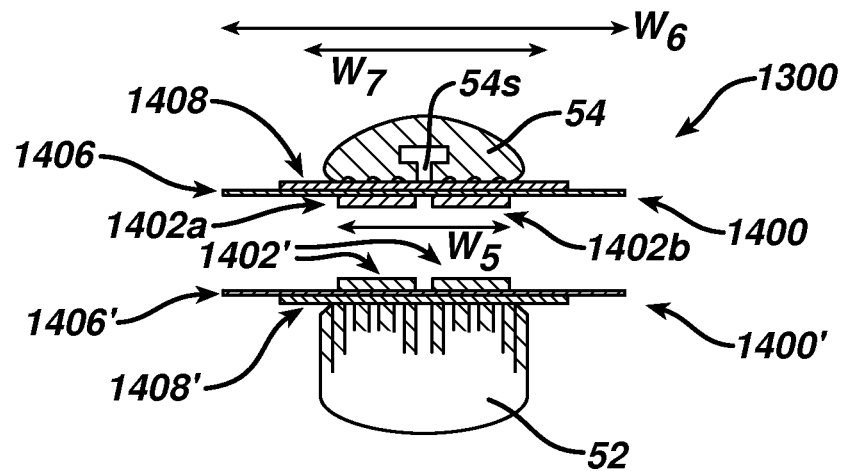
FIG. 33A is an end view of a cartridge assembly and an anvil of a surgical stapler having a multi-layer adjunct material coupled thereto.
Figure 33B:
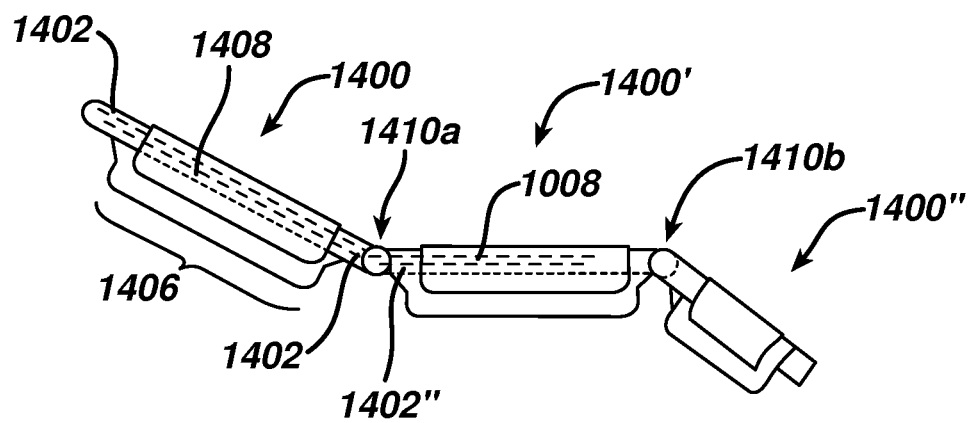
FIG. 33B is a side view of three adjuncts stapled onto tissue and having overlapping portions therebetween.
Figure 33C:
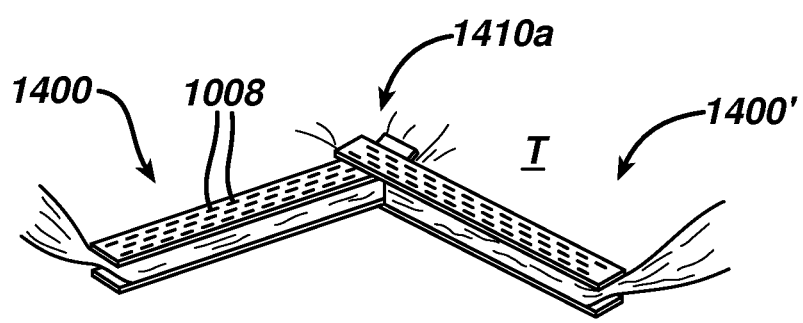
FIG. 33C is a perspective view of a first adjunct material and a second adjunct material stapled onto tissue and having first and second overlapping portions.

An adjunct material can include features facilitating multiple firings of staples along tissue. FIG. 33A illustrates an embodiment 1300 of an end effector 50 having first and second adjunct materials 1400, 1400', the first adjunct material 1400 being coupled to the anvil 54 and the second adjunct material 1400' being coupled to the cartridge assembly 52. As shown, each of the adjunct materials 1400, 1400' can include multiple layers, and the layers can have various widths in the direction transverse to a longitudinal axis (not shown) of the anvil/cartridge assembly 54, 52. A first tissue-contacting layer 1402, 1402' of each adjunct 1400, 1400' can be positioned adjacent to tissue (not shown) when tissue is grasped between the anvil 54 and the cartridge assembly 52. In certain aspects, the first tissue-contacting layer 1402, 1402' can be formed from a material configured to seal around a staple line, such as an elastomeric material. The first tissue-contacting layer 1402, 1402' can have a width W5 in a direction transverse to the longitudinal axis LA of the anvil 54 that is substantially equal to a width WA of the anvil 54, or the width W5 of the first layer 1402 can be less than the width WA of the anvil 54. As shown in FIG. 33A, the first tissue-contacting layer 1402 can include a first portion 1402a positioned on a first side of the cutting member slot 54s and a second portion 1402b positioned on a second side of the cutting member slot 54s rather than being formed from a continuous piece of material. In other aspects, the first layer 1402 can be a single continuous piece of material. A second layer 1406, 1406' can be positioned closer to the tissue-contacting surface of the anvil 54 and can be formed from a substantially rigid material. As shown, a width W6 of the second layer 1406 can be greater than the width WA of the anvil 54. This second layer 1406, 1406' can help prevent stretching of the tissue T near the staples 1008. A third layer 1408, 1408' can be positioned closest to the tissue-contacting surface of the anvil 54 such that the second layer 1406, 1406' is sandwiched between the first and third layers 1402, 1402' and 1408, 1408'. The third layer 1408, 1408' can have a width W7 that is greater than the width WA of the anvil 54, but less than the width W6 of the second layer 1406, as shown. This third layer 1408, 1408' can be semi-rigid to help relieve strain on tissue T as the tissue T expands and contracts. A longitudinal length of the layers can also vary, the length being measured in the direction transverse to the widths. Preferably, the third layer 1408, 1408' has a longest length measured along the longitudinal axis of the anvil 54 compared to a longitudinal length of each of the first and second layers 1402, 1402', 1406, 1406'. As shown in FIG. 33B, multiple adjuncts 1400, 1400', 1400" can be sequentially deployed onto tissue in a row and the longitudinal lengths of the layers can result in regions 1410a, 1410b where the first layer 1402 of one adjunct 1400 overlaps with a first layer 1402' of another adjunct 1400'. In this way, the staples 1008 can still penetrate through these overlapping regions than if multiple, e.g. three or more layers 1402, 1406, 1408 were positioned there. FIG. 33C illustrates two adjuncts 1400, 1400' stapled onto the tissue T at about a 90 degree angle relative thereto, the first adjunct 1400 having a first terminal end and the second adjunct 1400' having a second terminal end. The first and second terminal ends form the overlapping region 1410a, as shown. These adjuncts 1400, 1400' can be used to allow a user to deploy adjuncts to accommodate various geometries of tissue. These multilayer adjuncts 1400, 1400' can vary in any number of ways. While the layers 1402, 1406, 1408 can have various thicknesses, in the illustrated embodiment the second layer 1406 has a smaller thickness than a thickness of each of the first and third layers 1402, 1408. For example, the first layer 1402 can be in the range of about 3 to 15 mm, the second layer 1406 can be in the range of about 5 to 20 mm, and the third layer 1408 can be in the range of about 3 to 20 mm. In certain aspects, these layers 1402, 1404, 1406 and 1402', 1404', 1406' can be laminated together prior to being coupled to the anvil/cartridge assembly 54, 52. In certain aspects, layers 1406 and 1406' may be at least partially comprised of an absorbable material such as PDS®.

Reinforcing Tissue with Sealant and Adjuncts

Any of the adjuncts herein can be used in conjunction with a sealant to help maintain a seal around staples as the tissue expands and contracts following a surgery. A sealant can have various formulations and differing viscosity and curing behavior. Generally, a sealant can be made from a biocompatible and bioabsorbable material that can be configured to transition from a first, liquid state to a second, hardened state via a curing process, such as a polymerization reaction. The first state can be a softened state, e.g., a fluid, a gel, a foam, etc. and the second state can be a hardened state, e.g., a solid, a rigid member, etc. When the sealant is in the first, softened state, the sealant can flow through the delivery tube and into the sealing cuff, as described in greater detail below. The sealant can transition from the first, softened state to the second, hardened state after a predetermined amount of time. In certain aspects, the sealant can be formed from biologic material. In some embodiments, the sealant can assist in wound healing by releasing various chemical compounds, during and/or after curing of the sealant in a patient's body. By way of non-limiting example, the sealant can be configured to release a therapeutic drug, such as promoters of wound healing (e.g., transforming growth factor-beta, etc.), antibacterial agents (e.g., triclosean, ionized silver, etc.), and other known agents over time to aid the tissue in healing near the location of the sealant in a body. In one embodiment, a fibrin sealant can include two reactive components combined immediately prior to delivery into a patient, such as Thrombin and a biologically active component (BAC2), Fibrinogen and Factor XIII In certain aspects, the components can be provided in a 5:1 volumetric ratio of BAC2 to Thrombin. In an alternative embodiment, the material may be the fibrin sealant sold under the trade name Evicel®. In another embodiment, the sealant can be blood, such as autologous blood.

Figure 34A:
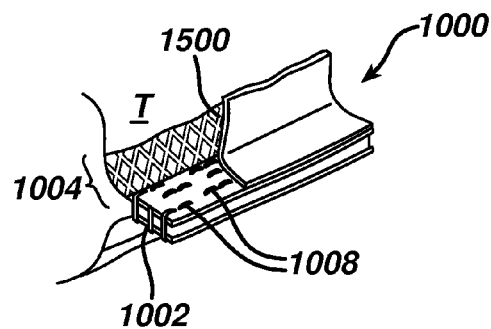
FIG. 34A is a perspective view of first and second adjunct materials stapled onto tissue and having a sealant delivered onto an outer surface of the first adjunct.

FIG. 34A illustrates the adjunct of FIG. 16B having sealant 1500 delivered thereon. As shown, the sealant 1500 can be delivered so that it substantially covers the central 1002 and wing regions 1004 of the adjunct 1000 or in another embodiment (not shown), the sealant 1500 can be selectively delivered onto only the central region 1002 and not onto the wing region 1004.

Figure 34B:
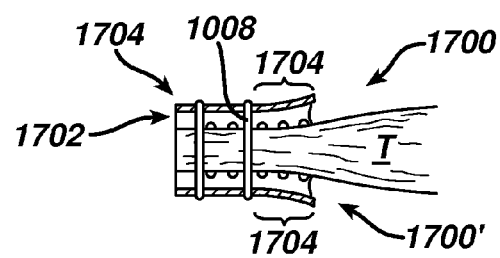
FIG. 34B is a side view of the first and second adjunct materials of FIG. 34A stapled to tissue.
Figure 34C:
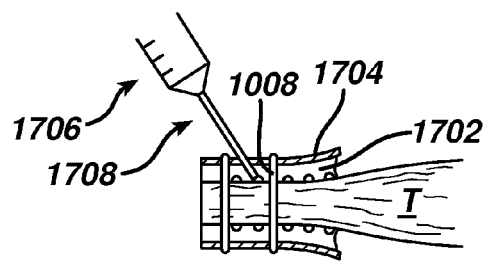
FIG. 34C is a side view of the first and second adjunct materials of FIG. 34A having sealant delivered to a space below an outer surface of the adjunct.
Figure 34D:
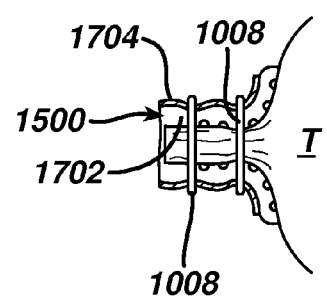
FIG. 34D is a side view of the first and second adjunct materials of FIG. 34A in an expanded position.

The sealant 1500 can be delivered to an adjunct in other ways, and need not be delivered to an outer surface of the adjunct 1000. For example, FIG. 34B illustrates multilayer adjuncts 1700, 1700' stapled onto tissue T. The layers 1702, 1704 can be formed from various materials, but in the illustrated embodiment include a first layer 1702 of fibrous scaffold positioned adjacent to the tissue T and a second layer 1704 consisting of an elastic film. A delivery tool 1706 having an injection needle 1708 can have a sealant 1500 disposed therein and can penetrate into the first layer 1702 of fibrous scaffold. The sealant 1500 can be delivered to this first layer 1702, as in FIG. 34C and the injection needle 1708 can be removed from the patient's body. The sealant 1500 can bind directly onto the tissue T and/or may be held in firm apposition to the tissue by layer 1704, and as in other embodiments, can have a wing region 1704, 1704' that distributes a strain to tissue beyond the staples 1008 at the staple line. When the sealant is Evicel®, the material forms a fibrin clot from fibrinogen. Without a loss in generality, other sealants form a hardened sealing structure by different mechanisms that are useful for sealing leak pathways. The combination of sealant 1500 and adjunct material 1700 can prevent formation of leaks as the tissue T expands and contracts. The adjuncts 1700' and layers 1702', 1704' can be substantially similar to the adjunct 1700 and 1702, 1704 layers previously described.

Figure 35A:
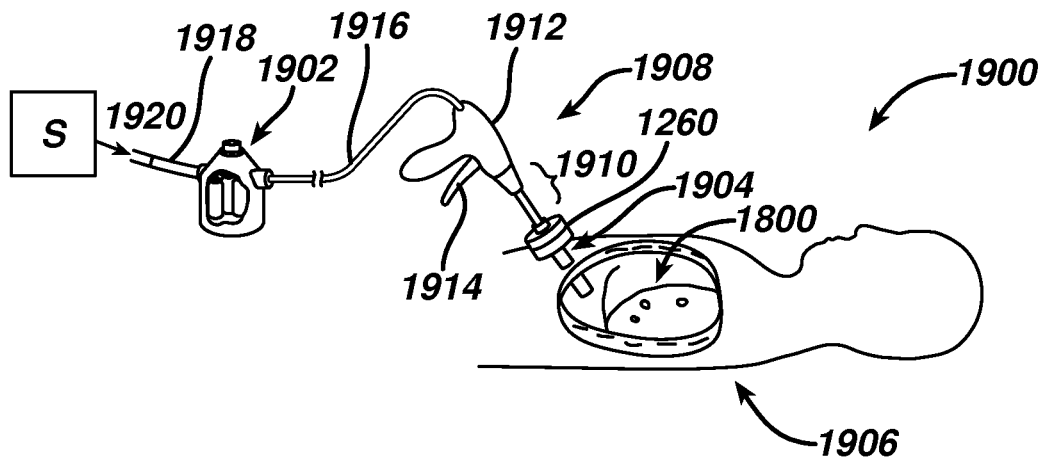
FIG. 35A is a perspective view a system for nebulizing a sealant which includes a container and an applicator tool extending through a trocar and into a patient.
Figure 35B:
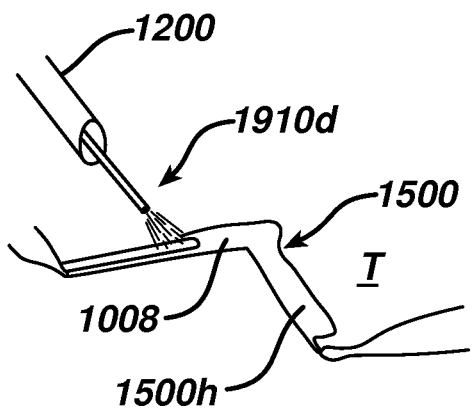
FIG. 35B is perspective view of the applicator tool of FIG. 35A delivering sealant to a staple line in tissue.
Figure 35C:
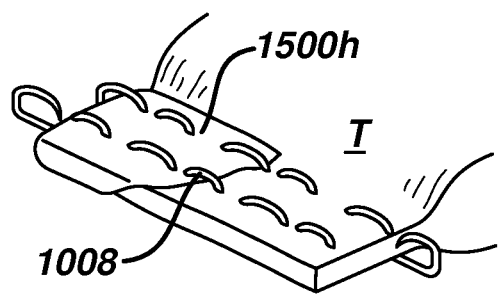
FIG. 35C is a perspective view of the nebulized sealant of FIG. 35A hardened onto the staple line.

A sealant can be used to reinforce tissue in other ways. For example, FIGS. 35A-35C illustrate sealant 1500 being delivered to a chest cavity 1800 of a patient. As shown in FIG. 35A, a system 1900 for delivering a sealant 1500 can include a container or canister 1902 for receiving components A, B, C of a sealant 1500 therein. In certain aspects, the components A, B, C can include acid solubilized collagen A, fibrinogen B, and thrombin C. A trocar 1200 can extend through an incision 1904 formed in a patient 1906 and into the chest cavity 1800. An applicator tool 1908 can have a shaft 1910 extending through the trocar 1200, a distal end 1910d of the shaft 1910 terminating in the chest cavity. A handle assembly can be formed on a proximal end 1910p of the shaft 1900 and can be configured to be grasped be a user. The handle assembly 1912 can be a pistol-grip type handle assembly and can include one or more actuators, such as a lever 1914 that can be pivoted to actuate the device 1908. The canister 1902 and the applicator tool 1908 can be coupled together in various ways, such as via a tube 1916. This tube 1916 can be substantially flexible to facilitate movement of the applicator tool 1908 during a procedure. The canister 1902 can have a second tube 1918 coupled thereto and connected to a gas source S so that gas 1920 can be delivered to the canister 1902. The gas 1920 can include, by way of non-limiting example, $CO_2$, $O_2$, etc. In certain aspects, the gas source S can be a continuous gas source such as a continuous $CO_2$ gas source available in hospital operating rooms. One or more valves (not shown) can be disposed in the tube 1916, in the handle assembly 1912, in the shaft 1910, or in any other portion of the system 1900 and can be selectively opened and closed by activating the actuator, such as by pivoting the actuator 1914 on the handle assembly 1912. For example, one valve can control influx of the gas 1920 into the canister 1902 and another valve can control delivery of the sealant 1500 into the applicator tool 1908. After tissue T is stapled, such as by deploying one or more cartridges of staples onto lung tissue, the distal end 1910d of the shaft 1910 of the applicator 1908 can be positioned near the staples 1008 as in FIG. 35B. Preferably, the distal end 1910d of the applicator tool 1908 is positioned about 5 to 30 mm away from a staple line depending on the size of the region to cover. A user can grasp the handle assembly 1912 of the applicator tool 1008 and activate the actuator 1914, such as by moving the pivotable lever 1914 proximally. This can open a valve disposed in the system 1900 and begin delivering the gas 1920 to the canister 1902 to nebulize the sealant 1500 so that it forms encapsulated liquid droplets that can be sprayed directly onto the tissue T, as shown. In this way, the sealant 1500 can be delivered onto the tissue along the staple line, as shown in FIG. 35C. The sealant 1500 can harden thereon, forming hardened regions 1500h facilitating formation and maintenance of a seal along the staples 1008. The sealant 1500 can also be delivered onto an adjunct rather than directly onto the tissue T, such as any of the adjuncts described herein. As will be appreciated by a person skilled in the art, sealant can be delivered to any portion of the tissue, such as only the tissue at the staple line and/or beyond the staple line.

Figure 36A:
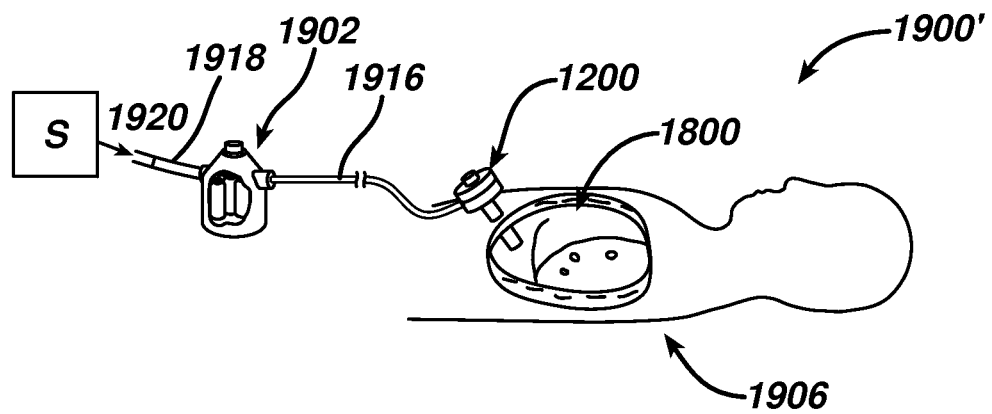
FIG. 36A is a perspective view of another exemplary system for nebulizing a sealant and delivering a nebulized sealant to a patient directly through a trocar and into a patient.
Figure 36B:
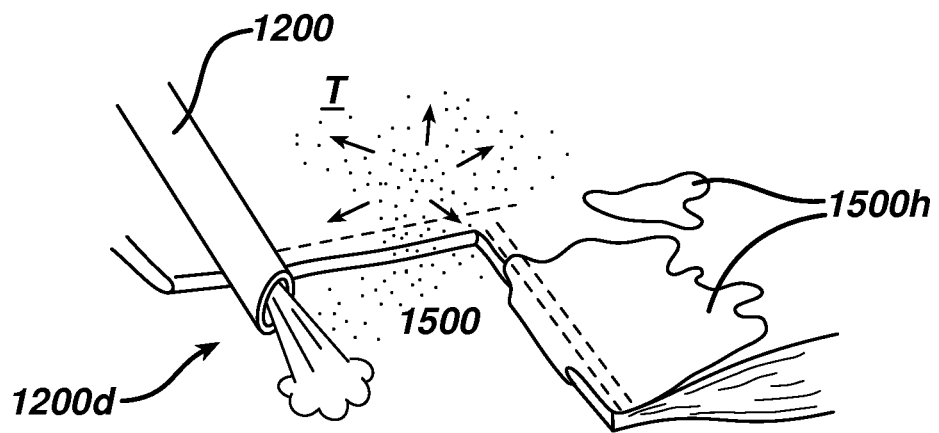
FIG. 36B is a perspective view of the trocar of FIG. 36A delivering nebulized sealant onto tissue at and beyond the staple line.

A sealant can be delivered in various ways. For example, a system 1900' for delivering a sealant 1500 is provided in FIG. 36A and includes many of the features of FIG. 35A, including a gas source, canister, etc. However, in this embodiment the system delivers a nebulized sealant 1500 directly through the trocar 1200 and does not include an applicator tool. In this embodiment, the system also need not include valves and the delivery of the gas 1920 to the canister 1902 can simply be controlled using a valve at the gas source. The delivery of gas into the canister 1902 can also nebulize the sealant 1500, but rather than form encapsulated liquid droplets, the gas 1920 can be delivered at a higher pressure and rate to create a nebulized fog of sealant 1600. As shown in FIG. 36B, this sealant fog 1500 can spread throughout the chest cavity of the patient and can harden on all surfaces of the tissue, such as forming hardened regions 1500h along all surfaces of the patient's lungs.

In an embodiment in which the sealant is blood, such as autologous blood, the blood can be harvested from the patient and applied to the adjunct material. By way of non-limiting example, the adjunct material can be ORC, a known hemostatic agent, and the application of the blood to the ORC adjunct will cause the formation of a clot, resulting in an effective sealing structure. A person skilled in the art will appreciate that blood, such as autologous blood can be applied to a variety of adjunct materials to provide an enhanced sealing structure. Further, a person skilled in the art will appreciate that the volume of blood applied to the adjunct will vary depending upon a number of factors, including the type and location of tissue as well, the age and condition of the patient, and the identity of the adjunct. Generally, however, when the adjunct is an ORC material, the blood can be applied in an amount in the range of about 5-10 cc per line of staple used to affix the adjunct to the tissue.

Adjuncts Having Tissue Reinforcement Features

Adjunct materials described herein may be used in any suitable type of surgery where a surgical stapler or other instrument is deployed to connect tissues. One advantage of tissue adjuncts is their propensity to prevent or minimize leaks, such as fluid or gas leaks. Tissue adjuncts can perform this function by one or more of the following mechanisms: plugging holes or tears that occur at the staple puncture sites; restricting movement of tissue around staple puncture sites to prevent an increase in the size of staple holes and/or to prevent tissue tears; and minimizing strain gradients that occur between constrained tissues within the staple line and free tissue adjacent to the staple line.

In some embodiments, adjunct materials described herein may be used for sealing staple punctures created when a surgical stapler is used in lung surgery. When surgery is performed on a lung, the lung is typically collapsed, and a required procedure, including application of the stapler to lung tissue, is then performed on the collapsed lung. After the procedure is completed, the collapsed lung is reinflated to a normal lung volume. The reinflation of the lung stretches the lung tissue (e.g., lung parenchyma), particularly in an area around a staple line, which may result in increased stress at a junction between the stapled tissue (which is restricted from stretching by the staples) and the surrounding tissue areas. Furthermore, an airtight sealing is required for the staple punctures of the lung. The sealing of a good quality may be difficult to achieve—while leaks around staple punctures typically seal within approximately five days, in some cases, staple punctures may persist for longer periods of time, such as, for example, six months or longer. In such circumstances, a lengthy hospitalization of a patient may be required.

Accordingly, applicants have recognized and appreciated that an end effector, such as a staple cartridge assembly for use with a surgical stapler, and/or its associated anvil, can include an adjunct material which may be used to seal punctures created by a surgical stapler used to secure lung or other types of tissue. The adjunct material can also reinforce the staple line, distribute stress load on the tissue near the staple line, and minimize tearing of the tissue—e.g., when the lung tissue is reinflated after the surgery to transition to its normal volume.

In some embodiments, the staple cartridge assembly can comprise a cartridge body of a surgical stapler and an adjunct material, which is interchangeably referred to herein as a tissue reinforcement construct. The tissue reinforcement construct can be removably attached to the cartridge body and is configured to be delivered to a surgical site by deployment of the staples of the surgical stapler. When the staples are deployed, the adjunct material can remain at the surgical site with the staples. In this way, the adjunct material can be used to help seal holes formed by staples and/or can be used to provide tissue reinforcement at the treatment site.

In some embodiments, the adjunct material can comprise a first, or outer, dissolvable and/or absorbable material encompassing a second, or inner, material. The first material can be selectively dissolvable and/or absorbable. In some embodiments, the first material may be brittle. The second material can be a swellable, hydrophilic material that is maintained within the first material in a constrained configuration and is configured to transition to a predetermined shape when exposed to moisture in an unconstrained configuration. Prior to deployment of the staples, the second material can be encompassed within the first material in an intact form.

In some embodiments, the first material can be less hydrophilic than the second material and can therefore serve as a moisture barrier. The second material may be compressed within the first material in a constrained configuration such that, when the first material is punctured by staples deployed to connect tissue or is otherwise penetrated (e.g., cut by a surgical knife or compressed between a cartridge and anvil), the second material is exposed to moisture from the surrounding environment of the patient's body and begins to swell. In this way, the second material gradually swells and expands to eventually transition to a predetermined shape. As the second inner material swells, it expands to seal the holes in the tissue created by the staples. The second material can swell at a rate that allows it to form a seal around a hole as the tissue, such as lung parenchyma that was deflated prior to a surgical procedure, is inflated back to its normal volume, while compressing the stretching tissue and restricting its deformation or preventing its tearing around the staple line.

In some embodiments, one or more portions of the first material, such as, for example, portions encompassing peripheral edges of the second material can be more dissolvable than portions of the first material encompassing a central portion of the second material. Additionally the portions of the first material encompassing the peripheral edges of the second material can be more absorbable than portions of the first material encompassing the central portion of the second material. After the integrity of the first material is broken and as the portions of the first material encompassing the peripheral edges of the second material are dissolved or absorbed by the patient's body, the second material enclosed within those portion is allowed to expand upon exposure to moisture to thus seal and reinforce the stapled tissue.

The first and second materials of the adjunct material may comprise any suitable materials. In some embodiments, it is advantageous to select a material that is absorbable and capable of bearing compressive and bending loads. The first material can be formed from a variety of materials. They may be present in continuous form so as to fully encapsulate the materials making up the center of the device, or alternately they might be present in a non-continuous form. These non-continuous forms include, but are not limited to, otherwise encapsulating forms with minute openings allowing water or bodily fluids to access the materials making up the center of the device to facilitate rapid hydration to allow expansion of the center material; melt blend nonwoven forms with controlled porosity; immiscible polymer blends having a major blend component an absorbable polymer and a minor component being a biocompatible water soluble polymer which is capable of rapidly dissolving creating conduits to the central material allowing for its rapid hydration to generate an external force on the tissue.

The absorbable polymer making up the outer layer, although not limited to, can be selected from among polydioxanone (also referred to as poly(1,4-dioxan-2-one), or poly(p-dioxanone)); polyglycolide (also referred to as polyglycolic acid), polylactide (also referred to as polylactic acid) in all its forms based on the ring-opening of the corresponding lactone monomers, L(−)-lactide, D(+)-lactide, and meso-lactide, as well as all of its forms based upon polycondensation of L(+)-lactic acid and D(−)-lactic acid (e.g., poly(L(−)-lactide), poly(D(+)-lactide), poly(meso-lactide), poly(racemic-lactide), poly(L-lactic acid), poly(D-lactic acid), etc.); the polycaprolactones, especially poly(epsilon-caprolactone); polyhydroxyalkanoate (PHA); the absorbable copolymers usually formed by the ring-opening polymerization of the lactone monomers, L(−)-lactide, (D+)-lactide, meso-lactide, glycolide, 1,4-dioxan-2-one, trimethylene carbonate, and the caprolactones, especially epsilon-caprolactone, in any molar combination or in an sequential distribution. These later copolymers include, but are not limited to epsilon-caprolactone/glycolide copolymers such as 25/75 poly(caprolactone-co-glycolide) (also referred to as poliglecaprone 25), 10/90 poly(L(−)-lacide-co-glycolide) (also referred to as polyglactin 910), polyglyconate, polyglycolide-trimethylene carbonate (PGA/TMC). The absorbable polymer can be a miscible or immiscible blend of the previously mentioned polymers (and copolymers thereof) in any combination. In other embodiments, the first material may be selected from biodegradable synthetic absorbable polymers such as a polydioxanon film sold under the trademark PDS® or with a Polyglycerol sebacate (PGS) film or other biodegradable films formed from PGA (Polyglycolic acid and various forms thereof, marketed under the trademarks Vicryl® and/or Neoveil®), PCL (Polycaprolactone), PLA or PLLA (Polylactic acid), PHA (polyhydroxyalkanoate), PGCL (poliglecaprone 25, sold under the trademark Monocryl®), PANACRYL® (Ethicon, Inc., Somerville, N.J.), polyglactin 910, poly glyconate, PGA/TMC (polyglycolide-trimethylene carbonate sold under the trademark Biosyn), polyhydroxybutyrate (PHB), poly(vinylpyrrolidone) (PVP), poly(vinyl alcohol) (PVA), absorbable polyurethanes, or a blend or copolymerization of any of the above. Blends and/or copolymerizations of any of the aforementioned materials can be tailored to have a desired molecular weight and/or degradation rate. It will be clear to one skilled in the art to select a biocompatible material.

The second material may be formed from a variety of materials. Advantageous materials include those that are absorbable and can undergo a controlled degree of swelling so as to create an external force on the tissue. Swelling might be accomplished by hydration based on an influx of water or bodily fluids. One class of materials that is particularly advantageous is absorbable dehydrated hydrogels. These include the materials described in U.S. Pat. No. 5,698,213, entitled "Hydrogels of Absorbable Polyoxaesters" and crosslinked aliphatic polyoxaesters containing amine and/or amido groups and blends thereof with other polymers as described in U.S. Pat. No. 5,700,583, each of which is incorporated herein by reference in its entirety. Other materials suitable for the second material include water soluble polymers such as poly(vinylpyrrolidone) (PVP), poly(vinyl alcohol) (PVA), and polyethylene glycol (PEG) or the higher molecular weight polyethylene oxide (PEO). Additionally suitable are absorbable polyurethanes. It is to be understood that suitable materials include copolymers that contain a hydrophilic section and an absorbable polyester section; this would include, by way of example, the copolymer made by reaction of a relatively low molecular weight alpha,omega-dihydroxy polyethylene glycol and a lactone monomer such as L(−)-lactide, (D+)-lactide, meso-lactide, glycolide, 1,4-dioxan-2-one, trimethylene carbonate, and the caprolactones, especially epsilon-caprolactone, in any molar combination or in an sequential distribution. Blends of materials and copolymers formed from a wide variety of suitable monomers, some already mentioned above, may be suitable. In one embodiment, the second material may also be a biologically derived material as described above such as ORC. It will be clear to one skilled in the art to select a biocompatible material.

The adjunct material described herein can be delivered to a treatment site using any suitable surgical stapling device, as embodiments are not limited to any specific methods of employing a surgical stapling device that in used in conjunction with the adjunct material. In some embodiments, tissue is engaged between a cartridge assembly and an anvil of a surgical stapler at a treatment site, wherein at least one of the cartridge assembly and anvil has an adjunct material removably retained thereon. The surgical stapler can then be actuated to eject staples from the cartridge assembly through the adjunct material and into the tissue. The adjunct material can help to reduce impact and trauma from the stapling and distribute stress load on the tissue near the staple line to reduce the possibility of tissue tearing.

Figure 37A:
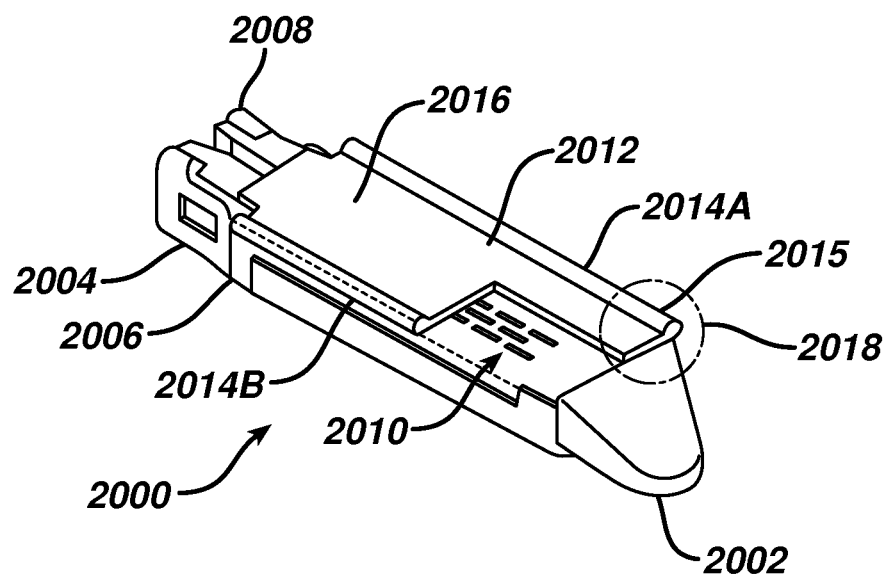
FIG. 37A is a perspective view of a staple cartridge assembly comprising an adjunct material, in accordance with some embodiments.

FIG. 37A illustrates an example of a portion 2000 of an end effector of a surgical stapler that can be used with one or more adjunct materials as described herein. In the example illustrated, the portion is a jaw 2000 having a distal end 2002, a proximal end 2004 and a cartridge body 2006. As shown in FIG. 37A, the surgical stapler includes a shaft 2008 that can be configured to couple the end effector with a handle assembly of the surgical stapler which is not shown for ease of illustration.

The jaw 2000 of the surgical stapler can be configured to support staples 2010 which can be arranged in any suitable configuration. In this example, the staples 2010 are arranged in rows and create a staple line when deployed to engage tissue. However, it should be appreciated that the staples 2010 may be arranged in a circular or any other configuration, as embodiments are not limited in this respect.

As shown in FIG. 37A, the jaw 2000 serving as a cartridge assembly can be associated with an adjunct material 2012, also referred to interchangeably herein as a tissue reinforcement construct. The adjunct material 2012 can be removably retained on the cartridge body 2006 so as to be positioned over the staples 2010 in any suitable manner. In some embodiments, the cartridge body 2006 can be preloaded with an adjunct material such as the material 2012. In other embodiments, the adjunct material 2012 can be positioned on the cartridge 2006 (e.g., by a surgeon or other medical professional) prior to a surgical procedure.

The adjunct material 2012 can have a configuration such that at least one of peripheral edge portions 2014A and 2014B has a cross section that is larger than a cross-section of a central portion 2016 the adjunct material 2012. The central portion 2016 of the adjunct material 2012 can be defined as a portion that is closer to a longitudinal axis of the cartridge body 2006 than the peripheral edges of the cartridge body. The central portion 2016 and the peripheral edge portions 2014A and 2014B can have any suitable widths. Moreover, the peripheral edge portions 2014A and 2014B can have the same or different widths.

In should be appreciated that the tissue reinforcement construct in accordance with some embodiments can be advantageously used to reinforce a staple line created by the surgical stapler with improved quality relative to existing approaches. For example, in some embodiments, the tissue reinforcement construct can be used to reinforce the staple line 270 degrees around its perimeter. In particular, referring to FIG. 37A, the adjunct material 2012 can be configured such that the peripheral edge portions 2014A and 2014B and a distal portion 2015 have properties such that the staple line created by the staples 2010 can be reinforced. For example, the larger cross-section of the peripheral edge portions 2014A and 2014B makes the adjunct material able to reduce or prevent damage to tissue—e.g., to sensitive tissue in thoracic cavity. Further, in some embodiments, the peripheral edge portions 2014A and 2014B and the distal portion 2015 can be more flexible or stretchable than the central portion 2016 of the adjunct material 2012, which can further help to compress tissue such as the lung parenchyma as it is reinflated after surgery. Additionally or alternatively, in some embodiments, some or all of the peripheral edge portions 2014A and 2014B and the distal portion 2015 can degrade at a faster rate than the central portion 2016, which can lead to a faster rate of release of the inner material of the adjunct material 2012 encompassed within those portions. In this way, tissue in the area around the staple line can be reinforced in an atraumatic way almost immediately after the tissue is penetrated by the staples and/or a knife.

It should be appreciated that the adjunct material 2012 can have any other features that facilitate its use with the surgical stapler. For example, in some cases, the adjunct material 2012 can have cut-out tabs that can be pressed or slid into a knife slot or cartridge of the surgical stapler. When the knife cuts down in the middle of the adjunct material, the tabs are cut out and separated from the stapler.

Figure 37B:
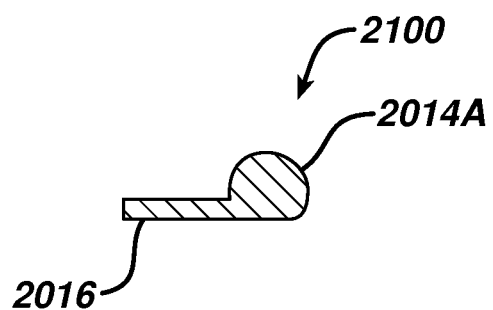
FIG. 37B is a cross-sectional view of a portion of the adjunct material of FIG. 37A, in accordance with some embodiments.

FIG. 37B illustrates an enlarged view 2100 of a cross section 2018 of a portion of the adjunct material 2012 of FIG. 37A. As shown in FIG. 37B, a peripheral edge, such as, for example, the peripheral edge 2014A, may have a larger cross sectional dimension than that of the central portion 2016. The larger cross sectional thickness of the edge portion allows to better seal the areas around the holes created by the staples and prevent tissue tearing. As shown in FIG. 37A, the adjunct material 2012 can be releasably positioned on the cartridge body 2006 so that one or both of the peripheral edge portions 2014A and 2014B extend beyond the cartridge body 2006. This can further improve the way in which the adjunct material 2012, when in an unconstrained configuration upon exposure to moisture, expands and provides effective sealing of a staple line created by the surgical stapler against air or fluid leakage and prevents tearing of the tissue near the staple line.

Figure 38:
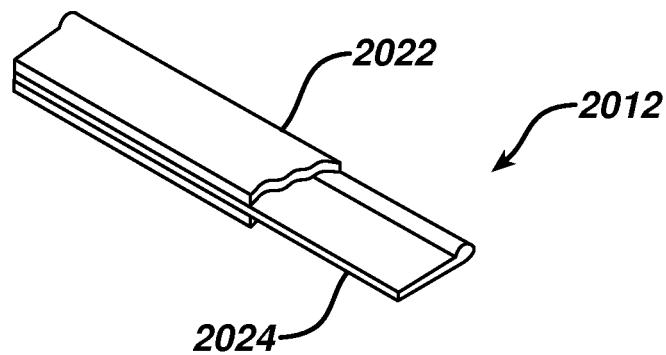
FIG. 38 is a perspective, partially cut-away view of the adjunct material, in accordance with some embodiments.

In some embodiments, the adjunct material 2012 may comprise an outer material that encompasses an inner material maintained within the outer material in a constrained configuration. FIG. 38 shows by way of example that the adjunct material 2012 can comprise a first, outer material 2022 and a second, inner material 2024. The first material 2022 may be a suitable dissolvable and/or absorbable material. The second material 2024 may be a suitable hydrophilic, swellable material. The properties of the first and second material may be uniform throughout or may vary. For example, the first material 2022 may be selectively dissolvable and/or absorbable. Similarly, different portions of the second material 2024 can have different hydrophilicity. For example, in some cases, peripheral edge portions of the second material 2024 can be more hydrophilic than a central portion of the second material 2024.

The first material 2022 may envelop the second material 2024 and, prior to delivering staples (e.g., staples 2010 in FIG. 37A) to the tissue, serve as a moisture barrier. The first material 2022 may be at least partially stretchable or may have any other properties that can be selected based on a clinical application of the adjunct material. For example, in some embodiments, the first material 2022 may be at least partially brittle.

The first material 2022 can prevent exposure of the second material 2024 to moisture for a certain time period—e.g., until the adjunct material 2012 is delivered to the surgical site in the patient's body. When the staples are deployed and the adjunct material 2012 is thus pierced or otherwise penetrated, the second material 2024 begins to swell upon exposure to moisture that passes to the second material 2024 through punctures in the first material 2022. Additionally or alternatively, the first material 2022 can be cut by a knife of the surgical stapler upon its deployment. Furthermore, in some embodiments, the properties of the first material 2022 may be such that the material can crack or otherwise lose its integrity due to compression when it is pressed between the cartridge and anvil of the surgical stapler. For example, if the first material 2022 is brittle, it can be broken by compression.

As discussed above, the first and second materials can be made from a number of suitable biologic materials and/or synthetic materials.

In some embodiments, the first and second material may be selected such that the first material is less hydrophilic than the second material. The same materials (e.g., polymers) may be used to manufacture the first and second materials, but the molecular weight of the source materials may be adjusted differently to produce materials suitable for the first material and materials suitable for the second material. The molecular weight of the polymers can be altered so that to obtain materials having desired degradation properties, as discussed above. For example, mixtures of PGA (Polyglycolic acid and various forms thereof, marketed under the trademarks Vicryl® and/or Neoveil®), and PLA or PLLA (Polylactic acid) can absorb at a relatively fast rate. Similarly, polyhydroxyalkanoate (PHA) can dissolve quickly and the materials made from PHA can begin to degrade within 20 to 30 minutes after attachment to tissue via contact with heat and/or water.

The degradation rates of the first and second material may be selected based on the desired clinical application—e.g., based on a type of treated tissue and/or an amount of time that the adjunct material is desired to remain at the surgical site. For example, a first material for an adjunct material intended to be used in lung surgeries may have a slower degradation rate than that of a first material for the adjunct material to be used to staple vessels. It should be appreciated, however, that embodiments are not limited to materials having any specific degradation rates or any other properties.

Figure 39:
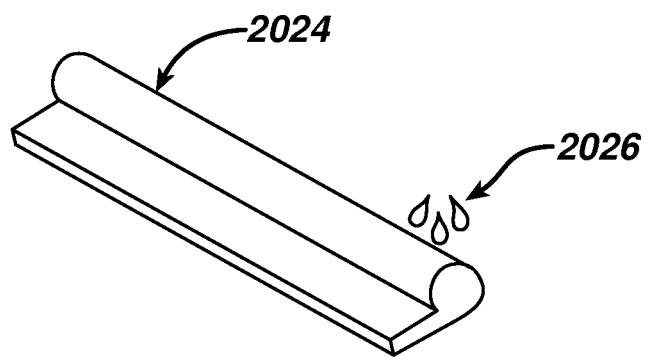
FIG. 39 is a perspective view of an interior hydrophilic, swellable material included in the adjunct material, in accordance with some embodiments.

FIG. 39 illustrates the second material 2024 that can be maintained within the first material 2022 in a constrained configuration—e.g., in a compressed or otherwise constrained configuration. In some embodiments, the second material 2024 can be a hydrophilic foam. The second material 2024 may comprise any suitable material(s) and, in some embodiments, may include one or more therapeutic agents, such as, for example, drugs, promoters of healing, antibacterial agent(s), and antimicrobial agent(s). The therapeutic agent can be configured to be released over time to aid the tissue in healing, for example. In embodiments where more than one therapeutic agent is employed, different therapeutic agents can be configured to release at different rates.

Upon exposure to moisture schematically shown in FIG. 39 as moisture 2026, the second material 2024 can absorb moisture and thus swell and expand. Additionally, if the second material 2024 includes one or more therapeutic substance(s), these substances can begin to elute once the second material 2024 is exposed to moisture. The moisture 2026 can be blood, other bodily fluid, or any other liquid. The adjunct material 2012 can be manufactured such that one or more portions of the second material 2024, can, upon exposure to moisture, expand to transition to a preconfigured shape. The shape of the second material 2024 prior to and after exposure to moisture can be selected so as to provide a good quality seal around the punctures in the tissue created by the staples and provide reinforcement to the staple line against the tissue to prevent tears in the tissue or pulling of the staples through the tissue. For example, as illustrated in FIG. 39, the second material 2024 can have a shape such that its peripheral edges have a larger cross-section than its central portion.

Although FIGS. 37A-39 illustrate the adjunct material 2012 having a shape such that the peripheral edges portions have a larger cross-section than that of the central portion of the adjunct material, it should be appreciated that the adjunct material 2012 can have any suitable shape, as embodiments are not limited in this respect. For example, the adjunct material can have a uniform thickness throughout, or the thickness of the adjunct material can vary in any suitable manner. Regardless of the shape and size of the adjunct material, in some embodiments, the adjunct material can be configured such that one or more portions of the first material are selectively dissolvable and/or selectively absorbable by the patient's body. Furthermore, one or more portions of the second material can be selectively swellable.

Figure 40:
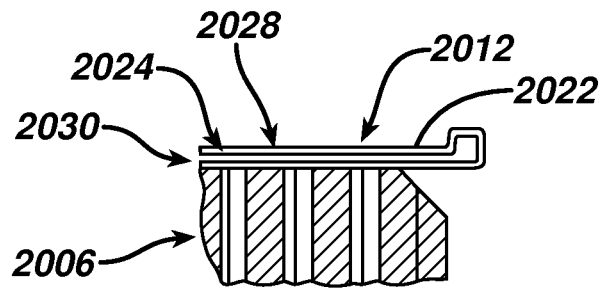
FIG. 40 is a perspective view of the adjunct material before penetration by surgical staples, in accordance with some embodiments.

FIG. 40 is a side view of the adjunct material 2012 removably attached to the cartridge body 2006, prior to deployment of staples supported by the cartridge body 2006. The first material 2022 of adjunct material 2012 comprises a top layer 2028 and a bottom layer 2030, with the second material 2024 sealably enclosed therebetween. As illustrated, a peripheral edge portion of the adjunct material 2012 extends beyond the cartridge body 2006. Such disposition of the adjunct material 2012 with respect to the cartridge body 2006 enhances tissue reinforcement and offers improved resistance to air and fluid leaks around staple holes.

In some embodiments, adjunct materials as described herein may be used in a surgical stapling device that is employed in lung surgery, such as in surgery to treat lung cancer, lung volume reduction surgery, or any other type of surgery. Prior to such surgery, the lung is deflated, and then reinflated to its normal volume after the required procedure is completed. A common complication after such a surgery is that air or fluid can leak though the punctures or holes created by the staples. Moreover, as the lung is being reinflated and the tissue stretches, holes can increase in size (through stretching) or tears can occur in the tissue areas around the staple holes. Accordingly, the described adjunct material can be used to reinforce the tissue around the staple holes and compress the tissue as the lung stretches to assume its normal volume. It should be appreciated, however, that the adjunct material can also be used to seal punctures created by surgical staplers used to secure any other type of tissue, such as, gastrointestinal tissue and vessels (e.g., intestine, stomach and esophagus).

Additionally, in some embodiments, an adjunct material can comprise one or more therapeutic substances, or agents, that can be eluted when the staples are deployed to help healing the tissue at the treatment site, or to prevent or combat infection. The therapeutic substances can be released at different rates to provide the desired action at the treatment site.

Figure 41A:
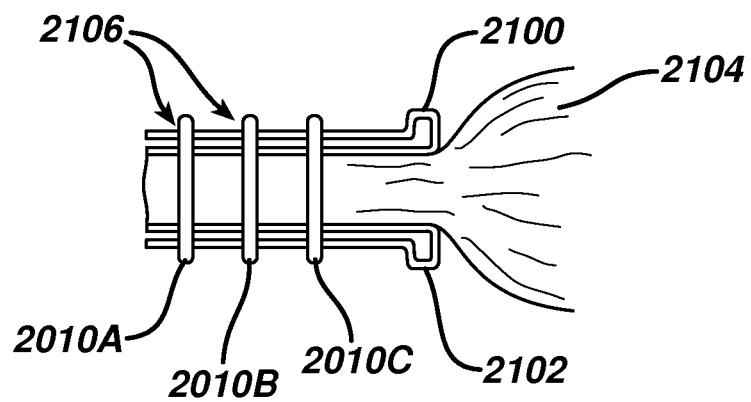
FIG. 41A is a side view of tissue and adjunct materials retained to both the cartridge assembly and anvil of a surgical stapler, after penetration by the surgical staples, in accordance with some embodiments.
Figure 41B:
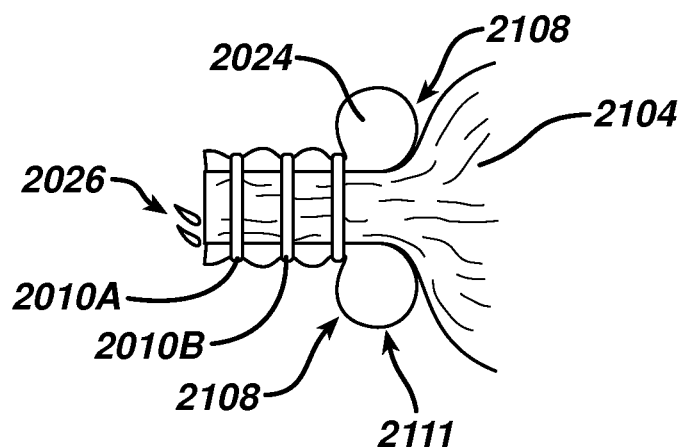
FIG. 41B is another side view of tissue and adjunct materials retained to both the cartridge assembly and anvil of a surgical stapler, after penetration by the surgical staples, in accordance with some embodiments.

In some embodiments, either or both of the cartridge and anvil of the end effector of a surgical stapler can have removably attached thereto an adjunct material such as, for example, the adjunct material 2012. Accordingly, FIGS. 41A and 41B show that two adjunct materials 2100 and 2102 can be used with the surgical stapler to reinforce tissue at a treatment site. When the staples (e.g., staples 2010A-2010C in FIGS. 41A and 41B) are deployed to engage tissue 2104, each of them can create a corresponding puncture in the adjunct material. FIGS. 41A and 41B illustrate by way of example punctures 2106 in the adjunct material 2100. It should be appreciated, however, that the adjunct material 2102 is similarly punctured by the staples 2010A-2010C. In addition, it should be appreciated that only three staples 2010A-2010C are shown for the purpose of illustration only, as embodiments are not limited to any specific number of staples that can be seated in the cartridge body.

The staples deployed to engage the tissue can remain with the tissue until they are removed using an instrument, absorbed by the patient's body or otherwise removed from the treatment site. The adjunct material is maintained at the treatment site by the staples for a certain period of time which can depend on a number of factors—e.g., a period during which the staple holes are expected to heal, a time required for one or more portions of the adjunct materials to disintegrate, and any other suitable factors. Furthermore, one or both of the first and second materials of the adjunct material can be dissolvable and/or (bio)absorbable materials that are gradually absorbed or eliminated in other ways from the patient's body.

FIG. 41A shows the staples 2010A-2010C retaining the adjunct materials 2100 and 2102 at the treatment site of the engaged tissue 2104 at a period of time shortly after the staples are deployed. Because the staples 2010A-2010C penetrate the adjunct materials 2100 and 2102, the integrity of the first layer of the adjunct materials is disturbed, and moisture can pass to activate the second material 2024 encompassed within the first material 2022.

In some embodiments, as shown in FIG. 41B, after a certain time period (which can be of any suitable duration), tissue 2104 begins to expand—e.g., lung parenchyma expands to eventually reach its normal volume, after a surgery was performed on a collapsed lung. At the same time, the second material 2024, which can be hydrophilic, begins to swell upon contact with moisture. As the tissue 2104 expands, the second material 2024 can swell gradually, to transition to a large radius (denoted by way of example using reference numeral 2108 in FIG. 41B) at peripheral edges portions 2109 and 2111 of the adjunct materials 2100 and 2102, respectively.

The first material 2022 encompassing peripheral edge and distal portions of the second material 2024 can stretch to accommodate the expanding volume of the second material 2024. Further, one or more portions of the first material 2022 can be dissolvable and/or absorbable so that the first material 2022 gradually disintegrates as the second material 2024 swells and expands from its constrained form to a predefined shape. In particular, in the embodiment of FIG. 41B, the portions of the first material 2022 at the peripheral edge portions 2109 and 2111 can be configured to dissolve at a faster rate than portions of the first material encompassing a central portion of the second material 2024. Additionally or alternatively, the portions of the first material 2022 at the peripheral edge portions 2109 and 2111 can be configured to absorb at a faster rate than portions of the first material encompassing the central portion of the second material 2024. The described configuration of the first material, where the staple holes in the tissue are sealed and the tissue area surrounding a large portion of the staple line is compressed by the swollen hydrophilic material allows reinforcing the tissue in an effective, atraumatic manner. In this way, the sensitive lung tissue can be sealed so as to prevent bleeding, tearing, and/or leakage of the treated tissue. The ability to create an airtight seal while allowing the tissue to safely stretch around the staple line (e.g., as the lung is reinflated) is particularly useful because the success of the patient's recovery is largely based on how fast the tissue at the surgical site can heal.

As discussed above, in some embodiments, the first, outer material of the adjunct material described herein can have properties that are not uniform throughout. For example, as also discussed above the first material may be selectively dissolvable and/or selectively absorbable. In some embodiments, one or more portions of the first material can be adapted to dissolve at a faster rate than other portions of the first material. Additionally or alternatively, one or more portions of the first material can be adapted to absorb at a faster rate than other portions of the first material. The portions of the first material that are adapted to dissolve and/or absorb at a faster rate can be, for example, peripheral edge portions of the first material, or any other portions.

Figure 42A:
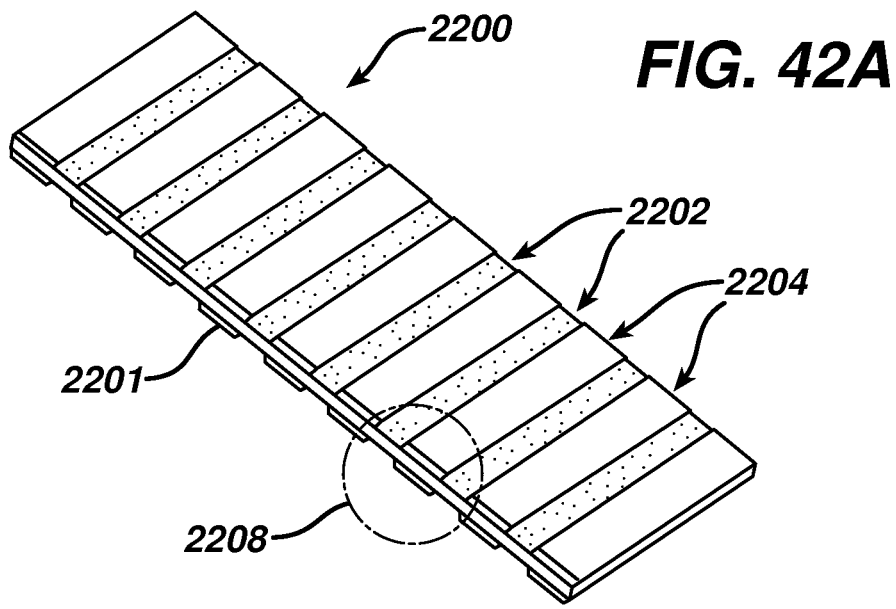
FIG. 42A is a perspective view of the adjunct material including portions of an outer material having different characteristics, in accordance with some embodiments.

FIG. 42A illustrates an example of a first material 2201 of an adjunct material 2200 that has portions 2202 adapted to dissolve and/or absorb at a faster rate than portions 2204 of the first material 2200. In this example, the adjunct material 2200 has a uniform, or approximately uniform, thickness throughout. However, it should be appreciated that the thickness of the adjunct material can vary from one portion to another. It should also be appreciated that the alternating portions 2202 and 2204 are shown by way of example only, as the first material can be partitioned into the portions having different dissolution rates and/or portions having different absorption rates in any suitable manner. For example, as mentioned above, the portions of the first material encompassing the peripheral edge portions of the second material can be adapted to dissolve at a faster rate than portions of the first material encompassing the central portions of the second material.

Furthermore, the portions of the first material encompassing the peripheral edge portions of the second material can be configured to absorb at a faster rate than portions of the first material encompassing the central portions of the second material. Additionally, the portions 2202 and 2204 can have different widths, as embodiments as not limited in this respect. By varying the number, length, width and other properties (e.g., materials) of the portions of the first material configured to dissolve and/or absorb at different rates, the second material can be configured to expand at different rates. Different materials can be selected for the first and second materials to obtain desired degradation rates. Depending upon the desired clinical application, different rates at which the second material swells and expands can be controlled to distribute load around the staple line and decrease the possibility of tissue tearing. Additionally, a time during which the adjunct material remains at the treatment site can be adjusted by varying properties of the first and second materials.

Figure 42B:
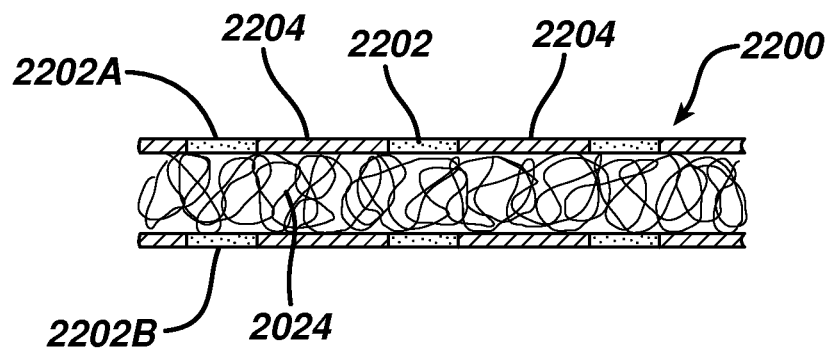
FIG. 42B is a side view of the adjunct material of FIG. 42A, in accordance with some embodiments.

FIG. 42B shows an enlarged cross-sectional view of a portion 2208 of the adjunct material 2200 of FIG. 42A. The first material 2201 of the adjunct material 2200 encloses the second material 2206 which may be a hydrophilic foam comprising any suitable material. Similar to FIG. 42A, FIG. 42B also demonstrates that the first material 2201 can comprise portions 2202 configured to dissolve and/or absorb at a faster rate than portions 2204. It should be appreciated that FIG. 42B shows that portions 2202 located on different sides of the second materials 2206 (e.g., portions 2202A and 2202B) are shown to be aligned with each other by way of example only, as embodiments are not limited in this respect.

Figure 43:
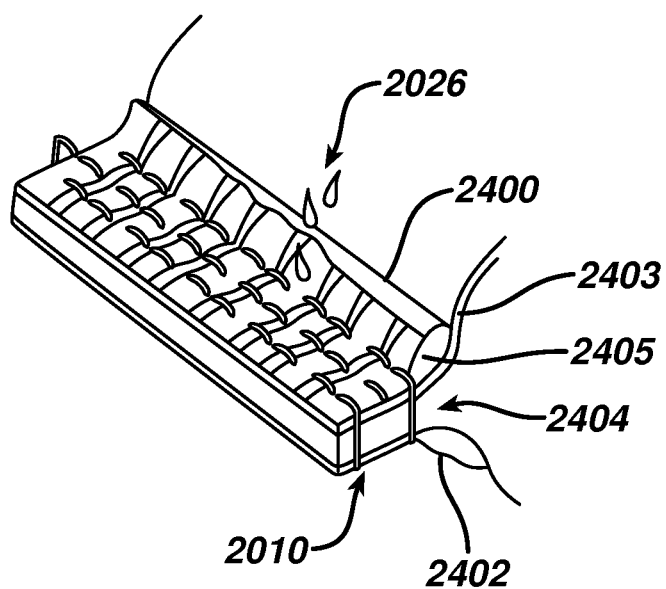
FIG. 43 is a perspective view of the adjunct material illustrating a peripheral edge portion of the adjunct material after penetration by the surgical staples, in accordance with some embodiments.

FIG. 43 illustrates an example in accordance with some embodiments where both a cartridge and anvil side of the surgical stapler can have an adjunct material removably retained thereon. Accordingly, in this example, adjunct materials 2400 and 2402 (e.g., adjunct materials 2200 or any other suitable adjunct materials) are employed to seal punctures in tissue 2404 created by the staples 2010. As shown, when the adjunct materials 2400 and 2402 are pierced by the staples 2010, moisture 2026 from the surrounding environment (e.g., blood, other bodily fluid, water, medication, etc.) passes through the staple holes (e.g., a hole 2408 in FIG. 44) to the inner hydrophilic material (e.g., the second material 2206 of FIGS. 42A and 42B) maintained within an outer layer of the adjunct material.

FIG. 43 also shows that peripheral edge portions of the adjunct materials which, prior to deployment of the staples, extend beyond the cartridge body and/or anvil, can transition to a large radius which may reinforce the tissue 2404. In particular, a peripheral edge portion 2403 of the adjunct material 2400 can transition to a large radius 2405. For example, the portion 2403 can transition from a radius roughly equal to half the thickness of the adjunct (about 0.025 to 1.0 mm) to a radius up to about 5 times the initial size of the feature. However, it should be appreciated that the adjunct material described herein can have any suitable dimensions and, when in an unconstrained form, can transition to a radius of any suitable size, as embodiments are not limited in this respect.

Additionally, a portion of a first material of the adjunct material 2400 (e.g., the first material 2201 of FIGS. 42A and 42B) at the peripheral edge portion 2403 can be such that it dissolves and/or absorbs at a faster rate than other portions of the first material. In this way, the peripheral edge portion 2403 of the adjunct material can disintegrate faster than other areas of the first material, thus allowing the second material encompassed within that portion to swell and expand at a faster rate than the central portion of the second material. As discussed above, the adjunct materials can expand to transition to a predetermined shape, which can be selected based on a clinical application, type of wound to be sealed, and any other factors.

Figure 44:
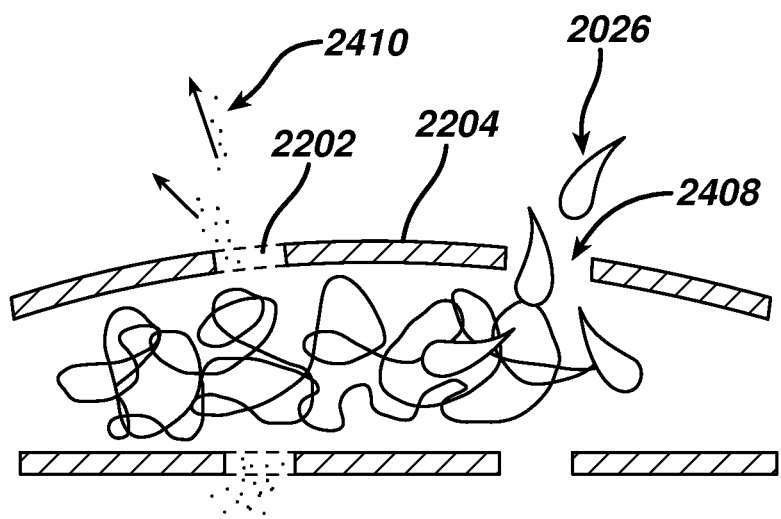
FIG. 44 is a perspective view of the adjunct material of FIG. 43, in accordance with some embodiments.

Additionally, because the outer layer of the adjunct material, such as, for example, the first material 2201, can be at least partially hydrophilic and/or absorbable, one or more portions of this layer, which may or may not be pierced by a staple, can begin to disintegrate as indicated by reference numeral 2410, as schematically shown in FIG. 44 upon exposure to moisture 2026.

The adjunct material described herein may comprise a first material, which is a material encompassing a second material, that can have various properties. For example, as discussed above, the first material can have portions that dissolve at different rates, portions that absorb at different rates, portions of varying widths, etc. The first and second materials can comprise different materials.

Figure 45:
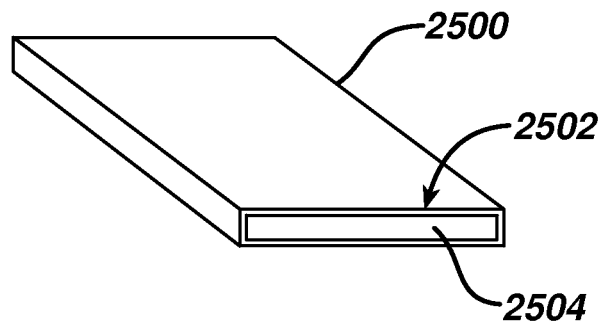
FIG. 45 is a perspective view of an adjunct material having a uniform thickness, in accordance with some embodiments.

An adjunct material 2500 shown in FIG. 45 may have a thickness that is the same or substantially the same along a cross-section of the adjunct material. In this example, a first (outer) material 2502 of the adjunct material 2500 may be brittle. It should be appreciated, however, that the adjunct material in accordance with some embodiments having any suitable shape can be brittle.

The first material 2502 can encompass a second material 2504 which may be a hydrophilic foam made of any suitable material. Additionally, in some embodiments, the second material 2504 may comprise one or more therapeutic substances. The non-limiting examples of the therapeutic substance include fibrin, thrombin, antibiotics, antimicrobial, and antibacterial agents. Suitable agents can include, but are not limited to, triclosean, and silver and copper ions and nanoparticles. It should be appreciated that any number of any suitable therapeutic substances can be included with the second material 2504 and can be eluted with the second material 2504 is exposed to moisture and/or heat in the patient's body.

In some embodiments, tissue is engaged between a cartridge assembly and an anvil of a surgical stapler at a treatment site, wherein at least one of the cartridge assembly and anvil has an adjunct material removably retained thereon. The surgical stapler can then be actuated to eject staples from the cartridge assembly through the adjunct material and into the tissue. The adjunct material can help to reduce impact and trauma from the stapling, distribute stress load on the tissue near the staple line—e.g., as the tissue such as lung parenchyma is stretched after the surgery to its normal volume. It should be appreciated, however, that the adjunct material described herein can be employed in any type of surgery, and embodiments are not particularly limited to lung surgeries.

Figure 46:
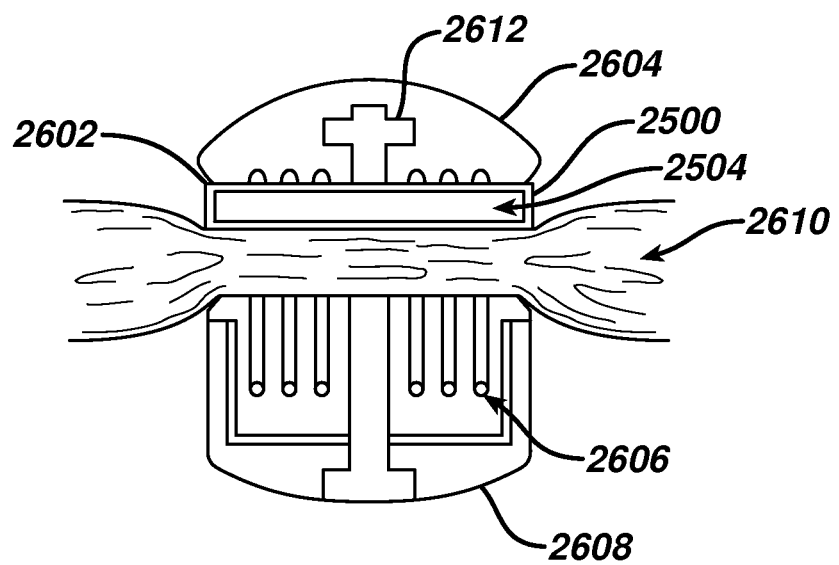
FIG. 46 is a cross-sectional view of tissue and an anvil of a surgical stapler having an adjunct material retained thereon, before penetration of the tissue by surgical staples, in accordance with some embodiments.

In the example illustrated in FIG. 46, an adjunct material 2500 can be positioned on a tissue facing side 2602 of an anvil 2604 of a surgical stapler. When staples 2606 supported by a cartridge body 2608 (which may be similar to the cartridge body 2006 in FIG. 37A) are deployed to engage tissue 2610, the first material 2502 of the adjunct material 2500 can fracture so as to expose the second material 2504 to moisture. Additionally or alternatively, the adjunct material 2500 can fracture by being compressed between the anvil 2604 and the cartridge assembly 2608. Furthermore, in embodiments as shown in this example in which the surgical stapler includes a knife 2612, the knife 2612 can also be used to cut the adjunct material 2500 thus exposing the second material 2504 to moisture. Although adjunct material 2500 is shown in FIG. 46 as being disposed on an anvil 2604 of a surgical stapler, adjunct material 2500 may be placed on one or both tissue facing surfaces of opposed jaws of a surgical stapler.

Figure 47:
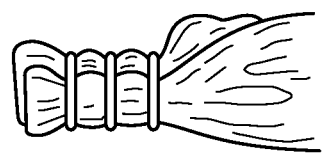
FIG. 47 is a side view of the tissue penetrated by the surgical staples and the adjunct material penetrated and retained by surgical staples, in accordance with some embodiments.

Regardless of the way in which the second material 2504 of the adjunct material 2500 is exposed to moisture, the second material 2504 expands to seal staple holes or prevent them from forming and the therapeutic substance is released to provide the desired effect on the tissue 2610, as shown in FIG. 47.

Woven Adjunct Materials

Adjunct materials are provided for sealing of a staple line against fluid leakage. One advantage of tissue adjuncts is their propensity to prevent or minimize leaks, such as fluid or gas leaks. Tissue adjuncts can perform this function by one or more of the following mechanisms: plugging holes or tears that occur at the staple puncture sites; restricting movement of tissue around staple puncture sites to prevent an increase in the size of staple holes and/or to prevent tissue tears; and minimizing strain gradients that occur between constrained tissues within the staple line and free tissue adjacent to the staple line.

A woven adjunct material can provide reinforcement to the staple line and can prevent tears in the tissue or pulling of the staples through the tissue by distributing stress along the tissue near a staple line. Further, a woven adjunct material can absorb impact from stapling and reduce trauma at and/or beyond the staple line. In certain aspects, the woven adjunct material can act as a medium into which staples can penetrate into when tissue at the staple site is thin or diseased. A woven adjunct material can thus be configured to both distribute the compressive load and to compensate for variable tissue thickness. In certain aspects, an adjunct material can include a plurality of layers, at least one of which is woven, such as a core and one or more layers. A size, shape, and a composition of the material forming each these layers can be selected in various ways to influence mechanical properties of the resulting adjunct material, such as a compressibility and fluid absorption capability of the adjunct.

An adjunct material can be inserted into a patient and deployed at a surgical site in various ways. For example, an adjunct material can be releasably coupled to an end effector of a surgical stapler, the end effector including a cartridge assembly and an anvil. When the end effector is positioned adjacent to a surgical site, tissue can be engaged between the cartridge assembly and the anvil. Actuation of the surgical stapler can eject staples from the cartridge assembly, through the adjunct material, and into the tissue grasped between the jaws. The adjunct material can help to reduce trauma from the stapling and distribute stress load across the tissue near the staple line to reduce a likelihood that the tissue will tear. In certain aspects, the adjunct material can elute a therapeutic agent, serve to absorb fluid, adjust for variations in material thickness, or perform various other functions when the adjunct is deployed onto tissue.

Figure 48A:
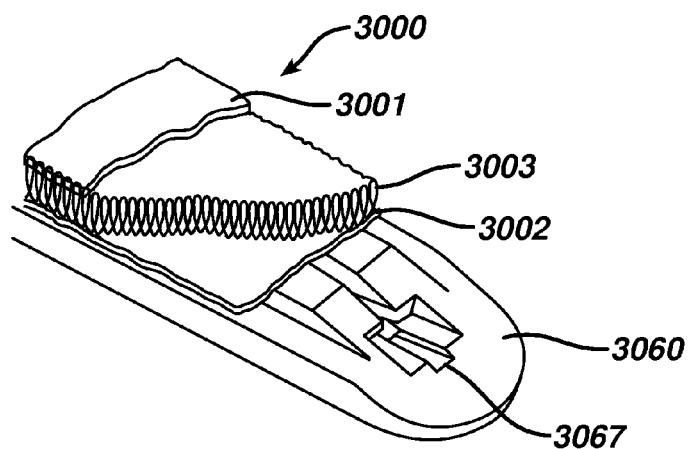
FIG. 48A is a perspective view of a woven adjunct material loaded onto a cartridge assembly of a surgical stapler.
Figure 48B:
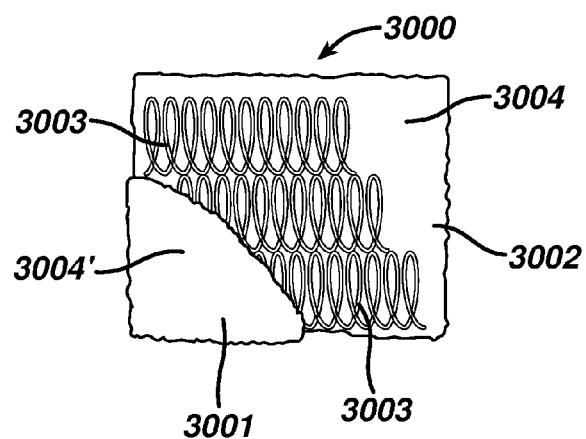
FIG. 48B is a top view of the woven adjunct material of FIG. 48A.

A woven adjunct material can have various sizes, shapes, and configurations. In one embodiment, a woven adjunct material includes an inner core layer and at least one outer layer of material. The outer layer of material can be positioned on one or more sides of the core layer, e.g., top, bottom, and/or lateral sides of the core layer. In one embodiment, a flexible support layer can surround all sides of the elastic core layer so as to envelop the elastic core. The core layer and flexible support layers can be formed from various materials. For example, the elastic core layer can be a layer of loosely woven material, and a tightly woven material can surround the elastic core layer on at least one side and can act as a flexible support layer. Each of the flexible support layers can include fibers 3004, which can be the same as or different than fibers 3005 in the elastic core layer 3003. FIG. 48B illustrates one exemplary embodiment of a woven adjunct material 3000 in which flexible support layers 3001, 3002, are positioned on the top and bottom of the elastic core layer 3003, respectively.

The woven adjunct material can be configured to releasably couple to an end effector of a surgical instrument, such as a cartridge assembly and/or anvil of a surgical stapler. For example, FIG. 48A shows the woven adjunct 3000 including the two flexible support layers 3001, 3002 on the top and bottom of the elastic core layer 3003 and coupled to a cartridge assembly 3060 having a knife slot 3067 and a plurality of staple cavities (not shown). The woven adjunct can be releasably retained on any of the end effectors of the surgical staplers provided herein e.g., staplers 10, 100, 200, an open linear cutting stapler.

Figure 48C:
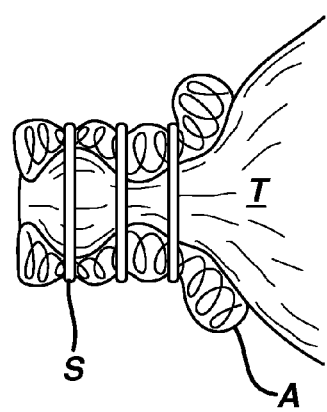
FIG. 48C is a side view of the woven adjunct material of FIG. 48A stapled onto tissue.

The adjunct material can deliver various benefits to the tissue when the adjunct material is stapled to the tissue. FIG. 48C shows the effects of an adjunct material A on a tissue T. As illustrated in FIG. 48C, the adjunct material A can compensate for variable thickness of the tissue at the staples S by compressing under the load of the staples S. The adjunct material A can distribute a strain on the tissue T from the staples S to a portion of the tissue T positioned beyond the staple line to prevent tearing along the tissue T at or beyond the staple line.

FIGS. 49A-C show a behavior of an adjunct material 3000 when a compressive force is applied and then released. More specifically, FIG. 49A shows the adjunct material 3000 before application of a compressive force. FIG. 49B shows the adjunct material 3000 having a compressive force applied thereto which decreases a thickness of the adjunct. FIG. 49C shows the adjunct material 3000 after the compressive force is released therefrom, which increases a thickness of the adjunct. This compression and expansion capability can result from the structure of the adjunct material.

The support layer(s) of the woven material 3000 can be formed in a variety of weave patterns and geometries to provide desired mechanical properties, such as flexibility, pressure distribution, homeostasis, and pneumostasis. The weave pattern used to form support layer(s) can vary and can include, by way of non-limiting example, those achieved by flat knitting processes with various needles, circular knitting processes with various needles, double knitting, warp knits, weft, knits, plain weaves, pile weaves, etc. The flexible support layer 3001, 3002 and the elastic core layer 3003 can have the same weave pattern or the flexible support layer and the elastic core layer can have different weave patterns to achieve a desired property for each layer. Additional processes can be applied to a layer to adjust its size, density, mechanical properties, surface properties, appearance, etc. These processes include the application of heat, the application of heat under a boundary condition such as force or displacement, a chemical treatment (e.g., scouring, mercerizing, singeing, raising, calendaring, sanforizing, etc.). A person of skill in the art will appreciate that the structure of the flexible support layer(s) of the woven adjunct can be adjusted to achieve desired properties. For example, the flexible support layer(s) can have a tighter weave than a weave of the core layer. In certain aspects, the flexible support layer(s) can be densely woven. Regarding a relative density of the support layer and the core layer, the support layer(s) can be in the range of about 2 to 10 times more densely woven than the elastic core layer.

FIG. 50 illustrates an exemplary weave of fibers used to form the support layers 3001, 3002 of FIGS. 48A-48C. As shown, fibers 3004 can be woven into loops which interlock in both the X and Y directions. A weave density of the flexible support layers 3001, 3002 can be sufficiently dense so that the support layers 3001, 3002 are not transparent to light. The weave density can be characterized in various ways, such as by a degree of binding between adjacent fibers. The fibers can be interlocked, as shown, or knotted together, such that there is substantially no relative motion between the fibers when a force is applied to the layer. Fibers 3004 may be comprised of a braided mix of multiple smaller fibers made of one or more materials. The selection or materials, fiber diameter, and ratios of different fiber constituents (e.g., five fibers of a first material for every one fiber of a second material) can impact the behavior of fibers 3004.

One skilled in the art will appreciate that the flexible support layer(s) 3001, 3002 can be formed from various types of fibers that are biocompatible and bioabsorbable. Examples of such materials include various materials from which sutures are made, including naturally occurring fiber materials and synthetic fibers. Exemplary materials include polydioxanon (sold under the trademark PDS®), Polyglycerol sebacate (PGS), PGA (Polyglycolic acid and various forms thereof, marketed under the trademarks VICRYL® and/or NEOVEIL®), PCL (Polycaprolactone), PLA or PLLA (Polylactic acid), PHA (Polyhydroxyalkanoate), PGCL (Poliglecaprone 25, sold under the trademark MONOCRYL®, PANACRYL® (Ethicon, Inc., Somerville, N.J.), polyglactin 910, polyglyconate, PGA/TMC (polyglocolide-trimethylene carbonate sold under the trademark BIOSYN®), polyhydroxybutyrate (PHB), poly(vinylpyrrolidone) (PVP), poly(vinyl alcohol) (PVA), absorbable polyurethanes, regenerated cellulose, and oxidized regenerated cellulose fibers (ORC). Blends and/or copolymerizations of any of the aforementioned materials can be tailored to have a desired molecular weight, mechanical properties, and/or degradation rate. In one embodiment, the flexible support layers(s) 3001, 3002 can be formed as a non-woven structure derived from the aforementioned materials. These materials may be in the form of a foam and/or film. In one embodiment, the flexible support layers(s) are at least partially comprised of PDS® to facilitate adherence to elastic core layer 3003. In one embodiment, fiber 3004 is a braided filament comprised of five Vicryl® fibers and one PDS® fiber.

In one embodiment, the flexible support layer(s) 3001, 3002 can be formed from a combination of synthetic fibers and naturally occurring fibers. For example, a naturally occurring fiber or fibers can be woven into the tissue contacting surface of a flexible support layer primarily comprising synthetic fibers. Exemplary naturally occurring materials include oxidized regenerated cellulose fibers (ORC) and regenerated cellulose. The naturally occurring material, particularly ORC, can be advantageous as it can function to form a seal with the tissue as it tends to gelatinize upon contact with a liquid.

A size of the fibers in the flexible support layer(s) can be selected to achieve desired mechanical properties. An exemplary composition of the flexible support layer is fibers 3004 in the support layer(s) can be in the range of about 10-0 to 24-0 in size, i.e., about 0.024 mm to 0.3 mm. In addition, the fibers of the flexible support layer(s) can be of various fiber types including monofilament and braided.

The elastic core layer 3003 can have various sizes, shapes, and configurations, and the material of the elastic core layer can be selected to achieve desired mechanical properties. The elastic core layer 3003 can include a knitted or woven structure that is loose in one direction (the direction of deformation) that readily compress when a compressive force is applied and then can expand when the compressive force is no longer applied. Increasing resistance to compression (in the direction of deformation) can be achieved by compacting the structure in the plane perpendicular to the direction of primary deformation. This compact structure can be achieved by post-knitting process steps such as heating, mechanical compression, etc. Further, the fibers in the elastic core layer can be loosely woven such that the fibers are able to move relative to one another more readily than the interlocked or knotted fibers in the support layer. As such, the weave density of the elastic core layer 3003 is typically significantly less dense in at least one direction than that of the support layers 3001, 3002. By way of example, the relatively low weave density of the elastic core layer 3003 can be characterized in terms of the weave density being sufficiently low so as to permit it to be transparent to light. An alternative description would be a deformation inducing a stretch ratio of approximately 0.5 requires a pressure of approximately 3 g/mm².

Like the flexible support layer(s), the elastic core layer can be formed from various types of fibers that are biocompatible and bioabsorbable. Examples of such materials include various materials from which sutures are made, including naturally occurring fiberous materials and synthetic fibers. Exemplary materials include polydioxanon (sold under the trademark PDS®), Polyglycerol sebacate (PGS), PGA (Polyglycolic acid and various forms thereof, marketed under the trademarks VICRYL® and/or NEOVEIL®), PCL (Polycaprolactone), PLA or PLLA (Polylactic acid), PHA (Polyhydroxyalkanoate), PGCL (Poliglecaprone 25, sold under the trademark MONOCRYL®, PANACRYL® (Ethicon, Inc., Somerville, N.J.), polyglactin 910, polyglyconate, PGA/TMC (polyglocolide-trimethylene carbonate sold under the trademark BIOSYN®), polyhydroxybutyrate (PHB), poly(vinylpyrrolidone) (PVP), poly(vinyl alcohol) (PVA), absorbable polyurethanes, regenerated cellulose, and oxidized regenerated cellulose fibers (ORC). Blends and/or copolymerizations of any of the aforementioned materials can be tailored to have a desired molecular weight, mechanical properties, and/or degradation rate. In one embodiment, the elastic core layer 3003 can be at least partially comprised of PDS® to facilitate adherence to flexible support layer(s) 3001, 3002. In one embodiment, fiber 3005 is a braided filament comprised of five Vicryl® fibers and one PDS® fiber.

A size of the fibers in the elastic core layer can affect the properties of the adjunct material, such as elasticity, compressibility, and resiliency of the adjunct. In one embodiment, the fibers in the elastic core layer 3005 can have a greater diameter than the fibers in the flexible support layers 3004. The fibers of the elastic core can be braided or can be a monofilament. While a size of the fiber forming the elastic core can vary, in one embodiment the elastic core can be formed from fibers made of suture materials having a size in the range of about 10-0 to 2-0 in size, i.e., about 0.02 mm to 0.3 mm.

The elastic core layer and the flexible support layer(s) can be connected in various ways. For example, the elastic core layer and flexible support layer(s) can be directly connected, e.g., woven together. As shown in FIGS. 51A and 51B, the fibers 3004 of the flexible support layers 3001, 3002 can be woven around and interlocked with the fibers 3005 of the elastic core layer 3003. In another embodiment, (not shown), the elastic core and flexible support layers can be bonded together my melting one or more constituents (e.g., PDS®, etc.) comprising fibers 3004 of the flexible support layers 3001, 3002 and fibers 3005 of the elastic core layer 3003. In another embodiment (not shown), the elastic core and flexible support layers can be bonded together using any known manufacturing technique, such as using felting or otherwise adhering the layers together.

A thickness of an adjunct material, including the elastic core and the flexible support layer(s), can vary depending on the intended clinical application. In general, an adjunct material can be at least as thick as a height of a staple in its formed state. If a single adjunct material is coupled to one portion of an end effector, e.g. a cartridge assembly or an anvil, the adjunct material can be about 3.5 mm thick. Alternatively, if an adjunct material is present on both the anvil and the cartridge, each piece of adjunct material can be about one half of the height of the staple in its formed state. The flexible support layers typically have a thickness equal to about the diameter of two of the fibers used for the flexible support layer, typically from about 0.16 to 0.6 mm thick. The elastic core typically comprises the remainder of the thickness dimension of the adjunct material. Generally, the thickness of the elastic core can be in the range of about 2 to 3 mm.

Woven three-dimensional structures can be formed in such a way and using such materials that they will have desired mechanical properties. The adjunct material generally will have a number of desired properties that will vary depending upon the claimed application. One of skill in the art will understand that the material can be varied in accordance with the description above to modify these desired properties. Typically, however, when compressed and held at a height of 2 mm in a 37° C. PBS solution, the adjunct material construct can provide a minimum pressure of 3.0 gf/mm2 from the time of compression (t=0) through 72 hours. When compressed and held at a height of 2 mm in a 37° C. PBS solution, the adjunct material construct can provide pressure that does not go below the line defined by 3.0 gf/mm$^2$ @ 72 hours and 0.0 gf/mm$^2$ at day 28. When compressed to 1.0 mm, held for 15 seconds, and then released, the adjunct material can return to 2.0 mm height with at least 2.0 gf/mm$^2$ within 30 seconds. The adjunct material can be able to compress without excessive pressure to around 0.75 mm. The adjunct material should be fully reabsorbed in about 120 days.

Figure 52A:
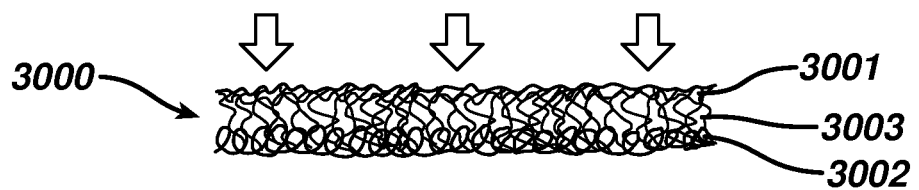
FIG. 52A is a side view of the woven adjunct material of FIG. 51A in compressed state.
Figure 52B:
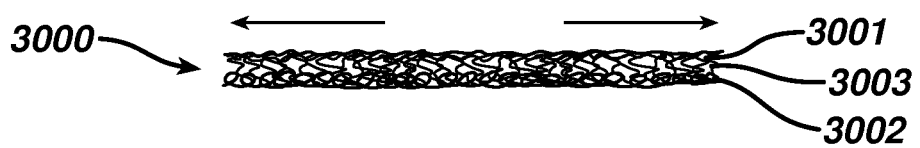
FIG. 52B is a side view of the woven adjunct material of FIG. 51A in an expanded state.

FIGS. 52A-52B show typical behavior of the adjunct material under compressive and elongation forces, respectively. FIG. 52A shows the adjunct material 3000 with a compressive force applied thereto, while FIG. 52B shows the adjunct material 3000 with an elongation force applied thereto. As shown, the adjunct material 3000 has sufficient integrity and structure such that it is not compromised by the application of these forces. The amount of material and degree of compression to be applied can determine the mechanical properties of the resultant brick. Accordingly, one of skill in the art will understand that the amount of material and degree of compression can be varied in order to modify these properties.

With the above teachings, one skilled in the art will recognize that adjunct 3000 may be comprised of one or more elastic core layers 3003 as well as one or more flexible support layers 3001, 3002. The order and number of layers as well as their orientation result in multiple combinations that are conceived within this disclosure. For example, the adjunct can include two external support layers connected by a single, central flexible layer. One skilled in the art will also appreciate that the adjunct 3000 can be formed of sandwiches of multiple flexible support layers (e.g., three layers) with a number of (e.g., two) elastic core layers.

Fibrous Adjunct Materials

In another embodiment, non-woven fibrous materials can form all or portions of an adjunct material. Like a woven adjunct material, the mechanical properties of a fibrous adjunct material can be influenced by the shape of the adjunct, the type of fibers used, and the density of the fibers.

The resulting material properties may also be influenced by process steps used to create the adjunct. For example, FIG. 54A illustrates an adjunct material 3100 with a central region that is more dense than regions adjacent the perimeter of the structure. FIG. 54D shows pre-processed adjunct material 3100D prior to a compressive processing step that creates adjunct material 3100. Pre-processed adjunct material 3100D is comprised of (woven or non-woven) fibers of a generally homogeneous structure and generally uniform density. By compressing the central region 3110 of 3100D to the flat height of adjunct material 3100, a central region is created that is more dense than the perimeter region.

FIG. 54B shows a wider structure 3100B being compressed to a more narrow structure (by force or by shrinkage through heat) resulting in an aligned fiber pattern with anisotropic material properties.

FIG. 54C shows a block 3100C that is pressed to increase the width resulting in an anisotropic material with an aligned fiber pattern perpendicular to that of the adjunct 3100B of FIG. 54B.

The construction of non-woven adjunct materials can be selected in various ways, but can include a fleece (e.g., a material that is similar to the fine web of cotton or wool removed by the doffing knife from the cylinder of a carding machine) and/or melt blown fibers.

A non-woven adjunct material can be formed from various types of fibers that are biocompatible and bioabsorbable. Examples of such materials include various materials from which sutures are made, including naturally occurring fiber materials and synthetic fibers. Exemplary materials include polydioxanon (sold under the trademark PDS®), Polyglycerol sebacate (PGS), PGA (Polyglycolic acid and various forms thereof, marketed under the trademarks VICRYL® and/or NEOVEIL®), PCL (Polycaprolactone), PLA or PLLA (Polylactic acid), PHA (Polyhydroxyalkanoate), PGCL (Poliglecaprone 25, sold under the trademark MONOCRYL®, PANACRYL® (Ethicon, Inc., Somerville, N.J.), polyglactin 910, polyglyconate, PGA/TMC (polyglocolide-trimethylene carbonate sold under the trademark BIOSYN®), polyhydroxybutyrate (PHB), poly(vinylpyrrolidone) (PVP), poly(vinyl alcohol) (PVA), absorbable polyurethanes, regenerated cellulose, and oxidized regenerated cellulose fibers (ORC). Blends and/or copolymerizations of any of the aforementioned materials can be tailored to have a desired molecular weight, mechanical properties, and/or degradation rate.

One of skill in the art will understand that the fiber size of the non-woven adjunct can be optimized in order to achieve desired properties. In a preferred embodiment, the fibers can be suture fibers from about 10-0 to 2-0 in size, i.e., about 0.02 mm to 0.3 mm. In a more preferred embodiment, the fibers can be size 7-0, i.e., about 0.15 mm.

Adjuncts Having Mesh and Fibrous Layers

In other embodiments, the adjunct material can have other constructions, such as a woven or non-woven adjunct material surrounded by a mesh. For example, FIG. 55 shows a mesh 3200 formed from fibers 3201, can surround adjunct material 3100. The mesh 3200 can have various configurations, and can include a plurality of fibers 3201 arranged in a repeating pattern such as a honeycomb structure, as shown. The size of mesh, and type of mesh can be varied, in addition to the construction of the non-woven material described above, to modify the mechanical properties of the non-woven material as described above. A mesh can be positioned around a core layer similar to the core layers previously described. For example, the mesh can surround a fleece core layer, or one made from melt blown fibers. The mesh may be used to constrain adjunct material 3100 in a desired state for use. Further, the mesh may be used to facilitate attachment to a stapling device.

In general, the mesh can be a loosely woven mesh of fibers. The mesh can be a mesh of fibers woven in a geometry that is transparent to light. The mesh can have a wide range of pore sizes, such as in the range of about 0.5 to 5 mm.

In general, the mesh material can be a mesh that is suitable for surgical implantation. The mesh can be biocompatible and may be bioabsorbable. In one exemplary embodiment, the mesh can be PROCEED® or PHYSIOMESH®, both of which are manufactured by Ethicon, Inc. of Somerville, N.J.

In certain aspects, the mesh surrounding the fleece material can be coated with a therapeutic agent such that the mesh can elute or release the therapeutic agent to a patient when the adjunct is positioned in a patient's body. The therapeutic agent may be a drug that promotes a beneficial outcome such as healing, or prevents infection.

Coating an Adjunct with a Theraputic Substance

Figure 53A:
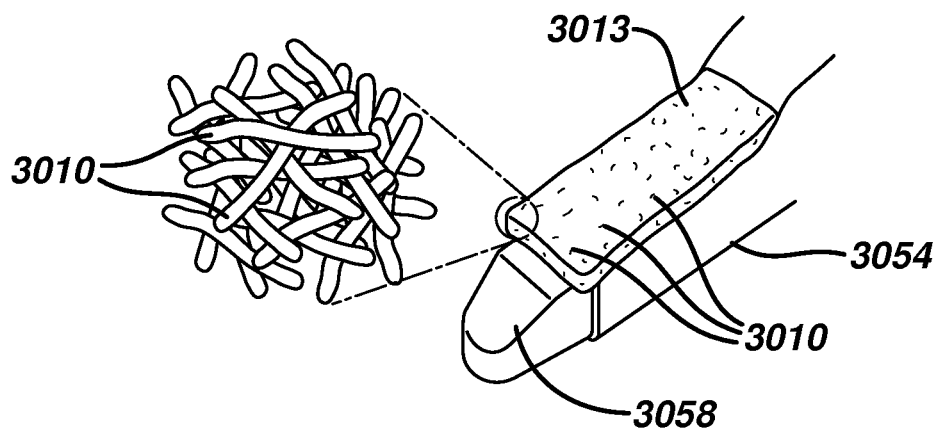
FIG. 53A is a perspective view of an end effector with partial detail of a fibrous adjunct material loaded onto the cartridge assembly.
Figure 53B:
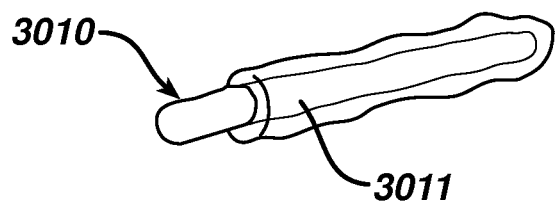
FIG. 53B illustrates a fiber of the adjunct material of FIG. 53A coated with a drug.

The fibers of an adjunct material can be coated with a therapeutic substance i.e., one that can aid in healing and/or combat or prevent infection and that can be effective to be released upon implantation of an adjunct material. For example, FIG. 53A shows an adjunct material 3013, loaded on the tissue facing surface 3058 of an anvil 3054 in which the adjunct material includes fibers 3010 coated with a therapeutic substance 3011 as shown in FIG. 53B. In another embodiment (not shown), the fibers in a woven adjunct material can be coated with a therapeutic substance. One skilled in the art will appreciate that the number/percentage of fibers coated with a therapeutic substance can vary. In another embodiment (not shown), only a small percentage of the fibers of the adjunct material are coated, e.g., in the range of about 5 to 50% of the fibers by volume can be coated.

In some embodiments, the adjunct material may include one or more therapeutic agents, such as, for example, drugs, clotting or sealing agents, antibacterial agent(s), and antimicrobial agent(s). It should be appreciated that any number of any suitable therapeutic substances can be included on an adjunct material. The therapeutic agent can be configured to be released over time to aid the tissue in healing, for example. In embodiments where more than one therapeutic agent is employed, different therapeutic agents can be configured to release at different rates.

Therapeutic substance coated onto the fibers can have various properties. Exemplary therapeutic substances that can be employed can include those that expedite binding as well as antibiotics, and antimicrobials. Exemplary therapeutic substances can include a mixture of fibrinogen and thrombin. In one embodiment, fibrinogen and thrombin can be used as therapeutic substances for coating the VICRYL® suture which forms the adjunct material because lyophilized fibrinogen and thrombin (human or animal derived) are known to adhere to VICRYL® fibers when released from a fluid suspension VICRYL® fibers can be used in the tissue contacting surface. In another embodiment a small number of VICRYL® fibers can be used. In another embodiment, VICRYL® fibers can be woven (e.g., needle punch) into the structure of the adjunct material, e.g. at the core or on the support layers, and can be coated with a therapeutic substance. In certain aspects, when thrombin coated onto a woven adjunct, the thrombin can comprise about 1% or less of the woven adjunct.

As previously mentioned, various antimicrobials can be coated onto the fibers of woven or non-woven adjunct material. Exemplary include, by way of non-limiting example, triclosean and ionized silver. In another embodiment, antibiotics can be deposited only onto a woven layer of an adjunct material. Where a woven layer of an adjunct material includes an antibiotic, antimicrobial, or antibacterial woven therein or coated onto the fibers, the antibiotic/antimicrobial/antibacterial can comprise about 0.5% or less of the adjunct material.

A therapeutic substance can be coated on the fibers of the elastic core layer of a woven adjunct material. When the therapeutic substance is deposited on the fibers of the elastic core, the therapeutic substance can be in liquid form and can be absorbed into the elastic core layer. This can allow the therapeutic substance to disperse into the tissue following implantation of the adjunct material.

An adjunct material can include various other layers. In another embodiment, (not shown), the elastic core layer can have a film coupled to at least one side of the core layer. In an exemplary embodiment the film is made of PDS®. In another embodiment, the film can include PGA/PCL 75/250 polymeric fibers.

Modifying Region(S) of an Adjunct Material Based on Features of a Surgical Device The adjunct material on the cartridge assembly can have varied properties throughout or particular regions of the adjunct material can be modified to correspond to a portion of the end effector to which the adjunct will be coupled. For example, when the adjunct material is to be used on a surgical stapler having a knife, e.g. surgical staplers 10, 100, and 200, the properties of the adjunct can be modified in the region in which the knife will cut through the adjunct material. Such a modification can include thinning out the flexible support layer, using less material, the core layer only at this region, having a more loosely woven layer than other layers of the adjunct, or removing excess material with a laser. In another embodiment, felting can be applied to specified regions of the adjunct so that the knife can more easily penetrate and cut through the adjunct material. In another embodiment, the properties of the adjunct can be modified by either adding or removing fibers from the woven structure to make it stiffer or more flexible, respectively. A zone of increased stiffness may be useful for attachment to the stapling device. In addition, zones of increased flexibility may be help to promote optimal tissue interactions.

A felting process can be used to control dimensions and/or adjust a local density of the adjunct material, such as to decrease a density of a single layer or multiple layers of an adjunct material. Felting can include applying heat to a specific section of the adjunct material at a temperature between the material's glass transition temperature and its melting temperature. By applying heat above the glass transition temperature, and below the melting temperature the structure of the material can be altered. With this process it is possible to decrease the density of the material while avoiding changes associated with complete melting of the material.

Figure 56A:
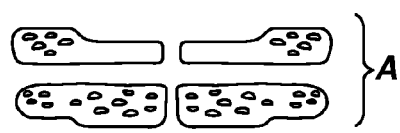
FIG. 56A is a perspective view of four adjunct materials for loading onto an end effector of a stapler.
Figure 56B:
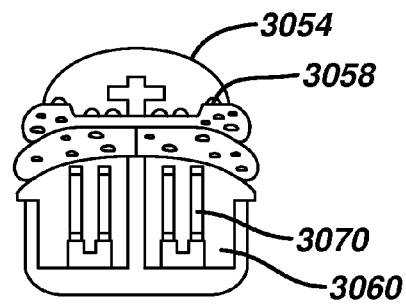
FIG. 56B is an end, sectional view of adjunct materials loaded onto both the anvil and cartridge assembly of a stapler.

In an alternative embodiment, the adjunct material can be used on both the anvil and cartridge side of a surgical stapler. For example, FIGS. 56A and 56B demonstrate the use of adjunct material A on both the tissue facing surface 3058 of the anvil portion 3054, and the cartridge assembly 3060, wherein the staples 3070 are covered by the adjunct material so that when deployed, the staples can pierce the adjunct material. A thickness of the adjunct material thickness can be varied across a lateral or longitudinal (not shown) length of the anvil and the cartridge assembly, such as by using methods described above. Such an asymmetric geometry on both tissue facing surfaces of the anvil and cartridge may be useful for tissue facing surfaces that are not flat, which may be useful when staples 3070 are of varying unformed height, formed heights, or both unformed and formed heights. In such an arrangement, it is important to note that the geometry of an adjunct material on the first opposing jaw is not necessarily symmetric with the geometry of an adjunct material on the second opposing jaw. In one embodiment the combined thickness of both adjunct materials across a lateral distance is approximately the same. In another embodiment, the combined thickness of both adjunct materials across a lateral distance is not the same.

Stapling Adjunct Material onto Tissue

The adjunct material described herein can be deployed onto tissue using a surgical stapling device, e.g., surgical staplers 10, 100, 200, open linear cutting stapler. In use, tissue can be engaged between a cartridge assembly and an anvil of a surgical stapler at a surgical site, wherein at least one of the cartridge assembly and anvil has an adjunct material releasably retained thereon. The surgical stapler can be actuated to eject staples from the cartridge assembly, through the adjunct material, and into the tissue. The adjunct material can help to reduce impact and trauma from the stapling, evenly distribute strain along the staple line, and can compensate for variable tissue thickness and allow staples secure onto thin or diseased areas of tissue. Different areas of the adjunct material can perform different functions when the adjunct material is stapled onto tissue.

Figure 57A:
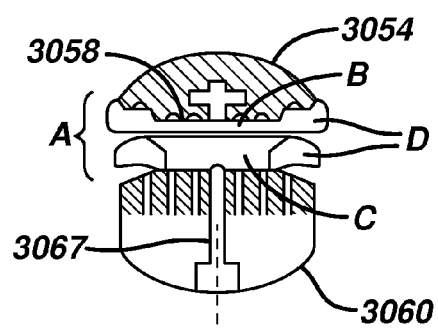
FIG. 57A is a front sectional view of adjunct materials loaded onto both the anvil and cartridge assembly of an end effector.
Figure 57B:
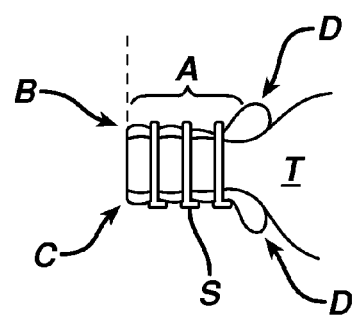
FIG. 57B is a side sectional view of the adjunct material of FIG. 57A stapled onto tissue.

FIG. 57A shows four adjunct materials that can be releasably coupled to an end effector of a surgical stapler. First and second adjunct materials can couple to a tissue facing surface 3058 of the anvil 3054 and second and third adjunct materials can coupled to the cartridge assembly 3060. Three regions of the adjunct material identified as B, C, and D, can each perform a different function. For example, the B region can be used for staple sealing, the D region can be used for stress relief and collateral damage reduction, and the C region can be used for variable thickness compensation. Accordingly, it can be possible to select the adjunct material used in each region to meet desired surgical outcomes. When the adjunct material is deployed onto the tissue T and coupled thereto via the staples S, the adjunct material can be positioned along an outer surface of the tissue, as shown in FIG. 57B. The adjunct material can seal the staples, provide stress relief and reduce collateral damage to nearby tissue, and/or can compensate for variable tissue thickness.

Crown-Side Staple-Specific Adjuncts

Figure 58:
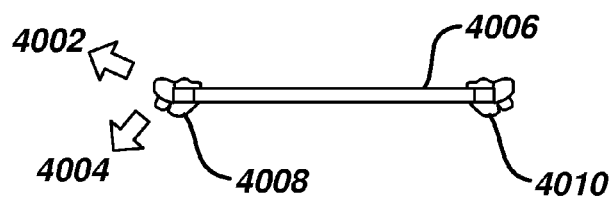
FIG. 58 is a top view of tissue damage that can occur near staple legs.

As mentioned above and shown in FIG. 58, punctures formed by staples fired from a surgical stapler may result in the leakage of blood, air, or other fluids depending on the type of tissue being stapled. More particularly, tissue can stretch in any of a variety of directions 4002, 4004 after a staple 4006 is implanted therein, thereby stretching punctures 4008, 4010 formed by the staple legs. In some cases, bleeding or other leakage through staple punctures can be present even though a stapled end of a vessel or other body lumen is successfully sealed.

One advantage of tissue adjuncts is their propensity to prevent or minimize leaks, such as fluid or gas leaks. Tissue adjuncts can perform this function by one or more of the following mechanisms: plugging holes or tears that occur at the staple puncture sites; restricting movement of tissue around staple puncture sites to prevent an increase in the size of staple holes and/or to prevent tissue tears; and minimizing strain gradients that occur between constrained tissues within the staple line and free tissue adjacent to the staple line.

Embodiments of the devices and methods described herein can address leakage from these punctures by providing one or more adjuncts that are coupled to a staple and configured to plug or seal the punctures 4008, 4010. As described above, the adjuncts can be formed from viscous coatings (e.g., bio-absorbable urethane, etc.) disposed in staple cavities of a cartridge body containing staples. Upon ejection from the cartridge body, the adjunct coatings can become plugs that fill punctures 4008, 4010 formed by the staple legs. The plugs can be compressed when the staples are formed through tissue, and as the adjunct material is compressed it can expand and fill any defects in the tissue that could create leak paths. The adjunct plugs can also serve to distribute pressure applied by the staple, thereby reducing the possibility of a staple pulling through the tissue and failing to fasten the tissue as intended (so-called "cheese wiring"). Still further, a viscous coating used as an adjunct material can also include other healing properties, as described above (e.g., antimicrobial properties, hemostats, etc.) or other features to help with the formation of staples (e.g., lubricants, etc.).

Figure 59A:
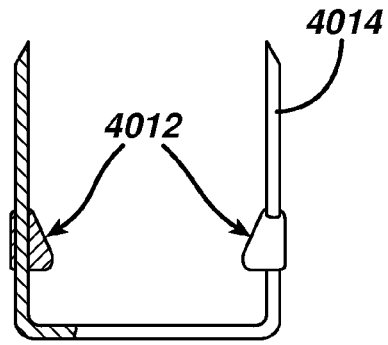
FIG. 59A is a side view of one embodiment of adjuncts coupled to a staple.

FIG. 59A illustrates one embodiment of adjuncts 4012 disposed about legs of a surgical staple 4014. The illustrated adjuncts 4012 are in the form of plugs disposed about each leg of the staple, that is, they have a tapered cylindrical shape configured to wedge into a puncture created by a staple leg as it passes through tissue. The adjuncts 4012 can be formed at any point along the legs of the staple 4014 and, in some embodiments, can be configured to slide along the legs, as described in more detail below.

Figure 59B:
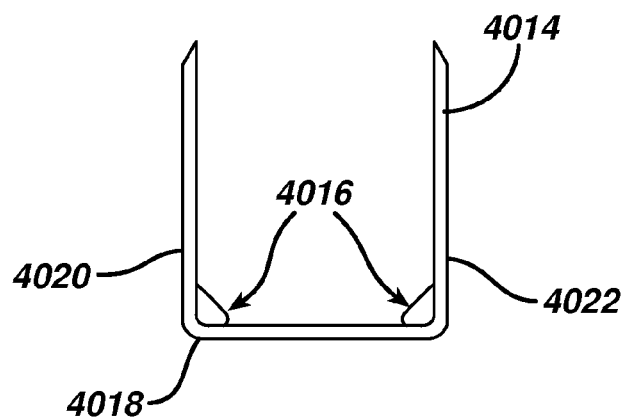
FIG. 59B is a side view of an alternative embodiment of adjuncts coupled to a staple.

In the embodiment shown in FIG. 59B, adjuncts 4016 can be positioned at a junction between a crown 4018 of the staple 4014 and each staple leg 4020, 4022. The adjuncts 4016 can again have a shape that tapers from the crown 4018 toward a distal end of the staple legs 4020, 4022 such that the adjunct forms a plug configured to be received within a puncture in tissue. The adjuncts 4016 can further be formed from a flowable material, e.g., a hydrogel, which can retain its shape prior to implantation but can become more flowable upon implantation in tissue to fill a puncture or other defect in the tissue. In other embodiments, a swellable material can be employed, i.e., a material that increases in volume upon contact with water or other bodily fluid.

Figure 60:
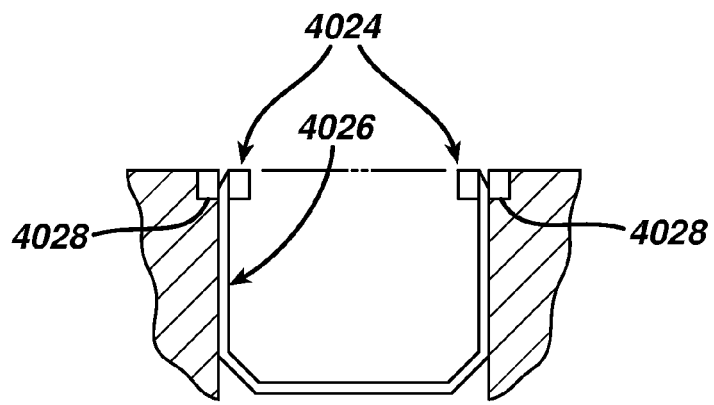
FIG. 60 is a cross-sectional view of one embodiment of adjuncts coupled to a staple.
Figure 61:
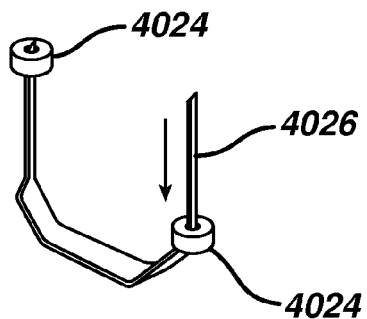
FIG. 61 is a perspective view of the adjuncts and staple of FIG. 60.

FIG. 60 illustrates an alternative embodiment of adjuncts 4024 disposed around legs of staple 4026. In this embodiment, the staple 4026 is housed within a staple cavity of a surgical stapler's cartridge body 4028. Adjunct plugs 4024 are disposed around each leg of the staple 4026 at a distal end thereof. In some embodiments, the adjuncts 4024 can be seated in small cut-outs or shelves formed in the cartridge body 4028 (compare to FIG. 62). The adjuncts 4024 can be configured to slide over the legs of staple 4026, as shown in FIG. 61.

In use, as shown in FIG. 62, tissue 4030 can be clamped between the cartridge body 4028 and an anvil 4032 and the staple 4026 can be ejected out of the cartridge body through the tissue and into the anvil. The adjuncts 4024 can abut against the tissue 4030 and begin to slide over the legs of the staple 4026 as it is ejected from the cartridge body (see FIG. 61). Ultimately the adjuncts 4024 can end up compressed between the tissue 4030 and a crown of the staple 4018. Because the adjuncts 4024 can be formed from a material that becomes flowable upon contact with water or other bodily fluid, or under compressive forces, the cylindrically-shaped adjuncts 4024 shown in FIG. 61 can flow into the punctures in the tissue 4030, as shown in FIG. 62.

Viscous coatings and other flowable or swellable materials can be suitable choices for an adjunct material because they can adapt to varying forces experienced by tissue at different locations within the body. FIGS. 63A and 63B illustrate that such adjunct materials can be used to effectively seal staple leg punctures that expand inward toward one another, as can be the case when the tissue is under compression, as well as staple leg punctures that expand outward away from one another, as can be the case when the tissue is under tension. By way of example, tissue under tension can often be found in the thoracic cavity, e.g., lung tissue and/or cardiovascular tissue (FIG. 63B), while tissue under compression can often be found outside of the thoracic cavity (FIG. 63A).

Figure 64A:
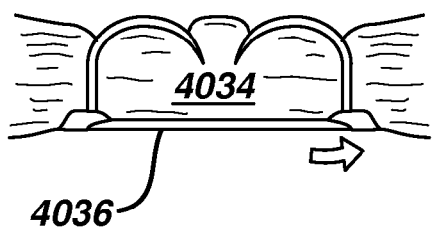
FIG. 64A is a side view of one embodiment of adjunct operation in tissue.
Figure 64B:
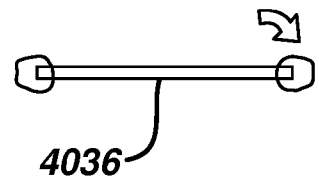
FIG. 64B is a top view of the adjunct operation shown in FIG. 64A.

FIGS. 64A and 64B provide alternative views of the configuration shown in FIG. 63B. Tissue 4034 that is under tension can cause staple leg punctures to expand outward from the staple 4036. Accordingly, flowable adjunct plugs 4038 in the form of gel plugs disposed around each leg of the staple 4036 can be pushed outward by compression between the crown of the staple and the tissue 4034 into the punctures. The gel can seal the expanded punctures, thereby preventing any leakage therethrough.

Figure 65:
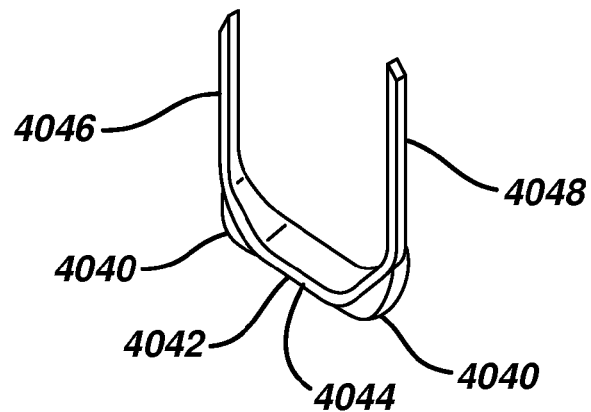
FIG. 65 is a perspective view of one embodiment of adjuncts coupled to a staple.

As noted above, FIGS. 59A-64B show adjunct material disposed around legs of a surgical staple or formed at an inner junction between a crown of the staple and the staple legs. In an alternative embodiment shown in FIG. 65, adjunct material 4040 can be coupled to an outer surface of the staple 4042 at the junction between a crown 4044 of the staple and each staple leg 4046, 4048. The adjunct material 4040 can be a flowable or swellable material in some embodiments, such as a hydrogel. Such a material can expand outward upon contact with tissue and fill the punctures formed by the staple legs 4046, 4048. The adjunct material 4040 in FIG. 65 is in the shape of a cylindrical plug, however any of a variety of other shapes are also possible. As mentioned above, other possible shapes can include taper along a leg of the staple, or entirely different shapes can be utilized, such as a cube, hexagonal extrusion, etc.

Figure 66:
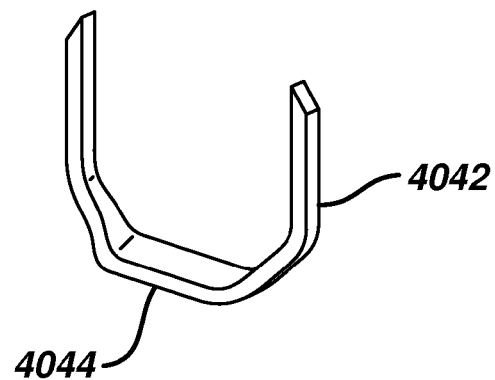
FIG. 66 is a perspective view of the staple of FIG. 65.
Figure 67A:
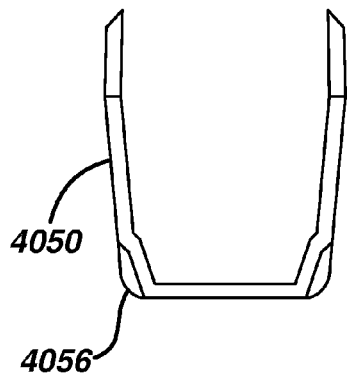
Figure 67B:
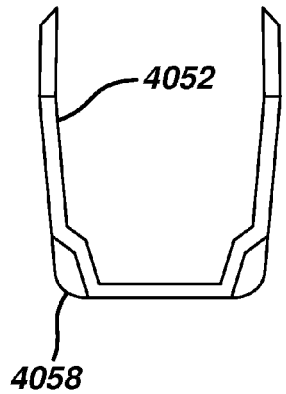
Figure 67C:
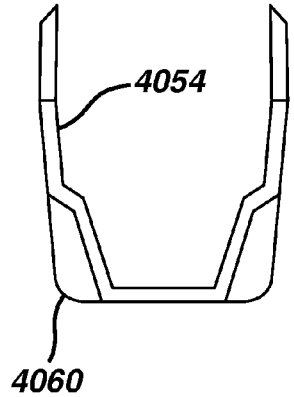

A shape of the staple 4042 can be modified to accommodate the adjunct material 4040, as shown in FIG. 66. In some embodiments, for example, right-angle corners of the staple 4014 shown in FIGS. 59A and 59B can be chamfered to provide attachment surfaces for the adjunct material 4040. The crown 4044 of the staple 4042 also has a broader, flat shape, as opposed to the cylindrical rod or square cross-sectional shape of the staple 4014 in FIG. 59. In addition, both the staple 4042 and the adjunct material 4040 can have any of a variety of sizes. FIGS. 67A-67C illustrate embodiments of staples 4050, 4052, and 4054 that have a same width and leg length, but accommodate increasing amounts of adjunct material 4056, 4058, 4060.

Figure 68A:
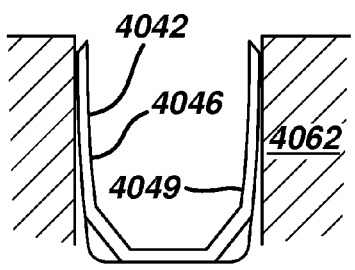
Figure 68B:
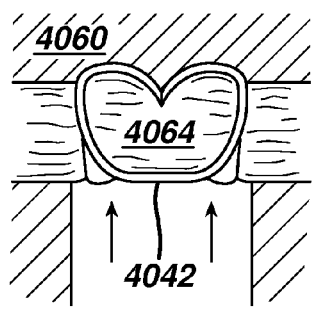
Figure 68C:
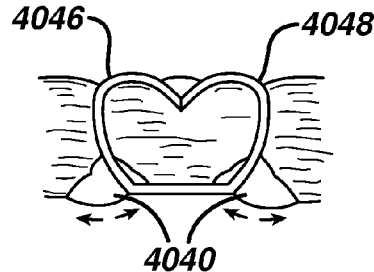

FIGS. 68A-68C illustrate the implantation of the staple 4042 shown in FIG. 65 in a patient's lung. The staple 4042 can be initially stored within a staple cavity of a surgical stapler cartridge body 4062. Once tissue 4064 is disposed between the cartridge body 4062 and an anvil 4066, the staple 4042 can be ejected from the staple cavity through the tissue and into the anvil. Upon contact with the lung tissue 4064, the hydrogel adjunct material 4040 can expand to fill any gaps or defects surrounding the punctures formed by the staple legs 4046, 4048.

Figure 69A:
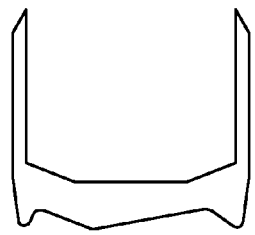
Figure 69B:

The flattened-crown staple of FIG. 65 is just one embodiment of a staple that can accommodate attachment of adjunct material thereto. FIGS. 69A and 69B illustrate still other alternative staple geometries that can have adjunct material coupled thereto, e.g., disposed about a leg thereof, or coupled to an outer or inner surface of a crown. U.S. patent application Ser. No. 14/138,516, filed on Dec. 23, 2013, the entirety of which is incorporated herein by reference, discloses still further staple geometries that can be combined with the adjunct materials disclosed herein. Regardless of the particular staple geometry or attachment mechanism for an adjunct material, the adjunct material can be configured to fill and seal individual punctures formed by the staple legs.

Figure 71A:
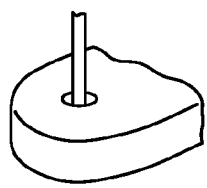
Figure 71B:
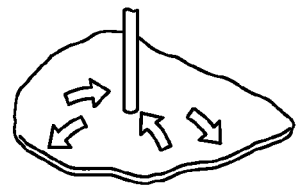

FIG. 70 illustrates an alternative embodiment of an adjunct in the form of a pledget 4066 that is configured to seal around both a first leg and a second leg of a surgical staple 4068. The pledget 4066 is shown pressed against a crown (not shown) of the staple 4068 and can be formed from a flowable and/or swellable material, such as a hydrogel or other gel, as discussed above. The gel can be configured to retain its shape when disposed within a surgical stapler cartridge body, as shown in FIG. 71A, but to become more flowable in all directions upon contact with tissue, water, or other fluid, as shown in FIG. 71B.

FIGS. 72A and 72B show the surgical staple 4068 and adjunct pledget 4066 from a side view before and after implantation. As shown in FIG. 72B, the pledget 4066 has expanded outward and flowed into tissue 4070 upon contact therewith. The gel material of the pledget 4066 can thereby seal the punctures formed by the staple 4068, as well as distribute pressure applied to the tissue by the a crown 4072 of the staple 4068.

In still other embodiments, adjunct material can be in the form of a coating disposed over all or a portion of a surgical staple, as shown in FIGS. 73 and 74. In particular, staple 4074 of FIG. 73 includes a coating 4076 of an adjunct material disposed over an entire outer surface thereof. The adjunct material employed in the coating 4076 can be configured to swell upon contact with tissue or bodily fluid, such that once the staple 4074 is implanted in tissue the coating will expand away from the staple and fill any gaps that may be present. FIG. 74 illustrates a side cross-sectional view of tissue 4078 having multiple rows of staples 4074 disposed therein. The staples 4074 can seal the tissue 4078 together at the center of the figure, such that fluid cannot pass and the tissue could be transected between the staples 4074.

Other non-flowable materials can also be employed as adjuncts in some embodiments. For example, a compressible foam can be used as an adjunct material in combination with a gel or other flowable material, or on its own. FIG. 75 illustrates one embodiment of a staple 4080 having a foam adjunct 4082 disposed around both legs of the staple. Attempts to utilize foam in combination with staples may sometimes encounter a problem wherein the foam rotates about a crown of the staple during implantation. The staple 4080 addresses this problem, and minimizes this possibility, by incorporating an additional pledget 4084 between a crown of the staple and the foam adjunct 4082. The pledget 4084 can provide support to the foam adjunct 4082 during implantation to prevent it from rotating about the crown of the staple. The pledget 4084 can be formed from a rigid biocompatible material, or can be formed from a flowable material as described above. In the latter embodiment, a gel or other flowable material can retain its shape prior to implantation so as to provide the necessary support for the foam adjunct 4082, and subsequently flow into defects in tissue after implantation. U.S. Pat. Pub. No. 2011/0192882 to Hess et al., the entirety of which is incorporated herein by reference, discloses additional techniques for coupling staples to rigid pledgets and incorporating them into a cartridge body that can be combined with the adjunct materials disclosed herein.

In some embodiments, it can be desirable to prevent any adjunct material from coming into contact with the cartridge body of the surgical stapler during implantation of a staple. If there is contact between the cartridge body and adjuncts, it is possible that the adjunct material can be scraped off the staple as it is ejected from the cartridge body. In embodiments where the adjunct material is a hydrogel or other flowable and/or swellable material, it is further possible that the adjunct material could interfere with ejection of a staple if it was, for example, scraped off into a staple cavity and left to expand there or flow into neighboring portions of the surgical stapler. Accordingly, in certain embodiments sealing adjuncts disposed within a staple cavity of a surgical stapler cartridge body can be configured to be ejected therefrom along with a staple without contacting the cartridge body.

There are a number of ways to ensure that the adjuncts do not contact the cartridge body. In one embodiment, adjunct material can be coupled to a staple such that the staple shields the adjunct from contact with the cartridge body during ejection. The staple shown in FIG. 65 is one example of a staple that shields adjunct material from contact with the cartridge body because the adjunct material is essentially behind the staple as it is ejected from the cartridge body. In other embodiments, adjunct material can be tucked into an area extending between the legs of a staple, such as in the staple shown in FIG. 59B. This configuration can also shield the adjunct material from contacting the cartridge body during ejection from a staple cavity.

In other embodiments, the staple cavity openings in the cartridge body can be shaped to accommodate passage of at least one sealing adjunct coupled to a surgical staple. FIG. 76 illustrates one embodiment of a cartridge body 4086 that includes a plurality of staple cavities 4088 having openings shaped to accommodate the staple 4080 and foam adjunct 4082 shown in FIG. 75.

FIG. 77 illustrates an alternative embodiment of a cartridge body 4090 having a plurality of staple cavities 4092 shaped to accommodate a staple 4094 having a plurality of adjuncts 4096 coupled to an outer portion of each staple leg. FIGS. 78A-78C illustrate various embodiments of staple cavity openings that are configured to allow for passage of one or more adjuncts coupled to a surgical staple. In the top view of FIG. 78A, for example, a deck 4098 of the cartridge body is shown having an opening 4100 formed therein. The opening 4100 can include cut-outs 4102, 4104 formed at opposite ends thereof that are sized to accommodate sealing adjuncts 4106, 4108 that are coupled to a flat form staple 4110 that is similar to the staple shown in FIG. 65. In the alternative embodiments of FIGS. 78B and 78C, additional cut-outs are provided surrounding the legs of the staple 4110 to accommodate different configurations of adjunct material coupled thereto.

Anvil-Side Segmented Adjuncts

Certain embodiments of the methods and devices described herein include one or more adjunct segments disposed on an anvil-side of a surgical stapler, that is to say on an opposite side of staple tissue from the crown-side adjuncts described above. These anvil-side adjuncts can be used in addition to the crown-side adjuncts. While the crown-side adjuncts serve to prevent leakage caused by tissue deformation around the staple legs, the anvil-side adjuncts described below can prevent tissue damage from strain caused by the staple and the staple-line as a whole.

Adjunct segments disposed on the anvil-side of a surgical stapler can include sheets of biocompatible or bioresorbable material, discrete adjunct segments each designed to interact with legs of an individual staple, discrete adjunct segments each designed to interact with legs of multiple staples, discrete adjunct segments attached to each other, or any suitable combination thereof. In some embodiments, each adjunct can be of a size that when placed adjacent the anvil-side of a surgical stapler, each adjunct spans only a single staple-forming opening. Further, in some embodiments, each adjunct can be of a size that when placed adjacent the anvil-side of a surgical stapler, each adjunct spans multiple single staple-forming openings.

In addition to preventing damage from the staple in the stapled tissue, adjunct segments disposed on the anvil-side of a surgical stapler can serve to hold together staples that do not interact with tissue during a stapling procedure, that is to say excess staples. For example, in embodiments where the anvil-side adjuncts include sheets of material, adjunct segments that are each designed to interact with the legs of multiple staples, or adjunct segments that are attached to each other, a surgical stapler can be fitted across a segment of tissue, such as a portion of intestinal tissue or a vessel, whose diameter is shorter than the length of the staple line created by the surgical stapler. In that case, there will be staples that do not pass through tissue. Removal of those excess staples that are not securing tissue from the patient is facilitated if they remain attached to the tissue through the adjunct segments. The surgeon or stapler operator can then sever select adjuncts to detach the excess staples and he or she can remove all of the excess staples while minimizing the potential for loss of an excess staple inside the patient.

Though, as described in more detail below, some embodiments of the segmented adjuncts described herein can be used on a cartridge, adjunct segments can be deposited to the anvil-side of the surgical stapler in the staple shaping depressions in the anvil-side of the surgical stapler as a liquid that hardens over time or after exposure to curing radiation. Adjuncts can also be supplied as discrete adjuncts attached to a sheet. The sheet can be a connective film, such as continuous film. The sheet can be a woven mesh. In some embodiments, a plurality of discrete adjuncts can be connected through a plurality of connecting branches, through a plurality of threads, or other suitable means for connecting the adjuncts with biocompatible or bioresorbable material that does not impede the functioning of the staples or irritate the tissue once the staples are applied. When the adjuncts used are connected through a plurality of connecting branches, the surgical stapler can include one or more features to sever the connecting branches as the staples are deployed into tissue.

FIG. 79 shows a top view of one embodiment of a plurality of adjunct segments coupled to one another 4112, such as might be seated in a cartridge for use with a surgical stapler or seated directly in a surgical stapler. The individual adjunct segments 4114 are shown to span a plurality of staple forming openings 4116, and when applied to tissue, as seen in the top portion of the figure on the right, there can be excess adjunct segments that do not attach to tissue 4120. The individual adjunct segments 4114 are joined together through branches 4118. The branches 4118 can be made of a similar material as the adjuncts, but made thinner than the adjuncts and of a diameter that allows for the branches 4118 to be broken 4122 by the application of force. In this way, excess adjunct segments 4120 can be removed.

FIG. 80 shows a perspective view of an alternative embodiment of a plurality of adjunct segments 4124 applied on the anvil-side of a surgical stapler. The plurality of adjunct segments 4124 shown are held together by connecting threads of filaments 4126 between individual adjunct segments 4128. Each adjunct segment 4128 is configured to span a plurality of staple forming openings 4132.

A film that may include a woven material 4130 can overlay the individual segmented adjuncts 4128. The film, optionally including a woven material 4130, can help to mitigate the damage to stapled tissue by distributing forces.

FIG. 81A shows a view of one embodiment of surgical end effector 4134 having a plurality of adjunct segments 4124. The surgical end effector 4134 is shown accepting a vessel 4136. In FIG. 81B, the surgical end effector 4134 is shown transecting the vessel 4136, causing staples to engage with the adjunct segments 4124 of FIG. 81A. FIG. 81C shows the vessel 4136 and adjuncts 4124 after transection of the vessel 4136. Filaments or threads 4126 can connect the adjuncts 4124, and the filaments or threads 4126 can aid in the application of the plurality of adjuncts 4124 to the surgical end effector 4134. Yet the filaments or threads 4126 can be torn when separating the ends of the transected vessel 4136. The filaments or threads 4126 can hold excess adjunct segments 4138 in place until removed by a surgeon.

FIG. 82 shows another embodiment of segmented adjuncts 4140 disposed on the anvil-side of a surgical stapler 4142. Each individual adjunct segment 4144, 4146 spans multiple staple forming openings. As shown, each adjunct segment 4144, 4146 can have a distinct configuration from that of the adjunct segments adjacent to it. However, each adjunct segment 4144, 4146 interlocks with its neighbors. In this way, it may be possible to have some degree of adhesion between adjacent adjunct segments 4144, 4146 so that no filaments or branches are needed, and so that no filaments or partial branches will be exposed after the excess adjunct segments are removed from stapled tissue. Additionally, the adjuncts are shown as including a woven material.

FIG. 83 shows a portion of a surgical staple anvil 4148 with a plurality of staple forming openings filled with a viscous sealant material 4150. Some of the ways in which the material arrives in the staple forming openings of the staple anvil 4148 are shown in FIGS. 84-86D. FIG. 84 shows a surgical stapler anvil 4152 with staple forming openings in which pre-formed sealing gel 4154 is placed, as described in greater detail below. FIG. 85 is a cross sectional view of an anvil 4156 with staple forming openings filled with a sealing liquid or gel 4158. The sealing liquid or gel 4158 has a film or layer 4160, above the bulk of the sealing material, that is flush with the surface of the anvil 4156. FIG. 86A shows the addition of the sealing material 4158 in a liquid or gel state to staple forming openings on an anvil 4156. FIG. 86B shows the staple forming openings filled with sealing liquid or gel, and FIG. 86C shows the creation of the film or layer 4160. A light source, such as a UV light source, provides lights at an energy level sufficient to cause partial curing of the sealing material 4158 to form the film or layer 4160.

In some embodiments, the staple forming openings of an anvil can contain completely cured sealing material 4162, as shown in FIG. 86D. Fully cured sealing material 4162 can have different materials properties than the partially cured material shown in FIG. 85A. FIG. 87 shows a staple 4164 that was shaped using a surgical stapler with partially cured sealing material in the staple forming openings of the stapler anvil. The staple 4164 has legs that pass through the cured layer 4160, into the uncured sealing material 4158, and back through the cured layer 4160, and in some embodiments, the end of each leg of the staple 4164 can end in tissue. The sealing material helps to prevent any passage of fluids through tissue, adjacent to the staple, as well as preventing undesirable deformation or damage to the tissue.

FIG. 88 shows an alternate way of delivering adjuncts for the anvil-side of surgical staples 4166 that includes multiple adjuncts 4168 that fit into staple forming openings on the anvil of a surgical stapler and a thin connecting film 4170. The thin connecting film 4170 can be a continuous film that allows for easy transport and placement of multiple adjuncts 4168 at once.

FIG. 89 is a perspective view of showing adjuncts 4172 with 4174 mesh material. FIG. 90 shows an exploded view of the view of FIG. 89. FIGS. 91A and 91B show adjuncts 4184 that are cured with a film above the adjuncts 4186, in which the film connects the adjuncts 4186, as well as discrete adjuncts which are not connected 4190 to each other. In the system of discrete adjuncts 4188, each adjunct 4190 has un-cured seal material that fits the within the staple forming openings of the anvil of a surgical stapler. Each adjunct also has a layer of cured material 4194 above the uncured sealing material 4192.

FIG. 92 shows a cross-sectional view of a surgical staple 4198 in a cartridge 4196 that is opposite the anvil 4202 of a surgical stapler. In the figure, tissue 4200 is between the cartridge 4196 and the anvil 4202. The anvil 4202 is shown to have multiple staple forming openings 4190, each opening filled with uncured sealing material 4192 and having a layer of cured sealing material 4194 over each staple forming opening 4190.

FIG. 93 is a cross-section view of a surgical staple 4198 inserted in tissue 4200 with an adjunct that includes both cured and uncured sealing material present on the free-ends of the legs of the staple. The legs of the staple have passed through the tissue, through a cured portion of the adjunct material 4204, through a portion of un-cured adjunct material 4206 and then back into the tissue 4200. FIG. 94 shows curing of the un-cured adjunct material 4206 in FIG. 93 so that it becomes a cured, conforming material 4210. A light source 4208 provides the appropriate radiation to cure the liquid or gel setting material 4206 after the material has spread to conform to the surface of the tissue 4200.

FIG. 95 shows a grouping 4212 of discrete adjunct segments 4214 that are joined by a plurality of connecting branches of adjunct material 4216. The adjunct segments 4214 in the grouping 4212 can be partially or fully cured, such that the grouping 4212 can be stored for long periods of time. FIG. 96 shows the adjunct grouping 4212 of FIG. 95 fitting over staple forming openings, or anvil pockets, 4220 on a surgical stapler anvil 4218.

FIG. 97 shows an anvil 4222 with adjunct-separating features 4226 between the staple forming openings 4224. FIG. 98 shows a side view of an embodiment of a surgical stapler that includes a staple 4228 in a staple cartridge 4230 and a plurality of adjunct segments 4214 coupled to the anvil 4222. The plurality of adjunct segments 4214 are joined by branches 4216. The branches 4216 are severed by the sharp features 4216 when the staple 4228 is inserted into the tissue (4232 in FIG. 99). FIG. 99 shows the staple 4228 as it is formed by actuation of the surgical staple, ad FIG. 100 show the staple 4228 after it is fully implanted in the tissue 4232, with the branches 4216 severed, making breaks 4234 in the branches, and with the adjunct segments 4214 between a portion of the ends of the legs of the staple 4228 and the tissue 4232.

FIG. 101 is a cross-sectional view of an embodiment of a retainer 4238 to hold adjunct material 4240 in place against a surgical stapler anvil 4236. FIG. 102A is a cross-sectional view of the retainer 4238 and anvil 4236 shown in FIG. 101, with adjunct material 4240 between the anvil and the retainer. FIG. 102B is a variation of the embodiment shown in FIG. 102A in which the adjunct material is present only as discrete adjuncts 4240, without any connecting material.

FIG. 103 is a cross-sectional view of an embodiment of a staple forming opening 4246 with bulge tabs 4244. The tabs 4244 are shaped during manufacturing into retainer features. FIG. 104 shows the staple forming opening 4246 of FIG. 103 filled with a plug element 4250, or adjunct material, and the bulge tabs 4244 shaped into trapping features 4248. FIG. 105 is a top view of the staple forming opening 4246 shown in FIG. 103. The line A-A is that along which the cross-sectional views are taken.

FIG. 106 shows a perspective view of one embodiment of a surgical stapler with adjunct segments 4256, 4258 associated with both the anvil 4254 and staple cartridge 4252. In this embodiment, the adjunct segments 4258 on the anvil 4254 have branches of adjunct material or filaments 4260 between the adjunct segments 4258. The adjunct segments 4256 on the staple cartridge 4252 interlock with each other, such that a notch 4262 in one adjunct segment receives a protrusion 4264 from its neighboring adjunct segment. In this way, additional means of holding together the adjuncts 4256 on the staple cartridge 4252, which is on the crown-side of the staples, are needed. Further, the adjuncts 4256 on the staple cartridge 4252 span more than one staple, so that two or more staples will be connected by each adjunct.

FIGS. 107 and 108 show an embodiment of a surgical stapler with an anvil 4266 that includes attachment 4272 and alignment features 4274 for adjunct material 4270. FIG. 107 is an exploded view of the anvil 4266 with staple forming openings 4268 and features 4274 on the side of the anvil for anchoring or interfacing with loops 4272 on a sheet of adjunct material 4270. FIG. 108 shows the adjunct material 4270 flush against the anvil 4266 with the loops 4272 attached to the features 4274 which are shown to be tabs or pegs that attach to the loops. Such features 4274 can be present on a staple cartridge and used with a similar type of adjunct material instead of or in addition to being used on the anvil 4266 of a surgical stapler.

FIGS. 109-111 show an embodiment of a surgical stapler 4276 with adjunct assemblies 4284, 4278 coupled to both the anvil 4282 and the staple cartridge 4280 of the stapler. The adjunct assemblies 4284, 4278 are shown to include adjunct segments 4286, 4288 that are joined by a sheet of adjunct material. On the anvil 4282, there are a plurality of staple forming openings 4290 which can accept adjunct segments 4286. FIG. 111 shows the relative thickness of an adjunct segment 4286 to that of the sheet of adjunct material. The adjunct segments 4286 on the stapler anvil 4282 can include partially cured or fully cured sealing material, as described above. The adjunct material 4278 for use with the staple cartridge 4280 has adjunct segments 4288 which can fit over the ends of the staples in the cartridge 4280, either in contact with or above the staple legs. In practice, using such a surgical stapler 4276 would insert staples into tissue in with adjunct material both at the crown of each staple and at the anvil-side of each staple, thus potentially reducing leaking and tissue damage caused by the staple.

FIG. 112 shows a cross-sectional view of one embodiment of a plurality of adjunct segments 4288 (e.g., micro-fingers) connected to one another by a film 4278. These adjunct segments 4288 may not correspond to individual features on a stapler anvil or a staple cartridge, but instead may serve to act as a cushion or a light-weight, highly conformable and compressible material. FIGS. 113A and 113B show cross-sectional views of a surgical stapler, similar to that shown in FIG. 109, with a staple 4294 in a cartridge 4292 with an adjunct material 4296 that includes a plurality of adjunct segments 4292 that can act as a light-weight, conformable and compressible material 4296. The anvil 4300 shown in FIG. 113A has staple forming openings 4302 in which include adjunct segments 4304 that are attached to a sheet of adjunct material 4306. FIG. 113B shows the staple 4294 after the stapler has been actuated on tissue 4308. The tissue 4308 contacts adjunct material with micro-fingers 4298 near the crown of the staple and thicker, continuous adjunct material 4304 at the anvil-side of the staple.

FIGS. 114A and 114B show an embodiment of a surgical stapler component 4310 that includes adjunct segments of varying thickness 4312. Each adjunct segment is discrete and spans only one staple. FIG. 114B shows that adjunct segments of greater thickness 4318 are located nearest the centerline of the stapler component 4310, and that the thinner adjunct segments 4316 correspond to staples further away from the centerline, where a cut in stapled tissue would be made.

FIG. 115 shows another embodiment of adjunct segments 4322, 4326 on one part of a surgical stapler. The adjunct segments 4322, 4324 are not of uniform thickness. Each adjunct segment has a thick side, 4328, 4330, and a thin side 4332, 4334. Each adjunct segment 4322, 4324 spans more than one staple 4326 location shown in the exemplary staple cartridge 4320. The adjunct segments are shown with their thick sides 4328, 4330 towards the center of the staple cartridge 4320. When the surgical stapler cuts through tissue after stapling the tissue, it will cut the tissue through the center of the cartridge, between the thick sides 4328, 4330 of the adjunct segments. In this way, the adjunct segments 4322, 4324 provide more support to the staples nearest the free ends of the tissue.

FIG. 116 shows a cross-sectional view of the stapler of FIG. 115. The staple cartridge 4320 holds staples 4336. Over the staples 4336 are adjunct segments 4334 and 4324 which have their thick sides 4330, 4328 near the center of the cartridge and their thin sides 4324, 4322 toward the outer edges of the cartridge 4320, over the outermost staples. The stapler anvil 4338 has staple forming openings 4340, over which are adjunct segments 4342, 4344. The anvil-side adjunct segments 4342, 4344, are shown to have their thick sides 4346, 4348 near the venter of the anvil, corresponding to the innermost staples. The thin sides 4350, 4352 of the anvil-side adjuncts 4342, 4344 are located toward the edges of the anvil such that the thin sides are associated with the outermost staples once the stapler is actuated.

FIG. 117 shows an embodiment of a surgical stapler component 4310 that includes adjunct segments of varying thickness 4312. Each adjunct segment is discrete and spans only one staple. Adjunct segments of greater thickness 4318 are located nearest the centerline of the stapler component 4310, and that the thinner adjunct segments 4316 correspond to staples further away from the centerline, where a cut in stapled tissue would be made. These adjunct segments are discrete, not interlocking as those shown in FIG. 115.

FIGS. 6118A and 118B show a multi-material adjunct 4354 that includes a film 4356 with openings 4360 and a base layer 4358 with connecting features 4362. The base layer 4358 can be a layer of elastomeric material. The connecting features 4362 can be shaped to fit through the openings 4360, for example the connecting features 4362 shown are columns and the openings 4360 are circular holes. The connecting features 4362 and openings 4360 can be any suitable shape, symmetrical or asymmetrical, as in when a particular orientation between the base layer 4358 and the film 4356 is desired. FIGS. 119A and 119B show the adjunct of FIGS. 118A and 118B in context, with a staple 4364 shown. FIG. 119A shows the staple prior to insertion into the adjunct 4354. The staple 4364 is shown as aligned with the connecting features 4362 so that each leg of the staple moves through a connecting feature 4362 when stapling tissue. FIG. 119B shows the staple 4364 after being moved toward an anvil of a surgical stapler.

FIGS. 120-122 show different embodiments of a surgical staple and adjunct in tissue, with the legs of the surgical staple shaped to retain the tissue in a particular configuration. FIG. 120 shows a staple 4368 in tissue 4370 with adjunct material 4372 near the anvil-side of the staple, such that the adjunct material 4372 acts as a seal to avoid leaking from the tissue 4368. FIG. 121 shows a staple 4374 in tissue 4376 with an adjunct on the anvil-side of the staple 4374. The adjunct includes a film 4378, a depression in the film 4382, and a thicker area in the adjunct 4380 into which the ends of the legs of the staple 4374 move when the staple forms. In FIG. 122, the staple 4374 is used with an adjunct with a film 4378, multiple depressions in the film per staple 4386, and a pair of thicker areas in the adjunct 4380 into which the ends of the legs of the staple 4374 move when the staple forms, one pair of thicker areas per staple.

FIGS. 123A-123E show different embodiments for a plurality of adjuncts coupled to a surgical stapler anvil. The adjunct array 4388 shown in FIG. 123A includes portions near the anvil edge 4392, portions near the anvil centerline 4390, and multiple adjunct segments 4394. The adjunct segments shown include openings 4400 for staple legs to pass through as they move toward the anvil and openings 4402 for staple legs to pass through as they move away from the anvil during staple forming. The adjunct segments 4394 connect to each other and to the portions of the adjunct array near the anvil edge 4392 and anvil centerline 4390 through branches of adjunct material 4398. The edge 4392 and centerline 4390 portions also have branches 4396 to connect to the adjunct segments 4394. FIG. 123B shows an adjunct assembly 4404 that is similar to that shown in FIG. 123A. The adjunct array 4404 shown in FIG. 123B includes portions near the anvil edge 4392, portions near the anvil centerline 4390, and multiple adjunct segments 4408. The adjunct segments shown include openings 4412 for staple legs to pass through as they move toward the anvil and openings 4414 for staple legs to pass through as they move away from the anvil during staple forming. The adjunct segments 4408 connect to each other and to the portions of the adjunct array near the anvil edge 4392 and anvil centerline 4390 through branches of adjunct material 4406. Unlike the adjunct array 4388 in FIG. 123A, the adjunct array 4404 has no connectors between rows of adjunct segments. The adjunct array 4416 of FIG. 123C is similar to that of FIG. 123B, in that there are no connectors between the rows of adjunct segments, only connectors 4420 between each adjunct segment 4418 and its neighboring segment. Each segment has openings 4422 for staple legs to pass through as they move toward the anvil and openings 4424 for staple legs to pass through as they move away from the anvil during staple forming. The adjunct array 4426 shown in FIG. 123D includes portions near the anvil edge 4428, portions near the anvil centerline 4430, and multiple adjunct segments 4432. The adjunct segments shown include openings 4438 for staple legs to pass through as they move toward the anvil and openings 4440 for staple legs to pass through as they move away from the anvil during staple forming. The adjunct segments 4432 connect to each other and to the portions of the adjunct array near the anvil edge 4428 and anvil centerline 4430 through branches of adjunct material 4434, 4436. The adjunct array 4442 shown in FIG. 123E is different from that shown in FIG. 123D and includes portions near the anvil edge 4444, portions near the anvil centerline 4446, and multiple adjunct segments 4452. The adjunct segments shown include openings 4458 for staple legs to pass through as they move toward the anvil and openings 4456 for staple legs to pass through as they move away from the anvil during staple forming. The adjunct segments 4452 connect to each other and to the portions of the adjunct array near the anvil edge 4444 and anvil centerline 4446 through branches of adjunct material 4448, 4454, 4450.

FIG. 124 shows a first side 4460 and a second side 4470 of a plurality of adjuncts 4464 that are connected in a row. The first side view 4460 show the adjunct segments 4464, their connectors 4462, the openings 4466 in the adjunct segments for when the legs move towards the stapler anvil during staple forming, and the openings 4468 in the adjunct segments for when the legs move away from the stapler anvil during staple forming. The second side view 4470 shows elements of the first side view 4460, but there is additional material on this side of the adjuncts 4464. Through this additional material, there are openings 4474 in the adjunct segments for when the legs move towards the stapler anvil during staple forming, and the openings 4472 in the adjunct segments for when the legs move away from the stapler anvil during staple forming.

FIGS. 125-129 show embodiments of adjuncts segments that overlap and interlock to some degree when in use with surgical staples. The configurations shown can be used to accommodate for movement in the tissue, such as expansion on contraction after stapling. In FIG. 125, there are two configurations of adjunct segments, 4512, 4514. The adjunct segments shown 4512, 4514 are minor images of each other. Each adjunct segment spans two staples. For example, as in FIG. 127, each adjunct segment is shown with two staple crowns in contact with each segment. However, it should be noted that in the configuration shown in FIGS. 126 and 127 each staple, aside from the staples at the end of the row, contacts two overlapping adjunct segments. In FIG. 126, the two adjunct segments 4512 and 4514 are seen in an extended configuration 4526 and in a compact configuration 4528. Openings are shown in the adjunct segments through which staple legs pass as staples are formed by moving from the staple cartridge toward the anvil in a surgical stapler. As can be seen, when the adjunct 4512, 4514 are overlaid, some of the openings overlap and align to allow a staple leg to pass through. Opening 4516 aligns with opening 4522, and opening 4520 aligns with opening 4518 at the bottoms of the adjunct segments. Opening 4518 is shown as not aligning with any other opening, but opening 4518 may align with opening 4525 of another adjunct segment that is similar to 4512. Similarly, opening 4524 is not shown aligning with any other opening, but it may align with opening 4516 of another adjunct segment that is similar to 4512. FIG. 126 shows that in an extended configuration 4526, adjacent openings on the top portions of the adjunct segments, 4525 and 4524, are further apart than in a compact configuration 4528. FIG. 128 shows the relative position of two adjacent adjunct segments that are similarly oriented 4514. In an extended configuration 4526 there is a gap or space between the adjunct segments 4514. In a compact configuration 4528 the adjacent adjunct segments 4514 are very close, in some instance touching, and in some instances slightly overlapping. FIG. 129 shows a compact configuration 4528 in which only half of the adjunct segments are visible, such as when the adjunct segments are opaque and only the topmost adjunct segments are visible.

FIGS. 130A-130C show embodiments of adjunct segments that connect adjacent surgical staples. FIG. 130A shows rows 4530 of surgical staples 4532 that are connected the next staple in the row via an adjunct segment 4534. The adjunct segments 4534 are shown as being in or on a supporting layer or film 4536. Such configurations, adjunct segments with supporting layers or films, are described in greater detail herein elsewhere. The adjunct segments 4534 shown in FIG. 130A are located near the anvil-side of the staples once the staples are deployed in tissue. FIG. 130B shows row 4540 of surgical staples 4542 in use with adjunct segments 4544 and a supporting film 4546. As in FIG. 130A, the adjunct segments 4544 are located near anvil-side of the staples 4542. However the adjunct segments 4544 of FIG. 130B are shaped differently from those in FIG. 130A, in that the openings for accepting staple legs are larger in FIG. 130B. This increased size can allow for slight contraction or expansion of the tissue and the corresponding motion of the staples. FIG. 130C shows another embodiment in which rows 4550 of surgical staples 4552 with adjunct segments 4554 and a support film 4556 are used together. The adjunct segments 4554 in FIG. 130C are different from those in FIGS. 130A and 130B because the adjunct segments 4554 are rings, allowing the maximum amounts of motion of the staple legs within the center 4558 of the adjunct segments 4554. This allows even greater motion of the each surgical staple with regards to its neighbor, and thus the stapled tissue can accommodate greater expansion and contraction.

FIGS. 131 and 132 show the adjunct segments 4534 and surgical staples 4532 of FIG. 80A. In FIG. 131, an artery 4560 has staples 4532 and adjunct segments 4543 seal a portion of the artery 4562. FIG. 132 shows the artery 4560, staples 4532, and adjuncts 4534. In both FIGS. 131 and 132, each staple 4532 is shown connected to its neighbor through opposite ends of an adjunct segment.

FIGS. 133-135 are similar to FIG. 131, except that each shows a different type or use of an adjunct segment. In FIG. 133, an artery or other type of tissue 4560 is sealed by two rows 4570 of staples 4572. The row of surgical staples 4572 at the free edge of the tissue 4562 has thick adjunct segments 4574. The row of surgical staples 4572 further away from the free edge of the tissue 4562 has thinner adjunct segments 4576. The adjunct segments 4574, 4576 connect each surgical staple 4572 to at least one neighboring staple. Also, the adjunct segments 4574, 4576 are near the crowns of the staples 4579 when the staples are deployed, as shown. Using different thickness adjunct segments 4574, 4576 can help to prevent tissue damage and can help to promote healing of the tissue 4560 after the stapling procedure. The embodiment of rows of staples 4580 shown in FIG. 134 is similar to that shown in FIG. 133, except that the adjunct segments 4584, 4586 are positioned near the anvil-side portions 4588 of the surgical staples 4582. The thickness of the adjunct segments 4584, 4586 are different, in that those adjunct segments nearest the free edge 4562 of the tissue are thicker adjunct segments 4584 and those away from are thinner 4586. FIG. 135 shows an embodiment of rows 4590 of surgical staples 4592 where thicker adjuncts 4594, 4595 are used closer to the free edge 4562 of the tissue 4560 and thinner adjuncts are used away from the free edge 4562 of the tissue 4560 to attach each staple 4592 to a neighboring staple along the length of the rows 4590. In the embodiment shown in FIG. 135, adjuncts 4594, 4595, 4596, 4597 are located near the crowns 4599 of the staples 4592, as well as near the anvil-side portions 4598 of the staples 4592.

Staple lines that include a plurality of surgical staples and adjunct segments that connect two surgical staples together can exhibit a myriad of configurations that correspond to a range of contraction or expansion of the underlying tissue. FIGS. 136-139 show exemplary configurations adjunct segments and surgical staples in which each staple connects two adjunct segments. FIG. 136 shows a staple cartridge 4600 with adjunct segments 4604 that contact two staples 4602 when forming a staple line. The staple line includes two rows of staples that are applied parallel to the surgical cut, with the first row adjacent to a surgical cut and the second row further away from the surgical cut. The staples in the first row are offset from the second row. Each adjunct segment 4604 connects a staple from the first row with a staple from the second row. Because of the offset, the adjunct segments 4606 are applied in a position that is tilted when compared to a line perpendicular to the surgical cut, and in a relaxed state, as shown, the adjunct segments 4616 are as close together as they can be, touching or nearly touching. FIG. 139 shows the progression of the configuration changes from a tensioned state 4620 to a fully relaxed state 4630. In an extremely tensioned state 4620, the adjunct segments 4616 are at an angle in the range of about 0° to 90° in a position that so that the adjunct segments 4616 are further away from each other than in the relaxed state 4630. In the intermediate state 4625 shown in FIG. 139, the adjunct segments 4616 are perpendicular to the surgical cut. The relaxed state 4630 is similar to that shown in FIG. 136.

FIG. 137 shows another configuration of adjunct segments 4608 and surgical staples 4606 in which the staples are applied along a surgical cut at an angle. In a relaxed state 4610, such as when first applied to tissue, the staples 4606 are between about 0° and 90° to the cut, such as at about 45° to the cut, and the adjunct segments 4608 are perpendicular to the cut. When the tissue stretches, the staples 4606 are at a different angle, such as about 30° from the cut. The adjunct segments 4608 move from a position substantially perpendicular to the surgical cut to one that is no longer perpendicular. FIG. 138A shows a side view of the relaxed configuration 4610, and FIG. 138B shows a side view of the tensioned configuration 4612 of staples 4606 and adjunct segments 4608.

FIGS. 140A-140B show an embodiment 4640 of surgical staples and adjunct segments 4652 connected by a serpentine connector 4646 on an optional support layer 4642. The support layer 4642 can also include adjunct segments 4644 that are not connected. The serpentine connector 4646 is connected to the adjunct segments 4652 at connection points 4648. The support and adjunct segments 4652 shown include openings for staple legs.

As shown in other figures described above, adjunct segments can have many configurations. FIGS. 141A-145D show four different configurations. FIGS. 141A-141D show an adjunct segment 4690 that is symmetric, such that the top view and the bottom view are similar. The adjunct segment 4690 includes openings 4692 for staple legs. FIG. 141A is a cross-sectional view of the adjunct segment 4690, FIG. 141B is an end view of the adjunct segment, FIG. 141C is a bottom view of the adjunct segment 4690, and FIG. 141D is a top perspective view of the adjunct segment 4690. FIGS. 142A-142D show an adjunct segment 4700 which includes a thicker portion 4704 in the center of the adjunct segment, between the openings 4702 for staple legs.

FIG. 143 shows an embodiment of a delivery configuration assembly 4710 for adjunct segments 4712. The adjunct segments 4712 can be made as individual components, not connected by branches or filaments, adhered to a compliant or removable backing 4714. The arrangement of the adjunct segments 4712 on the backing 4714 can be such that mating the delivery configuration assembly 4710 with a surgical stapler anvil or staple cartridge allows for perfect or near perfect alignment of the adjunct segments 4712 with the stapler features.

FIGS. 144A-144D show an embodiment for an adjunct segment 4715 that has a base portion 4717 and thicker portions 4716 with openings 4718. The openings 4718 go through the thicker portions 4716 as well as the base portion 4717. The thicker portions 4716 may be a different material than the base portion 4717 or the thicker and base portions may be of the same or similar materials. The thicker portions 4716 may prevent tissue damage from staple legs when the tissue expands or contracts. FIGS. 145A-145D show an adjunct segment 4720 that has a base portion 4722 with openings 4726 for staple legs and portions around the openings 4724. The openings portions around the openings 4724 may be of a different material than the base portion 4722, or they base 4722 and the portions surrounding the openings 4726 may be of the same material, but, because of their configuration, have different materials properties, such as they may act as cushions between the adjunct segment 4720 and a surgical staple or tissue.

Application of Adjunct Materials

Sealant materials can be applied to tissue that is treated with surgical staples directly, prior to or after being treated with a surgical stapler and endocutter as a film or a liquid as an alternative to being applied as an adjunct segment.

FIGS. 146-149C show an applicator for applying liquid or gel adjunct material 4899 directly to an anvil or a staple cartridge of a surgical stapler 4891. FIG. 146 shows an embodiment 4890 in which an adjunct material 4899 is applied from a tube 4896, through an applicator 4897 attached to the tube 4896. The adjunct material 4899 is shown on the anvil 4892. FIG. 147 shows a cross-sectional view of an applicator 4897 with gel adjunct material 4894 in contact with the anvil 4892 to fill staple forming openings 4893. FIG. 148 shows a view of an applicator 4897 with a squeegee feature 4898 to apply adjunct material 4894 to an anvil 4892 to fill staple forming openings 4893 with adjunct material. FIG. 149A shows an applicator 4909 for applying adjunct material 4906 from a reservoir 4908 to an anvil 4904 of a surgical stapler 4900. FIG. 149B shows an alternate type of applicator 4920 for applying adjunct material 4922 to an anvil 4914 of a surgical stapler 4910. The applied adjunct material 4922 is smoothed by the applicator 4920 into the staple forming openings 4916 to form adjuncts 4918. FIG. 149C shows the adjuncts 4918 in the staple forming openings 4916 in the anvil 4914.

FIGS. 150-154 show an applicator for applying an adjunct material directly to an anvil of a surgical stapler, in which the material is composed of two precursors or two materials which mix prior to application to the anvil or staple cartridge. FIG. 150 shows an embodiment 4930 of an applicator 4942 for an adjunct material from two materials 4936, 4940. The applicator 4942 includes a dual syringe set 4932 and a mixing nozzle 4944. The dual syringe set 4932 includes individual syringes 4934, 4938 that interface with the applicator nozzle 4946 through fittings, such as Luer fittings or threaded fittings. The individual syringes are shown as syringe A 4934, that can contain a first material 4936, such as fibrin; and syringe B 4938, that can contain a second material 4940, such as thrombin. A single plunger expels the first and second materials into the mixing nozzle 4994 before the adjunct material exits through the applicator nozzle 4946. FIG. 151 is a similar embodiment, but the diameters of the syringes 4952, 4954 in the syringe set 4950 are different, so that upon application of the plunger, a ratio of materials other than 1:1 exits the syringes and mixes in a common lumen, the mixing nozzle 4958, before exiting through the applicator nozzle 4959.

FIGS. 152A and 152B show the interface between a syringe or other container 4960 filled with an adjunct material 4962 and a portion of a mixing or applicator nozzle 4963. The interface includes a fitting between a threaded portion 4966 of the container 4960 of adjunct material 4962 and a threaded portion 4965 of the nozzle 4963. The container 4960 of adjunct material 4962 can include a seal 4961 that keeps the adjunct material 4962 within the container 4960 during shipping and storage. The nozzle 4963 includes a piercing feature 4964 to break the seal 4961 when the threaded portions 4965 and 4966 are fully engaged. When the threaded portions 4965 and 4966 are fully engaged the adjunct material 4962 flows from the container 4960 into the nozzle 4963. FIGS. 153 and 154 show a dual syringe set 4932 attached to a mixing nozzle 4944 and applicator nozzle 4946, as in FIG. 150, in use applying adjunct material 4969 to an anvil 4968 of a surgical stapler 4967.

FIGS. 155-160 show fittings and which can apply liquid or gel to a portion of a surgical stapler, either to the anvil or the staple cartridge and the resulting adjunct layer. In FIG. 155 and FIG. 156, the applicator nozzle 4977 is shown fitted over an anvil 4976. In FIG. 155, the adjunct material 4978 is a single adjunct material, that is to say that it is not a material that needed to be mixed immediately prior to application. The adjunct material 4979 shown in FIG. 156 includes two precursors or components that are mixed immediately prior to application of the adjunct material to the anvil. FIG. 157 shows an anvil 4980 with staple forming openings 4981 filled with adjunct material 4982 that was applied with a nozzle applicator, such as shown in FIG. 155 and FIG. 156.

Adjunct material can be applied to staple cartridges used with surgical staplers. FIG. 158 shows an applicator nozzle 4984 coupled to a staple cartridge 4983 to apply adjunct 4985 to staples 4986 loaded in the cartridge. FIG. 159 also shows an applicator nozzle 4988 fitted to a staple cartridge 4983. In FIG. 159, the adjunct material 4987 flowing over the staple 4986 is made of two constituents or components which are mixed immediately prior to application of the adjunct material to the cartridge. FIG. 160 provides a view of applied adjunct material 4989 on staples 4986 loaded in a stapler cartridge 4983.

FIG. 161 shows a surgical staple 4992 improperly situated inside of tissue 4991. Such a configuration 4990 can occur when no adjunct material is present to distribute forces from the staple on the tissue and prevent the staple from cutting through tissue or inappropriately compressing the tissue. FIG. 163 shows how the presence of adjunct material 4998 on the anvil-side of a staple 4997 can allow proper placement of the staple 4997 in tissue 4996.

FIG. 162 shows a stick of gel adjunct material 4994 that is applied to the anvil 4995 or staple cartridge of a surgical stapler 4993. This is an alternate embodiment for a method for applying, and an applicator of, adjunct material. In this way, a surgical stapler can be reloaded and prepared quickly, such as when a surgeon needs to use a single surgical stapler multiple times in a single procedure.

FIGS. 164A-164C show surgical staples 41010 used with adjuncts 41012 used with a surgical stapler 41000 to transect tissue 41002. In the surgical stapler 41000, the anvil 41004 can be loaded with adjunct segments 41012 which interact with the staples 41010 loaded in the staple cartridge 41006. The adjuncts 41012 in the anvil 41004 can hold staples 41010 that are not applied to tissue 41002, as shown in FIG. 164C.

Adjuncts for Anastomosis

Anastomosis is a process which requires creating a circular cut through a staple line in each end of the tissues to be connected. Cutting through a staple line can cause torn or partially cut staples. Dog ears of tissue at the corners of the staple line can have leaks or allow debris to collect, however, if it is not possible to eliminate dog ears altogether, then it sealing them to minimize leakage is desirable. Described below are adjunct assemblies for use with specific staple cartridge configurations that include seals for dog ears, as well as provide a minimal amount of staples through the area that is eventually cut by a circular cutting implement.

FIG. 165 shows an embodiment of a non-continuous adjunct 41020 for use in forming an anastomosis. The non-continuous adjunct 41020 includes a ring 41022, or washer, in the center of the adjunct. Attached on either side, 180° apart, are suture filaments 41026. The suture filaments connect to sealing material 41024. Each portion of sealing material 41024 is configured to seal a dog ear portion of the staple line by. The sealing material 41024 is configured to span multiple staples and once inserted into tissue, the staple can have the sealing material 41024 adjacent to the crown of the staple or adjacent to the anvil-side of the staple. In some embodiments, the sealing material 41024 is configured to be adjacent to the crown of staples deployed in tissue. Such sealing material can be complemented with sealing material, such as adjunct segments, on the anvil-side of the staple.

FIGS. 166 and 167 show a surgical staple cartridge 41028 and a staple pattern for use with the adjunct of FIG. 165. The staple pattern on the cartridge 41028 is shown to have areas of two or more rows of staples 41030 and areas with a single row of staples 41031. The single row of staples 41031 is intended to, or configured to, correspond to the portion of the tissue that will be cut through in forming a circular cut. The suture filament 41026 of the non-continuous adjunct 41020 is delivered parallel to this single row of staples 41030. The areas of two or more rows of staples 41030 correspond to where the dog ears in the tissue will be. The sealing material 41024 of the non-continuous adjunct 41020 is configured to be used with the two or more rows of staples 41030, as shown in FIG. 166.

In the staple cartridge 41028 shown in FIG. 166 and the staple pattern shown in FIG. 167, it can be seen that the single row of staples 41031 is centered with respect to the multiple rows of staples 41030 in the dog ear area. The suture filament 41026 of the non-continuous adjunct 41020 will not only be substantially parallel to the single row of staples 41031, but the suture filament 41026 will almost overlay the single row of staple 41031 once the adjunct 41020 is deployed with surgical staples into tissue. More than one non-continuous adjunct 41020 can be deployed at a time, and is shown in FIG. 166, in such situations, the non-continuous adjuncts 41020 can be substantially similar.

FIG. 168 is an illustration of an alternative embodiment of a non-continuous adjunct for use in forming an anastomosis. Shown are two non-continuous adjuncts 41040, 41050 that are minor images of each other. The non-continuous adjuncts 41040, 41050 each have a washer 41046, 41056, attached to suture filaments 41044, 41054. The suture filaments 41044, 41054 are attached to sealing material 41042, 41052 that is configured to span multiple surgical staples in the dog ear area of the stapled tissue.

FIGS. 169-173 show a surgical stapler cartridge 41060 for use with the adjuncts of FIG. 168, as well as further views of the non-continuous adjuncts 41040, 41050 of FIG. 168. The stapler cartridge 41060 is symmetric about a centerline, where a cut through stapled tissue can be made. The cartridge 41060 has areas for a single row of staples 41064 and for multiple rows of staples 41062 on each half of the cartridge. The multiple rows of staples 41062 are at the ends of the staple line and are where the dog ear portion of the tissue will be. The single rows of staples 41064 are off-center with respect to the multiple rows of staples 41062, such that the single rows of staples 41064 are located towards the edges of the cartridge 41060. When the non-continuous adjuncts 41040, 41050 are overlaid onto the cartridge, the sealing material 41042, 41052 corresponds to the areas on the cartridge 41060 with multiple rows of staples 41062, the washers 41046, 41056 are each in the center of a single row of staples 41064, each on one half of the cartridge 41060. The suture filaments 41046, 41056 are substantially parallel to the single rows of staples 41064, but do not overlay them. FIG. 171 shows the relative positioning of the non-continuous adjuncts 41040, 41050 and staples, showing the unsealed staples 41066 of the single rows of staples. These unsealed staples 41066 can be cut through or removed when an anastomosis is formed. FIG. 172 shows the view of FIG. 171 overlaid on the view of FIG. 170. FIG. 173 includes depressions in the staple cartridge 41060 underneath the washers 41046, 41056.

FIG. 174 shows an embodiment of an adjunct washer 41066 before and during actuation of a surgical stapler. The washer 41066 can be one similar to any of the previously discussed washers, 41022, 41046, 41056. The washer 41066 is shown in a recess in a stapler cartridge 41064. Suture filaments 41068 connect to the washer 41066. When the adjunct is placed in the surgical stapler, before staple deployment, the washer 41066 is substantially circular in cross-section. During staple deployment, the washer 41066 compresses under pressure 41070 from the surgical stapler. The washer 41066 then has a substantially elliptical cross-section. Under pressure, the washer 41066 becomes flush, or nearly flush, with an upper portion of the staple cartridge while filling, or nearly filling, the recess.

FIG. 175 shows an embodiment of a surgical staple cartridge for use in forming an anastomosis. This side view allows a comparison for the tips of a standard staple cartridge 41072 and that of a LAR 41074. A person skilled in the art will appreciate that it could be useful in LAR procedures to reduce the length of the end effector distal to an articulation joint in the stapler. It is believed that reducing the distance from a distal most staple in the cartridge to the distal most location on the staple cartridge will enable this effort as shown in FIG. 175. A person skilled in the art will be able to ascertain the appropriate relative distances.

FIG. 176 shows a body lumen transected by a surgical stapler with an adjunct, such as the one shown in 118. The tissue 41076 is shown with non-continuous adjuncts 41040, 41050 in place. The washers 41046, 41056 align, and alongside each washer 41046, 41056 and the suture filaments 41044, 41054 connected to each washer is a single row of staples 41066 that is not sealed by adjunct material. Sealing material 41042, 41052 prevents leaks in the dog ear portions of tissue with multiple rows of staples.

FIGS. 177A-177C shows a cross-sectional view of the use of an adjunct 41050, such as the one shown in FIG. 168 and a circular stapler trocar 41078. FIG. 177A shows the non-continuous adjunct in tissue 41076 with the washer 41056 above a staple line that includes the unsealed, single row of staples 41066. FIG. 177B shows the trocar 41076 approaching the staple line 41066 and washer 41056 as it moves through a lumen in the tissue 41076. FIG. 177C shows the engagement of the trocar 41078 with the washer 41066. FIG. 178 shows the relative positioning of all of the components of the adjunct 41505 when the trocar 41078 is engaged with the washer 41056.

FIGS. 178-186 shows a circular stapler trocar 41078 passing through a washer portion of a non-continuous adjunct 41050. FIG. 179 shows the non-continuous adjunct 41050 with a washer 41056, suture filaments 41054, and sealing material 41052 at the dog ears of the tissue 41076. A circular staple and cutting implement 41080 is inside the tissue 41076. A trocar 41078 is at the center of the staple and cutting implement 41080. The trocar 41078 extends through the washer 41056 toward a shaft 41084 that is connected to an anvil 41082 in another portion of the tissue 41076 that has been cut and sealed along a staple line 41088. The anvil 41082 is shown above a buttonhole that is adjacent the shaft 41084.

FIG. 180 shows an embodiment similar to that shown in FIG. 179. In FIG. 180 the non-continuous adjuncts 41040, 41050 are shown each with a washer 41046,41056, suture filaments 41044, 41054, and sealing material 41042,41052 at the dog ears of the tissue 41076. A single row of staples 41066 surrounds each of the washers 41046, 41056 near the suture filaments. A circular staple and cutting implement is inside the tissue 41076, and the trocar 41078 extends through one washer 41056 towards a mating shaft that extends through the other washer 41046.

FIGS. 181-183 show cross-sectional views of the movement of the sections of tissue 41076 toward each other, so that the tissue can be stapled (FIG. 185) and cut FIG. 186 to create an anastomosis. FIG. 181 is a cross-sectional view of FIG. 179, but with the shaft 41084 attached to the anvil 41082 fitted over the trocar 41078 and in contact with the washer 41056. FIG. 182 is a closer view of the shaft 41084 connected to the anvil and the center portion of the adjunct 41050, particularly the washer 41056 and suture filaments 41054. As the shaft 41084 moves down, so that the two portions of the tissue 41076 move together, the shaft 41084 moves the suture filaments 41054 downward so that the sealing material 41052 on the dog ears move closer together, as shown in FIG. 183. FIG. 184 shows the movement of the sealing material 41052 on the dog ears toward the trocar 41078 as the shaft moves the washer 41056 downward. FIG. 185 shows the tissue sections attached with staples 41100. The adjunct 41050, with the washer 41056 pushed down by the shaft and the sealing material 41052 at the dog ear portion, are shown in the center of the stapling and cutting implement 41080. FIG. 186 shows the tissue 41076 after the circular cut has been made. The tissue is joined with three rows of staples 41100 in a circular configuration with the previously stapled tissue, including the non-continuous adjunct 41050, removed. The adjuncts 41033, 41040, 41040 described above can be used interchangeably or in combination in the methods for creating an anastomosis shown in FIG. 176-186.

Various exemplary bronchus sealants and methods of sealing bronchial tubes are provided. In general, the bronchus sealants and methods of sealing bronchial tubes can facilitate sealing of stapled bronchial tubes. In some embodiments, a reinforcement material, e.g., a mesh (e.g., a knitted mesh, a non-woven mesh, or a woven mesh), a non-woven matrix, a film, a melt-blown non-woven material, a felt material, a closed-cell foam, an open-cell foam, a braided suture, or a sponge, can be introduced into a bronchial tube, and then the bronchial tube and the reinforcement material can be stapled using a surgical stapler. A sealant can be introduced into the bronchial tube and can harden therein, thereby helping to seal the bronchial tube where the bronchial tube was stapled. Prior to hardening, the sealant can seep or wick in a first state into the staple line, thereby facilitating complete sealing of the bronchial tube. The reinforcement material and the sealant can cooperate to provide a better, more complete seal of the staple line than if either of the reinforcement material and the sealant were used without the other. The reinforcement material at the staple line can cause inflammation of the bronchial tube, thereby causing the bronchial tube to encapsulate the reinforcement material as an irritant. Such encapsulation can facilitate long term sealing of the bronchial tube. The reinforcement material can thus take advantage of the bronchial tube's natural inflammatory response, and natural slow healing of the bronchial tube, to help seal the stapled bronchial tube. The sealant can facilitate short term sealing of the bronchial tube during the time the bronchial tube reacts to and encapsulates the reinforcement material, e.g., for a time period of up to about two weeks. The reinforcement material that has been stapled can extend from the staple line into the bronchial tubes passageway, thereby providing the sealant with a structure within the bronchial tube to help hold the sealant in position adjacent the applied staples while the sealant hardens within the bronchial tube and to help hold the sealant in position adjacent the applied staples after the sealant has hardened. By being held adjacent to the staple line by the reinforcement material, the sealant can be more likely to harden at and completely seal the staple line. The bronchial tube can thus be more likely to remain sealed during expansion and contraction of the lung during breathing.

The sealant can be introduced into the bronchial tube before the stapling of the bronchial tube and the reinforcement material, such as by the reinforcement material being imbibed with the sealant in a first state, e.g., as a softened state such as fluid, a gel, etc., or as a dry state, e.g., as a powder, etc. The reinforcement material being coupled to the sealant before stapling can facilitate delivery of the reinforcement material and the sealant into the bronchial tube by allowing the reinforcement material and the sealant to be simultaneously delivered thereto. Alternatively or in addition, the sealant can be introduced into the bronchial tube after the stapling of the bronchial tube and the reinforcement material, such as by injection of the sealant in a first state into the bronchial tube adjacent a staple line formed by the stapling. The sealant being delivered into the bronchial tube subsequent to the stapling can help prevent the sealant from hardening within the bronchial tube before the bronchial tube is stapled. If the sealant is delivered into the bronchial tube subsequent to the stapling, the same surgical instrument that delivered the reinforcement material into the bronchial tube can deliver the sealant, thereby making the surgical procedure easier to perform since only one delivery device need be introduced into the bronchial tube.

FIG. 187 illustrates one embodiment of a surgical instrument 5000 configured to deliver a reinforcement material (not shown) and a sealant (not shown) into a bronchial tube 5002 of lungs 5004 of a patient 5006. The instrument 5000 can include a proximal handle portion (not shown) configured to be held, e.g., handheld by a medical practitioner, held by a robotic surgical arm, etc., outside the patient 5006, as will be appreciated by a person skilled in the art. The instrument 5000 can be configured to be transorally advanced into the bronchial tube 5002, as shown in FIG. 187, by being advanced into a mouth 5008 of the patient 5006. The instrument 5000 can be advanced into the patient 5006 in other ways, as will be appreciated by a person skilled in the art. For example, the instrument 500 can be configured to be advanced into a patient through an introducer device, such as a trocar, inserted into the patient through an incision formed through skin of the patient.

As shown in FIG. 188, the instrument 5000 can include a scoping device 5010, e.g., an endoscope, a laparoscope, etc., and an end cap 5012 configured to be coupled to a distal end 5014 of the scoping device 5010. The scoping device 5010 in this illustrated embodiment has one working channel 5016 extending longitudinally therethrough, includes one visualization element 5058, e.g., a lens, etc., and includes two lights 5018, e.g., light emitting diodes (LEDs), etc. The lights 5018 and the viewing element 5058 can be distal-facing, as in the illustrated embodiment, which can facilitate visualization of a target surgical site distal to the instrument 5000. In other embodiments, a scoping device can have a plurality of working channels extending longitudinally therethrough and/or can have a different number of lights.

The end cap 5012 can be configured to be selectively attachable to the scoping device's distal end 5014, such as by being snap fit thereon, by being fit thereto via interference fit (as in the illustrated embodiment), by being threaded thereto, etc. In other words, the end cap 5012 can be configured to be removably and replaceably attachable to the scoping device 5010. The end cap 5012 being configured to be selectively attachable to the scoping device 5010 can allow the end cap to be disposable, can facilitate cleaning of the scoping device 5010 and/or the end cap 5012 before reuse with another patient, and/or can help prevent the scoping device 5010 from being damaged by sealant delivered using the instrument 5000. Exemplary embodiments of attachment techniques for attaching an end cap to a scoping device are described in further detailed in U.S. Pat. No. 8,551,058 entitled "Endoscopic Translumenal Surgical Systems" filed on Jul. 10, 2007, which is hereby incorporated by reference in its entirety.

The end cap 5012 can include a working port 5020, a window 5022, and a balloon 5024 around a perimeter thereof. The working port 5020 can be configured to be aligned with the scoping device's working channel 5016 when the end cap 5012 is attached to the scoping device 5010, which can allow a surgical device (not shown) to be advanced distally through the scoping device's working channel 5016 and through the end cap's working port 5020. The window 5022 can be configured to be aligned with the scoping device's lights 5018 when the end cap 5012 is attached to the scoping device 5010, thereby allowing the lights 5018 to shine through the window 5022 so as to illuminate a target surgical site distal to the instrument 5000.

The balloon 5024 can be configured to be selectively inflatable when the end cap 5012 is attached to the scoping device 5010. The balloon 5024 can be configured to move between an uninflated configuration, shown in FIG. 188 with the balloon 5024 in solid line 5026, and an inflated configuration, shown in FIG. 188 with the balloon 5024 in broken line 5028. When the balloon 5024 is in the uninflated configuration, the end cap 5012 can have a first diameter that is less than a second diameter of the end cap 5012 when the balloon 5024 is in the inflated configuration. The balloon 5024 can be configured to be selectively inflated and deflated in a variety of ways. As in this illustrated embodiment, the end cap 5012 can include an inflation line 5030 extending distally therefrom. The balloon 5024 can be in fluid communication with the inflation line 5030. The inflation line 5030 can be configured to extend through the working channel 5016 of the scoping device 5010 and couple to an inflation source (not shown) at a proximal end of the scoping device 5010, as will be appreciated by a person skilled in the art. In some embodiments, the inflation line 5030 can extend through the working channel 5016 of the scoping device 5010 and be configured to be attached to the end cap 5012 when the end cap 5012 is attached to the distal end 5014 of the scoping device 5010.

The end cap 5012 can include a cleaning mechanism (not shown) configured to clean a distal end of the instrument 5000, e.g., a distal end of the scoping device 5010 and/or a distal end of the end cap 5012, when the end cap 5012 is attached to the scoping device's distal end. The cleaning mechanism can allow for the instrument 5000 to be cleaned within a patient's body such that the instrument 5000 need not be removed for cleaning should the viewing element 5058, the lights 5018, and/or other feature become obscured, clogged, etc. during use due to fluid and/or other matter. Exemplary embodiments of cleaning mechanisms are described in further detailed in U.S. Pat. Pub. No. 2009/0270686 entitled "Methods And Devices For Maintaining Visibility During Surgical Procedures" filed on Apr. 29, 2008, and U.S. Pat. Pub. No. 2009/0234193 entitled "Apparatus For Keeping Clean A Distal Scope End Of A Medical Viewing Scope" filed on Mar. 13, 2008, which are hereby incorporated by reference in their entireties.

FIGS. 189-192 illustrate an exemplary embodiment of a surgical procedure for stapling and sealing the bronchial tube 5002 using the instrument 5000. Although the procedure is illustrated with respect to the surgical instrument 5000 of FIGS. 187 and 188, any of the surgical instruments discussed herein can be similarly used. Similarly, although the procedure is illustrated with respect to the bronchial tube 5002 of FIG. 187, another tubular anatomical structure, e.g., a blood vessel, etc., can be similarly treated. Also, although the procedure is illustrated with respect to stapling, a bronchial tube (or other anatomical structure) can be sealed as discussed herein in conjunction with a type of fastener other than staples, e.g., clips, sutures, energy, etc.

As shown in FIG. 189, the bronchial tube 5002 can include a tumor 5032. As will be appreciated by a person skilled in the art, treatment of the tumor 5032 can include removing a portion of the bronchial tube 5002 that includes the tumor 5032 and leaving another portion of the bronchial tube 5002 within the patient 5006.

As also shown in FIG. 189, a reinforcement material 5034 can be introduced into the bronchial tube 5002. The reinforcement material 5034 can include a flexible material configured to be stapled or otherwise fastened, e.g., using clips, etc., within the bronchial tube 5002. Examples of the reinforcement material 5034 include a mesh (e.g., a knitted mesh, a non-woven mesh, or a woven mesh), a non-woven matrix, a composite matrix including a non-woven polymer (e.g., polyglactin 910) and a knitted or woven backing material (e.g., oxidized cellulose), a film, a melt-blown non-woven material, a felt material, a closed-cell foam, an open-cell foam, a sponge, a braided suture, and oxidized cellulose (e.g., oxidized regenerated cellulose (ORC)). Various embodiments of multilayered dressings that can be used as the reinforcement material 5034 are described in U.S. Pat. Pub. No. 2006/0257458 entitled "Reinforced Absorbable Multilayered Hemostatis Wound Dressing" filed on Apr. 10, 2006, which is hereby incorporated by reference in its entirety. The reinforcement material 5034 can be absorbable or non-absorbable. The reinforcement material 5034 in this illustrated embodiment includes a mesh. The mesh can be formed from any one or more materials. In general, material suitable for implantation, such as material for a surgical suture, can be suitable for the mesh. Examples of absorbable materials that can be used, alone or in any combination thereof, to form the mesh include poliglecaprone (e.g., Monocryl® available from Ethicon, Inc. of Somerville, N.J.), polyglactin (e.g., polyglactin 910, such as Vicryl® available from Ethicon, Inc. of Somerville, N.J.), polydioxanone, collagen, oxidized cellulose, glycerol, glycolide, lactide, dioxanone, trimethylene carbonate, and gut suture. Examples of non-absorbable materials that can be used, alone or in any combination thereof, to form the mesh include polypropylene, polyethylene, polybutester fiber, stainless steel, nylon, polyester, silk, and polyvinylidene difluoride (PVDF). The reinforcement material 5034 in this illustrated embodiment has a rectangular shape, but the reinforcement material 5034 can have any shape, e.g., ovular, triangular, etc.

The reinforcement material 5034 can be introduced into the bronchial tube 5002 by being advanced through the working channel 5016 of the scoping device 5010, as also shown in FIG. 189. The end cap 5012 is not attached to the scoping device 5010 in FIG. 189. A grasper 5036 grasping the reinforcement material 5034 can be advanced through the scoping device's working channel 5016 so as to hold and pass the reinforcement material 5034 through the working channel 5016 and out a distal end thereof so as to position the reinforcement material 5034 within the bronchial tube 5002, as shown in FIG. 189. The reinforcement material 5034 can be introduced into the bronchial tube 5002 in another way, as will be appreciated by a person skilled in the art, such as by being advanced through a different scoping device, advancing the reinforcement material 5034 into the bronchial tube 5002 using the grasper 5036 without a scoping device, etc.

The reinforcement material 5034 can be positioned at a target site within the bronchial tube 5002 located on one side of the tumor 5032. The target site can be an area intended to be stapled with a surgical stapler 5038. The stapler 5038 can be any surgical stapler configured to staple a bronchial tube, such as a linear stapler, as shown in the illustrated embodiment. Exemplary embodiments of staplers are described in further detail in U.S. Patent Application entitled "Adjunct Materials and Methods of Using Same in Surgical Methods for Tissue Sealing" filed on even date herewith Atty. Dkt. No. 47059-253F01US (END7380USNP)), which is hereby incorporated by reference in its entirety.

The stapler 5038 can be located outside the bronchial tube 5002, as shown in FIG. 189. The stapler 5038 and the grasper 5036 can include a location mechanism configured to help position the stapler 5038 relative to the target site within the bronchial tube 5002 where the reinforcement material 5034 is positioned. The bronchial tube 5002 is a relatively hard member that can make it difficult, if not impossible, to locate the grasper 5036 and/or the reinforcement material 5034 therein by touch. In another, softer body lumen, such as the intestinal tract, the grasper 5036 and/or the reinforcement material 5034 could be located by external touch of the lumen, e.g., by touching the lumen with a finger, by gently pressing the stapler 5038 against the lumen, etc.

The location mechanism can have a variety of configurations. Exemplary embodiments of location mechanisms that can be used to facilitate positioning of a stapler are described in U.S. Pat. Pub. No. 2012/0024934 entitled "Transwall Visualization Arrangements And Methods For Surgical Circular Staplers" filed on Jul. 30, 2010, which is hereby incorporated by reference in its entirety.

For example, the location mechanism can include a light illuminated within the bronchial tube 5002 that can be detectable from outside the bronchial tube 5002. For example, the lights 5018 of the scoping device 5010 can be configured to be bright enough to be visually detectable from outside the bronchial tube 5002. For another example, the location mechanism can include a light (not shown) illuminated from outside the bronchial tube 5002 that can allow location of the grasper 5036 and/or the reinforcement material 5034 within the bronchial tube 5002 to be visually identified, such as by the stapler 5038 including a light (not shown) and/or a second scoping device (not shown) located outside the bronchial tube 5002 including one or more lights similar to the lights 5018 of the scoping device 5010. For yet another example, the location mechanism can include one or more magnets, such as rare earth magnets, located within the bronchial tube 5002, e.g., by being attached to the grasper 5036, by being attached to detection members (e.g., lights, extendable bumpers, etc.) coupled to the scoping device 5010, etc. A probe (e.g., a Hall effect sensor, etc.) positioned near the tumor 5032 side of the bronchial tube 5002 can be configured to measure a distance between the magnet(s) and the tumor 5032, thereby indicating a location for stapling of the bronchial tube 5002. The probe can be attached to the stapler, e.g., to a distal tip of an anvil of the stapler. The magnet(s) can be configured to alternate in polarity and/or vary in intensity, which can facilitate the probe's measurement of the distance by allowing the probe to detect distance and orientation.

In this illustrated embodiment, the location mechanism includes a magnet 5040 coupled to the grasper 5036 and a sensor (not shown), e.g., a proximity sensor, a Hall effect sensor, etc., coupled to the stapler 5038 and configured to sense the magnet 5040 coupled to the grasper 5036 when the sensor is within a certain predetermined distance of the magnet 5040. In this way, the sensor being positioned near the magnet 5040 disposed within the bronchial tube 5002, so as to sense the magnet 5040, can indicate that the stapler 5038 is adjacent the reinforcement material 5034 within the bronchial tube 5002. In other words, the detection of the magnet 5040 by the sensor can indicate that the stapler 5038 is at a position relative to the bronchial tube 5002 at which the stapler 5038 can staple the bronchial tube 5002. The sensor sensing the magnet 5040 can be configured to trigger a notification at a proximal end (not shown) of the stapler 5038 when the stapler's magnet is magnetically attracted to the magnet 5040, which can help indicate to a user of the stapler 5038 that the stapler 5038 is positioned adjacent the target site. The notification can include, e.g., a light, a sound, a vibration, etc. The grasper 5036 includes one magnet 5040 in this illustrated embodiment, but the grasper 5036 can each include any number of magnets. Although the grasper 5036 includes the magnet 5040 in this illustrated embodiment, another element, such as the scoping device 5010 (e.g., the distal end 5014 thereof), the reinforcement material 5034, etc., can include the magnet 5040 and/or can include one or more additional magnets. In an exemplary embodiment, the magnet 5040 can be coupled to an element that is not implanted within the bronchial tube 5002, e.g., on a surgical device used to deliver the reinforcement material 5034 and/or a sealant to the bronchial tube 5002, which can help prevent the location mechanism from interfering with any subsequent surgical procedures.

When the stapler 5038 is positioned at a desired location relative to the bronchial tube 5002, e.g., adjacent the target site where the reinforcement material 5034 is within the bronchial tube 5002, the stapler 5038 can staple the bronchial tube 5002 and the reinforcement material 5034 by ejecting one or more staples 5042 therefrom, as shown in FIG. 190. The stapler 5038 in this illustrated embodiment ejects six staples 5034, but the stapler 5038 can eject any number of staples, simultaneously or sequentially. The stapler 5038 can also, as will be appreciated by a person skilled in the art, cut the stapled bronchial tube 5002 using a knife or other cutting element. The cutting of the bronchial tube 5002 can result in a specimen portion 5044 of the bronchial tube 5002, which includes the tumor 5032 and which can be removed from the patient 5006, and a remainder portion 5046 of the bronchial tube 5002, which can remain within the patient 5006. As shown in FIG. 191, the stapling and cutting can form first and second staple lines 5052a, 5052b in the bronchial tube, with the first staple line 5052a being formed in the specimen portion 5044 and the second staple line 5052b being formed in the remainder portion 5052b.

As mentioned above, the stapler 5038 can staple the reinforcement material 5034 when the stapler 5038 staples the bronchial tube 5002. The stapler 5038 can thus cut the reinforcement material 5034 when the stapler 5038 cuts the bronchial tube 5002. A first portion 5048 of the reinforcement material 5034 can be in the specimen portion 5044 after being stapled and cut and can be removed from the patient 5006 with the specimen portion 5044. A second portion 5050 of the reinforcement material 5034 can be in the remainder portion 5046 and can remain in the bronchial tube 5002 after being stapled and cut, as shown in FIG. 191. The second portion 5050 of the reinforcement material 5034 within the bronchial tube 5002 can extend from the staple line 5052b into the bronchial tube 5002.

As shown in FIG. 191, a sealant 5054 can be introduced into the bronchial tube 5002. The sealant 5054 can include a material configured to transition from a first state to a second state in which the material is harder than in the first state. The first state can thus be a softened state or a dry state, and the second state can be a second, harder state, e.g., hardened as a solid, a rigid member. The sealant 5054 can be configured to transition from the first state to the second, harder state in a predetermined amount of time. As will be appreciated by a person skilled in the art, the predetermined amount of time can vary based on the substance(s) forming the sealant 5054. Examples of the sealant 5054 include one or a combination of one or more of an adhesive, fibrin thrombin, a hydrogel, fibronectin, gelatin, collagen, Factor XIII, transglutaminase, polyethylene glycol (e.g., Progel® Pleural Air Leak Sealant available from Davol Inc. of Providence, R.I.), alginate, carboxymethylcellulose, methylcellulose, hydroxypropylmethyl cellulose, pectin, polyvinyl alcohol, polyvinylpyrrolidone, benzocaine (e.g., Projel-20™ available from Septodont of Lancaster, Pa.), cyanoacrylate, polyglycolic acid, hyaluronic acid, magnesium peroxide, 2 octyl cyanoacrylate (e.g., Dermabond® available from Ethicon, Inc. of Somerville, N.J.), and hydrogen peroxide. In another embodiment, the sealant can be blood, such as autologous blood. Exemplary embodiments of sealants are described in further detail in U.S. Patent Application entitled "Methods And Devices For Sealing A Body Lumen" filed on even date herewith (Atty. Dkt. No. 47059-254F01US (END7381USNP)), which is hereby incorporated by reference in its entirety.

The sealant 5054 can be introduced into the bronchial tube 5002 by being advanced through the working channel 5016 of the scoping device 5010, as also shown in FIG. 191. The sealant 5054 can be advanced into the bronchial tube 5002 in the first state, as also shown in FIG. 191.

The end cap 5012 can be attached to the scoping device 5010 when the sealant 5054 is delivered into the bronchial tube 5002, as also shown in FIG. 191. If the end cap 5012 is not already attached to the scoping device 5010, e.g., when the reinforcement material 5034 is introduced into the bronchial tube 5002, the scoping device 5010 can be removed from the bronchial tube 5002 after delivering the reinforcement material 5034, and the end cap 5012 can be attached to the distal end 5014 of the scoping device 5010. The end cap 5012 being attached to the scoping device 5010 when the sealant 5054 is delivered into the bronchial tube 5002 can help protect the scoping device 5010 from damage by helping to keep the sealant 5054 from contacting the scoping device 5010 and hardening thereon. Hardened sealant 5054 on the scoping device 5010 can cause damage to the scoping device 5010 by, e.g., clogging the working channel 5016 and/or obscuring the lights 5018. If the sealant 5054 contacts the end cap 5012 and hardens thereon, the end cap 5012 can be disposed of at typically much lower monetary cost than disposing the scoping device 5010 and/or the end cap 5012 can be more easily cleaned than the scoping device 5010 since, e.g., the end cap 5012 is smaller than the endoscope 5010.

An applicator 5056 can be slidably advanced through the scoping device's working channel 5016 and deliver the sealant 5054 therethrough. The applicator 5056 can have a variety of configurations. In this illustrated embodiment, the applicator 5056 includes an elongate tube through which the sealant 5054 can pass.

The sealant 5054 can be directed toward the staple line 5052b. The sealant 5054 can thus be directed toward the second portion 5050 of the reinforcement material 5034 extending from the staple line 5052b. The applicator 5056 can be advanced through the scoping device's working channel 5016 and out the end cap's working port 5020, as shown in FIG. 191, to facilitate directing the sealant 5054 toward the reinforcement material 5034. The lights 5018 of the scoping device 5010 can be on and can shine through the end cap's window 5022, as shown in FIG. 191, which can facilitate visualization of the applicator 5056, the reinforcement material 5034, and/or the sealant 5054 using the viewing element 5058, which can help the sealant 5054 be directed toward the staple line 5052b.

The sealant 5054 can be introduced into the bronchial tube 5002 so as to be applied to the reinforcement material 5034 and/or an interior tissue surface of the bronchial tube 5002. The reinforcement material 5034 can provide an object within the bronchial tube 5002 for the sealant 5054 to attach to, thereby helping to ensure that the sealant 5054 hardens adjacent the staple line 5052b, thereby helping to seal the staple line 5052b. In an exemplary embodiment, the sealant 5054 is applied to both the reinforcement material 5034 and the interior tissue surface of the bronchial tube 5002, as shown in FIGS. 191 and 192.

The sealant 5054 can be configured to transition from the first state in which it is delivered into the bronchial tube 5002, as shown in FIG. 191, to the second, harder state, as shown in FIG. 192. The sealant 5054 being introduced into the bronchial tube 5002 in the first state can allow the sealant 5054 to seep or wick into the staple line 5052b and into the reinforcement material 5034, which can facilitate sealing of the staple line 5052b so as to help prevent a leak. The sealant 5054 in the hardened state being coupled to the reinforcement material 5034, as shown in FIG. 192, can help keep the sealant 5054 in position within the bronchial tube 5002 where the sealant 5054 is helping to seal the staple line 5052b.

The balloon 5024 can be in the inflated within the bronchial tube 5002 when the sealant 5054 is being advanced out of the applicator 5056, as shown in FIG. 191. In other words, the balloon 5024 can be in the inflated configuration during delivery of the sealant 5054 into the bronchial tube 5002. The balloon 5024 being inflated during delivery of the sealant 5054 can help prevent the sealant 5054 from blowing back proximally after being advanced distally from the applicator 5056 by filling any excess space between the end cap 5012 and the interior surface of the bronchial tube 5002, can help prevent the sealant 5054 from hardening within the bronchial tube 5002 at a location that could potentially interfere with the bronchial tube's ordinary function during breathing, can help hold the end cap 5012 in a fixed position relative to the bronchial tube 5002 during delivery of the sealant 5054 so as to facilitate introduction of the sealant 5054 into the bronchial tube 5002 at a desired location, and/or can help direct all of the sealant 5054 toward the staple line 5052*b*.

The balloon 5024 can be in the uninflated configuration when the end cap 5012 is advanced into bronchial tube 5002 and can be moved from the uninflated configuration to the inflated configuration after the end cap 5012 has been positioned within the bronchial tube 5002 adjacent the staple line 5052*b*. The balloon 5024 can be expanded within the bronchial tube 5002 using the inflation line 5030, e.g., by passing a fluid (e.g., air, water, etc.) through the inflation line 5030 and into the balloon 5024. The balloon 5024 being in the uninflated configuration during advancement of the end cap 5012 through the patient's mouth 5008 and through advancement of the end cap 5012 to the target site within the bronchial tube 5002 can allow the end cap 5012 to have a smaller outer diameter, which can facilitate passage of the end cap 5012 through the patient's body.

If the end cap 5012 is attached to the scoping device 5010 when the reinforcement material 5034 is advanced into the bronchial tube 5002, the balloon 5024 can be in the inflated configuration when the reinforcement material 5034 is being advanced into the bronchial tube 5002. The balloon 5024 being inflated during delivery of the reinforcement material 5034 can help prevent the reinforcement material 5034 from blowing back proximally after being advanced distally from the scoping device 5010 by filling any excess space between the end cap 5012 and the interior surface of the bronchial tube 5002 and/or can help hold the end cap 5012 in a fixed position relative to the bronchial tube 5002 during delivery of the reinforcement material 5034 so as to facilitate positioning the reinforcement material 5034 at a desired location.

After the sealant 5054 has been delivered into the bronchial tube 5002, the scoping device 5010, the end cap 5012 (if attached to the scoping device 5010 during sealant 5054 delivery), and any devices within the scoping device's working channel 5016, e.g., the applicator 5056, can be removed from the bronchial tube 5002. FIG. 192 shows the removal of the scoping device 5010, the end cap 5012, and the applicator 5056 from the bronchial tube 5002 in a direction shown by a retraction arrow 5060. The applicator 5056 is removed from the bronchial tube 5002 simultaneously with the scoping device 5010 and the end cap 5012 in this illustrated embodiment, but the applicator 5056 can be removed from the bronchial tube 5002 before the scoping device 5010 and the end cap 5012, e.g., by being withdrawn from the working channel 5016. Although FIG. 192 shows the scoping device 5010, the end cap 5012, and the applicator 5056 being removed from the bronchial tube 5002 after the sealant 5054 has transitioned from the first state to the second, harder state, any of the scoping device 5010, the end cap 5012, and the applicator 5056 can be removed prior to the sealant 5054 completing the transition to the hardened state. Keeping at least the scoping device 5010 within the bronchial tube 5002 until the sealant 5054 has transitioned to the hardened state can help ensure that the sealant 5054 hardens in the proper location adjacent the staple line 5052*b*, e.g., by allowing visualization of the sealant 5054 within the bronchial tube 5002 using the viewing element 5058.

In some embodiments, the reinforcement material 5034 can include sealant coupled thereto prior to the reinforcement material 5034 being stapled. For example, the reinforcement material 5034 can have a sealant coupled thereto, e.g., imbibed therein, soaked therein, coated thereon, etc., when the reinforcement material 5034 is advanced into the bronchial tube 5002. For another example, the reinforcement material 5034 can include a composite matrix (e.g., the composite matrix mentioned above including a non-woven polymer and a knitted or woven backing material) coated or impregnated with a sealant such as lyophilized fibrinogen and thrombin, a non-woven support. By the reinforcement material 5034 including sealant prior to the stapling thereof, the surgical procedure can include fewer steps since sealant need not be separately delivered after the stapling. However, even if the reinforcement material 5034 includes sealant prior to the stapling thereof, sealant can be delivered after the stapling, which can help ensure complete sealing of the staple line 5052*b*. For example, sealant coupled to the reinforcement material 5034 can include a first component, and sealant delivered subsequent to delivery of the reinforcement material 5034 can include a second component configured to activate the first component when in contact therewith. The second component activating the first component can trigger the transitioning from the first state to the hardened state so as to create a third material that acts as the sealant. In this way, timing of hardening of the sealant can be user-controlled by preventing hardening of the sealant until the second component is introduced to the first component, which can help prevent premature hardening of the sealant before the reinforcement material 5034 is desirably positioned and/or before stapling occurs. Delivering the sealant as multiple components can ease delivery of the sealant through the relatively small diameter bronchial tube 5002 by allowing the sealant to be introduced therein in multiple parts. In other words, less sealant material can be passed through the tube 5002 at any given time. Delivering the sealant as multiple components can be less expensive monetarily than introducing a singular sealant material into the bronchial tube 5002 since amounts of the sealant introduced can be better controlled and/or less of a more expensive component can be introduced than a less expensive component. Exemplary embodiments of multi-component sealants configured to be activated are described in further detail in previously mentioned U.S. Patent Application entitled "Methods And Devices For Sealing A Body Lumen" filed on even date herewith (Atty. Dkt. No. 47059-254F01US (END7381USNP)), which is hereby incorporated by reference in its entirety.

FIGS. 193 and 194 illustrate another embodiment of a reinforcement material 5062 and a sealant 5064. In this illustrated embodiment, as shown in FIG. 193, the reinforcement material 5062 is coupled to the sealant 5064 prior to stapling of the reinforcement material 5062 and a bronchial tube 5066 within which the reinforcement material 5062 can be positioned. The reinforcement material 5062 in this illustrated embodiment includes a sponge. The sealant in 5064 in this illustrated embodiment includes a therapeutic agent, e.g., a biologic, soaked into the sponge. The sealant 5064 being coupled to the reinforcement material 5062 prior to stapling thereof can help the sealant 5064 seal a staple line in the bronchial tube 5066 since the sealant 5064 can be positioned within the bronchial tube 5066 at a location of the staple line prior to formation of the staple line. The sealant 5064 including a therapeutic agent can help facilitate healing, as will be appreciated by a person skilled in the art.

The reinforcement material 5062 can be advanced into the bronchial tube 5066 similar to that discussed above regarding the reinforcement material 5034 of FIGS. 189-192. The scoping device 5010 of FIGS. 188-192 and the grasper 5036 of FIGS. 189 and 190 are shown advancing the reinforcement material 5062 into the bronchial tube 6066, but these and/or other devices can be used to introduce the reinforcement material 5062 into the bronchial tube 5066, as discussed above. Similarly, the stapler 5038 of FIGS. 189 and 190 is shown stapling the bronchial tube 5066, the reinforcement material 5062, and the sealant 5064 in FIG. 194, but a different stapler or a device applying a different type of fastener can be used to cut and secure a portion of the bronchial tube 5066. The bronchial tube 5066 in this illustrated embodiment has a tumor 5068 therein that is being excised, thereby prompting introduction of the reinforcement material 5062 and the sealant 5064 therein, but a bronchial tube can be treated for this and/or another reason using any reinforcement material and any sealant described herein.

The sealant 5064 can be sufficient sealant to seal the staple line formed by the stapler 5038. However, as mentioned above, additional sealant (not shown), such as an activator of the sealant 5064 previously delivered, can be introduced into the bronchial tube 5066 and delivered adjacent to the staple line so as to facilitate sealing thereof. The additional sealant can be advanced into the bronchial tube 5066 in a variety of ways, such as by the using the applicator 5056 of FIGS. 191 and 192 discussed above.

In some embodiments, a bronchial tube can be stapled, or otherwise cut and fastened, before a reinforcement material or a sealant are introduced into the bronchial tube. Stapling or otherwise fastening the bronchial tube before introducing the reinforcement material or the sealant are introduced therein can allow the bronchial tube to be stapled without a chance of the bronchial tube being stapled at a location where the reinforcement material is not positioned.

FIG. 195 illustrates another embodiment of a surgical instrument 5070 configured to deliver a reinforcement material (not shown) and a sealant (not shown). The instrument 5070 can include a proximal handle portion 5074 configured to be held outside the patient 5072. The instrument 5070 can be configured to be transorally advanced into the patient 5072, as shown in FIG. 195, by being advanced into a mouth 5076 of the patient 5072, although the instrument 5070 can be advanced into the patient 5072 in other ways that will be appreciated by a person skilled in the art.

The instrument 5070 can be configured to deliver the reinforcement material and the sealant into a bronchial tube after the bronchial tube has been stapled or otherwise cut and fastened. FIG. 196 shows an embodiment of a stapler 5078 including a pair of jaws 5080*a*, 5080*b* positioned on opposite sides of a bronchial tube 5082 of the patient 5072. As mentioned above, the stapler 5078 can have a variety of configurations. FIG. 197 shows the bronchial tube 5082 after being stapled by the stapler 5078. The stapler 5078 can cut the bronchial tube 5082 when stapling and accordingly create first and second staples lines 5084*a*, 5084*b* at facing ends of the cut bronchial tube 5082. The cutting of the bronchial tube 5082 by the stapler 5078 can result in a specimen portion 5082*a* of the bronchial tube 5082, which includes the first staple line 5084*a* and can be removed from the patient 5072, and a remainder portion 5082*b* of the bronchial tube 5082, which can include the second staple line 5084*b* and can remain within the patient 5072.

As shown in FIG. 198, the instrument 5070 can be configured to be advanced into the remainder portion 5082*b* of the bronchial tube 5082. A distal end 5070*d* of the instrument 5070, also shown in FIG. 199, can be positioned adjacent the second staple line 5084*b*. The instrument 5070 can include a first chamber 5090 configured to have a sealant 5086 disposed therein when the distal end 5070*d* is advanced into the bronchial tube 5082, and can include a second chamber 5092 configured have a reinforcement material 5088 disposed therein when the distal end 5070*d* is advanced into the bronchial tube 5082. In this illustrated embodiment, the sealant 5086 includes a fibrin and the reinforcement material 5088 includes ORC, but as mentioned above, the sealant 5086 and the reinforcement material 5088 can have other configurations. When the reinforcement material 5088 is acidic, such as when it includes ORC, the reinforcement material 5088 can provide an anti-microbial benefit during healing of the bronchial tube 5082, which can help reduce infection and/or other complications from the stapling. The first chamber 5090 in this illustrated embodiment includes a passageway of a tubular shaft 5094 extending longitudinally through the instrument 5070. The second chamber 5092 in this illustrated embodiment includes a cavity formed in a distal-most portion of the instrument 5070. The instrument 5070 can also include a piston 5096 configured to release the reinforcement material 5088 from the second chamber 5092, as discussed further below. In general, the piston 5096 can be slidably movable relative to the tubular shaft 5094 so as to move the reinforcement material 5088 out of the second chamber 5092 and out of the instrument 5070.

The instrument 5070 can be configured to advance the sealant 5086 and the reinforcement material 5088 into the bronchial tube 5082 adjacent the staple line 5082*b*. As shown in FIG. 200, when the instrument's distal end 5070*d* is positioned adjacent the staple line 5084*b*, the sealant 5086 can be released from the first chamber 5090 so as to be delivered into the bronchial tube 5082 at the staple line 5086. The sealant 5086 can seep or wick into the staple line 5082*b*, as discussed above. The sealant 5086 can be released from the first chamber 5090 in a variety of ways, as will be appreciated by a person skilled in the art. For example, a force can be applied to the first chamber 5090 in a distal direction, e.g., air pushed into the first chamber 5090 through an open proximal end (not shown) of the tubular shaft 5094 so as to push the sealant 5086 out a distal end of the tubular shaft 5094. All of the sealant 5086 can be released from the first chamber 5090 or, as shown in FIG. 200, only a portion of the sealant 5086 can be released from the first chamber 5090 so as to be disposed within the bronchial tube 5082.

As shown in FIGS. 200 and 201, when the instrument's distal end 5070*d* is positioned adjacent the staple line 5084*b*, the reinforcement material 5088 can be released from the second chamber 5092 so as to be delivered into the bronchial tube 5082 at the staple line 5086. The reinforcement material 5088 can be released from the second chamber 5092 in a variety of ways, as will be appreciated by a person skilled in the art. For example, the piston 5096 can be advanced distally, as shown by directional arrows 5098 in FIG. 200, so as to push the reinforcement material 5088 out an open distal end of the instrument 5070. The piston 5096 can be slidably disposed around the tubular shaft 5094, as mentioned above, and slid relative thereto to release the reinforcement material 5088 without also causing release of the sealant 5086. All of the reinforcement material 5088 can be released from the second chamber 5092, as in this illustrated embodiment, or only a portion of the reinforcement material 5088 can be released from the second chamber 5092 so as to be disposed within the bronchial tube 5082.

The sealant 5086 can be applied only before the reinforcement material 5088, the sealant 5086 can be applied only after the reinforcement material 5088, or the sealant 5086 can be applied both before and after the reinforcement material 5088. Application of the sealant 5086 after the application of the reinforcement material 5088 can allow the sealant 5086 to seep or wick into any space between the reinforcement material 5088 and an internal surface of the bronchial tube 5082, thereby further facilitating sealing. In this illustrated embodiment, the sealant 5086 is applied both before and after the reinforcement material 5088. FIG. 200 shows a first application of the sealant 5086 before application of the reinforcement material 5088, and FIG. 201 shows a second application of the sealant 5086 after the application of the reinforcement material 5088.

In an embodiment in which the sealant is blood, such as autologous blood, the blood can be harvested from the patient and applied to the adjunct material. By way of non-limiting example, the adjunct material can be ORC, a known hemostatic agent, and the application of the blood to the ORC adjunct will cause the formation of a clot, resulting in an effective sealing structure. A person skilled in the art will appreciate that blood, such as autologous blood can be applied to a variety of adjunct materials to provide an enhanced sealing structure. Further, a person skilled in the art will appreciate that the volume of blood applied to the adjunct will vary depending upon a number of factors, including the type and location of tissue as well, the age and condition of the patient, and the identity of the adjunct. Generally, however, when the adjunct is an ORC material, the blood can be applied in an amount in the range of about 5-10 cc per line of staple used to affix the adjunct to the tissue.

A person skilled in the art will appreciate that the methods, devices, systems, and apparatus described herein application in conventional minimally-invasive and open surgical instrumentation as well application in robotic-assisted surgery.

As will be appreciated by persons skilled in the art, various surgical staplers known in the art can be used to form an anastomosis. In general, referring back to FIG. 7, a surgical stapler 200 includes a handle assembly 212 with a shaft 214 extending distally therefrom, an end effector 250 being disposed on a distal end thereof for treating tissue. The end effector 250 can include a cartridge assembly 252 and an anvil 254, each having a tissue-contacting surface 260*p*, 260*d* that is substantially circular in shape. The cartridge assembly 252 and anvil 254 can be coupled together via a shaft 262 extending from the anvil 254 to the handle assembly 212 of the stapler 200, and manipulating an actuator 222 on the handle assembly 220 can retract and advance the shaft 262 to move the anvil 254 relative to the cartridge assembly 252. In one embodiment, the shaft 262 can be formed of first and second portions (not shown) configured to releasably couple together to allow the anvil 254 to be detached from the cartridge assembly 252, allowing greater flexibility in positioning the anvil 254 and the cartridge assembly 252 in a body. For example, the first portion of the shaft can be disposed within the cartridge assembly 252 and extend distally outside of the cartridge assembly 252, terminating in a distal mating feature. The second portion of the shaft 214 can be disposed within the anvil 254 and extend proximally outside of the cartridge assembly 252, terminating in a proximal mating feature. In use, the proximal and distal mating features can be coupled together to allow the anvil 254 and cartridge assembly 252 to move relative to one another. The anvil 254 and cartridge assembly 252 can perform various functions and can be configured to capture tissue therebetween, staple the tissue by firing of staples from a cartridge assembly 252 and/or can create an incision in the tissue. In general, the cartridge assembly 252 can house a cartridge containing the staples and can deploy staples against the anvil 254 to form a circular pattern of staples around a circumference of a tubular body organ.

The handle assembly 212 of the stapler 200 can have various actuators disposed thereon that can control movement of the stapler. For example, the handle assembly 212 can have a rotation knob 226 disposed thereon to facilitate positioning of the end effector 250 via rotation, and/or a trigger 222 for actuation of the end effector 250. Movement of the trigger 222 through a first range of motion can actuate components of a clamping system to approximate the jaws, i.e. move the anvil 254 toward the cartridge assembly 252. Movement of the trigger 222 through a second range of motion can actuate components of a firing system to cause the staples to deploy from the staple cartridge assembly 252 and/or cause advancement of a knife to sever tissue captured between the cartridge assembly 252 and the anvil 254.

The surgical stapler 200 is only one example of many different staplers that can be used in conjunction with the sealant and sealing cuffs disclosed herein. Further detail on the illustrated embodiment, as well as additional exemplary embodiments of surgical staplers, components thereof, and their related methods of use, that can be used in accordance with the present disclosure include those devices, components, and methods provided for in U.S. Publication No. 2013/0256377, U.S. Pat. Nos. 8,393,514, 8,317,070, 7,143, 925, each of which is incorporated by reference herein in its entirety.

Sealing Cuff

A sealing cuff is provided herein that can be positioned around a tubular body organ and can act as a mold for a sealant when the sealant is in the first, liquid state. The sealing cuff can have various sizes, shapes, but is generally configured to be positioned around an anastomosis of a tubular organ. In general, the sealing cuff can be formed from a spherical-shaped member with truncated proximal and distal ends. The sealing cuff can include a central portion and first and second flared portions. The central portion of the cuff can correspond to a shape of a tubular body organ, while the first and second flared portions can facilitate movement of the cuff along the tubular organ before sealant is delivered thereto. In one embodiment shown in FIGS. 202A-202C, a sealing cuff 6000 can have a substantially circular cross-sectional shape taken along a central longitudinal axis LC of the cuff 6000. The central portion 6002 of the sealing cuff 6000 can have an inner surface 6004 configured to directly contact or be positioned adjacent to an outer surface of a tubular body organ (not shown). The inner surface 6004 can define an interior chamber 6006 for receiving a sealant therein. For example, the inner surface 6004 of the sealing cuff 6000 can have a substantially concave shape that defines the interior chamber 6006. As a result, sidewall edges of the sealing cuff can contact tissue to hold a sealant within the interior chamber of the cuff. The sealing cuff 6000 can have various features for facilitating even distribution of sealant within the interior chamber 6006. For example, the sealing cuff 6000 can include any number of protrusions 6008 formed on the inner surface 6004 of the sealing cuff 6000. In general, the protrusions 6008 can be configured to directly contact an outer surface of a tubular body organ when the sealing cuff 6000 is positioned around the organ and can prevent gravity from pulling sealant toward a low portion of the sealing cuff 6000. The protrusions 6008 can be shaped in various ways, such as cylindrical, spherical, conical, etc., and can have a radial height selected so that a terminal end 6008*t* of the protrusion 6008 directly contacts the outer surface of the tubular body organ. The protrusions 6008 can also be spaced apart in various ways, such as around a circumference of the sealing cuff 6000 in a single row or in multiple rows, e.g. two rows, three rows, four rows, etc. The protrusions 6008 can be spaced evenly around the circumference in a single plane or can be spaced in any other pattern configured to facilitate an even distribution of sealant within the interior chamber 6006 of the sealing cuff 6000. The protrusions can have a radial height substantially equal to or larger than a radial thickness between the inner surface of the sealing cuff and the outer surface of the body lumen to help achieve a uniform thickness of sealant around the circumference of the cuff. As shown in FIG. 202C, the sealing cuff 6000 can further include first and second flared portions positioned 6010*a*, 6010*b* on either side of the central portion 6002 of the cuff 6000 and having an inner diameter DF that is greater than the inner diameter DI of the central portion 6002 of the cuff 6000. These flared portions 6010*a*, 6010*b* can facilitate sliding the cuff around a tubular body organ, as will be discussed in greater detail. By way of non-limiting example, the inner diameter DF of the flared portions can be about 95% of the inner diameter DI of the central portion of the cuff. The sealing cuff 6000 can have a relatively thin wall, for example, with a thickness in the range of about 1 to 5 mm. An inner diameter DI of the cuff can correspond to, e.g. be greater than or equal to, an outer diameter of a tubular body organ. For example, the inner diameter DI of the sealing cuff 6000 can be in the range of about 19 to 35 mm.

The sealing cuff can have variety of features that allow it to be positioned around a tubular organ and then removed from the organ. For example, the sealing cuff 6000 in FIGS. 202A-202C can be substantially ring-shaped when the cuff 6000 inserted in a patient. One or more reinforcement ribs 6012, 6014 can extend between and substantially perpendicular to the first and second flared portions 6010*a*, 6010*b*. In order to facilitate removal of the cuff 6000 from an organ, the sealing cuff 6000 can have a breakaway portion (not shown) configured to fracture or tear when a pulling force is applied to the cuff 6000. This breakaway portion can be positioned in the narrow space between the first and second reinforcement ribs 6012, 6014, as shown in FIG. 202B. As will be appreciated by persons skilled in the art, the breakaway portion can be formed from a different, weaker material than the remaining portion of the sealing cuff 6000, e.g. different from the material forming central portion 6002 of the sealing cuff 6000 and/or the reinforcement ribs 6012, 6014. The sealing cuff 6000 can further include a plurality of tabs that can be grasped by a tool to help position the sealing cuff 6000 and/or remove the sealing cuff 6000 from an organ. For example, as shown in FIG. 202A, a first tab 6012*a* can be formed on a first terminal end of the first reinforcement rib 6012 and a second tab 6012*b* can be formed on a second terminal end of the first reinforcement rib 6012. Similarly, a third tab 6014*a* can be formed on a first terminal end of the second reinforcement rib 6014 and a fourth tab 6014*b* can be formed on a second terminal end 6014*b* of the second reinforcement rib 6014. Each of the tabs 6012*a*, 6012*b*, 6014*a*, 6014*b* can have a substantially rectangular cross-sectional shape with a relatively thin thickness so that the tabs 6012*a*, 6012*b*, 6014*a*, 6014*b* can be grasped by one or more tools.

The sealing cuff can be configured to move in other ways and need not include a breakaway portion. For example, the sealing cuff can pivot between an open position in which first and second ends of sealing cuff are separated and a closed position in which first and second ends of sealing cuff are joined together. In this way, when the sealing cuff is in the closed position, the sealing cuff is ring-shaped and defines the interior chamber for receiving sealant. The sealing cuff can include any number of features to facilitate pivotable movement of the sealing cuff, such as a pivot-type hinge and one or more locking mechanisms configured to lock the sealing cuff in the closed position.

A sealing cuff can include one or more ports for receiving sealant therein and for directing the sealant to the interior chamber of the cuff. For example, the sealing cuff 6000 of FIG. 202A includes a port 6024 having a delivery tube 6026 coupled thereto for delivering sealant to the cuff 6000. The port 6024 can be positioned so that it extends substantially parallel to the central longitudinal axis LC of the sealing cuff 6000 so as to minimize a diameter DP of the sealing cuff 6000 at the port 624. As shown in FIG. 202C, the port 6024 can include a passageway 6028 extending into the inner surface 6004 of the cuff 6000, the passageway 6028 having a mating feature 6030 configured to mate with the delivery tube 6026. The delivery tube 6026 can be configured to couple to the mating feature 6030 in various ways, such as via a press-fit or a snap-fit, so that the delivery tube 6026 can be removed and cleaned or replaced after a single use. The passageway 6028 can be shaped in various ways, but in the illustrated embodiment includes a first portion 6028*a* that is perpendicular to a second portion 6028*b* for receiving fluid from the port, the second portion 6028*b* directing the fluid substantially toward a central inner diameter of the sealing cuff and thus, toward a staple line of an anastomosis. As will be appreciated by persons skilled in the art, while the sealing cuff is shown with only one port, the cuff can include any number of ports for delivering sealant to the cuff.

The sealing cuff can have other features that facilitate positioning of the sealing cuff around a tubular body organ. As shown in FIG. 203, a sealing cuff 6100 can have one or more extension ports 6114, 6116 formed in an outer surface 6112. One or more of the extension ports 6114, 6116 can have an inner diameter DP sized and shaped to receive a grasping tool therein. The extension ports can have various features. As shown, the extension port 6114 can have an inner lumen 6118 that determinates on the outer surface 6112 of the sealing cuff 6100 so as to not interfere with the interior chamber 6106 of the cuff 6100. In another embodiment, the inner lumen 6118 of the extension port 6114 can be in communication with the interior chamber 6106 of the cuff such that fluid can be delivered into the interior chamber 6106 therethrough, such as through a tube (not shown) extending between the inner lumen 6118 and an outer. Any number of the extension ports can have an inner lumen configured to deliver fluid to the interior chamber 6106. The inner lumen 6118 can be substantially perpendicular to the outer surface 6112 of the sealing cuff 6000 or can be disposed at other angles relative to the outer surface 6112 of the cuff 6000. For example, as shown in FIG. 203, the sealing cuff 6100 can include the first and second extension ports 6114, 6116, the first extension port 6114 being positioned about 90 degrees relative to the second extension port 6116. In another embodiment (not shown), any number of extension ports can include features for angularly positioning the extension port relative to the outer surface of the cuff, such as a ball and socket joint. The extension ports can include locking mechanisms configured to lock the port at a desired position. As will be appreciated by a person skilled in the art, the sealing cuff 6100 can include any number of extension ports positioned at any number of locations around the sealing cuff selected so as to not substantially interfere with delivery of the cuff 6100 into a patient's body. The inner lumen 6118 can be cylindrical in shape and the inner diameter DP can be in the range of about 19 to 35 mm. The second extension port 6116 can include an inner lumen 6120 being sized and shaped substantially the same as the inner lumen 6118, or the inner lumen 6120 can have a different size and shape. A sealing cuff can include features that facilitate a user locating a position of the cuff when the cuff is in a patient. For example, the cuff and/or the graspers can be configured to emit light.

A sealing cuff can include other features that help hold the sealant in a desired position between the tubular body organ and the inner surface of the sealing cuff. For example, FIG. 204A illustrates a perspective, partial cross-sectional view of a sealing cuff 6200 having suture 6232 woven across an inner surface 6204 of the sealing cuff 6200. The strand of suture 6232 can be provided in a criss-crossed pattern forming intersecting triangles across the inner surface 6204 of the cuff. In another embodiment (not shown), the strand of suture 6232 can include multiple strands of suture that can be woven in various patterns across the inner surface 6204 of the cuff 6200. In general, this suture 6232 can be used to hold the sealant away from the inner surface 6204 of the sealing cuff 6200 to prevent sealant from solidifying thereon and can therefore facilitate removal of the cuff 6200 from a patient's body. The suture 6232 can be attached to the sealing cuff 6200 in various ways. For example, a plurality of attachment points 6234 can be formed on a proximal end 6200*p* of the cuff 6200 and spaced equally about the circumference of the proximal end 6200*p* of the cuff 6200. As shown in FIG. 204B, a passageway 6236 can be formed around the circumference of the proximal end 6200*p* of the cuff 6200 and can have an elongate member 6238, e.g. a second strand of suture, extending therethrough. The passageway 6236 can further include a plurality of radial openings formed therein, each radial opening 6240 being substantially perpendicular to the passageway 6236, as shown in FIG. 204B. Each radial opening 6240 can allow the first strand of suture 6232 to pass therethrough from the inner surface 6204 of the cuff 6200, around the second strand of suture 6236, and back through the radial opening 6249 toward the inner surface 6204 of the cuff 6200, as shown in FIG. 204B. In use, the second strand of suture 6236 can be cut to release the first strand of suture 6232 from the inner surface 6204 of the cuff.

A sealing cuff according to any of the exemplary embodiments can be formed from various materials. Preferably, the sealing cuff is formed from a substantially rigid material so that it is configured to withstand the forces applied to the cuff sealant is injected through the delivery tube and into an anastomosis. A sealing cuff can be formed into a single, unitary structure, such as via injection molding, or into multiple pieces joined together using any known fixation techniques.

Sealants

A sealant can have various formulations and differing viscosity and curing behavior. Generally, a sealant can be made from a biocompatible and bioabsorbable material that can be configured to transition from a first, liquid state to a second, solidified state via a curing process, such as a polymerization reaction. The first state can be a softened state, e.g., a fluid, a gel, a foam, etc. and the second state can be a hardened state, e.g., a solid, a rigid member, etc. When the sealant is in the first, softened state, the sealant can flow through the delivery tube and into the sealing cuff, as described in greater detail below. The sealant can transition from the first, softened state to the second, solidified state after a predetermined amount of time. In certain aspects, the sealant can be formed from biologic material. In some embodiments, the sealant can assist in wound healing by releasing various chemical compounds, during and/or after curing of the sealant in a patient's body. By way of non-limiting example, the sealant can be configured to release a therapeutic drug, such as fibrin, thrombin, etc. over time to aid the tissue in healing near the location of the sealant in a body. In one embodiment, a fibrin sealant can include two reactive components combined immediately prior to delivery into a patient, such as Thrombin and a biologically active component (BAC2), Fibrinogen and Factor XIII. In certain aspects, the components can be provided in a 5:1 volumetric ratio of BAC2 to Thrombin. While the resulting sealant can have different viscosity and curing behavior depending on its formulation, this exemplary formulation of sealant can have a viscosity in the range of about 1 cp to 90 cp after the components have been mixed and the polymerization reaction has started, and the sealant can cure to a solidified state in about 3 minutes.

FIG. 205A illustrates a first component 6340 of a sealant 6300 positioned in an injection syringe 6342. As shown, the syringe can include a plunger 6341 for drawing the component 6340 therein. The syringe 6342 can be configured to introduce gas, e.g. air, into the component 6340 through various techniques. For example, an opening 6344 can be formed in a needle 6346 of the injection syringe 6342 so that air can be introduced into the component 6340 as it is drawn into the syringe 6342. This first component 6340 can be mixed with one or more additional components (not shown) immediately prior to or during injection into a patient, and these additional components can also have gas introduced therein. The presence of gas in one or more of the components of the sealant 6300 can form air pockets/closed cells 6348 as the sealant 6300 has solidified into a staple line 6350, as shown in FIG. 205B, resulting in a sealant 6300 that has increased flexibility in its solidified form than if the sealant 6300 lacked these air pockets/closed-cells 6348. This can allow the sealant 6300 to move radially and longitudinally, in coordination with a movement of a tubular body organ, as the organ radially expands, contracts, and/or twists during normal bodily function. Further, this preparation technique can decrease an amount of sealant 6300 that is applied to a sealing cuff because the gas can form the closed-cells 6348 in the sealant 6300 that increase the overall volume for a given mass of sealant 6300. The presence of these closed-cells 6348 can act as a visual indicator to a user regarding the location and/or thickness of the sealant 6300.

Expandable Devices

An expandable device can be used in conjunction with a sealing cuff to hold the sealant in a desired position as the sealant cures from the liquid state to the solidified state. In general, the expandable devices provided herein can be positioned inside of a tubular body organ in a compressed position and can move to an expanded position in which the devices expand against an inner surface of the tubular body organ. This can force an outer surface of the tubular organ toward the inner surface of sealing cuff and can help hold the sealant in this position to achieve a complete seal around the anastomosis. An expandable device can have various sizes, shapes, and configurations. In some embodiments, an expandable device can include first and second expandable members so that the first expandable member can be positioned on a first side of anastomosis and the second expandable member can be positioned on second side of the anastomosis. In certain aspects, the expandable device can be expanded/inflated by delivering liquid or gas to the expandable members. In one embodiment shown in FIG.

206A, an expandable device 6400 can include first and second expandable members 6410, 6412, i.e. inflatable balloons, coupled to an elongate member 6416, such as a cylindrical rod, via a coupling mechanism 6417. The elongate member 6416 can be configured to mate with a distal end 6418d of a scoping device 6418, as shown, to allow a user to visualize the expandable members 6410, 6412 when the expandable device 6400 is positioned inside of a tubular body organ (not shown). The first and second expandable members 6410, 6412 can be fixedly coupled to the elongate member 6416 and spaced apart along an axial length of the elongate member 6416. The first and second expandable members 6410, 6412 can be sealed around the elongate member 6416 using any attachment mechanism known in the art, such as an adhesive. As a result, the elongate member 6416 can extend through a central longitudinal axis of each of the first and second expandable members 6410, 6412 without interfering with the expansion and compression of the expandable members 6410, 6412. As will be appreciated by a person skilled in the art, the elongate member 6416 can be made from various materials and can be flexible or semi-flexible so as to allow the elongate member to navigate a tortuous tubular body organ.

The device can include various features for delivering fluid, e.g. liquid or gas, to the expandable members. As shown in FIG. 206A, the elongate member 6416 can have proximal and distal terminal ends 6416p, 6416d, and an inner lumen extending 6420 therethrough from the proximal terminal end 6416p of the elongate member 6416 and terminating proximal to the distal terminal end 6416d. The inner lumen 6420 of the elongate member 6416 can have one or more inflation lumens disposed therein for delivering fluid, e.g. liquid or gas such as saline, oxygen, carbon dioxide, etc., to one or both of the expandable members. For example, the device of FIG. 206A includes first and second inflation lumens 6422, 6424. The first inflation lumen 6422 can be configured to deliver fluid therethrough and into a first exit port (not shown) formed in the elongate member 6416, the first expandable member 6410 being disposed around the first exit port. Similarly, the second inflation lumen 6424 can be configured to deliver fluid therethrough and into a second exit port (not shown) formed in the elongate member 6416, the second expandable member 6412 being disposed around the second exit port. Each of the first and second inflation lumens 6422, 6424 can be coupled to first and second fluid sources (not shown) that can allow for selective inflation of the expandable members 6410, 6412, e.g. simultaneous inflation of the first and second expandable members 6410, 6412 or sequential inflation of the expandable members 6410, 6412 in any order. As will be appreciated by a person skilled in the art, the expandable device can have any number of inflation lumens, such as one inflation lumen in fluid communication with first and second expandable members. The expandable devices can include other features for facilitating moving the expandable members from a compressed position to an expanded position by inflating and deflating the expandable members. For example, the expandable members can include one or more valves (not shown) positioned in any of their respective inflation lumens. In certain aspects, the valves can be configured to close when the expandable member achieves a certain inflation volume to prevent liquid or gas from flowing out of the expandable members. After a procedure is performed, the valves can be opened to allow the expandable members to deflate to the compressed position to facilitate removal of the device from the patient's body.

The expandable members can have various sizes and shapes in the expanded and compressed positions. When the expandable members of FIG. 206A are in an expanded position, the expandable members 6410, 6412 can be substantially disc-shaped. The expandable members can have any size and shape configured to expand a tubular body organ, such as spherical, tubular, etc. In general, each of the expandable members can have a maximum diameter in the expanded position that is greater than an inner diameter of the tubular body organ in its resting state, such as in the range of about 110 to 115% greater than the inner diameter of the tubular body organ. As explained in further detail below, this can facilitate positioning of the sealant between an outer surface of the tubular body organ and an inner surface of the sealing cuff. The expandable members can be formed from various materials that can be inflated, such as rubber, silicone, PET, and Teflon.

FIG. 206B illustrates another embodiment of an expandable device having a first expandable member 6410', e.g. a first inflatable balloon, fixedly coupled to a flexible tether 6416'. A second expandable member 6412', e.g. a second inflatable balloon, can be positioned over a proximal terminal end 6416p' of a tether 6416' and can slide along an axial length of the tether 6416' in a compressed position so as to allow a user to selectively position the second expandable member 6412' relative to the first expandable member 6410'. The second expandable member 6412' can include an inflation lumen 6422' that can be integrally formed thereon or the inflation lumen 6422' can consist of a tube removably attachable to the second expandable member 6412'. As in the previous embodiment, an inflation source (not shown) can be coupled to the inflation lumen 6422'. The proximal terminal end 6416p' of the tether 6416' can also be coupled to an inflation source (not shown) while a distal terminal end 6416d' of the tether 6416' can be inserted into the tubular body organ with the first expandable member 6410' fixedly coupled thereto. In certain aspects, the distal terminal end 6416d' of the tether 6416' can be attached to an anvil of a circular stapler to allow the expandable device 6400' to be positioned inside of the tubular body organ as the anastomosis is being formed, as will be described in greater detail below. The tether 6416' can have anti-tangle features, such as being biased to a coiled position, and can be formed from a flexible material configured to navigate a tortuous tubular body organ. The tether 6416' can include a location device (not shown) such as a magnet, disposed thereon and positioned proximal to the second expandable member 6412', the location device allowing a surgeon to determine a location of the tether 6416' relative to an anastomosis.

An expandable device can vary in any number of ways and can include a single expandable member rather than a plurality of expandable members, as shown in FIGS. 206C and 206D. In the illustrated embodiments, expandable devices 6500, 6500' can perform many of the functions of the previous expandable devices 6400, 6400' using different features. For example, expandable members 6510, 6510' are a single balloon fixedly coupled to an elongate member, such as the scope 6418 at proximal fixation points 6526p, 6526p' and distal fixation points 6528p, 6528p'. Each expandable member 6510, 6510' includes a single inflation lumen 6522, 6522' that can extend along an outer surface 6418, 6418' of the scope 6418. Alternatively, the expandable member can have an inflation lumen extending through the scope 6418 rather than along an outer surface of the elongate member. The expandable members 6510, 6510' can be shaped in various ways. For example, FIG. 206C illustrates the expandable member 6510 having proximal and distal expandable portions 6510*p*, 6510*d* that form a substantially dumbbell-shape when the expandable member 6510 is in the expanded position and having a nonexpandable central portion 6510*c*. FIG. 206D illustrates an expandable member 6510' having a substantially cylindrical shape when it is in the expanded position. As in the previous embodiments, a maximum diameter of each of the expandable members 6510, 6510' can be selected so that the maximum diameter is greater than an inner diameter of the tubular body organ in its resting state, that is, before the expandable members 6510, 6510' are positioned therein in the expanded position. In another embodiment shown in FIG. 207, the expandable device 6600 can include the first and second expandable members 6410, 6412, and can include first and second inflation lumens 6622, 6624 terminating in distal ends 6622*d*, 6624*d* delivered to direct fluid to the first expandable member 6410 and the second expandable member 6412, respectively. The expandable device 660 can further include a third inflation lumen 6626 having a distal end 6626*d* configured to deliver liquid or gas to a central portion of the device, i.e. to the space in between the first and second expandable members 6410, 6412. As will be described in greater detail below, this lumen 6626 can deliver liquid or gas to the inner wall of the anastomosis to allow a user to test leakage therefrom.

As will be appreciated by persons skilled in the art, various inflation fluids (liquid and/or gas) can be delivered to the expandable member(s), such as air, carbon dioxide, saline, water. Additionally, the inflation fluid can be colored, such as by adding methylene blue to the inflation fluid prior to injection, and can be any biocompatible contrast material known in the art to facilitate visualization of the surgical procedure.

In other embodiments, the expandable devices can be configured to move to an expanded position without the use of liquid and inflation lumens. For example, FIGS. 208A-208C, illustrate various embodiments of stents in their expanded positions. In general, the stents can be configured to move between a compressed position and an expanded position, but can generally be biased to the expanded position. To facilitate delivery of the stent into a tubular body organ, the expandable stents can be positioned within an elongate sheath (not shown) that holds the stent in the compressed condition and can be removed once the stent is in a desired position relative to an anastomosis. As in the previous devices, the expandable stents can have various sizes, shapes, and configurations in the expanded position. For example, a stent 6700 of FIG. 208A has first and second expandable members 6710, 6712, each having a frustoconical shaped terminal portion 6732, 6734 and a central cylindrical portion 6736, 6738 configured to contact an inner wall of a tubular body organ adjacent to the anastomosis when the stent 6700 is in the expanded position. The stent 6700 can be coupled to an elongate member 6716 or rod having an actuator 6740 extending through the elongate member 6716. The actuator 6740 can be configured to be pulled proximally relative to the elongate member 6716 to deploy the expandable members 6710, 6712 to the expanded position of FIG. 208A. A stent 6700' of FIG. 208B can include first and second expandable portions 6710', 6712' being substantially funnel shaped and having a smaller diameter at a central portion 6736' thereof than at terminal ends 6732', 6734', the terminal ends 6732', 6734' being configured to contact an inner wall of the tubular body organ at a distance from the anastomosis. The expandable portions 6710', 6712' can be coupled to a flexible body, such as a tether 6716 that can have one or more location features (not shown) disposed thereon. A stent 6700" of FIG. 208C can include elongate bundles of wire 6742 extending along a longitudinal axis of the body organ and coupled to an elongate member 6716", the bundles of wire 6742 defining a first expandable portion 6710 and second expandable portion 6712. The proximal and distal ends 6742*p*, 6742*d* of the loops can be configured to expand against an inner wall of the tubular body organ while central portions of the loops have a same diameter in the expanded and compressed positions, i.e. have a smaller diameter than the tubular body organ at the anastomosis. As will be appreciated by persons skilled in the art, the expandable stents can be formed from various materials, such as Nitinol, metal wire, plastics, etc. While the expandable stents shown in FIGS. 208A-208C all include central portions having a maximum diameter less than a diameter of the organ at the anastomosis, the stents can include expandable central portions. The stents can vary in any number of ways and can have any combination of features, such as being coupled to a scope rather than an elongate member.

An expandable device can include features that facilitate a user locating a position of the device when it is positioned in a patient. For example, the expandable device can be configured to emit light, such as by being formed from a material that can emit light.

Delivery of Cuff to an Organ

A surgical procedure can be performed on a patient and can include removing a section of a tubular body organ that has an obstruction or tumor therein. This procedure can include, by way of non-limiting example, a lower anterior resection (LAR) of a rectum. Similarly, although the procedure is illustrated with respect to a tubular body organ, i.e. a rectum, another tubular anatomical structure, can be similarly treated such as entero-entero anastomosis of an intestine, uretero-uretero anastomosis of a kidney duct, esophagogastric anastomosis in the thorax or neck, aorto-iliac anastomosis, etc. After the section of the tubular body organ is removed, the procedure can include reattaching two sections of the tubular, e.g. performing a lumen-to-lumen anastomosis, such as using a circular surgical stapler. As will be appreciated by persons skilled in the art, the procedure can be an open surgical procedure, but is preferably a minimally invasive, laparoscopic and endoscopic surgical procedure in which multiple incisions are formed in a patient, the stomach cavity is insufflated with gas, and one or more trocars extend into the incisions and define a working channel for instruments to be inserted therethrough. A scope can be inserted through one of the incisions to allow a surgeon to visualize the surgical site. Alternatively or additionally, a scope can be inserted through a patient's body, i.e. through an anus to facilitate visualization of the surgical site. As described in greater detail below, various devices can be delivered endoscopically to the surgical site, including the expandable devices and the circular surgical stapler.

FIGS. 209A-209E illustrate an exemplary embodiment of a surgical procedure for stapling and sealing a tubular body organ using the sealing cuff. Although the procedure is illustrated with respect to the sealing cuff 6000 of FIGS. 202A-202C and the surgical stapler 200 of FIG. 207, the sealing cuff 6000 can include any combination of features described herein. Although the procedure is illustrated with respect to stapling, a tubular body organ can be sealed as discussed herein in conjunction with a type of fastener other than staples, e.g., clips, sutures, etc. While the surgical procedure is shown without an expandable device positioned inside of the tubular body organ, any of the devices herein can be used to expand the organ and force the outer surface of the organ toward the inner surface of the cuff to hold the sealant therebetween.

FIG. 209A illustrates first and second sections 6800a, 6800b of a tubular body organ 6800 after a portion of the organ 6800 has been removed and prior to the first and second sections 6800a, 6800b being joined in an anastomosis. The first section 6800a of the tubular body organ 6800 includes the cartridge assembly (not shown) of the surgical stapler 200 positioned therein and having a first shaft portion 262a extending therefrom. As shown in FIG. 209B, the cartridge assembly can be held within the first section 6800a of the organ 6800a via one or more strands of suture 6802a. The second section 6800b of the tubular body organ 6800 includes the anvil (not shown) of the surgical stapler 200 positioned therein and having the second shaft portion 262b extending therefrom. The anvil can also be held within the second section 6800b of the organ via one or more strands of suture 6802b. Prior to joining the two sections 6800a, 6800b, the sealing cuff 6000 can be introduced onto the tubular body organ 6800 by sliding the cuff 6000 over the second shaft portion 262b and the second section 6800b of the tubular body organ.

With the sealing cuff 6000 positioned on the second section 6800b of the tubular body organ 6800, the sealing cuff 6000 can optionally be held in position by inserting a first grasper tool 6818 directly through a first incision in a patient (without a trocar) or through a trocar 6804 and into a first extension port 6114 formed on the sealing cuff 6000, as shown in FIG. 209B. Optionally, a second grasper tool (not shown) can be inserted directly through a second incision in a patient (without a trocar) through a second trocar (not shown) and into the second extension port 6116. The grasper tools can be manipulated to move the sealing cuff 6000 axially along the tubular body organ 6800 and/or can rotate the sealing cuff 6000 relative to the organ 6800. In certain aspects, when the extension ports include a joint that allows angle(s) of the extension ports to be adjusted relative to an outer surface of the cuff, the grasper tools can be used to change an angle of one or more of the ports relative to the outer surface of the cuff, and each of the ports can be locked in an angulated position when a desired angle is achieved. With the sealing cuff 6000 positioned away from terminal ends 6806a, 6806b of the first and second sections 6800a, 6800b of the tubular organ 6800, the anvil 254 and the cartridge assembly 252 can be joined together, capturing tissue therebetween to begin forming an anastomosis. As shown in FIG. 209C, the first and second sections 6800a, 6800b of the tubular organ 6800 can be moved toward one another and the first and section portions 262a, 262b of the shaft 262 can then be coupled together to prepare the surgical stapler 200 to form an anastomosis. As shown, the anvil 254 and the cartridge assembly 252 of the stapler 200 can then be separated at a distance. The actuator (not shown) on the stapler 200 can be manipulated by a user, and this can retract the anvil 254 toward the cartridge assembly 252 until the anvil 254 and cartridge assembly 252 capture a portion of the tubular body organ 6800 therebetween, as shown in FIG. 209D. With the anvil 254 and cartridge assembly 252 positioned adjacent to one another, the device 200 can fire staples from the cartridge assembly 252 in a circular pattern around a circumference of the tubular body organ 6800, forming an anastomosis 6808. After the anastomosis 6808 is formed, the surgical stapler 200 can be removed from the patient, such as by retracting the stapler 200 proximally and out of the rectum of the patient.

The sealing cuff 6000 can be positioned over the anastomosis 6808 in various ways and can be moved toward the anastomosis 6808, such as by sliding the cuff 6000 relative thereto, as shown in FIG. 209E. The interior chamber 6006 of the sealing cuff 6000 can be positioned over the anastomosis 6808 so that the sealing cuff 6000 can direct the sealant 6300 toward the anastomosis 6808. For example, the sealing cuff 6000 can be substantially centered over the anastomosis 6808, that is, the second portion 6028b of the passageway 6028 can be aligned with a central longitudinal axis LA of the anastomosis 6808 to facilitate delivery of the sealant 6300 thereto. If the sealing cuff is configured to emit light, as previously mentioned, a user can visually monitor a position of the cuff based in part on a location of the emitted light. As shown in FIG. 209F, with the sealing cuff 6000 in the desired position, the sealant 6300 can be introduced into the delivery tube 6026 when the sealant 6300 is in a liquid state and can pass through the port 6024 and into the interior chamber 6306 of the cuff 6000. The sealant 6300 can seep into the staple line of the anastomosis 6808 and can solidify therein so as to prevent leaks. As will be appreciated by persons skilled in the art, a sufficient volume of the sealant 6300 can be delivered into the interior chamber 6306 so that the sealant 6300 is positioned 360 degrees around the anastomosis 6808. The protrusions 6008 formed on the inner surface 6004 of the sealing cuff 6000 can help distribute the sealant 6300 evenly across the anastomosis 6808 and can ensure that gravity does not pull the sealant 6300 toward a portion of the sealing cuff 6000 closest to the ground. The sealing cuff 6000 can remain positioned around the anastomosis 6808 until the sealant 6300 transitions from the liquid state to the solidified state for a predetermined amount of time, at least as long as the curing time of the sealant 6300. In certain aspects, the sealing cuff 6000 can be rotated around the body lumen as the sealant 6300 is curing from the liquid to the solidified state to facilitate uniform coverage of the sealant 6300 around the anastomosis. After the sealant 6300 has cured and is in its solidified state, one or more grasping tools (not shown) can contact and grasp the sealing cuff 6000 at various locations, such as along the tabs 61012a, 6012b, 6014a, 6014b or in the extension ports 6114, 6116. The grasping tools can be used to pull apart the sealing cuff 6000 and remove the breakaway sections so that the first reinforcement rib 6012 is detached from the second reinforcement rib 6014, the sealing cuff 6000 having a C-shaped profile, as in FIG. 209G. If the cuff includes suture woven on an inner surface thereof, as in the cuff 6200 previously described, the second strand of suture 6236 can be cut to release the first strand of suture 6232 from the inner surface 6204 of the cuff 6000, thereby releasing the solidified sealant 6300 from the cuff 6000. The sealing cuff 6000 can be removed from the tubular body organ 6800 and withdrawn from the patient's body, leaving a substantially ring-shaped structure of solidified sealant 6300b around the anastomosis 6808. The sealant 6300b can be absorbed into the body after a predetermined amount of time, such as after two weeks. Preferably, this time is selected so that the tubular body organ 6800 is substantially healed at the anastomosis 6808.

Delivery of Expandable Devices to an Organ

While the surgical procedure of FIGS. 209A-209G includes formation of the anastomosis and positioning of the sealing cuff around an anastomosis, the expandable devices disclosed herein can be used in conjunction with the sealing cuff to hold the sealant between the outer surface of the organ and the inner surface of the cuff. An expandable device can be delivered to the anastomosis in various ways, such as via the circular surgical stapler or a scope. For example, as shown in FIG. 210A, the anvil 254 of a surgical stapler 200 can be used to facilitate positioning of the expandable members 6410, 6412 inside of the tubular body organ 6800 prior to an anastomosis being formed. A tether 6416' and two expandable members 6410, 6412 can be coupled to a distal terminal end 254d of the anvil 254, as shown in FIG. 210B. The tether 6416' can be in a coiled position to prevent the tether 6416' from tangling around structures in the tubular body organ 6800. The tether 6416' can optionally include a location device 6430, such as a magnet, configured to allow a surgeon to visually monitor a position of the tether 6416' relative to the anastomosis. After the surgical stapler 200 fires the staples and forms the anastomosis 6808, the proximal end 6416p' of the tether 6416' can be detached from the anvil 254 and pulled proximally through the tubular body organ 6800 until the proximal end 6416p' is positioned outside of a patient's body. Alternatively, as shown in FIG. 210C, the tether 6416' and the expandable members 6410, 6412 can be coupled to the distal terminal end 6418d of the scoping device 6417 via the elongate member 6416 or rod. The scope 6418, elongate member 6416, and the expandable members 6410, 6412 can be inserted trans-anally through the tubular body 6800 and after a user confirms a positioning of the expandable members 6410, 6412 near the anastomosis 6800, the tether 6416' can be detached from the scoping device 6418. Any of the expandable devices/expandable members can be configured to emit light, and a user can include locate a position of the expandable device/expandable members relative to the anastomosis based in part on a location of the emitted light. The tether 6416' can be pulled proximally until the proximal end 6416p' of the tether 6416' is positioned outside of a patient's body. In both of these embodiments, a surgeon can position the first expandable member 6410 on a first side of the anastomosis 6808, i.e. distal to the anastomosis 6808, while the surgeon can position a second expandable member 6412 on a second side of the anastomosis 6808, i.e. proximal to the anastomosis 6808. With the expandable members 6410, 6412 so positioned, the proximal end 6416p' of the tether 6416' can be coupled to one or more inflation sources (not shown) and can deliver gas or liquid to the expandable members 6410, 6412. For example, a first inflation source (not shown) can be fluidly coupled to a first inflation lumen 6422 and can inflate the first expandable member 6410 to the expanded position, as shown in FIG. 210D. After the first expandable member 6410 is in the expanded position, a second inflation source (not shown) can be coupled to a second inflation lumen 6424 to inflate the second expandable member 6412 to the expanded position, as shown in FIG. 210E. The order of the steps can vary in any number of ways, for example, the first expandable member 6410 can be inflated at the same time as the second expandable member 6412 is inflated or the expandable members 6410, 6412 can be inflated sequentially, and this can be repeated any number of times until a desired amount of force is exerted on the tubular body organ 6800. In another embodiment shown in FIGS. 211A-211B, a scope such as a sigmoidoscope can be inserted trans-anally into the tubular body organ and can have the single expandable member 6500 positioned thereon. When the scope is inserted in the anus, as shown in FIG. 211A, the expandable member 6500 can be in the compressed position. More specifically, a surgeon can insert the expandable member 6500 into the anus of a patient so that the first coupling member 6526d is positioned on a first side of the anastomosis 6808, i.e. distal to the anastomosis 6808, and so that the second coupling member 6526p is positioned on a second side of the anastomosis 6808, i.e. proximal to the anastomosis 6808. The central portion 6510c of the expandable member 6500 can be axially aligned with a central portion of the sealing cuff 6000, as shown in FIG. 211B. Further, the sealing cuff 6000 can be substantially centered over the anastomosis 6808, that is, the second portion of the passageway of the cuff 6000 can be aligned with a central longitudinal axis LA of the anastomosis 6808 to facilitate delivery of the sealant 6300 to the interior chamber 6006 of the cuff 6000 and to the anastomosis 6808. A surgeon can confirm a positioning of these devices using visualization techniques known in the art. The central portion 6510c of the expandable member 6500 can be positioned adjacent to the anastomosis 6800. As in the other devices, the expandable member 6500 and sealing cuff 6000 can be positioned so that the cuff 6000 is substantially centered over the anastomosis 6808. As shown in FIG. 211C, as gas or fluid is delivered to the expandable member 6500 through the inflation lumen 6522, the first and second expandable portions 6510p, 6510d exert a force against an inner surface of the tubular body organ 6800 and increase an outer diameter of the tubular body organ 6800. This forces the outer surface of the tubular body organ 6800 toward the inner surface 6004 of the sealing cuff 6000. As will be appreciated by a person skilled in the art, the fluid can be delivered to the expandable member 6500 until a desired volume or pressure is achieved. After the sealant has substantially cured to its solidified state, the expandable member 6500 can be moved to the compressed position by releasing the fluid therefrom, and then retracted proximally and removed from the patient's body.

Any of the expandable devices disclosed herein can be positioned proximate to the anastomosis and can move from a compressed position to an expanded position to increase an outer diameter of portions of the tubular body organ adjacent to or surrounding the anastomosis. This includes the expandable devices and the expandable stents previously described. For another example, the expandable device 6400' of FIG. 206B can be used to increase an outer diameter of the tubular body organ 6800 adjacent to or surrounding the anastomosis 6808. In this embodiment, a surgeon can selectively position the second expandable member 6412' relative to the first expandable member 6410'. More specifically, a surgeon can position the first expandable member 6410' on the first side, i.e. distal to the anastomosis 6808 and the location of the expandable member 6410' can be monitored using the scope 6418, as shown in FIG. 212A. Alternatively or additionally, a surgeon can monitor the location of the expandable member 6410' using known imaging techniques to identify the location device 6430, e.g. magnet, coupled to the proximal end 6416p' of the tether 6416' and to the distal end 6416d of the elongate member 6416. A surgeon can detach the tether 6416' from the elongate member 6416 using various techniques, such as by inserting a grasper tool (not shown) into the tubular body organ 6808 and severing the tether 6416', and the scope 6418 can be retracted proximally until it is positioned outside of the patient, as in FIG. 212B. An inflation source (not shown) can be coupled to the proximal end 6416p' of the tether 6416' and can deliver liquid or gas to expand the expandable member 6410'. As shown in FIG. 212C, the scope 6418 can be inserted into the tubular body organ 6800 and can monitor a degree of inflation and positioning of the first expandable member 6410' relative to the anastomosis 6808. The second expandable member 6412', e.g. a second inflatable balloon, can be positioned over the proximal terminal end 6416p' of the tether 6416' when the proximal terminal end 6416p' is positioned outside of the patient's body, and the second expandable member 6412' can slide along an axial length of the tether 6416' in a compressed position. In this way, a user can selectively position the second expandable member 6412' relative to the first expandable member 6410' and relative to the anastomosis 6800, and the user can monitor this positioning using the scope 6418. After the second expandable member 6412' is in a desired position, the proximal terminal end 6416p' of the tether 6416' can be coupled to an inflation source (not shown) and can be activated to expand the second expandable member 6412', as shown in FIGS. 212D and 212E. The scope 6418 can be retracted proximally and removed from the patient's body. As a procedure is performed on the tubular body organ 6800, such as delivering sealant 6300 into the sealing cuff 6000 positioned around the anastomosis 6808, a volume of the expandable members 6010', 6012' can be adjusted as desired to ensure that the outer surface of the tubular body organ 6800 and the sealing cuff 6000 hold the sealant 6300 during the curing process. After the sealant 6300 has substantially cured to its solidified state, the first and second expandable members 6010', 6012' can be deflated to the compressed position and then retracted proximally and removed from the patient's body.

Methods for Testing a Seal of an Organ

Methods for testing a seal of an anastomosis can improve a surgical outcome by providing feedback to a surgeon as to the effectiveness of a seal along an anastomosis. More specifically, this can allow a surgeon to intervene and correct any leaks prior to completing the procedure. A leak test can be performed before a sealant is applied to an anastomosis and if liquid or gas fails to leak out of the staple line of the anastomosis, a surgeon may determine that it is not necessary to apply a reinforcing sealant to the anastomosis. As another example, the leak test can be performed after the sealant is applied to allow a surgeon to confirm that the sealant has penetrated the staple line and cured to its solidified state. While any of the expandable members provided herein can be modified to include an additional lumen for delivering liquid or gas to the portion of the tubular body organ adjacent to the anastomosis, specific reference is made to the expandable device of FIG. 207 for performing a leak test. After fluid has been delivered to the device so that the expandable members 6410, 6412 are in their expanded position, as shown in FIG. 213, fluid or gas can be delivered to the third inflation lumen 6626. This fluid can be trapped between first and second expandable members 6410, 6412, thereby exerting pressure on the anastomosis 6808. With the expandable members 6410, 6412 so positioned, leaks are more likely to occur at the staple line due to stretching of the tissue. As the surgeon continues to deliver the liquid or gas to this portion of the anastomosis 6808 until a desired volume and pressure is achieved in the expandable members 6410, 6412, any leaks can be observed using known imaging techniques. For example, a surgeon can confirm the presence of leaks by visually identifying gas bubbles or liquid moving out of the tubular body organ 6800 through the staple line. As previously mentioned, the use of dyes or contrast material can assist a surgeon with visually identify these leaks. The method can further include delivering therapeutic agents through the tubular body organ 6800 and into the anastomosis 6808 using the inflation lumen 6626. Such therapeutic agents can include, by way of non-limiting example, additional sealant material, adhesives, coagulants, promoters of healing, oncologic medicines, and colonic stents. The method can be performed in other ways. For example, a fourth lumen (not shown) can also be provided in the expandable device 6600 and a surgeon can use this fourth lumen to drain gas or liquid from the space between the expandable members 6410, 6412, such as to allow the leak test to be performed multiple times and/or to deliver various therapeutic agents, gas, liquid, etc. to the anastomosis 6808.

Other methods for performing a leak test are also shown in FIGS. 214A and 214B, which illustrate pressure being applied to the anastomosis 6808 at various locations. For example, FIG. 214A illustrates an expandable device 6900 having first and second mandrels 6910, 6912 having a thickness that increases from a central portion of the mandrels 6910, 6912 to an outer circumference thereof for facilitating a seal between the expandable device 6900 and the tubular body organ 6800. As shown, a side portion 6910s, 6912s of the mandrels 6910, 6912 can have an increased thickness near the inner wall of the tubular body organ 6800 so that a greater surface area of the expandable member 6910, 6912 contacts the inner surface of the organ 6800. In this way, the expandable device 6900 can withstand increased pressures and maintain in a substantially fixed position relative to the anastomosis 6808 as the fluid is delivered into a sealed space 6914 in between the first and second expandable mandrels 6910, 6912. As in the previous embodiment, the first expandable member 6910 can be inflated by delivering fluid thereto via a first inflation lumen 6922 and the second expandable member can be inflated by delivering fluid thereto via a second inflation lumen 6924 simultaneously or successively in any order. As shown in FIG. 214A, once the expandable mandrels 6910, 6912 are in the expanded positions, fluid such as gas can be delivered into the space 6914 between the mandrels 6910, 6912 via a third inflation lumen 6926. This can ensure that fluid does not leak out proximal or distal to the anastomosis 6808, as such leaking could decrease a pressure being applied to the anastomosis 6808 and thus, decrease an effectiveness of the leak test.

FIG. 214B illustrates a method for performing a leak test that includes a single expandable mandrel 6900' having proximal and distal portions 6912', 6910', sized and shaped similar to the expandable mandrels 6910, 6912 of FIGS. 214A. Fluid can be delivered to the expandable mandrel 6900' via the first inflation lumen 6922' to expand the mandrel 6900'. In the expanded position, the expandable mandrel 6900' has an enlarged central portion 6900c' positioned adjacent to and in direct contact with the anastomosis 6800. The central portion 6900c' of the expandable mandrel 6900' can exert a force perpendicular to the anastomosis 6808 and forming a staple line support zone, as shown. In this way, the expandable mandrel 6900' can prevent the anastomosis 6808 from compressing radially inward as the sealant 6300 is curing therearound and held in position in the cuff 600. Radial compression of the staple line is undesirable because it could decrease a diameter of the tubular body organ 6800 and prevent liquids and solids from passing therethrough. When the expandable mandrel 6900' is so positioned, fluid can be delivered to a first chamber 6902' positioned distal to the anastomosis 6808 via a second inflation lumen 6924', the first chamber 6902' being positioned between the distal portion 6910' and the anastomosis 6808. Simultaneously or sequentially, fluid can be delivered to a second chamber 6904' positioned proximal to the anastomosis 6808 via a third inflation lumen 6926', the second chamber 6904' being positioned between the proximal portion 6912' and the anastomosis 6808. As in the previous embodiments, a surgeon can visually identify any leaks from the anastomosis 6808. If leaks are observed, a surgeon can apply sealant 6300 to the anastomosis using a sealing cuff 6000, etc. and perform the leak test any number of times until the surgeon determines that the leaks are repaired.

After the leak test is performed and/or where a sealant has been cured to reinforce the anastomosis, the liquid or gas can be removed from the expandable member so that the expandable member is in the compressed position and the expandable device can be retracted proximally and out of the patient's body.

Reprocessing

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

In some embodiments, devices described herein can be processed before surgery. First, a new or used instrument, which can include an adjunct material, is obtained and if necessary cleaned. The instrument can then be sterilized. In some embodiments, the instrument can be dried, e.g., in an oven, together with a desiccant item, which can have a greater affinity for moisture than the adjunct material. In one sterilization technique, the instrument is placed in a closed and sealed container, such as a plastic or TYVEK bag or a foil bag. The container and instrument are then placed in a field of radiation that can penetrate the container, such as gamma radiation, x-rays, or high-energy electrons. The radiation kills bacteria on the instrument and in the container. In another sterilization technique, the instrument is placed in a first container, such as a plastic or TYVEK bag, having a vapor permeable backing. The first container can then be packaged in a second container, e.g., a foil bag, which can be left open. The first and second containers, together with the instrument, can undergo ethylene oxide sterilization. The second container can then be sealed to prevent moisture exposure. Prior to sealing, a desiccant item may be included in at least one of the first and second containers to further prevent changes to one or more device components. In both techniques, the sterilized materials can then be stored in the sterile container(s) to keep the materials sterile until the container(s) is/are opened in the medical facility.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
stapling a first adjunct material and a second adjunct material to a tissue surface at a treatment site with a plurality of staples, the first and second adjunct materials having a first layer that forms a seal around plurality of staples extending therethrough, a second layer that prevents stretching of tissue adjacent thereto, and a third layer that relieves strain on tissue adjacent thereto, wherein only the first layer of the first adjunct material overlies only the first layer of the second adjunct material to form an overlapping region, and wherein the staples extend through the overlapping region and the first layer in the overlapping region forms a seal around staples extending therethrough.

2. The method of claim 1, wherein the first layer is formed from an elastomeric material.

3. The method of claim 1, wherein at least one of the first and second adjunct materials is formed of oxidized regenerated cellulose.

4. The method of claim 1, wherein at least one of the first and second adjunct materials is formed from biocompatible, absorbable suture material, selected from the group consisting of polydioxanon, Polyglycerol sebacate, Polyglycolic acid, Polycaprolactone, Polylactic acid, Polyhydroxyalkanoate, Poliglecaprone 25, polyglactin 910, polyglyconate, polyglocolide-trimethylene carbonate, polyhydroxybutyrate, poly(vinylpyrrolidone), poly(vinyl alcohol), absorbable polyurethanes, and regenerated cellulose.

5. The method of claim 1, wherein at least one of the adjunct materials includes a therapeutic agent.

6. The method of claim 1, wherein at least one of the adjunct materials is made of a bioabsorbable material or a biofragmentable material.

7. The method of claim 1, wherein the first and second layers of the first and second adjunct materials each have a thickness, and wherein the thickness of the first layer is greater than the thickness of the second layer.

8. The method of claim 1, wherein the second layer has a smaller thickness than a thickness of each of the first and third layers.

9. The method of claim 1, wherein the first layer has a thickness from about 3 to 15 mm, the second layer has a thickness from about 5 to 20 mm, and the third layer has a thickness from about 3 to 20 mm.

10. The method of claim 1, wherein at least one of the first, second, or third layers is laminated.

11. The method of claim 1, wherein at least one of the first, second, or third layers is at least partially comprised of an absorbable material.

12. The method of claim 1, wherein the second layer is sandwiched between the first and third layers.

* * * * *